(12) United States Patent
Oikawa et al.

(10) Patent No.: US 8,609,656 B2
(45) Date of Patent: Dec. 17, 2013

(54) HETEROARYLPHENYLUREA DERIVATIVE

(75) Inventors: Nobuhiro Oikawa, Kamakura (JP);
Eisaku Mizuguchi, Kamakura (JP);
Kenji Morikami, Kamakura (JP);
Nobuo Shimma, Kamakura (JP);
Nobuya Ishii, Kamakura (JP);
Toshiyuki Tsukaguchi, Kamakura (JP);
Sawako Ozawa, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1054 days.

(21) Appl. No.: 10/590,026

(22) PCT Filed: Feb. 23, 2005

(86) PCT No.: PCT/JP2005/002923
§ 371 (c)(1),
(2), (4) Date: Aug. 18, 2006

(87) PCT Pub. No.: WO2005/080330
PCT Pub. Date: Sep. 1, 2005

(65) Prior Publication Data
US 2008/0119466 A1 May 22, 2008

(30) Foreign Application Priority Data

Feb. 23, 2004 (JP) .................. 2004-047037
Aug. 27, 2004 (JP) .................. 2004-248856

(51) Int. Cl.
*A61K 31/535* (2006.01)
(52) U.S. Cl.
USPC .................................................. 514/234.2
(58) Field of Classification Search
None
See application file for complete search history.

(56) References Cited

U.S. PATENT DOCUMENTS

2001/0011135 A1    8/2001  Riedl et al.

FOREIGN PATENT DOCUMENTS

| JP | 2002-534468 | 10/2002 |
|---|---|---|
| JP | 2003-509427 | 3/2003 |
| JP | 2003-526613 | 9/2003 |
| WO | 96/25157 A | 8/1996 |
| WO | 97/17329 A | 5/1997 |
| WO | 98/52558 A1 | 11/1998 |
| WO | 98/52559 A1 | 11/1998 |
| WO | 99/00357 A1 | 1/1999 |
| WO | 99/32106 A1 | 7/1999 |
| WO | 99/32110 A1 | 7/1999 |
| WO | 99/32111 A1 | 7/1999 |

(Continued)

OTHER PUBLICATIONS

Khire et al Omega-carboxypyridyl substituted ureas as Raf kinase inhibitors: SAR of the amide substituent. (Biorg Med Chem Lett 14:783-786, 2004).*

(Continued)

*Primary Examiner* — Craig Ricci
(74) *Attorney, Agent, or Firm* — Browdy and Neimark, PLLC

(57) ABSTRACT

The present invention provides a compound represented by the formula (1):

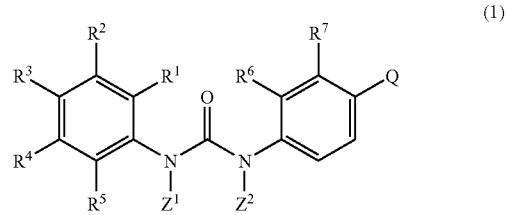

wherein $R^1$, $R^2$ and $R^5$ are each independently selected from a hydrogen atom, a halogen atom, a $C_1$-$C_6$ alkyl is substituted with a halogen atom and the like;

$R^3$ and $R^4$ are each independently selected from a hydrogen atom, a halogen atom, a substituted $C_1$-$C_6$ alkyl group and the like;

$R^6$ and $R^7$ are each independently selected from a hydrogen atom and a halogen atom;

$Z^1$ and $Z^2$ are each independently selected from a hydrogen atom, a hydroxyl group and —O(CHR$^{11}$)OC(=O)R$^{12}$;

Q is a group of the formula:

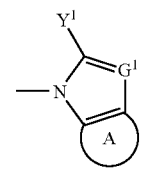

(wherein $G^1$ is C—$Y^2$ or N;

a ring A is a benzene ring or a 5- to 6-membered unsaturated heterocycle)

a pharmaceutically acceptable salt thereof or a prodrug thereof.

6 Claims, No Drawings

(56) References Cited

FOREIGN PATENT DOCUMENTS

| WO | 99/32436 A1 | 7/1999 | |
| --- | --- | --- | --- |
| WO | 99/32455 A1 | 7/1999 | |
| WO | 99/32463 A1 | 7/1999 | |
| WO | WO 99/32436 * | 7/1999 | ............ C07C 275/24 |
| WO | 00/41698 A1 | 7/2000 | |
| WO | 00/42012 A1 | 7/2000 | |
| WO | 00/43366 A1 | 7/2000 | |
| WO | WO 00/41698 A1 | 7/2000 | |
| WO | WO 01/19828 A2 | 3/2001 | |
| WO | 02/06275 A1 | 1/2002 | |
| WO | 02/32872 A1 | 4/2002 | |
| WO | 02/44156 A2 | 6/2002 | |
| WO | 02/088110 A1 | 7/2002 | |
| WO | 02/062763 A2 | 8/2002 | |
| WO | 02/085857 A2 | 10/2002 | |
| WO | 02/092576 A1 | 11/2002 | |
| WO | WO 03/029209 * | 4/2003 | |
| WO | WO 03/032989 * | 4/2003 | ............ C07D 471/04 |
| WO | 03/047579 A1 | 6/2003 | |
| WO | 03/068223 A1 | 8/2003 | |
| WO | 03/068228 A1 | 8/2003 | |
| WO | 03/068229 A1 | 8/2003 | |
| WO | 03/068746 A1 | 8/2003 | |
| WO | 03/080064 A1 | 10/2003 | |
| WO | 03/082272 A1 | 10/2003 | |
| WO | 03/099771 A2 | 12/2003 | |
| WO | 2005/042495 A1 | 5/2005 | |

OTHER PUBLICATIONS

Wolff, Manfred E ((Burger's Medicinal Chemistry 5ed, Part I) John Wiley & Sons, 1995, pp. 975-977).*
Banker ((Modern Pharmaceutics) Banker, G.S. et al, "Modern Pharmaceutics, 3ed.", Marcel Dekker, New York, 1996, pp. 451 and 596).*
Curtin et al (Bioorg Med Chem Lett 14:4505-4509, 2004).*
Anderson (Chem and Biol 10:787-797, 2003).*
Thiel (Nature Biotechnol 2:513-519, 2004).*

* cited by examiner

HETEROARYLPHENYLUREA DERIVATIVE

TECHNICAL FIELD

The present invention relates to a novel heteroarylphenylurea derivative, a pharmaceutically acceptable salt thereof, a synthetic intermediate of the derivative and a pharmaceutical composition comprising the derivative or its pharmaceutically acceptable salt.

Particularly, the present invention relates to a compound useful as a Raf inhibitor and an angiogenesis inhibitor. The above-described compound is useful for treating growth diseases, for example, cancer, psoriasis or atherosclerosis and is also useful for treating chronic rheumatoid arthritis and diabetes.

BACKGROUND ART

The Ras signal transduction pathway responds to various extracellular signals, for example, growth factors, cytokines and an extracellular matrix (ECM) through the cell-surface receptors to play an important role in regulation of proliferation, differentiation and transformation of cells.

The activation of the Ras protein in normal cells begins by the interaction of such extracellular signals as growth factors with the cell-surface receptors, and then the activated Ras protein interacts with Raf, a serine-threonine protein kinase, to activate Raf (see Non-patent Document 1 and Non-patent Document 2). It is known that with Raf, there are three types of isoforms of A-Raf of 68 Kd, B-Raf of 95 Kd and Raf-1 (c-Raf) of 74 Kd, and each is different in the aspects of the interaction with the Ras protein, the capacity of activating the substrate MEK, the expression and distribution in organs and the like, and the study with the use of a knockout mouse shows that all three A-Raf, B-Raf and Raf-1 are essential in survival. The activated Raf successively activates the substrate MEK by phosphorylation and the activated MEK activates ERK 1 and ERK 2 (MAPK). The activated ERK finally activates various substrates such as transcription factors in the cell nucleus and cytoplasma to bring about cellular changes (proliferation, differentiation and transformation) in response to the extracellular signals. These cellular changes including proliferation in normal cells are appropriately regulated but it is observed that in human cancer cells, about 20% of the Ras protein is mutated to be always in an activated state (GTP complex) and it is known that as a result, the growth signal to the Raf/MEK/ERK cascade is maintained to play an important role in the growth of human cancer cells (see Non-patent Document 3). Further, in the recent study, it is reported that the mutation of B-Raf is confirmed in 66% of melanomas, 15% of colon cancers and 14% of liver cancers, and the Raf/MEK/ERK cascade is in an activated state (see Non-patent Document 4).

In addition to the role as a direct downstream effector of the Ras protein in the Raf/MEK/ERK cascade as described above, the Raf kinase is known to play a key role in controlling the apoptosis of cells by various mechanisms (see Non-patent Document 5).

Thus, the techniques of blocking the Ras signal transduction pathway which plays an important role in the proliferation of cancer cells by inhibiting the Raf kinase as a target can be thought useful. Actually, it is reported that by inhibiting the expression of Raf with the RNA antisense, the growth of various human cancers is inhibited in vitro and in vivo (see Non-patent Document 6).

Cancer cells take in oxygen and nutrients necessary for survival and growth from the surrounding environment. In a solid tumor, these substances are supplied by simple diffusion until the solid cancer reaches a certain size. However, as the solid tumor grows to form a region 1 to 2 mm or more apart from the nearest blood vessel, this region forms a hypoxia region where the oxygen concentration is low, the nutrients are poor and the pH is low. Against to these stresses, tumor cells respond by various angiogenesis factors to stimulate the formation of a new blood vessel from the neighboring vascular endothelial cells. The angiogenesis thus started is thought to be essential in the growth of the solid tumors. There are a number of reports which suggests the relationship between VEGF (vascular endothelial growth factor), which is a growth factor specific for the vascular endothelial cells, and cancers, and the drugs which target VEGF or the tyrosine kinase activity of its receptors have recently been developed (see Non-patent Document 7 and Non-patent Document 8). Up to now, it is known that VEGF bonds to three types of receptor tyrosine kinases i.e. VEGFR-1 (flt-1), VEGFR-2 (KDR) and VEGF-3 (Flt-4), and since KDR performs strongly ligand-dependent autophosphorylation, KDR is thought to be essential to VEGF-dependent biological responses including angiogenesis.

On the other hand, a number of factors, which are involved in angiogenesis, are known in addition to VEGF and they act on vascular endothelial cells that play a key role in angiogenesis. The development of inhibitors of proliferation and function of vascular the endothelial cells that specifically act on vascular endothelial cells is strongly desired as therapeutic agents for angiogenic diseases such as cancers.

With respect to the relationship between the two cancer treatment targets, i.e. Raf and angiogenesis, an interesting report has recently been made. The activation of B-Raf and Raf-1 depends on not only the Ras protein but also growth factor signals. Basic fibroblast growth factor (b-FGF) activates Raf-1 through PAK-1 (p21-activated protein kinase-1) by the phosphorylation of serine 338 and 339 of Raf-1 to protect endothelial cells from apoptosis non-dependently to MEK 1. The VEGF signal activates Raf-1 through Src kinase by phosphorylation of tyrosine 340 and 341 of Raf-1 to protect endothelial cells dependently to MEK 1. By this report, it has been clarified that Raf plays a key role in not only the growth of cancer cells but also the control of survival of endothelial cell on angiogenesis (see Non-patent Document 9).

Further, angiogenesis is a physiological phenomenon essential in embryonic formation of the fetal period, wound healing of an adult, the menstrual period of an adult female and the like but it is reported that abnormality of angiogenesis in an adult individual relates to psoriasis, atherosclerosis, chronic rheumatoid arthritis and diabetic diseases (see Non-patent Document 10 and Non-patent Document 11), and inhibition of angiogenesis is useful for treating these diseases with the abnormality of angiogenesis.

Heretofore, a number of urea compounds which exhibit anticancer action by inhibiting any of Raf and kinases relating to angiogenesis (see Patent Documents 1 to 13). However, these compounds have a problem of solubility in water due to the high hydrophobicity and high crystallinity attributed to the phenylurea skeleton. Particularly in the case of oral drugs, the property of inferior solubility in water tents to lead to severe problems in clinical development such as poor bioavailability, unstable efficacy due to the individual difference in PK among patients or tendency of accumulation (see Non-patent Document 11 and Non-patent 13). For example, it is reported that the following compound Bay 43-9006 (Patent Document 5, Example 41):

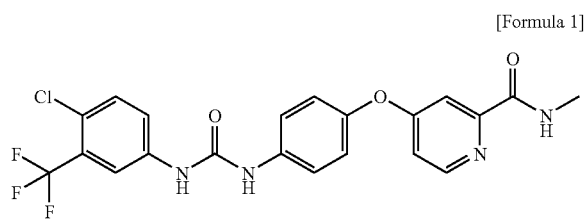

[Formula 1]

is a Raf-1 and B-RAF inhibitor and is also an inhibitor of kinases relating to the angiogenesis and the progression of a cancer including KDR, VEGFR-3, Flt-3, c-KIT and PDGFR-β (see Non-patent Document 14). However, the results of the phase I clinical study of the compound are reported (see Non-patent Document 15) and the compound is pointed out to have problems of high interpatient PK variability, tendency of accumulation upon multiple dosing and the like, which are due to high lipophilicity and low water solubility.

Patent Document 1: International Publication No. 98/52559 Pamphlet
Patent Document 2: International Publication No. 99/32106 Pamphlet
Patent Document 3: International Publication No. 99/32436 Pamphlet
Patent Document 4: International Publication No. 99/32455 Pamphlet
Patent Document 5: International Publication No. 00/42012 Pamphlet
Patent Document 6: International Publication No. 02/62763 Pamphlet
Patent Document 7: International Publication No. 02/85857 Pamphlet
Patent Document 8: International Publication No. 03/47579 Pamphlet
Patent Document 9: International Publication No. 03/68223 Pamphlet
Patent Document 10: International Publication No. 03/40228 Pamphlet
Patent Document 11: International Publication No. 03/40229 Pamphlet
Patent Document 12: International Publication No. 03/68746 Pamphlet
Patent Document 13: International Publication No. 03/80064 Pamphlet
Non-patent Document 1: Trends Biochem. Sci., Vol. 19, 474-480, 1994
Non-patent Document 2: Science, Vol. 264, 1463-1467, 1994
Non-patent Document 3: Annual Reports in Medicinal Chemistry, Vol. 29, 165-174, 1994
Non-patent Document 4: Nature, Vol. 417, 949, 2002
Non-patent Document 5: Biochemical Pharmacology, Vol. 66, 1341-1345, 2003
Non-patent Document 6: Nature, Vol. 349, 426-429, 1991
Non-patent Document 7: J. Clinical Oncology, Vol. 21, 60-65,
Non-patent Document 8: Expert Opinion Investigational Drugs, Vol. 12, 51-64, 2003,
Non-patent Document 9: Science, Vol. 301, 94-96, 2003
Non-patent Document 10: New England Journal of Medicine, Vol. 333(26), 1757-63, 1995
Non-patent Document 11: Angiogenesis, Vol. 5(4), 237-256,
Non-patent Document 12: Pharmazeutische Industrie, Vol. 64(8), 800-807, 2002
Non-patent Document 13: Pharmazeutische Industrie Vol. 64(9), 985-991, 2002
Non-patent Document 14: AACR-NCI-EORTC International Conference on Molecular Targets and Cancer Therapeutics, Proceedings, p. 69, No. A78
Non-patent Document 15: American Society of Clinical Oncology, Annual Meeting (May 18 to May 21, 2002) Abstracts, Nos. 121, 1816 and 1916, 2002.

DISCLOSURE OF THE INVENTION

Problem to be Solved by the Invention

An object of the present invention is to provide a compound which has high Raf inhibition activity and angiogenesis inhibition activity and is useful as an effective therapeutic and preventive agent for a disease with pathologic angiogenesis, for example, cancer and metastasis of cancer, a process for preparing them, an intermediate compound useful for its preparation and furthermore a pharmaceutical composition containing these compounds.

Means to Solve the Problem

As the results of strenuously developing heteroarylphenylurea derivatives having excellent Raf and angio-genesis inhibition effects by the present inventors, it has been found that derivatives having a specified structure not only exhibit excellent both inhibition actions but also excel in solubility in water and shows high and stable oral bioavailability and are useful as preventive or therapeutic agents (in particular, therapeutic agents) excellent in safety for proliferative diseases, and the present invention has been completed.

Compared to BAY 43-9006 disclosed in Patent Document 5 (International Publication No. 00/42012 Pamphlet), the compounds of the present invention have excellent solubility in water. Therefore, the compounds of the present invention are expected to have less interpatient variability in PK parameters such as Cmax, AUC value and half-life, and excellent and stable oral absorption, when administered orally. Further, the compounds of the present invention cause less body weight reduction in a dosage to exhibit the same therapeutic effect as BAY 43-9006 in an animal model and accordingly are useful as safer therapeutic or preventive agents (therapeutic agents, especially).

Namely, according to one aspect of the present invention, there is provided a compound represented by formula (1):

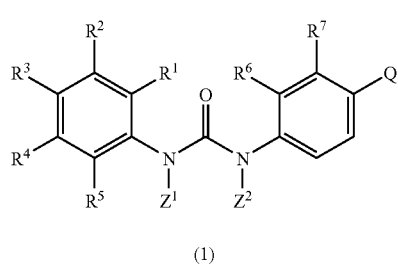

[Formula 2]

(1)

wherein
$R^1$, $R^2$ and $R^5$ are each independently selected from a hydrogen atom, a halogen atom, a $C_1$-$C_6$ alkyl group which may be substituted with one or more halogen atoms and a $C_1$-$C_6$ alkoxy group which may be substituted with one or more halogen atoms;
$R^3$ and $R^4$ are each independently selected from a hydrogen atom, a halogen atom, —NRfRg, —CONRfRg, —CH═NORe, a $C_1$-$C_6$ alkoxy group, a $C_1$-$C_6$ alkyl group and -T-$(CH_2)_k$—V, wherein the alkyl group and the alkoxy group may be substituted with one or more substituents selected from a hydroxyl group, a $C_1$-$C_6$ alkoxy group, a halogen atom and —NRfRg;
wherein Re is selected from a hydrogen atom and $C_1$-$C_6$ alkyl, wherein the alkyl group may be substituted with one to three substituents selected from a hydroxyl group, a $C_1$-$C_6$ alkoxy group, a halogen atom and —NRhRi, Rf and Rg are each independently selected from a hydrogen atom, $C_1$-$C_6$ alkyl group and $C_1$-$C_6$ alkylcarbonyl group, wherein the alkyl group and the alkylcarbonyl group may be substituted with one to three substituents selected from a hydroxyl group, a $C_1$-$C_6$ alkoxy group, a halogen atom and —NRhRi, Rh and Ri are each independently selected from a hydrogen atom and $C_1$-$C_6$ alkyl group, wherein the alkyl group may be substituted with one to three substituents selected from a hydroxyl group, a halogen atom and a $C_1$-$C_6$ alkoxy group, or Rf and Rg, and Rh and Ri together with a nitrogen atom to which they are attached may form a 4- to 7-heterocycle, wherein the heterocycle may be substituted with a $C_1$-$C_6$ alkyl group, T is an oxygen atom or a single bond; k is an integer selected from 0 to 4;

V is a 5- to 6-membered heterocyclyl group which may be substituted with one or more $Y^3$, —NRaRb, —CONRaRb, —OC(═O)NRaRb, —SO$_2$NRaRb, —N(—Ra)C(═O)NRa'Rb', —N(—Ra)C(═O)ORd, —C(═O)ORd, —S(═O)$_m$-Rd, —O-Rd, —OC(═O)Rc, —N(—Ra)C(═O)Rc, —N(Ra)SO$_2$Rc, —C(═NRa)NRa'Rb', —C(═NORa)Rc or —C(═O)Rc;

$R^6$ and $R^7$ are each independently selected from a hydrogen atom and a halogen atom;

$Z^1$ and $Z^2$ are each independently selected from a hydrogen atom, a hydroxyl group and —O(CHR$^{11}$)OC(═O)R$^{12}$;
wherein $R^{11}$ is a hydrogen atom or a $C_1$-$C_6$ alkyl group; and $R^{12}$ is a pyrrolidinyl group, a piperidinyl group, a morpholinyl group, a piperazinyl group, an amino $C_1$-$C_6$ alkyl group, a mono- or di($C_1$-$C_6$ alkyl)amino $C_1$-$C_6$ alkyl group, an amino $C_1$-$C_6$ alkylamino group or a mono- or di($C_1$-$C_6$ alkyl)-amino $C_1$-$C_6$ alkylamino group;

Q is a group of the formula:

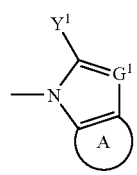

[Formula 3]

wherein $G^1$ is C—$Y^2$ or N;

ring A is a benzene ring or a 5- to 6-membered unsaturated heterocycle; a nitrogen atom present in the heterocycle may be an N-oxide; and the ring A may be substituted with one to three same or different substituents W;

$Y^1$ and $Y^2$ are each independently selected from a hydrogen atom, a halogen atom, a $C_1$-$C_6$ alkyl group, a $C_2$-$C_6$ alkenyl group, a $C_1$-$C_6$ alkoxy group, a mono- or dihydroxy $C_1$-$C_6$ alkyl group, a $C_1$-$C_6$ alkoxy $C_1$-$C_6$ alkoxy group, an amino $C_1$-$C_6$ alkoxy group, a ($C_1$-$C_6$ alkyl)amino $C_1$-$C_6$ alkoxy group, a di($C_1$-$C_6$ alkyl)amino $C_1$-$C_6$ alkoxy group, a $C_1$-$C_6$ alkoxy $C_1$-$C_6$ alkyl group, an amino $C_1$-$C_6$ alkyl group, a ($C_1$-$C_6$ alkyl)amino $C_1$-$C_6$ alkyl group, a di($C_1$-$C_6$ alkyl)amino $C_1$-$C_6$ alkyl group, an amino group, a ($C_1$-$C_6$ alkyl)amino group and a di($C_1$-$C_6$ alkyl)amino group;

W is a halogen atom, a nitro group, a cyano group, a hydroxyl group, —NRaRb, —N═C(-Rc)NRaRb, —CONRaRb, —OC(═O)NRaRb, —SO$_2$NRaRb, —N(—Ra)C(═O)NRa'Rb', —N(—Ra)C(═O)ORd, —N[C(═O)ORd][C(═O)ORd'], —C(═O)ORd, —S(═O)$_m$-Rd, —O-Rd, —OC(═O)Rc, —N(—Ra)C(═O)Rc, —N[C(═O)Rc][C(═O)Rc'], —N(—Ra)SO$_2$Rc, —N(SO$_2$Rc)(SO$_2$Rc'), —C(═NORd)NRa'Rb', —C(═NRa)NRa'Rb', —C(═NORa)Rc, —C(═O)Rc, a $C_1$-$C_6$ alkyl group which may be substituted with one or more $Y^3$, a $C_2$-$C_7$ alkenyl group which may be substituted with one or more $Y^3$, a $C_2$-$C_7$ alkynyl group which may be substituted with one or more $Y^3$, an aryl group which may be substituted with one or more $Y^3$ or a heteroaryl group which may be substituted with one or more $Y^3$;

Ra, Ra', Rb, Rb', Rc, Rc', Rd and Rd' are each independently selected from a hydrogen atom, a $C_1$-$C_{10}$ alkyl group, a $C_3$-$C_8$ cycloalkyl group, a $C_2$-$C_8$ alkenyl group, a $C_2$-$C_8$ alkynyl group, —[($C_1$-$C_6$ alkylene)-O]$_n$—($C_1$-$C_3$ alkyl), a tetrahydropyranyl group, a tetrahydrofuranyl group, an aryl group, a heteroaryl group, a nitrogen-containing heterocyclyl group (wherein the nitrogen atom on the heterocyclyl group may be substituted with a $C_1$-$C_3$ alkyl group); or Ra and Rb, Ra' and Rb', Ra and Rd, Ra and Ra', Ra and Rc, Rc and Rc' or Rd and Ra' may form a saturated or unsaturated 5- to 6-membered heterocycle by ring-closing at the bonding position of each of these two groups and the heterocycle may be substituted with a $C_1$-$C_6$ alkyl group;

Ra, Ra', Rb, Rb', Rc, Rc', Rd and Rd' each may be substituted with one to three same or different substituents selected from $Y^3$;

m is an integer selected from 0 to 2;

n is an integer selected from 1 to 4;

$Y^3$ is a halogen atom, —NRxRy, —C(═O)ORz, —C(═O)Rz, —ORz, —C(═O)NRxRy, —OC(═O)NRxRY, —SO$_2$NRxRy, —N(-Rx)C(═O)NRx'Ry', —N(-Rx)C(═O)ORz, —S-Rz, —SO-Rz, —SO$_2$-Rz, —OC(═O)Rz, —N(Rx)C(═O)Rz, —C(═NORz)NRx'Ry', —C(═NRx)NRx'Ry', —C(═NORx)Rz, —[O—($C_1$-$C_6$ alkylene)]1-O($C_1$-$C_3$ alkyl), —N(-Rx)-($C_1$-$C_6$ alkylene)-O($C_1$-$C_3$ alkyl), —C(═O)Rz, a $C_1$-$C_6$ alkyl group, a $C_2$-$C_8$ alkenyl group, a $C_2$-$C_8$ alkynyl group, an aryl group or a heteroaryl group;

Rx, Rx', Ry, Ry' and Rz are each independently selected from a hydrogen atom and a $C_1$-$C_4$ alkyl group;

Rx and Ry, Rx and Rx', Rx and Rz or Rz and Rx' may form a saturated or unsaturated 5- to 6-membered heterocycle by ring-closing at the bonding position of each of these two groups;

a pharmaceutically acceptable salt thereof or a prodrug thereof.

According to another aspect of the present invention, there is provided a compound represented by formula (1):

[Formula 4]

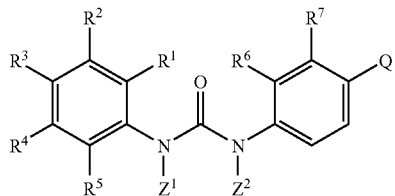

(1)

[wherein
$R^1$, $R^2$, $R^3$, $R^4$ and $R^5$ are each independently selected from a hydrogen atom, a halogen atom, a $C_1$-$C_6$ alkyl group which may be substituted with one or more halogen atoms and a $C_1$-$C_6$ alkoxy group which may be substituted with one or more halogen atoms;

$R^6$ and $R^7$ are each independently selected from a hydrogen atom and a halogen atom;

$Z^1$ and $Z^2$ are each independently selected from a hydrogen atom, a hydroxyl group and —O(CHR$^{11}$)OC(=O)R$^{12}$ (wherein $R^{11}$ is a hydrogen atom or a $C_1$-$C_6$ alkyl group; and $R^{12}$ is a pyrrolidinyl group, a piperidinyl group, a morpholinyl group, a piperazinyl group, an amino $C_1$-$C_6$ alkyl group, a mono- or di($C_1$-$C_6$ alkyl)amino $C_1$-$C_6$ alkyl group, an amino $C_1$-$C_6$ alkylamino group or a mono- or di($C_1$-$C_6$ alkyl)-amino $C_1$-$C_6$ alkylamino group);

Q is a group of the formula:

[Formula 5]

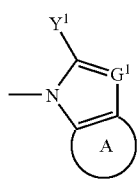

(wherein
$G^1$ is C—$Y^2$ or N;

ring A is a benzene ring or a 5- to 6-membered unsaturated heterocycle; a nitrogen atom present in the heterocycle may be an N-oxide; and the ring A may be substituted with one to three same or different substituents W;

$Y^1$ and $Y^2$ are each independently selected from a hydrogen atom, a $C_1$-$C_6$ alkyl group, a $C_1$-$C_6$ alkoxy group, a hydroxy $C_1$-$C_6$ alkyl group, a $C_1$-$C_6$ alkoxy $C_1$-$C_6$ alkyl group, an amino $C_1$-$C_6$ alkyl group, a ($C_1$-$C_6$ alkyl)amino $C_1$-$C_6$ alkyl group, a di($C_1$-$C_6$ alkyl)amino $C_1$-$C_6$ alkyl group, an amino group, a ($C_1$-$C_6$ alkyl)amino group and a di($C_1$-$C_6$ alkyl)amino group;

W is a halogen atom, a nitro group, a cyano group, a hydroxyl group, —NRaRb, —N=C(-Rc)NRaRb, —CONRaRb, —OC(=O)NRaRb, —SO$_2$NRaRb, —N(—Ra)C(=O)NRa'Rb', —N(—Ra)C(=O)ORd, —N[C(=O)ORd][C(=O)ORd', —C(=O)ORd, —S(=O)$_m$-Rd, —O-Rd, —OC(=O)Rc, —N(—Ra)C(=O)Rc, —N[C(=O)Rc][C(=O)Rc'], —N(—Ra)SO$_2$Rc, —N(SO$_2$Rc)(SO$_2$Rc'), —C(=NORd)NRa'Rb', —C(=NRa)NRa'Rb', —C(=NORa)Rc, —C(=O)Rc, a $C_1$-$C_6$ alkyl group which may be substituted with $Y^3$, a $C_2$-$C_7$ alkenyl group which may be substituted with $Y^3$, a $C_2$-$C_7$ alkynyl group which may be substituted with $Y^3$, an aryl group which may be substituted with $Y^3$ or a heteroaryl group which may be substitute with $Y^3$;

Ra, Ra', Rb, Rb', Rc, Rc', Rd and Rd' are each independently selected from a hydrogen atom, a $C_1$-$C_{10}$ alkyl group, a $C_3$-$C_8$ cycloalkyl group, a $C_2$-$C_8$ alkenyl group, a $C_2$-$C_8$ alkynyl group, —[($C_1$-$C_6$ alkylene)-O]$_n$—($C_1$-$C_3$ alkyl), an aryl group, a heteroaryl group, a pyrrolidinyl group and a piperidinyl group (wherein the nitrogen atom on the pyrrolidinyl group or the piperidinyl groups group may be substituted with a $C_1$-$C_4$ alkyl group); or Ra and Rb, Ra' and Rb', Ra and Rd, Ra and Ra', Ra and Rc, Rc and Rc' or Rd and Ra' may form a saturated or unsaturated 5- to 6-membered heterocycle by ring-closing at the bonding position of each of these two groups;

Ra, Rb, Ra', Rb', Rc, Rc', Rd and Rd' each may be substituted with one to three same or different substituents selected from $Y^3$;

m is an integer selected from 0 to 2;

n is an integer selected from 1 to 4;

$Y^3$ is a halogen atom, —NRxRy, —C(=O)ORz, —ORz, —CONRxRy, —OC(=O)NRxRy, —SO$_2$NRxRy, —N(-Rx)C(=O)NRx'Ry', —N(-Rx)C(=O)ORz, —S-Rz, —SO-Rz, —SO$_2$-Rz, —O(C=O)Rz, —N(Rx)C(=O)Rz, —C(=NORz)NRx'Ry', —C(=NRx)NRx'Ry', —C(=NORx)Rz, —[O—($C_1$-$C_6$ alkylene)]$_n$-O($C_1$-$C_6$ alkyl), —N(-Rx)-($C_1$-$C_6$ alkylene)-O($C_1$-$C_6$ alkyl), —CORz, a $C_1$-$C_6$ alkyl group, a $C_2$-$C_8$ alkenyl group, a $C_2$-$C_8$ alkynyl group, an aryl group or a heteroaryl group;

Rx, Rx', Ry, Ry' and Rz are each independently selected from a hydrogen atom and a $C_1$-$C_4$ alkyl group;

Rx and Ry, Rx and Rx', Rx and Rz or Rz and Rx' may form a saturated or unsaturated 5- to 6-membered heterocycle by ring-closing at the bonding position of each of these two groups)], a pharmaceutically acceptable salt thereof or a prodrug thereof.

In the above-described formula (1), $Y^2$ is preferably a hydrogen atom. Further, $R^{11}$ is preferably a hydrogen atom or a methyl group, and $R^{12}$ is preferably a pyrrolidinyl group or a piperazinyl group. Further, $R^2$ is preferably a halogen atom, a trifluoromethyl group or a trifluoromethoxy group.

According to another aspect of the present invention, there is provided a compound of formula (1), a pharmaceutically acceptable salt thereof or a prodrug thereof wherein Q is a group of the formula selected from:

[Formula 6]

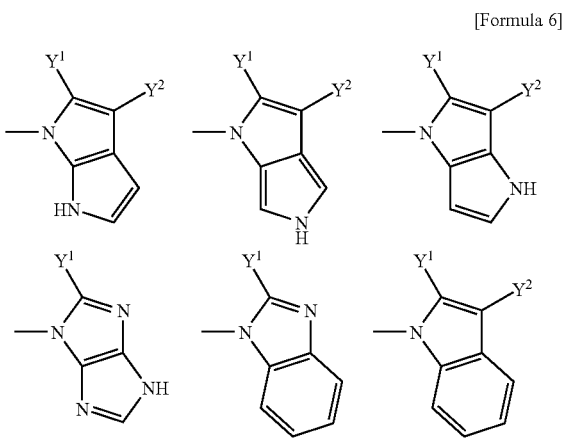

-continued

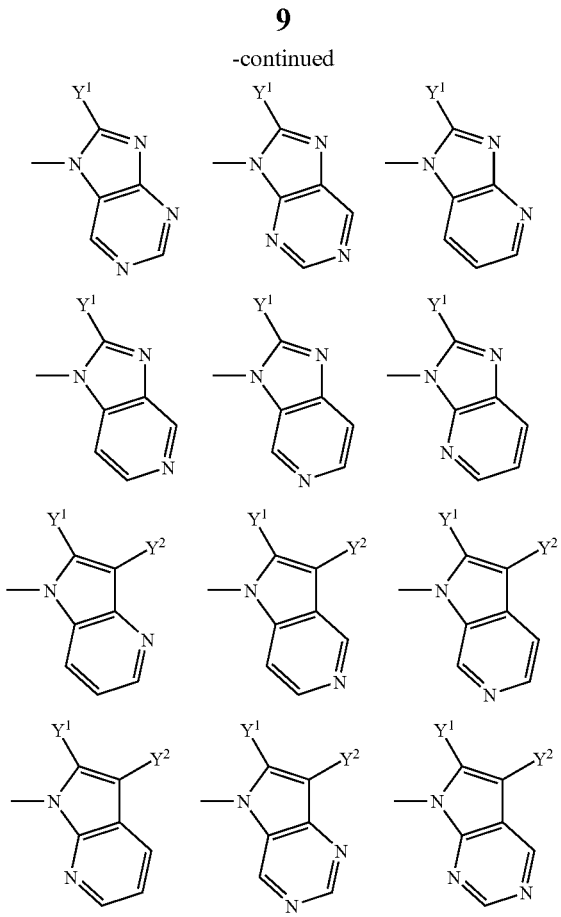

which may be substituted with one to three same or different substituents W.

Herein, Q may be a group of the formula selected from:

[Formula 7]

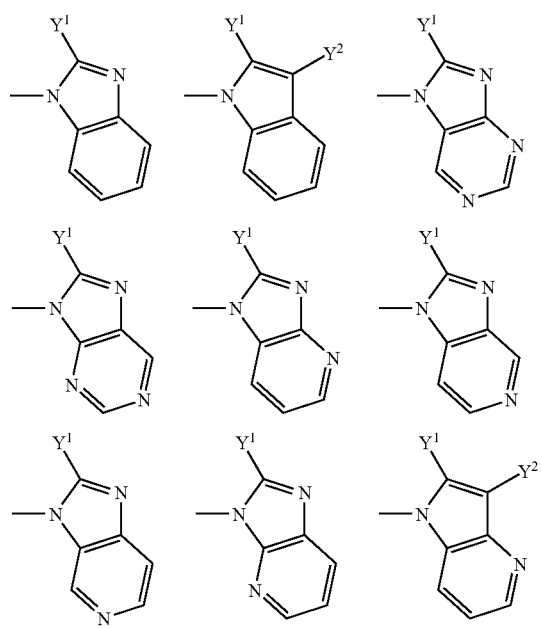

-continued

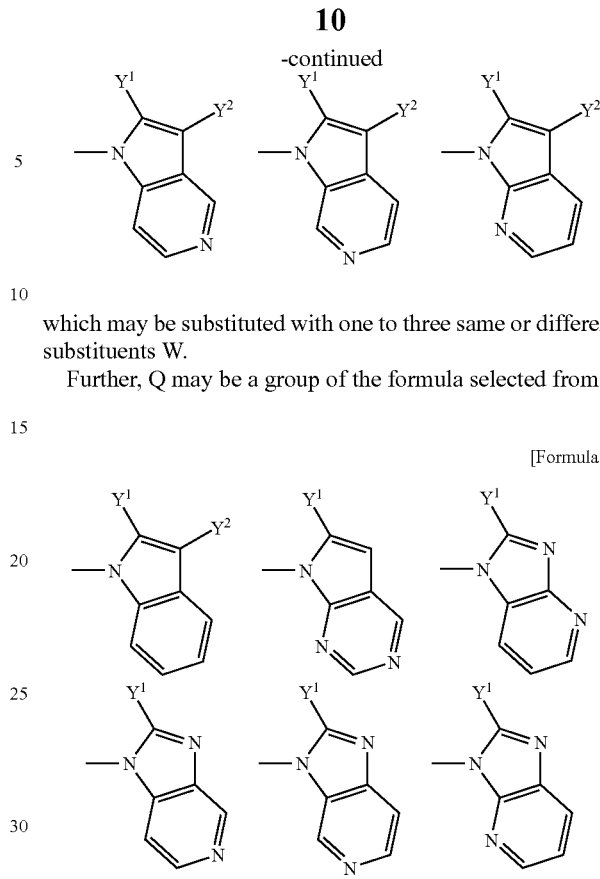

which may be substituted with one to three same or different substituents W.

Further, Q may be a group of the formula selected from:

[Formula 8]

which may be substituted with one to three same or different substituents W.

Furthermore, Q is preferably an imidazo[4,5-c]pyridin-1-yl group and a purin-9-yl group. More specifically, Q is preferably an imidazo[4,5-c]pyridin-1-yl group substituted at the 4-position with W and a purin-9-yl group which is substituted at the 6-position with W which are represented by the formulae:

[Formula 9]

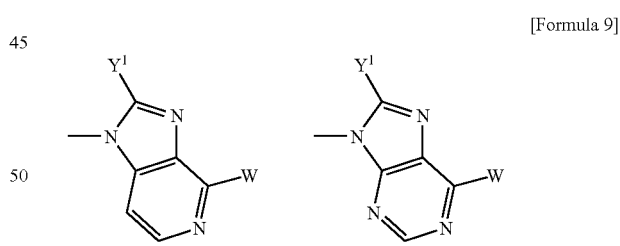

According to a further aspect of the present invention, there is provided a compound of formula (1), a pharmaceutically acceptable salt thereof or a prodrug thereof, wherein
$R^1$, $R^2$, $R^3$, $R^4$ and $R^5$ are each independently selected from a hydrogen atom, a chlorine atom, a fluorine atom, a bromine atom and a trifluoromethyl group;
$R^6$ and $R^7$ are hydrogen atoms; and
$Z^1$ and $Z^2$ are each independently selected from a hydrogen atom and a hydroxyl group.

According to a still further aspect of the present invention, there is provided a compound of formula (1) defined in claim 1, a pharmaceutically acceptable salt thereof or a prodrug thereof, wherein R$^1$, R$^2$, R$^5$, R$^6$, R$^7$, Z$^1$, Z$^2$ and Q are the same as already defined;

R$^3$ and R$^4$ are each independently selected from a hydrogen atom, a halogen atom, a C$_1$-C$_6$ alkyl group which may be substituted with one or more hydroxyl groups or halogen atoms, a C$_1$-C$_6$ alkoxy group which may be substituted with one or more halogen atoms, and -T-(CH$_2$)$_k$—V;

T is an oxygen atom or a single bond; k is an integer selected from 0 to 4;

V is a 5- to 6-membered heterocyclyl group which may be substituted with one or more substituents selected from a hydroxy group, an amino group, C$_1$-C$_6$ alkyl group, C$_1$-C$_6$ alkoxy group and C$_1$-C$_6$ alkyl carbonyl group.

Examples of groups represented by "-T-(CH$_2$)$_k$—V" include a heterocyclyl C$_1$-C$_6$ alkyl group which may be substituted with one or more substituents selected from a hydroxyl group, an amino group, a C$_1$-C$_6$ alkyl group and a C$_1$-C$_6$ alkylcarbonyl group; a heterocyclyl C$_1$-C$_6$ alkoxy group which may be substituted with one or more substituents selected from a hydroxyl group, an amino group, a C$_1$-C$_6$ alkyl group and a C$_1$-C$_6$ alkylcarbonyl group; and a heterocyclyloxy group which may be substituted with one or more substituents selected from a hydroxyl group, a C$_1$-C$_6$ alkyl group and a C$_1$-C$_6$ alkoxy group.

According to another aspect of the present invention, the above-described compound of formula (1), a pharmaceutically acceptable salt thereof or a prodrug thereof which has Raf inhibition and angiogenesis inhibition actions and is used in treating a cancer, psoriasis, atherosclerosis, chronic rheumatoid arthritis and diabetes is provided.

According to a further aspect of the present invention, a pharmaceutical composition comprising the above-described compound of formula (1), a pharmaceutically acceptable salt thereof or a prodrug thereof as an active ingredient is provided.

According to a still further aspect of the present invention, a Raf inhibitor or an angiogenesis inhibitor comprising the above-described compound of formula (1), a pharmaceutically acceptable salt thereof or a prodrug thereof as an active ingredient is provided.

According to a further aspect of the present invention, a preventive or therapeutic agent for a disease selected from cancer, psoriasis, atherosclerosis, chronic rheumatoid arthritis and diabetes which contains the above-described compound of formula (1), a pharmaceutically acceptable salt thereof or a prodrug thereof as an active ingredient is provided.

Effect of the Invention

According to the present invention, a preventive or a therapeutic agent (particularly a therapeutic agent) which not only has the existing Raf inhibition and angiogenesis inhibition actions but also excels in the solubility in water to show highly stable oral bioavailability and excels in the safety for proliferative diseases is provided. Further, according to the present invention, a compound useful for therapeutic and preventive agent effective for proliferative diseases such as cancer and cancerous metastasis, a process for producing thereof, an intermediate useful for production thereof, and furthermore a pharmaceutical composition comprising these compounds are provided.

WORKING MODE OF THE INVENTION

The term "halogen", as used in the present invention, means a fluorine atom, a chlorine atom, a bromine atom and iodine atom.

The term "C$_1$-C$_3$ alkyl group", as used in the present invention, means a straight-chain or branched-chain alkyl group having 1 to 3 carbon atoms and includes, for example, methyl, ethyl, n-propyl and i-propyl.

The term "C$_1$-C$_4$ alkyl group", as used in the present invention, means a straight-chain or branched-chain alkyl group having 1 to 4 carbon atoms and include, for example, methyl, ethyl, n-propyl, i-propyl, n-butyl, i-butyl, sec-butyl and tert-butyl.

The term "C$_1$-C$_6$ alkyl group", as used in the present invention, means a straight-chain or branched-chain alkyl group having 1 to 6 carbon atoms and includes, for example, "C$_1$-C$_4$ alkyl group" such as methyl, ethyl, n-propyl, i-propyl, n-butyl, s-butyl, i-butyl and t-butyl, and further includes n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl and 2-ethylbutyl.

The term "C$_1$-C$_{10}$ alkyl group", as used in the present invention, means a straight-chain or branched-chain alkyl group having 1 to 10 carbon atoms and includes, for example, "C$_1$-C$_4$ alkyl group" and "C$_1$-C$_6$ alkyl group", and further includes n-heptyl, n-octyl, n-nonyl and n-decanyl.

The term "C$_3$-C$_8$ cycloalkyl group", as used in the present invention, means as cyclic or partially cyclic alkyl group having 3 to 8 carbon atoms and includes, for example, cyclopropyl, cyclobutyl, cyclopentyl, cyclohexyl, cycloheptyl, cyclooctyl, cyclopropylmethyl, cyclohexylmethyl, cyclopropyl substituted with a C$_1$-C$_5$ alkyl, cyclopentyl substituted with a C$_1$-C$_3$ alkyl group and cyclohexyl substituted with a C$_1$-C$_2$ alkyl group.

The term "C$_1$-C$_6$ alkoxy group", as used in the present invention, means an alkyloxy group having a straight-chain or branched-chain alkyl group having 1 to 6 carbon atoms as an alkyl moiety and includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methyl-pentoxy, 2-methylpentoxy, 1-methylpentoxy, 3-ethylbutoxy and 2-ethylbutoxy.

The term "C$_2$-C$_8$ alkenyl group", as used in the present invention, means a straight-chain or branched-chain alkenyl group having 2 to 8 carbon atoms and include, for example, ethenyl (vinyl), 1-propenyl, 2-propenyl (allyl), propen-2-yl and 3-butenyl (homoallyl).

The term "C$_2$-C$_8$ alkynyl group", as used in the present invention, means a straight-chain or branched-chain alkynyl group having 2 to 8 carbon atoms and include, for example, ethynyl, 1-propynyl, 2-propynyl, 1-butynyl, 2-butynyl and 3-butynyl.

The term "aryl group", as used in the present invention, means a C$_6$-C$_{10}$ aromatic hydrocarbon group and include, for example, phenyl, 1-naphthyl and 2-naphthyl.

The term "heteroaryl group", as used in the present invention, means a 5- to 10-membered aromatic heterocyclyl group containing one or more heteroatoms selected from an oxygen atom, a nitrogen atom and a sulfur atom and include, for example, furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidinyl, pyrazinyl, pyridazinyl, indolyl and quinolyl. The substituting position of the heteroaryl group may be any substitutable position on a carbon atom or a nitrogen atom and is not particularly limited.

The term "unsaturated 5- to 6-membered heterocycle", as used in the present invention, means a heterocycle which contains one or more heteroatoms selected from an oxygen atom, a nitrogen atom and a sulfur atom and has an unsaturated bond and 5 to 6 atoms present in the ring and includes an aromatic heterocycle. Specifically "unsaturated 5- to 6-membered heterocycle" includes, for example, pyrrole, imidazole, pyrazole, pyrazoline, pyridine, pyrazine, pyrimidine, pyridazine, triazine, furan, thiophene, oxazole and thiazole. The substituting position of the heterocyclyl group may be any substitutable position on a carbon atom or a nitrogen atom and is not particularly limited.

The term "saturated or unsaturated 5- to 6-membered heterocycle", as used in the present invention, means a saturated or unsaturated heterocycle which contains one or more heteroatoms selected from an oxygen atom, a nitrogen atom and a sulfur atom and has 5 to 6 atoms present in the ring and includes an aromatic heterocycle. Specifically "saturated or unsaturated 5- to 6-membered heterocycle" includes, for example, pyrrolidine, piperidine, piperazine, pyrrole, imidazole, imidazoline, pyrazole, pyrazoline, oxazoline, morpholine, thiomorpholine, pyridine, pyrazine, pyrimidine, pyridazine, hexamethylene-imine, furan, tetrahydrofuran, thiophene, tetrahydro-thiophene, dioxolane, oxathiolane and dioxane. The substituting position of the heterocyclyl group may be any substitutable position on a carbon atom or a nitrogen atom and is not particularly limited.

The term "5- to 6-membered heterocyclyl group", as used in the present invention, means a saturated or unsaturated heterocyclic group which contains one or more heteroatoms selected from a nitrogen atom, an oxygen atom and a sulfur atom and has 5 to 6 atoms present in the ring. The heterocyclyl group includes, for example, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, pyridyl, pyrazinyl, pyrimidinyl and pyridazinyl. The nitrogen-containing heterocyclyl group is preferably pyridyl, pyrrolidinyl, morpholinyl, piperazinyl or piperidinyl.

The term "nitrogen-containing heterocyclyl group", as used in the present invention, means a saturated or unsaturated heterocyclic group which contains one or more nitrogen atoms and optionally further one or more heteroatoms selected from a nitrogen atom, an oxygen atom and a sulfur atom and has 5 to 6 atoms present in the ring. The nitrogen-containing heterocyclyl group includes, for example, pyrrolidinyl, piperidinyl, piperazinyl, pyrrolyl, imidazolyl, imidazolinyl, pyrazolyl, pyrazolinyl, oxazolinyl, morpholinyl, thiomorpholinyl, pyridyl, pyrazinyl, pyrimidinyl and pyridazinyl. The nitrogen-containing heterocyclyl group is preferably pyrrolidinyl, morpholinyl, piperazinyl or piperidinyl. The number of atom contained in the nitrogen-containing heterocyclyl group is not particularly limited, but for example 4 to 8, preferably 5 to 7, more preferably 5 to 6.

In the present invention, the "aryl group" and the "heteroaryl group" may optionally be substituted with at least one halogen atom, $C_1$-$C_6$ alkyl or $C_1$-$C_6$ alkoxy. The number of the substituent may be one to a possibly maximum number from a chemical structural standpoint. The number of the substituent is, for example, 1 to 5, preferably 1 to 3.

In the present invention, when the nitrogen atom present in the ring is an N-oxide, the N-oxide includes, for example, a pyridine-N-oxide, a pyrimidine N-oxide, pyridazine N-oxide and a triazine N-oxide.

The term "$C_1$-$C_6$ alkylene group", as used in the present invention, means a straight-chain or branched-chain divalent alkylene group having 1 to 6 carbon atoms and includes, for example, methylene, ethylene, propylene (including, for example, —$CH_2CH_2CH_2$—, —$CH(CH_3)CH_2$— and —$CH(CH_2CH_3)$—), butylenes (including, for example, —$CH_2CH_2CH_2CH_2$—, —$CH(—CH_3)CH_2CH_2$—, —$CH_2CH(—CH_3)CH_2$—, —$CH_2CH_2CH(—CH_3)$—, —$CH(—CH_2CH_3)CH_2$—, —$CH_2CH(—CH_2CH_3)$—, —$CH(—CH_2CH_2CH_3)$— and —$CH(—CH_3)CH(—CH_3)$—).

The term "hydroxyl $C_1$-$C_6$ alkyl group", as used in the present invention, means an alkyl group substituted with a hydroxyl group which has the already defined $C_1$-$C_6$ alkyl group as an alkyl moiety and includes, for example, hydroxymethyl, 2-hydroxyethyl, 1-hydroxyethyl, 3-hydroxypropyl, 2-hydroxypropyl, 1-hydroxypropyl, 2-hydroxyprop-2-yl and 1-hydroxy-prop-2-yl.

The term "$C_1$-$C_6$ alkoxy $C_1$-$C_6$ alkyl group", as used in the present invention, means an alkyl group substituted with an alkoxy group which has the already defined $C_1$-$C_6$ alkyl group as an alkyl moiety and the already defined $C_1$-$C_6$ alkoxy group as an alkoxy moiety and include, for example, methoxymethyl, 2-methoxyethyl, 1-methoxyethyl, 3-methoxypropyl, 2-methoxypropyl, 1-methoxypropyl, 2-methoxyprop-2-yl, 1-methoxy-prop-2-yl, ethoxymethyl, 2-ethoxyethyl, 1-ethoxyethyl, 3-ethoxypropyl, 2-ethoxypropyl, 1-ethoxypropyl, 2-ethoxy-prop-2-yl and 1-ethoxy-prop-2-yl.

The term "amino $C_1$-$C_6$ alkyl group", as used in the present invention, means an alky group substituted with an alkyl group which has the already defined $C_1$-$C_6$ alkyl group as an alkyl moiety and includes, for example, aminomethyl, 2-aminoethyl, 1-aminoethyl, 3-aminopropyl, 1-aminopropyl, 2-amino-pro-2-yl and 1-amino-pro-2-yl.

The term "($C_1$-$C_6$ alkyl)amino group", as used in the present invention, means an amino group substituted with an amino group which has the already defined $C_1$-$C_6$ alkyl group as an alkyl moiety and includes, for example, methylamino, ethylamino, n-propylamino and isopropylamino.

The term "di($C_1$-$C_6$ alkyl)amino group", as used in the present invention means an amino group substituted with an alkyl group which has the already independently defined two $C_1$-$C_6$ alkyl groups as alkyl moieties and includes, for example, dimethylamino, ethylmethylamino, diethylamino, di-n-propylamino, diisopropylamino, methyl-n-propylamino and methyl-isopropylamino.

The term "($C_1$-$C_6$ alkyl)amino $C_1$-$C_6$ alkyl", as used in the present invention, means an alkyl group substituted with an alkylamino group which has the already independently defined two $C_1$-$C_6$ alkyl groups as alkyl moieties and include, for example, (methylamino)methyl, 2-(methylamino)ethyl, 1-(methylamino)ethyl, 3-(methylamino)propyl, 2-(methylamino)propyl, 1-(methylamino)propyl, 2-(methylamino)prop-2-yl and 1-(methylamino)-prop-2-yl.

The term "di($C_1$-$C_6$ alkyl)amino $C_1$-$C_6$ alkyl", as used in the present invention, means an alkyl group substituted with an alkylamino group which has the already independently defined three $C_1$-$C_6$ alkyl groups as alkyl moieties and include, for example, (dimethylamino)methyl, 2-(dimethylamino)ethyl, 1-(dimethylamino)ethyl, 3-(dimethylamino)propyl, 2-(dimethylamino)propyl, 1-(dimethylamino)propyl, 2-(dimethylamino)prop-2-yl and 1-(dimethylamino)-prop-2-yl.

The term "amino $C_1$-$C_6$ alkylamino group", as used in the present invention, means an alkylamino group substituted with an amino group which has the already defined $C_1$-$C_6$ alkyl group as an alkyl moiety and includes, for example, (2-aminoethyl)amino, (3-aminopropyl)amino and (4-aminobutyl)amino.

The term "mono($C_1$-$C_6$ alkyl)amino $C_1$-$C_6$ alkyl group", as used in the present invention, means an alkylamino group substituted with an alkylamino group which has the already defined two $C_1$-$C_6$ alkyl group as alkyl moieties and includes, for example, (2-(methylamino)ethyl)amino, (2-(ethylamino)ethyl)amino and (3-(methylamino)propyl)amino and (3-(ethylamino)propyl)amino.

The term "di($C_1$-$C_6$ alkyl)amino $C_1$-$C_6$ alkyl group", as used in the present invention, means an alkylamino group substituted with an alkylamino group which has the already defined three $C_1$-$C_6$ alkyl group as alkyl moieties and includes, for example, (2-(dimethylamino)ethyl)amino, (2-(diethylamino)ethyl)amino, (3-(dimethylamino)propyl)amino and (3-(diethylamino)propyl)amino.

In the present invention, when Ra and Rb or Ra' and Rb' are bonded to the same nitrogen atom, Ra and Rb or Ra' and Rb' may form a saturated or unsaturated 5- to 6-membered heterocycle having at least one nitrogen. The heterocycle includes, for example, pyrrole, pyrrolidine, piperazine, pyridine, morpholine and thiomorpholine.

In the present invention, the —N(—Ra)C(=O)ORd group may be ring-closed at the bonding position of Ra and Rd to form a saturated or unsaturated 5- to 6-membered heterocycle. The heterocycle includes, for example, oxazolin-2-one and oxazolidin-2-one.

In the present invention, the —N(—Ra)C(=O)NRa'Rb' group may be ring-closed at the bonding position of Ra and Ra' to form a saturated or unsaturated 5- to 6-membered heterocycle. The heterocycle includes, for example, imidazolin-2-one and imidazolidin-2-one.

In the present invention, the —N=C(-Rc)NRaRb group may be ring-closed at the bonding position of Ra and Rc to form a saturated or unsaturated 5- to 6-membered heterocycle. The —N=C(-Rc)NRaRb on forming a heterocycle includes, for example, the formulae:

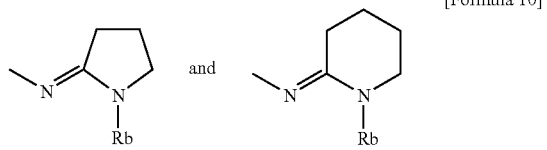

[Formula 10]

In the present invention, the —N(—Ra)C(=O)Rc group may be ring-closed at the bonding position of Ra and Rc to form a saturated or unsaturated 5- to 6-membered heterocycle. The heterocycle includes, for example, pyrrolin-2-one, pyrrolidin-2-one, piperidin-2-one and morpholin-3-one.

In the present invention, the —C(=NORa)Rc group may be ring-closed at the bonding position of Ra and Rc to form a saturated or unsaturated 5- to 6-membered heterocycle. The heterocycle includes, for example, isoxazole and isoxazoline.

In the present invention, the —N(—Ra)SO$_2$Rc group may be ring-closed at the bonding position of Ra and Rc to form a saturated or unsaturated 5- to 6-membered heterocycle. The heterocycle includes, for example, isothiazole-1,1-dioxide and isothiazoline-1,1-dioxide.

In the present invention, the —N[C(=O)Rc][C(=O)Rc'] group may be ring-closed at the bonding position of Rc and Rc' to form a saturated or unsaturated 5- to 6-membered heterocycle. The heterocycle includes, for example, pyrrolidin-2,5-dione and piperidine-2,5-dione.

In the present invention, the —C(=NORd)NRa'Rb' group may be ring-closed at the bonding position of Rd and Ra' to form a saturated or unsaturated 5- to 6-membered heterocycle. The heterocycle includes, for example, oxadiazoline.

The present invention includes a salt of the compound represented by formula (1) and a pharmaceutically acceptable salt of a prodrug of the compound. These salts are produced by bringing the compound or the prodrug of the compound into contact with an acid or a base usable in the production of drugs. The salts include, for example, a hydrochloride, a hydrobromide, a hydroiodide, a sulfate, a sulfonate, a phosphate, a phosphonate; a carboxylate such as an acetate, a citrate, a malate, a salicylate; an alkali metal such as a sodium salt and potassium salt; an alkaline earth metal salt such as a magnesium salt and a calcium salt; and an ammonium salt such as an ammonium salt, an alkylammonium salt, a dialkylammonium salt, a trialkylammonium salt and a tetraalkylammonium salt.

The term "prodrug", as used in the present invention, means a derivative of the compound of formula (1) which is converted into the compound of formula (1) or its pharmaceutically acceptable salts by enzymatic or non-enzymatic reaction under physiological conditions. When the prodrug is administered to a patient, it may be inactive, but in a living body, it is converted to be in the form of the compound of formula (1) which is active.

The term "prodrug" in the present invention includes, for example, that:

(1) when the compound of the formula (1) has a hydroxyl group in the molecule, the hydroxyl group is protected with a protective group;

(2) when the compound of the formula (1) has a —NH— group or an amino group in the molecule a compound, the —NH-group or the amino group is protected with a protective group; and (3) when the compound of the formula (1) has a carboxyl group in the molecule, the carboxyl group is converted to an ester group or an amide group which may be substituted.

Herein, examples of the protective group for the hydroxyl group include, for example, a $C_1$-$C_6$ alkylcarbonyl group, an arylcarbonyl group, a heteroarylcarbonyl group, a $C_1$-$C_6$ alkoxycarbonyl group, a $C_1$-$C_6$ alkylaminocarbonyl group, a di($C_1$-$C_6$ alkyl)aminocarbonyl group, an aryl $C_1$-$C_6$ alkyl group, a heteroaryl $C_1$-$C_6$ alkyl group, an aryl $C_1$-$C_6$ alkylaminocarbonyl group, —P(=O)(OH)$_2$, —CH$_2$OP(=O)(OH)$_2$, a $C_1$-$C_6$ alkyl group, a $C_1$-$C_6$ alkylsulfonyl group, an ((amino $C_1$-$C_6$ alkyl)carbonyloxy)$C_1$-$C_6$ alkyl group and an unsaturated heterocyclic carbonyloxy $C_1$-$C_6$ alkyl group. Further, the protected hydroxyl group may be an ester of a natural type or non-natural type amino acid, an ester of a dipeptide, an ester of a tripeptide or an ester of tetrapeptide. Preferred protective groups for the hydroxyl group include, for example, an acetyl group, a glycidyl group, a sarcosyl group, an alanyl, group, a leucyl group and a (5-methyl-2-oxo-1,3-dioxolo-4-yl)methyl group.

Examples of the protective group for the —NH— group or amino group include, for example, a $C_1$-$C_6$ alkylcarbonyl group, an arylcarbonyl group, a heteroarylcarbonyl group, a $C_1$-$C_6$ alkoxycarbonyl group, a $C_1$-$C_6$ alkylaminocarbonyl group, a di($C_1$-$C_6$ alkyl)aminocarbonyl group, an aryl $C_1$-$C_6$ alkyl group, a heteroaryl $C_1$-$C_6$ alkyl group, an (aryl $C_1$-$C_6$ alkyl)aminocarbonyl group, —P(=O)(OH)$_2$, —CH$_2$OP(=O)(OH)$_2$, a $C_1$-$C_6$ alkyl group and a $C_1$-$C_6$ alkylsulfonyl group. Further, the protected —NH— group or amino group may be an amide of a natural type or non-natural type amino acid, an amide of a dipeptide, an amide of a tripeptide amide or an amide of a tetrapeptide. Preferred protective groups for the amino group include, for example, an acetyl group, glycidyl group, sarcosyl group, an alanyl group, a leucyl group, and a (5-methyl-2-oxo-1,3-dioxolo-4-yl)methyl group.

Further, the amino group may form a saturated or unsaturated heterocyclyl group such as a phthalimide group, a succinimide group, a glutarimide group or a 1-pyrrolyl group by the protection.

When the carboxyl group is converted to an ester group or an amide group which may be substituted, examples of the ester group include, for example, a $C_1$-$C_6$ alkyl ester, an aryl ester, a heteroaryl ester, an aryl $C_1$-$C_6$ alkyl ester, a heteroaryl $C_1$-$C_6$ alkyl ester, a $C_1$-$C_6$ alkoxy $C_1$-$C_6$ alkyl ester, an aryloxy $C_1$-$C_6$ alkyl ester, an aryl $C_1$-$C_6$ alkyloxy $C_1$-$C_6$ alkyl ester, a hydroxyl $C_1$-$C_6$ alkyl ester, an amino $C_1$-$C_6$ alkyl ester, a $C_1$-$C_6$ alkylamino $C_1$-$C_6$ alkyl ester and a di($C_1$-$C_6$ alkyl)amino $C_1$-$C_6$ alkyl ester. Preferred ester groups are a methyl ester group, an ethyl ester group, 2-hydroxyethyl ester and a 2-(dimethylamino)ethyl ester group.

The amide group is, for example, an amide group represented by —C(=O)NR$^{21}$R$^{22}$, and R$^{21}$ and R$^{22}$ can be independently selected from a hydrogen atom, a $C_1$-$C_6$ alkyl group, an aryl group, a heteroaryl group, an aryl $C_1$-$C_6$ alkyl group, a heteroaryl $C_1$-$C_6$ alkyl group, a $C_1$-$C_6$ alkoxy $C_1$-$C_6$ alkyl group, an aryloxy $C_1$-$C_6$ alkyl group, an aryl $C_1$-$C_6$ alkyloxy $C_1$-$C_6$ alkyl group, a hydroxyl $C_1$-$C_6$ alkyl group, an amino $C_1$-$C_6$ alkyl group, a $C_1$-$C_6$ alkylamino $C_1$-$C_6$ alkyl group, a di($C_1$-$C_6$ alkyl)amino $C_1$-$C_6$ alkyl group, a hydroxyl group and an alkoxy group. R$^{21}$ and R$^{22}$ are preferably each a methyl group, an ethyl group, a 2-hydroxyethyl group or a 2-(dimethylamino)ethyl group.

As more specific examples of the compound represented by formula (1) of the present invention, the compounds as described below can be exemplified but the present invention is not limited to them.

TABLE 1

| | Structural formula | Name of compound | Example No. |
|---|---|---|---|
| 1 | | 1-(4-Chloro-3-(trifluoromethyl)phenyl)-3-(4-imidazo[4,5-c]pyridin-1-ylphenyl)urea | Example 1 |
| 2 | | 1-(4-Chloro-3-(trifluoromethyl)phenyl)-3-(4-imidazo[4,5-c]pyridin-3-ylphenyl)urea | Example 2 |
| 3 | | 1-(4-Chloro-3-(trifluoromethyl)phenyl)-3-(4-indol-1-ylphenyl)urea | Example 3 |
| 4 | | 1-(4-Chloro-3-(trifluoromethyl)phenyl)-3-(4-purin-7-ylphenyl)urea | Example 4 |
| 5 | | 1-(4-Chloro-3-(trifluoromethyl)phenyl)-3-(4-purin-9-ylphenyl)urea | Example 5 |

TABLE 1-continued

| | Structural formula | Name of compound | Example No. |
|---|---|---|---|
| 6 | | 1-(4-Chloro-3-(trifluoro-methyl)phenyl)-3-(4-pyrrolo-[2,3-b]pyridin-1-ylphenyl)urea | Example 6 |
| 7 | | 1-(4-Chloro-3-(trifluoro-methyl)phenyl)-3-(4-imidazo-[4,5-b]pyridin-1-ylphenyl)urea | Example 7 |
| 8 | | 1-(4-Chloro-3-(trifluoro-methyl)phenyl)-3-(4-imidazo-[4,5-b]pyridin-1-ylphenyl)urea | Example 8 |
| 9 | | 1-(4-Chloro-3-(trifluoro-methyl)phenyl)-3-[4-(5-cyano-indol-1-yl)phenyl]urea | Example 9 |
| 10 | | 1-(4-Benzimidazol-1-ylphenyl)-3-(4-chloro-3-(trifluoro-methyl)phenyl)urea | Example 10 |
| 11 | | 1-{4-[3-(4-Chloro-3-(trifluoro-methyl)phenyl)ureido]phenyl}-1H-indole-5-carboxylic acid methylamide | Example 11 |
| 12 | | 1-{4-[3-(4-Chloro-3-(trifluoro-methyl)phenyl)ureido]phenyl}-1H-indole-4-carboxylic acid methylamide | Example 12 |

TABLE 1-continued

| | Structural formula | Name of compound | Example No. |
|---|---|---|---|
| 13 | | 1-{4-[3-(4-Chloro-3-(trifluoromethyl)phenyl)ureido]phenyl}-1H-indole-6-carboxylic acid methylamide | Example 13 |
| 14 | | 1-{4-[3-(4-Chloro-3-(trifluoromethyl)phenyl)ureido]phenyl}-1H-indole-5-carboxylic acid thiazol-2-ylamide | Example 14 |
| 15 | | 1-{4-[3-(4-Chloro-3-(trifluoromethyl)phenyl)ureido]phenyl}-1H-benzimidazole-5-carboxylic acid methylamide | Example 15 |
| 16 | | 1-{4-[3-(4-Chloro-3-(trifluoromethyl)phenyl)ureido]-2-fluorophenyl}-1H-indol-5-yl)carbamic acid tert-butyl ester | Example 16 |
| 17 | | 1-[4-(5-Aminoindol-1-yl)-3-fluorophenyl]-3-(4-chloro-3-(trifluoromethyl)phenyl)urea hydrochloride | Example 17 |
| 18 | | Acetic acid 1-{4-[3-(4-chloro-3-(trifluoromethyl)phenyl)ureido]phenyl}-1H-indol-4-yl ester | Example 18 |
| 19 | | 1-(4-Chloro-3-(trifluoromethyl)phenyl)-3-[4-(4-hydroxyindol-1-yl)phenyl]urea | Example 19 |

TABLE 1-continued

| | Structural formula | Name of compound | Example No. |
|---|---|---|---|
| 20 | | [2-(1-{4-[3-(4-Chloro-3-(tri-fluoromethyl)phenyl)ureido]-phenyl}-1H-indol-4-yloxy)ethyl]-methylcarbamic acid tert-butyl ester | Example 20 |
| 21 | | 1-(4-Chloro-3-(trifluoromethyl)-phenyl)-3-{4-[4-(2-methylamino-ethoxy)indol-1-yl]phenyl}urea hydrochloride | Example 21 |
| 22 | | 1-(4-Chloro-3-(trifluoromethyl)-phenyl)-3-{4-[4-(2-morpholin-4-ylethoxy)indol-1-yl]phenyl}urea | Example 22 |
| 23 | | 1-{4-Chloro-3-(trifluoromethyl)-phenyl}-3-{4-[4-(2-piperazin-1-ylethoxy)indol-1-yl]phenyl}urea hydrochloride | Example 23 |
| 24 | | 1-{4-[3-(4-Chloro-3-(trifluoro-methyl)phenyl)ureido]phenyl}-N-hydroxy-1H-indole-5-carboxami-dine | Example 24 |
| 25 | | 1-{4-[3-(3-(trifluoromethyl)-phenyl)ureido]phenyl}-1H-indole-5-carboxamidine | Example 25 |
| 26 | | 1-(4-Chloro-3-(trifluoromethyl)-phenyl)-3-{4-[5-[5-methyl-[1,2,4]oxadiazol-3-yl]indol-1-yl]phenyl}urea | Example 26 |

TABLE 1-continued

| | Structural formula | Name of compound | Example No. |
|---|---|---|---|
| 27 | | 1-{4-[5-(5-tert-Butyl-[1,2,4]-oxadiazol-3-yl)indol-1-yl]phenyl}-3-(4-chloro-3-(trifluoromethyl)phenyl)urea | Example 27 |
| 28 | | 1-(4-Chloro-3-(trifluoromethyl)-phenyl)-3-{4-[5-(5-oxo-4,5-dihydro-[1,2,4]oxadiazol-3-yl]-phenyl}urea | Example 28 |
| 29 | | 1-(4-Chloro-3-(trifluoromethyl)-phenyl)-3-{4-[6-(di-tert-butoxycarbonylamino)purin-9-yl]-phenyl}urea | Example 29 |
| 30 | | 1-[4-(6-Aminopurin-9-yl)phenyl]-3-(4-chloro-3-(trifluoromethyl)-phenyl)urea hydrochloride | Example 30 |
| 31 | | 1-[4-(6-Aminopurin-9-yl)phenyl]-3-(3,5-bis-(trifluoromethyl)-phenyl)urea hydrochloride | Example 31 |
| 32 | | 1-[4-(6-Aminopurin-9-yl)phenyl]-3-(2-chloro-5-(trifluoromethyl)-phenyl)urea hydrochloride | Example 32 |

TABLE 1-continued

| | Structural formula | Name of compound | Example No. |
|---|---|---|---|
| 33 | 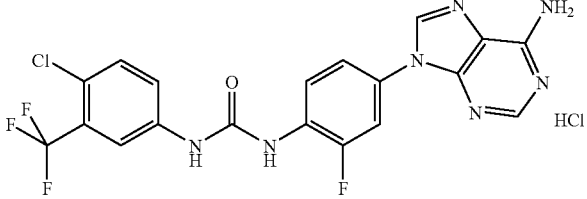 [SMILES: Nc1ncnc2c1ncn2-c1ccc(NC(=O)Nc2ccc(Cl)c(C(F)(F)F)c2)c(F)c1 ; Cl] | 1-[4-(6-Aminopurin-9-yl)-2-fluorophenyl]-3-(4-chloro-3-(trifluoromethyl)phenyl)urea hydrochloride | Example 33 |
| 34 | 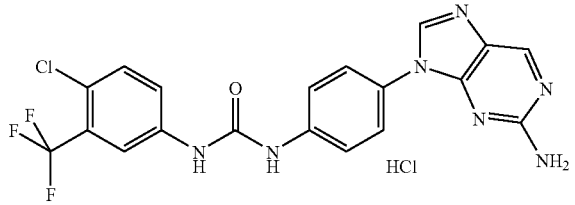 [SMILES: Nc1ncc2ncn(-c3ccc(NC(=O)Nc4ccc(Cl)c(C(F)(F)F)c4)cc3)c2n1 ; Cl] | 1-[4-(2-Aminopurin-9-yl)phenyl]-3-(4-chloro-3-(trifluoromethyl)-phenyl)urea hydrochloride | Example 34 |
| 35 | 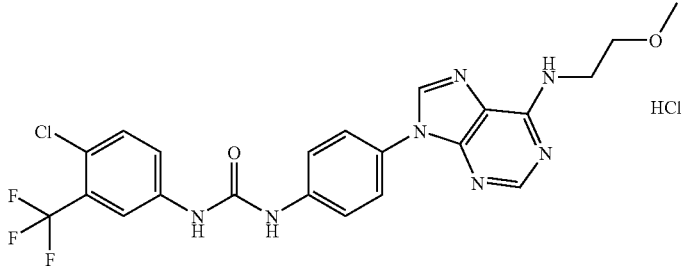 [SMILES: COCCNc1ncnc2c1ncn2-c1ccc(NC(=O)Nc2ccc(Cl)c(C(F)(F)F)c2)cc1 ; Cl] | 1-(4-Chloro-3-(trifluoromethyl)-phenyl)-3-{4-[6-(2-methoxy-ethylamino)-purin-9-yl]phenyl}-urea hydrochloride | Example 35 |
| 36 | 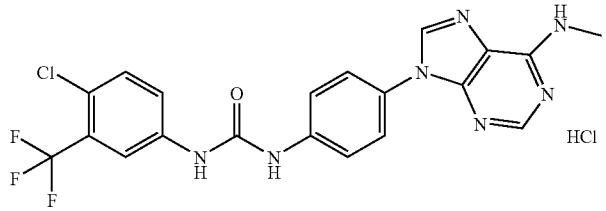 [SMILES: CNc1ncnc2c1ncn2-c1ccc(NC(=O)Nc2ccc(Cl)c(C(F)(F)F)c2)cc1 ; Cl] | 1-(4-Chloro-3-(trifluoromethyl)-phenyl)-3-[4-(6-(methylamino)-purin-9-yl)phenyl]urea hydrochloride | Example 36 |
| 37 | 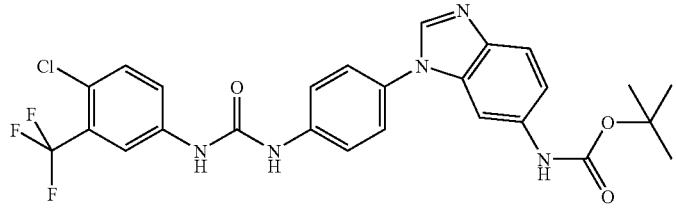 [SMILES: CC(C)(C)OC(=O)Nc1ccc2ncn(-c3ccc(NC(=O)Nc4ccc(Cl)c(C(F)(F)F)c4)cc3)c2c1] | (3-{4-[3-(4-Chloro-3-(trifluoromethyl)phenyl)ureido]phenyl}-3H-benzimidazol-5-yl)carbamic acid tert-butyl ester | Example 37 |
| 38 | 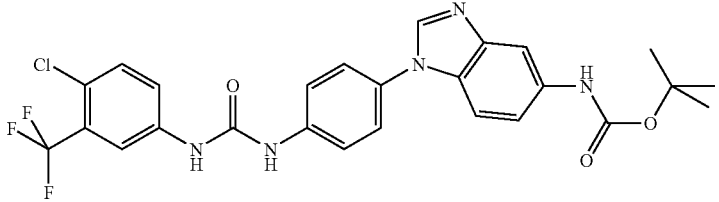 [SMILES: CC(C)(C)OC(=O)Nc1ccc2c(c1)ncn2-c1ccc(NC(=O)Nc2ccc(Cl)c(C(F)(F)F)c2)cc1] | (1-{4-[3-(4-Chloro-3-(trifluoromethyl)phenyl)ureido]phenyl}-1H-benzimidazol-5-yl)carbamic acid tert-butyl ester | Example 38 |

TABLE 1-continued

| | Structural formula | Name of compound | Example No. |
|---|---|---|---|
| 39 | 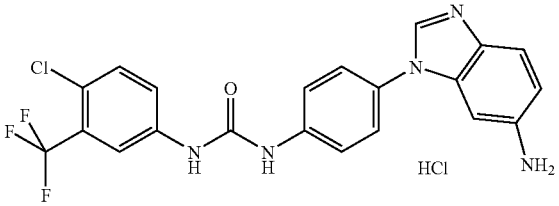 [SMILES: Nc1ccc2ncn(-c3ccc(NC(=O)Nc4ccc(Cl)c(C(F)(F)F)c4)cc3)c2c1 ; Cl] | 1-[4-(6-Aminobenzimidazol-1-yl)-phenyl]-3-(4-chloro-3-(trifluoromethyl)phenyl)urea hydrochloride | Example 39 |
| 40 | 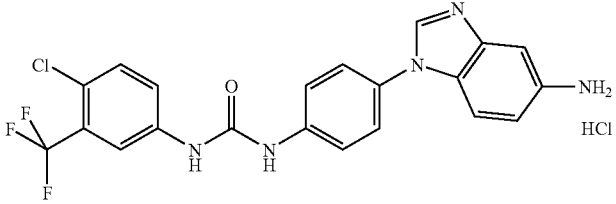 [SMILES: Nc1ccc2c(c1)ncn2-c1ccc(NC(=O)Nc2ccc(Cl)c(C(F)(F)F)c2)cc1 ; Cl] | 1-[4-(5-Aminobenzimidazol-1-yl)-phenyl]-3-(4-chloro-3-(trifluoromethyl)phenyl)urea hydrochloride | Example 40 |
| 41 | 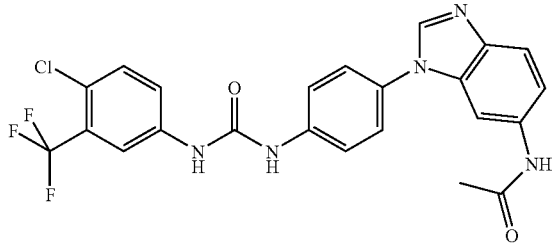 [SMILES: CC(=O)Nc1ccc2ncn(-c3ccc(NC(=O)Nc4ccc(Cl)c(C(F)(F)F)c4)cc3)c2c1] | N-(3-{4-[3-(4-Chloro-3-(trifluoromethyl)phenyl)ureido]phenyl}-3H-benzimidazol-5-yl)acetamide | Example 41 |
| 42 | 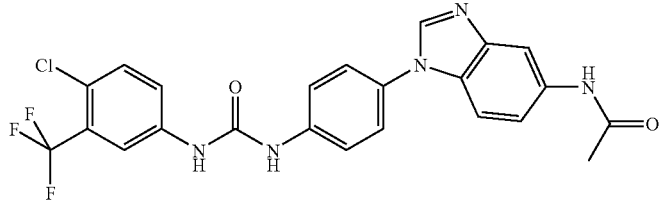 [SMILES: CC(=O)Nc1ccc2c(c1)ncn2-c1ccc(NC(=O)Nc2ccc(Cl)c(C(F)(F)F)c2)cc1] | N-(1-{4-[3-(4-Chloro-3-(trifluoromethyl)phenyl)ureido]phenyl}-1H-benzimidazol-5-yl)acetamide | Example 42 |
| 43 | 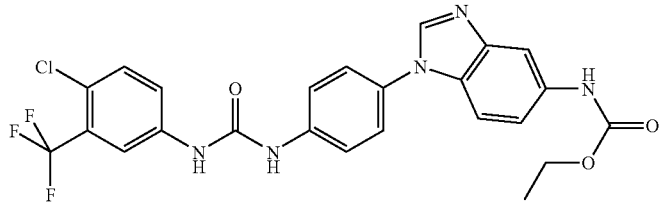 [SMILES: CCOC(=O)Nc1ccc2c(c1)ncn2-c1ccc(NC(=O)Nc2ccc(Cl)c(C(F)(F)F)c2)cc1] | (1-{4-[3-(4-Chloro-3-(trifluoromethyl)phenyl)ureido]phenyl}-1H-benzimidazol-5-yl)carbamic acid ethyl ester | Example 43 |
| 44 | 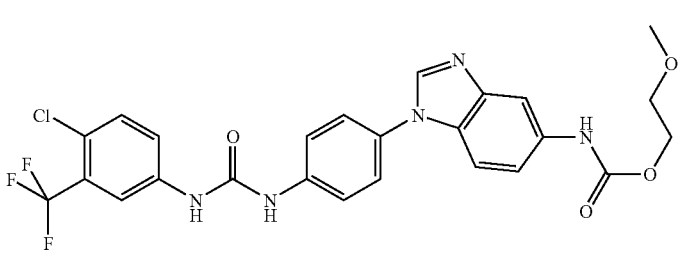 [SMILES: COCCOC(=O)Nc1ccc2c(c1)ncn2-c1ccc(NC(=O)Nc2ccc(Cl)c(C(F)(F)F)c2)cc1] | (1-{4-[3-(4-Chloro-3-(trifluoromethyl)phenyl)ureido]phenyl}-1H-benzimidazol-5-yl)carbamic acid 2-methoxyethyl ester | Example 44 |

TABLE 1-continued

| | Name of compound | Example No. |
|---|---|---|
| 45 | 1-(4-Chloro-3-(trifluoromethyl)phenyl)-3-hyrdoxy-3-(4-imidazo[4,5-c]pyridin-3-yl-phenyl)urea | Example 45 |
| 46 | 1-(4-Chloro-3-(trifluoromethyl)phenyl)-3-hyrdoxy-3-(4-purin-7-ylphenyl)urea | Example 46 |
| 47 | 1-(4-Chloro-3-(trifluoromethyl)phenyl)-3-hyrdoxy-3-(4-purin-9-ylphenyl)urea | Example 47 |
| 48 | 1-(4-Chloro-3-(trifluoromethyl)phenyl)-3-{4-[6-(di-tert-butoxycarbonylamino)purin-9-yl]phenyl}-3-hydroxyurea | Example 48 |
| 49 | 1-[4-(6-Aminopurin-9-ylphenyl]-3-(4-chloro-3-(trifluoromethyl)phenyl)-1-hydroxyurea hydrochloride | Example 49 |
| 50 | 3-(4-Chloro-3-(trifluoromethyl)phenyl)-1-hydroxy-1-[4-(6-methylpurin-9-yl]phenyl)-urea | Example 50 |

TABLE 1-continued

| | Structural formula | Name of compound | Example No. |
|---|---|---|---|
| 51 | | 3-[4-Chloro-3-(trifluoro-methyl)phenyl]-1-hydroxy-1-(4-imidazo[4,5-b]pyridin-1-yl-phenyl)urea | Example 51 |
| 52 | | 1-[4-(6-Chloropurin-9-yl)-phenyl]-3-(4-chloro-3-(tri-fluoromethyl)phenyl)-1-hydroxy-urea | Example 52 |
| 53 | | 3-(4-Chloro-3-(trifluoro-methyl)phenyl)-1-hydroxy-1-[4-(6-(methylamino)purin-9-yl]-phenyl)urea | Example 53 |
| 54 | | 1-{4-[6-(benzyl-methylamino)-purin-9-yl]phenyl}-3-(4-chloro-3-(trifluoromethyl)phenyl)-1-hydroxyurea | Example 54 |
| 55 | | 1-(4-Chloro-3-(trifluoro-methyl)phenyl)-3-hydroxy-3-[4-(6-morpholin-4-ylpurin-9-yl)-phenyl]urea | Example 55 |
| 56 | | 3-(4-Chloro-3-(trifluoro-methyl)phenyl)-1-[4-(6-dimethylamino-purin-9-yl)-phenyl]-1-hydroxyurea | Example 56 |

TABLE 1-continued

| | Structural formula | Name of compound | Example No. |
|---|---|---|---|
| 57 | | 1-(4-Chloro-3-(trifluoro-methyl)phenyl)-3-hydroxy-3-(4-{6-[(2-hydroxyethyl)-methyl-amino]purin-9-yl}phenyl)urea | Example 57 |
| 58 | | (1-{4-[3-(4-Chloro-3-(tri-fluoromethyl)phenyl)-1-hydroxy-ureido]phenyl}-1H-indol-5-yl)-carbamic acid tert-butyl ester | Example 58 |
| 59 | | 1-4-(5-Aminoindol-1-yl)phenyl]-3-(4-chloro-3-(trifluoro-methyl) phenyl)-1-hydroxyurea hydrochloride | Example 59 |
| 60 | | (1-{4-[3-(4-Chloro-3-(tri-fluoromethyl)phenyl)-1-hydroxy-ureido]phenyl}-1H-indol-4-yl)-carbamic acid tert-butyl ester | Example 60 |
| 61 | | 1-[4-(4-Aminoindol-1-yl)-phenyl]-3-(4-chloro-3-(tri-fluoromethyl)phenyl)-1-hydroxy-urea hydrochloride | Example 61 |
| 62 | | 1-(4-Chloro-3-(trifluoro-methyl)phenyl)-3-{4-[6-(di-tert-butoxycarbonylamino)-purin-9-yl]phenyl}-1-hydroxy-urea | Example 62 |

TABLE 1-continued

| | Structural formula | Name of compound | Example No. |
|---|---|---|---|
| 63 | 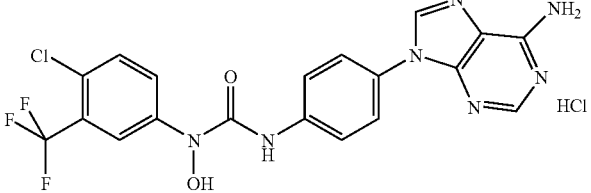 | 1-[4-(6-Aminopurin-9-yl)-phenyl]-3-(4-chloro-3-(tri-fluoromethyl)phenyl)-3-hydroxy-urea hydrochloride | Example 63 |
| 64 | 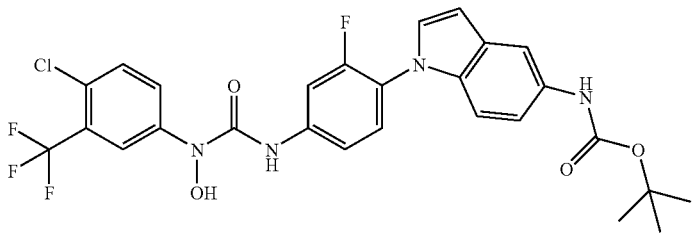 [SMILES: CC(C)(C)OC(=O)Nc1ccc2c(ccn2-c2ccc(NC(=O)N(O)c3ccc(Cl)c(C(F)(F)F)c3)cc2F)c1] | (1-{4-[3-(4-Chloro-3-(tri-fluoromethyl)phenyl)-3-hydroxy-ureido]-2-fluorophenyl}-1H-indol-5-yl)carbamic acid tert-butyl ester | Example 64 |
| 65 | 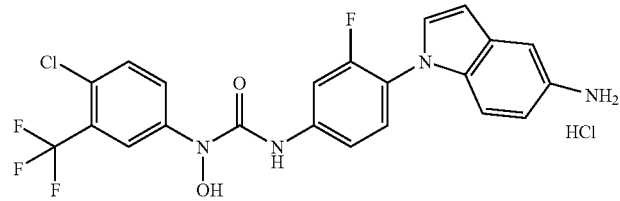 [SMILES: Nc1ccc2c(ccn2-c2ccc(NC(=O)N(O)c3ccc(Cl)c(C(F)(F)F)c3)cc2F)c1 ; Cl] | 3-[4-(5-Aminoindol-1-yl)-3-fluorophenyl]-1-(4-chloro-3-(trifluoromethyl)phenyl)-1-hydroxyurea | Example 65 |
| 66 | 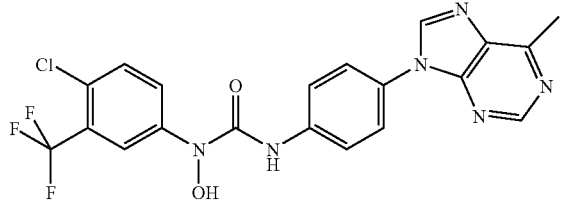 [SMILES: Cc1ncnc2c1ncn2-c1ccc(NC(=O)N(O)c2ccc(Cl)c(C(F)(F)F)c2)cc1] | 3-(4-Choloro-3-(trifluoro-methyl)phenyl)-3-hydroxy-1-[4-(6-methylpurin-9-yl)phenyl]urea | Example 66 |
| 67 | 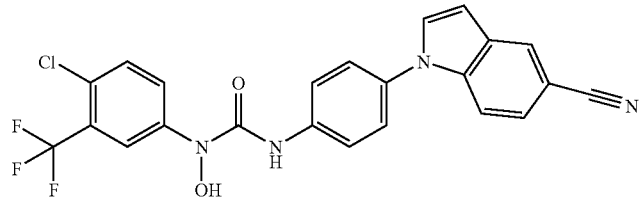 [SMILES: N#Cc1ccc2c(ccn2-c2ccc(NC(=O)N(O)c3ccc(Cl)c(C(F)(F)F)c3)cc2)c1] | 1-(4-Choloro-3-(trifluoro-methyl)phenyl)-3-[4-(5-cyano-indol-1-yl)phenyl]-1-hydroxy-urea | Example 67 |
| 68 | 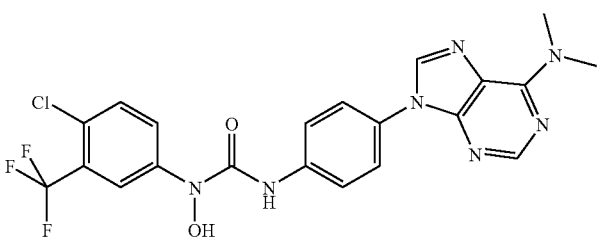 [SMILES: CN(C)c1ncnc2c1ncn2-c1ccc(NC(=O)N(O)c2ccc(Cl)c(C(F)(F)F)c2)cc1] | 3-(4-Choloro-3-(trifluoro-methyl)phenyl)-1-[4-(6-di-methylaminopurin-9-yl)phenyl]-3-hydroxyurea | Example 68 |
| 69 | 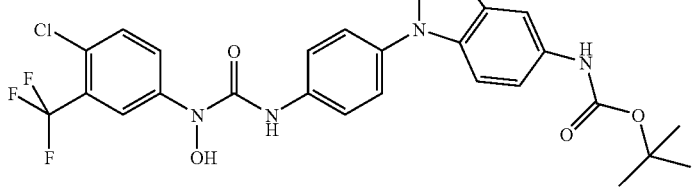 | (1-{4-[3-(4-Chloro-3-(tri-fluoromethyl)phenyl)-3-hydroxy-ureido]phenyl}-1H-indol-5-yl)-carbamic acid tert-butyl ester | Example 69 |

TABLE 1-continued

| | Structural formula | Name of compound | Example No. |
|---|---|---|---|
| 70 | | 1-[4-(5-Aminoindol-1-yl)-phenyl]-3-(4-chloro-3-(trifluoromethyl)phenyl)-3-hydroxyurea hydrochloride | Example 70 |
| 71 | | 1-[4-(4-Aminoindol-1-yl)-phenyl]-3-(4-chloro-3-(trifluoromethyl)phenyl)-3-hydroxyurea hydrochloride | Example 71 |
| 72 | | (1-{4-[3-(4-Chloro-3-(trifluoromethyl)phenyl)-3-hydroxy-ureido]phenyl}-1H-indole-5-carboxylic acid methylamide | Example 72 |
| 73 | | N-(1-{4-[3-(4-Chloro-3-(trifluoromethyl)phenyl)-3-hydroxy-ureido]phenyl}-1H-indol-5-yl)-2,2-dimethylpropionamide | Example 73 |
| 74 | | N-(4-{3-[4-Chloro-3-(trifluoromethyl)phenyl)-3-hydroxy-ureido]phenyl}-1H-indol-5-yl)-acetamide | Example 74 |
| 75 | | N-(1-{4-[3-(4-Chloro-3-(trifluoromethyl)phenyl)-3-hydroxy-ureido]phenyl}-1H-indol-5-yl)-pentanamide | Example 75 |
| 76 | | N-(1-{4-[3-(4-Chloro-3-(trifluoromethyl)phenyl)-3-hydroxy-ureido]phenyl}-1H-indol-5-yl)-decanamide | Example 76 |

TABLE 1-continued

| | Structural formula | Name of compound | Example No. |
|---|---|---|---|
| 77 | | (1-{4-[3-(4-Chloro-3-(tri-fluoromethyl)phenyl)-3-hydroxy-ureido]phenyl}-1H-indol-5-yl)-carbamic acid methyl ester | Example 77 |
| 78 | | (1-{4-[3-(4-Chloro-3-(tri-fluoromethyl)phenyl)-3-hydroxy-ureido]phenyl}-1H-indol-5-yl)-carbamic acid ethyl ester | Example 78 |
| 79 | | (1-{4-[3-(4-Chloro-3-(tri-fluoromethyl)phenyl)-3-hydroxy-ureido]phenyl}-1H-indol-5-yl)-carbamic acid pentyl ester | Example 79 |
| 80 | | (1-{4-[3-(4-Chloro-3-(tri-fluoromethyl)phenyl)-3-hydroxy-ureido]phenyl}-1H-indole-5-yl)-carbamic acid decyl ester | Example 80 |
| 81 | | N-{1-(4-(3-(4-Chloro-3-(tri-fluoromethyl)phenyl)-3-hydroxy-ureido]phenyl}-1H-indol-5-yl)-3-methylbutylamide | Example 81 |
| 82 | | N-(1-{4-[3-(4-Chloro-3-(tri-fluoromethyl)phenyl)-3-hydroxy-ureido]phenyl}-1H-indol-5-yl)-3,3-dimethylbutylamide | Example 82 |
| 83 | | (1-{4-[3-(4-Chloro-3-(tri-fluoromethyl)phenyl)-3-hydroxy-ureido]phenyl}-1H-indol-5-yl)-carbamic acid 2-methoxyethyl ester | Example 83 |

TABLE 1-continued

| | Structural formula | Name of compound | Example No. |
|---|---|---|---|
| 84 | | 3-(1-{4-[3-(4-Chloro-3-(trifluoromethyl)phenyl)-3-hydroxyureido]phenyl}-1H-indol-5-yl)-3,3-dimethylurea | Example 84 |
| 85 | | Morpholine-4-carboxylic acid (1-{4-[3-(4-chloro-3-(trifluoromethyl)phenyl)-3-hydroxyureido]phenyl-1H-indol-5-yl)-amide | Example 85 |
| 86 | | (2S,3S)-2-Amino-3-methylpentanoic acid (1-{4-[3-(4-chloro-3-(trifluoromethyl)-phenyl)-3-hydroxyureido]-phenyl}-1H-indol-5-yl)-amide | Example 86 |
| 87 | | (S)-2-Amino-N-(1-(4-[3-(4-chloro-3-(trifluoromethyl)-phenyl)-3-hydroxyureido]-phenyl}-1H-indol-5-yl)-3-methylbutylamide | Example 87 |
| 88 | | 1-(4-Choloro-3-(trifluoromethyl)phenyl)-1-hydroxy-3-(4-[4-(2-morpholin-4-yl-ethoxy)-indol-1-yl]phenylurea | Example 88 |
| 89 | | 1-(4-Chloro-3-(trifluoromethyl)phenyl)-3-[4-(5-oxyimidazo[4,5-c]pyridin-1-yl)phenyl]urea | Example 89 |
| 90 | | 1-[4-(4-Chloro-imidazo[4,5-c]-pyridin-1-yl)phenyl]-3-(4-chloro-3-(trifluoromethyl)-phenyl)urea | Example 90 |

TABLE 1-continued

| | Structural formula | Name of compound | Example No. |
|---|---|---|---|
| 91 | | 1-(4-Chloro-3-(trifluoromethyl)phenyl)-3-[4-(4-cyanoimidazo-[4,5-c]pyridin-l-yl)phenyl]urea | Example 91 |
| 92 | | 1-(4-[3-(4-Chloro-3-(trifluoro-methyl)phenyl)ureido]phenyl}-1H-imidazo[4,5-c]pyridine-4-carboxylic acid (2-dimethyl-aminoethyl)amide | Example 92 |
| 93 | | 1-{4-[3-(4-Chloro-3-(trifluoro-methyl)phenyl)ureido]phenyl}-1H-imidazo[4,5-c]pyridine-4-carboxylic acid methylamide | Example 93 |
| 94 | | 1-{4-[3-(4-Chloro-3-(trifluoro-methyl)phenyl)ureido]phenyl}-1H-imidazo[4,5-c]pyridine-4-carboxamidine hydrochloride | Example 94 |
| 95 | | N'-(9-{4-[3-(4-Chloro-3-(tri-fluoromethyl)phenyl)ureido]-phenyl}-9H-purin-6-yl}-N,N-dimethylformamidine hydro-chloride | Example 95 |
| 96 | | (S)-2-Amino-4-methyl-pentanoic acid 9-{4-[3-(4-chloro-3-(tri-fluoromethyl)phenyl)ureido]-phenyl)-9H-purin-6-yl)amide hydrochloride | Example 96 |

TABLE 1-continued

| | Structural formula | Name of compound | Example No. |
|---|---|---|---|
| 97 | | 2-Amino-N-(9-{4-[3-(4-chloro-3-(trifluoromethyl)phenyl)-ureido]phenyl)-9H-purin-6-yl)-acetamide hydrochloride | Example 97 |
| 98 | | N-(9-{4-[3-(4-Chloro-3-(tri-fluoromethyl)phenyl)ureido]-phenyl}-9H-purin-6-yl)-2-methylaminoacetamide hydrochloride | Example 98 |
| 99 | | (S)-2-Pyrrolidine-2-carboxylic acid 9-{4-[3-(4-chloro-3-(tri-fluoromethyl)phenyl)ureido]-phenyl}-9H-purin-6-yl)amide hydrochloride | Example 99 |
| 100 | | (S)-2-Amino-N-(9-{4-[3-(4-chloro-3-(trifluoromethyl)-phenyl)ureido]phenyl}-9H-purin-6-yl)propionamide hydrochloride | Example 100 |
| 101 | | (S)-2-Amino-N-(9-{4-[3-(4-chloro-3-(trifluoromethyl)-phenyl)ureido]phenyl}-9H-purin-6-yl)-3,3-dimethylbutylamide hydrochloride | Example 101 |
| 102 | | (R)-2-Amino-N-(9-{4-[3-(4-chloro-3-(trifluoromethyl)-phenyl)ureido]phenyl}-9H-purin-6-yl)-3-methylbutylamide hydrochloride | Example 102 |

TABLE 1-continued

| | Structural formula | Name of compound | Example No. |
|---|---|---|---|
| 103 | | (S)-4-Amino-4-(9-{4-[3-(4-chloro-3-(trifluoromethyl)-phenyl)ureido]phenyl}-9H-purin-6-ylcarbamoyl)butanoic acid hydrochloride | Example 103 |
| 104 | | (S)-2-Amino-4-(9-{4-[3-(4-chloro-3-(trifluoromethyl)-phenyl)ureido]phenyl}-9H-purin-6-ylcarbamoyl)butanoic acid hydrochloride | Example 104 |
| 105 | | (S)-2,6-Diaminohexanoic acid (9-{4-[3-(4-chloro-3-(tri-fluoromethyl)phenyl)ureido]-phenyl}-9H-purin-6-yl)amide hydrochloride | Example 105 |
| 106 | | (S)-4-Methyl-2-methylamino-pentanoic acid (9-{4-[3-(4-chloro-3-(tri-fluoromethyl)-phenyl}ureido]phenyl}-9H-purin-6-yl)amide hydrochloride | Example 106 |
| 107 | | Pentanoic acid (9-{4-[3-(4-chloro-3-(trifluoromethyl)-phenyl)ureido]phenyl}-9H-purin-6-yl)amide | Example 107 |
| 108 | | N-(9-{4-[3-(4-Chloro-3-(tri-fluoromethyl)phenyl)ureido]-phenyl}-9H-purin-6-yl)-2,2-dimethylpropionamide | Example 108 |

TABLE 1-continued

| | Structural formula | Name of compound | Example No. |
|---|---|---|---|
| 109 | | N-(9-{4-[3-(4-Chloro-3-(tri-fluoromethyl)phenyl)ureido]-phenyl}-9H-purin-6-yl)-2-[2-(2-methoxyethoxy)ethoxy]acetamide | Example 109 |
| 110 | | 1-(4-Chloro-3-(trifluoro-methyl)phenyl)-3-{4-[6-(di-methanesulfonylamino)purin-9-yl]phenyl}urea | Example 110 |
| 111 | | (9-{4-[3-(4-Chloro-3-(tri-fluoromethyl)phenyl)ureido]-phenyl}-9H-purin-6-yl)carbamic acid pentyl ester | Example 111 |
| 112 | | (9-{4-[3-(4-Chloro-3-(tri-fluoromethyl)phenyl)ureido]-phenyl}-9H-purin-6-yl)carbamic acid ethyl ester | Example 112 |
| 113 | | (9-{4-[3-(4-Chloro-3-(tri-fluoromethyl)phenyl)ureido]-phenyl}-9H-purin-6-yl)carbamic acid isobutyl ester | Example 113 |
| 114 | | (9-{4-[3-(4-Chloro-3-(tri-fluoromethyl)phenyl)ureido]-phenyl}-9H-purin-6-yl)carbamic acid allyl ester | Example 114 |

TABLE 1-continued

| | Structural formula | Name of compound | Example No. |
|---|---|---|---|
| 115 | | (9-{4-[3-(4-Chloro-3-(tri-fluoromethyl)phenyl)ureido]-phenyl}-9H-purin-6-yl)carbamic acid 2-methoxyethyl ester | Example 115 |
| 116 | | 1-(4-Chloro-3-(trifluoro-methyl)phenyl)-3-{4-[6-(2-oxo-oxazolidin-3-yl)purin-9-yl]phenyl}urea | Example 116 |
| 117 | | (9-{4-[3-(4-Chloro-3-(tri-fluoromethyl)phenyl)ureido]-phenyl}-9H-purin-6-yl)carbamic acid 2-methylamino-ethyl ester hydrochloride | Example 117 |
| 118 | | (9-{4-[3-(4-Chloro-3-(tri-fluoromethyl)phenyl)ureido]-phenyl}-9H-purin-6-yl)carbamic acid 2-amino-ethyl ester hydrochloride | Example 118 |
| 119 | | 1-(9-{4-[3-(4-Chloro-3-(tri-fluoromethyl)phenyl)ureido]-phenyl}-9H-purin-6-yl)-3-propylurea | Example 119 |
| 120 | | 1-(9-{4-[3-(4-Chloro-3-(tri-fluoromethyl)phenyl)ureido]-phenyl}-9H-purin-6-yl)-3-cyclohexylurea | Example 120 |

TABLE 1-continued

| | Structural formula | Name of compound | Example No. |
|---|---|---|---|
| 121 | 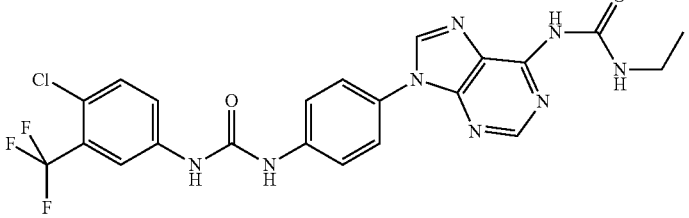 | 1-(9-{4-(3-(4-Chloro-3-(tri-fluoromethyl)phenyl)ureido]-phenyl}-9H-purin-6-yl)-3-ethylurea | Example 121 |
| 122 | 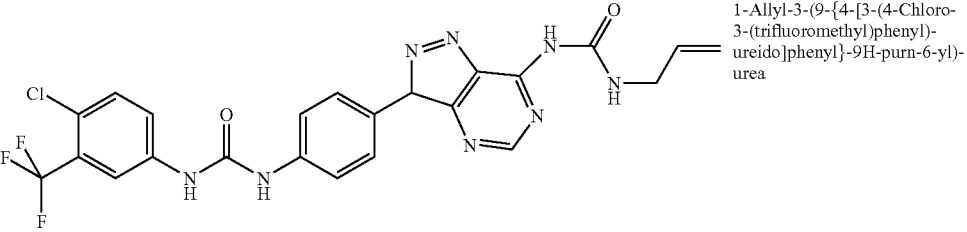 | 1-Allyl-3-(9-{4-[3-(4-Chloro-3-(trifluoromethyl)phenyl)-ureido]phenyl}-9H-purn-6-yl)-urea | Example 122 |
| 123 | 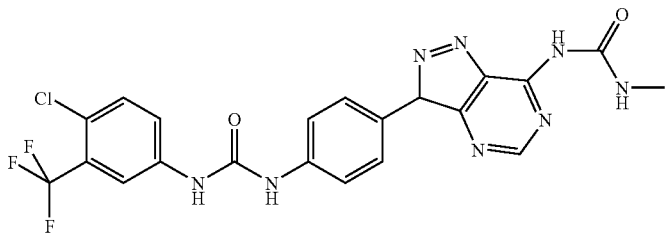 [SMILES: CNC(=O)Nc1ncnc2c1N=NC2c1ccc(NC(=O)Nc2ccc(Cl)c(C(F)(F)F)c2)cc1] | 1-(9-{4-[3-(4-Chloro-3-(tri-fluoromethyl)phenyl)ureido]-phenyl}-9H-purin-6-yl)-3-methylurea | |
| 124 | 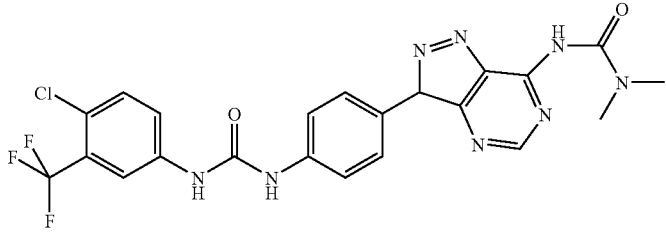 [SMILES: CN(C)C(=O)Nc1ncnc2c1N=NC2c1ccc(NC(=O)Nc2ccc(Cl)c(C(F)(F)F)c2)cc1] | 3-(9-{4-[3-(4-Chloro-3-(tri-fluoromethyl)phenyl)ureido]-phenyl}-9H-purin-6-yl)-1,1-dimethylurea | |
| 125 | 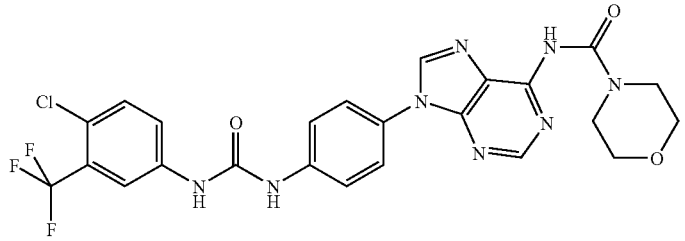 [SMILES: O=C(Nc1ccc(-n2cnc3c(NC(=O)N4CCOCC4)ncnc32)cc1)Nc1ccc(Cl)c(C(F)(F)F)c1] | Morpholine-4-carboxylic acid (9-{4-(3-(4-Chloro-3-(tri-fluoromethyl)phenyl)ureido]-phenyl}-9H-purin-6-yl)amide | |
| 126 | 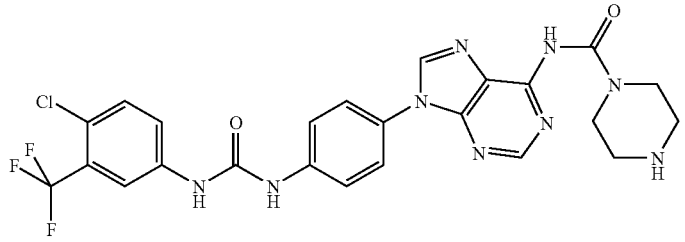 [SMILES: O=C(Nc1ccc(-n2cnc3c(NC(=O)N4CCNCC4)ncnc32)cc1)Nc1ccc(Cl)c(C(F)(F)F)c1] | Piperidine-1-carboxylic acid (9-{4-[3-(4-Chloro-3-(tri-fluoromethyl)phenyl)ureido]-phenyl}-9H-purin-6-yl)amide | |

TABLE 1-continued

| | Structural formula | Name of compound | Example No. |
|---|---|---|---|
| 127 | | 1-(9-{4-[3-(4-Chloro-3-(tri-fluoromethyl)phenyl)ureido]-phenyl}-9H-purin-6-yl)3-isopropylurea | |
| 128 | | 1-Butyl-3-(9-{4-[3-(4-chloro-3-(trifluoromethyl)phenyl)-ureido]phenyl}-9H-purin-6-yl)-urea | |
| 129 | | 1-tert-Butyl-3-(9-{4-[3-(4-chloro-3-(trifluoromethyl)-phenyl)ureido]phenyl}-9H-purin-6-yl)urea | |
| 130 | | 1-sec-Butyl-3-(9-{4-[3-(4-chloro-3-(trifluoromethyl)-phenyl)ureido]phenyl}-9H-purin-6-yl)urea | |
| 131 | | 1-(9-{4-[3-(4-Chloro-3-{tri-fluoromethyl)phenyl)ureido]-phenyl}-9H-purin-6-yl)-3-isobutylurea | |
| 132 | | 1-(9-{4-[3-(4-Chloro-3-(tri-fluoromethyl)phenyl)ureido]-phenyl}-9H-purin-6-yl)-1,3-dimethylurea | |

TABLE 1-continued

| | Structural formula | Name of compound | Example No. |
|---|---|---|---|
| 133 | 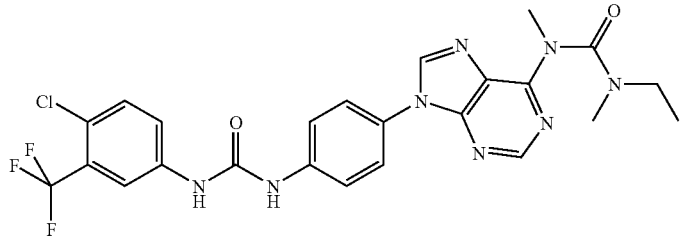 [SMILES: CCN(C)C(=O)N(C)c1ncnc2c1ncn2-c1ccc(NC(=O)Nc2ccc(Cl)c(C(F)(F)F)c2)cc1] | 1-(9-{4-[3-(4-Chloro-3-(tri-fluoromethyl)phenyl)ureido]-phenyl}-9H-purin-6-yl)-1,3,3-trimethylurea | |
| 134 | 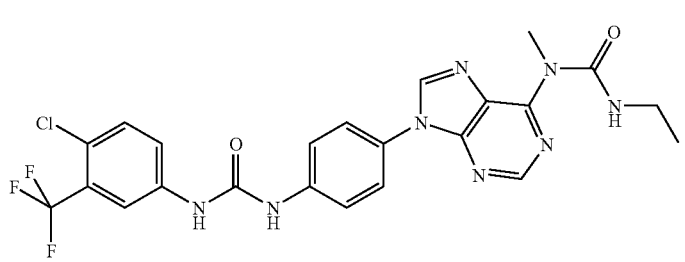 | 1-(9-{4-[3-(4-Chloro-3-(tri-fluoromethyl)phenyl)ureido]-phenyl}-9H-purin-6-yl)-3-ethyl-1-methylurea | |
| 135 | 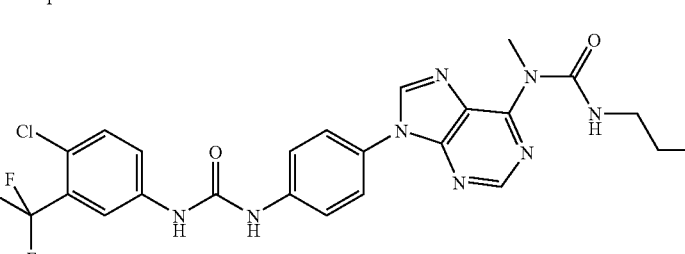 | 1-(9-{4-[3-(4-Chloro-3-(tri-fluoromethyl)phenyl)ureido]-phenyl}-9H-purin-6-yl)-1-methyl-3-propylurea | |
| 136 | 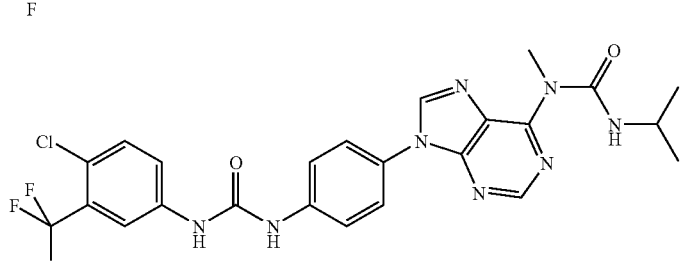 | 1-(9-{4-[3-(4-Chloro-3-(tri-fluoromethyl)phenyl)ureido]-phenyl}-9H-purin-6-yl)-3-isopropyl-1-methylurea | |
| 137 | 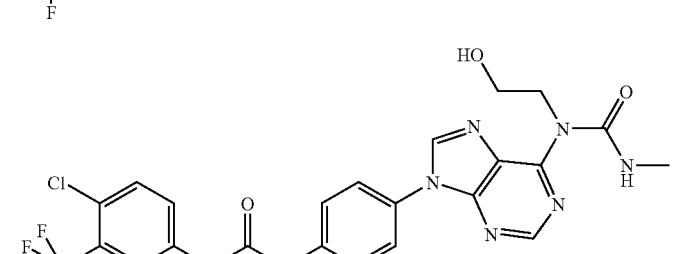 | 1-(9-{4-[3-(4-Chloro-3-(tri-fluoromethyl)phenyl)ureido]-phenyl}-9H-purin-6-yl)-1-(2-hydroxyethyl)-3-methylurea | |
| 138 | 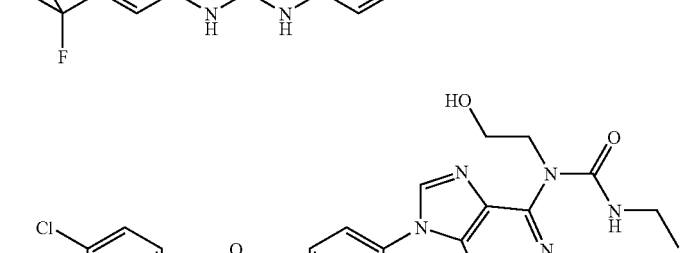 | 1-(9-{4-[3-(4-Chloro-3-(tri-fluoromethyl)phenyl)ureido]-phenyl}-9H-purin-6-yl)-3-ethyl-1-(2-hydroxyethyl)urea | |

TABLE 1-continued

| | Structural formula | Name of compound | Example No. |
|---|---|---|---|
| 139 | | 1-(9-{4-[3-(4-Chloro-3-(tri-fluoromethyl)phenyl)ureido]-phenyl}-9H-purin-6-yl)-1-(2-methoxyethyl)-3-methylurea | |
| 140 | | 1-(9-{4-[3-(4-Chloro-3-(tri-fluoromethyl)phenyl)ureido]-phenyl}-9H-purin-6-yl)-3-ethyl-1-(2-methoxyethyl)urea | |
| 141 | | 1-(9-{4-[3-(4-Chloro-3-(tri-fluoromethyl)phenyl)ureido]-phenyl}-9H-purin-6-yl)-1-(2-dimethylaminoethyl)-3-methyl-urea | |
| 142 | | 1-(9-{4-[3-(4-Chloro-3-(tri-fluoromethyl)phenyl)ureido]-phenyl}-9H-purin-6-yl)-1-(2-dimethylaminoethyl)-3-ethyl-urea | |
| 143 | | 1-(4-Chloro-3-(trifluoro-methyl)phenyl)-3-{4-[6-(2-oxo-imdazolin-1-yl)purin-9-yl]-phenyl}urea | |

TABLE 1-continued

| | Structural formula | Name of compound | Example No. |
|---|---|---|---|
| 144 | | 1-(4-Chloro-3-(trifluoro-methyl)phenyl)-3-{4-[6-(3-methyl-2-oxo-imidazolin-1-yl)purin-9-yl]phenyl}urea | |
| 145 | | 1-(9-{4-[3-(4-Chloro-3-(tri-fluoromethyl)phenyl)ureido]-phenyl}-9H-purin-6-yl)-3-(2-hydroxyethyl)urea | |
| 146 | | 1-(9-{4-[3-(4-Chloro-3-(tri-fluoromethyl)phenyl)ureido]-phenyl}-9H-purin-6-yl)-3-(2,3-dihydroxypropyl)urea | |
| 147 | | 1-(2-Aminoethyl)-3-(9-{4-[3-(4-chloro-3-(trifluoromethyl)-phenyl)ureido]phenyl}-9H-purin-6-yl)urea | |
| 148 | | 1-(9-{4-[3-(4-Chloro-3-(tri-fluoromethyl)phenyl)ureido]-phenyl}-9H-purin-6-yl)-3-(2-methylaminoethyl)urea | |
| 149 | | 1-(9-{4-[3-(4-Chloro-3-(tri-fluoromethyl)phenyl)ureido]-phenyl}-9H-purin-6-yl)-3-(2-dimethylaminoethyl)urea | |

TABLE 1-continued

| | Name of compound | Example No. |
|---|---|---|
| 150 | 1-(9-{4-[3-(4-Chloro-3-(tri-fluoromethyl)phenyl)ureido]-phenyl}-8-dimethylamino-9H-purin-6-yl)-3-ethylurea | |
| 151 | 1-(9-{4-[3-(4-Chloro-3-(tri-fluoromethyl)phenyl)ureido]-phenyl}-8-hydroxymethyl-9H-purin-6-yl)-3-ethylurea | |
| 152 | 1-(9-{4-[3-(4-Chloro-3-(tri-fluoromethyl)phenyl)ureido]-phenyl}-8-methoxymethyl-9H-purin-6-yl)-3-ethylurea | |
| 153 | 1-(9-{4-[3-(4-Chloro-3-(tri-fluoromethyl)phenyl)ureido]-phenyl}-8-dimethylaminomethyl-9H-purin-6-yl)-3-ethylurea | |
| 154 | 9-{4-[3-(4-Chloro-3-(tri-fluoromethyl)phenyl)ureido]-phenyl}-9H-purine-6-carboxylic acid methylamide | |
| 155 | 1-{4-[6-(2-Amino-ethylamino)-purin-9-yl]phenyl}-3-(4-chloro-3-(trifluoromethyl)-phenyl)urea | |

TABLE 1-continued

| | Structural formula | Name of compound | Example No. |
|---|---|---|---|
| 156 | 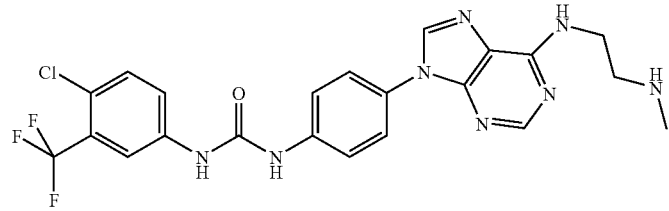 [SMILES: CNCCNc1ncnc2c1ncn2-c1ccc(NC(=O)Nc2ccc(Cl)c(C(F)(F)F)c2)cc1] | 1-(4-Chloro-3-(trifluoro-methyl)phenyl)-3-{4-(6-(2-methylamino-ethylamino)purin-9-yl)phenyl)urea | |
| 157 | 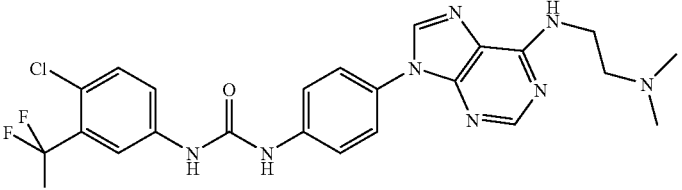 | 1-(4-Chloro-3-(trifluoro-methyl)phenyl)-3-{4-[6-(2-dimethylamino-ethylamino)-purin-9-yl]phenyl}urea | |
| 158 | 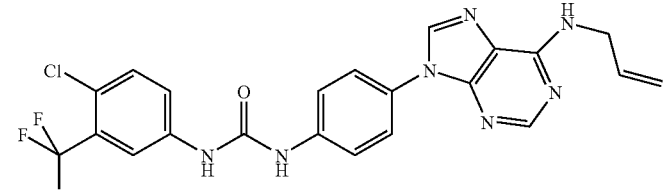 | 1-[4-(6-Allylamino-purin-9-yl)phenyl]-3-(4-chloro-3-(tri-fluoromethyl)phenyl)urea | |
| 159 | 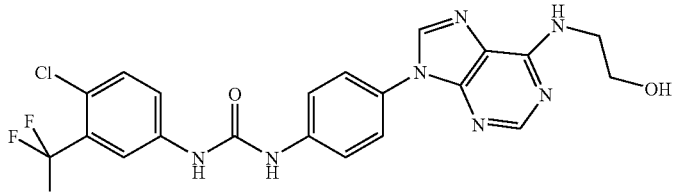 | 1-(4-Chloro-3-(trifluoro-methyl)phenyl)-3-{4-[6-(2-hydroxy-ethylamino)-purin-9-yl]phenyl}urea | |
| 160 | 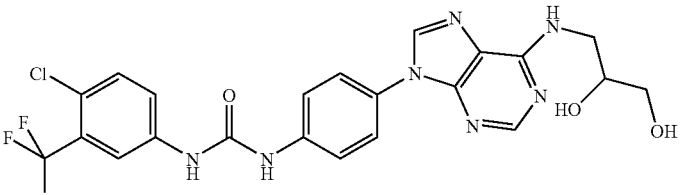 | 1-(4-Chloro-3-(trifluoro-methyl)phenyl)-3-{4-[6-(2,3-dihydroxy-propylamino)-purin-9-yl]phenyl}urea | |
| 161 | 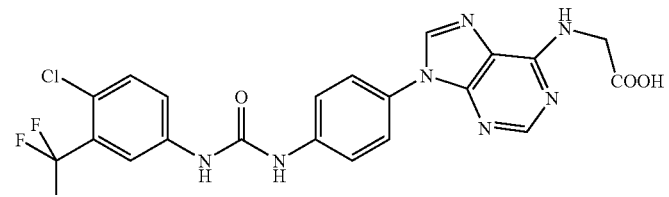 | (9-{4-[3-(4-Chloro-3-(tri-fluoromethyl)phenyl)ureido]-phenyl}-9H-purin-6-ylamino)-acetic acid | |
| 162 | 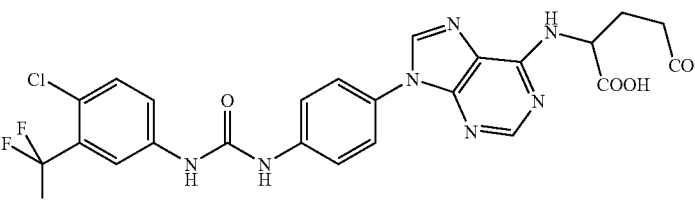 | 2-(9-{4-[3-(4-Chloro-3-(tri-fluoromethyl)phenyl)ureido]-phenyl}-9H-purin-6-ylamino)-pentanedicarboxylic acid | |

TABLE 1-continued

| | Structural formula | Name of compound | Example No. |
|---|---|---|---|
| 163 | | 1-[4-(4-Aminoimidazo[4,5-c]-pyridin-1-yl)phenyl]-3-(4-chloro-3-(trifluoromethyl)-phenyl)urea | |
| 164 | | 1-(4-Chloro-3-(trifluoro-methyl)phenyl)-3-[4-(4-methylamino-imidazo[4,5-c]-pyridin-1-yl)phenyl]urea | |
| 165 | | 1-(1-{4-[3-(4-Chloro-3-(tri-fluoromethyl)phenyl)ureido]-phenyl}-1H-imidazo[4,5-c]-pyridin-4-yl)-3-ethylurea | |
| 166 | | 1-(1-{4-[3-(4-Chloro-3-(tri-fluoromethyl)phenyl)ureido]-phenyl}-1H-imidazo[4,5-c]-pyridin-4-yl)-3-ethyl-1-methylurea | |
| 167 | | 1-(1-{4-[3-(4-Chloro-3-(tri-fluoromethyl)phenyl)ureido]-phenyl}-7-hydroxymethyl-1H-imidazo[4,5-c]pyridin-4-yl}-3-ethyurea | |
| 168 | | 1-(1-{4-[3-(4-Chloro-3-(tri-fluoromethyl)phenyl)ureido]-phenyl}-7-dimethylamino-methyl-1H-imidazo[4,5-c]-pyridin-4-yl)-3-ethylurea | |

TABLE 1-continued

| | Structural formula | Name of compound | Example No. |
|---|---|---|---|
| 169 | 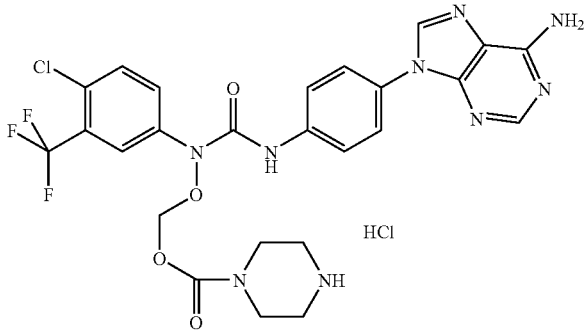 [SMILES: Nc1ncnc2c1ncn2-c1ccc(NC(=O)N(OCOC(=O)N2CCNCC2)c2ccc(Cl)c(C(F)(F)F)c2)cc1 ; Cl] | 3-[4-[6-Aminopurin-9-yl]-phenyl]-1-(4-chloro-3-(tri-fluoromethylphenyl)]1-(1-piperazinecarbonyloxy-methoxy)urea hydrochloride | |

TABLE 2

| | Structural formula | Name of Compound | Example No. |
|---|---|---|---|
| 1 | 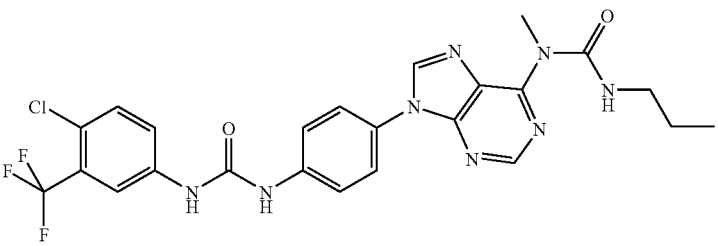 [SMILES: CCCNC(=O)N(C)c1ncnc2c1ncn2-c1ccc(NC(=O)Nc2ccc(Cl)c(C(F)(F)F)c2)cc1] | 1-(9-{4-[3-(4-Chloro-3-(tri-fluoromethyl)phenyl)ureido]-phenyl}-9H-purin-6-yl)-1-methyl-3-propylurea | Example 123 |
| 2 | 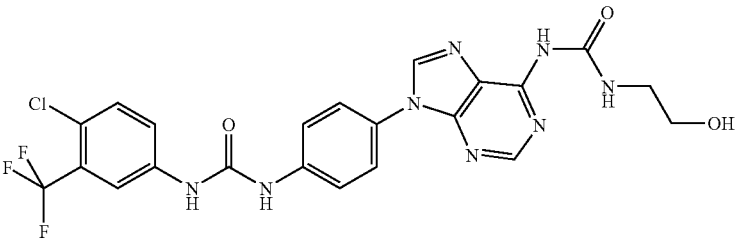 [SMILES: O=C(Nc1ccc(-n2cnc3c(NC(=O)NCCO)ncnc32)cc1)Nc1ccc(Cl)c(C(F)(F)F)c1] | 1-(9-{4-[3-(4-Chloro-3-(tri-fluoromethyl)phenyl)ureido]-phenyl}-9H-purin-6-yl)-3-(2-hydroxyethyl)urea | Example 124 |
| 3 | 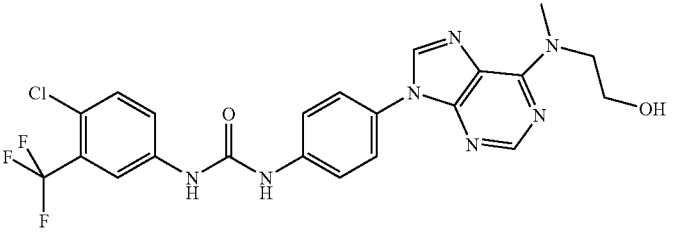 [SMILES: CN(CCO)c1ncnc2c1ncn2-c1ccc(NC(=O)Nc2ccc(Cl)c(C(F)(F)F)c2)cc1] | 1-(4-Chloro-3-(trifluoromethyl)-phenyl)-3-(4-{6-[(2-hydroxy-ethyl)-methylamino]purin-9-yl}-phenyl)urea | Example 125 |
| 4 | 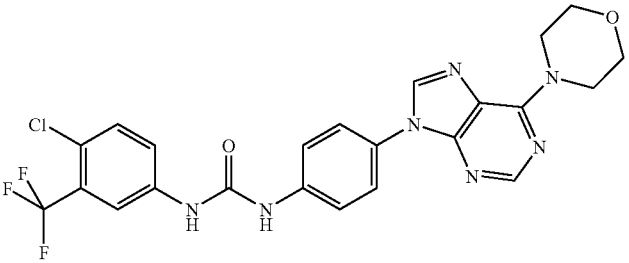 [SMILES: O=C(Nc1ccc(-n2cnc3c(N4CCOCC4)ncnc32)cc1)Nc1ccc(Cl)c(C(F)(F)F)c1] | 1-(4-Chloro-3(trifluoromethyl)-phenyl)-3-[4-(6-morpholin-4-yl-purin-9-yl)phenyl)urea | Example 126 |

TABLE 2-continued

| | Structural formula | Name of Compound | Example No. |
|---|---|---|---|
| 5 | | 1-(4-Chloro-3-(trifluoromethyl)-phenyl)-3-[4-[6-(pentylamino)-purin-9-yl]phenyl]urea | Example 127 |
| 6 | | 1-(4-Chloro-3-(trifluoromethyl)-phenyl)-3-[4-[6-piperazin-1-yl-purin-9-yl]phenyl]urea hydrochloride | Example 128 |
| 7 | | 1-[4-(6-Amino-8-iodopurin-9-yl)-phenyl]-3-(4-chloro-3-(trifluoromethyl)phenyl)urea | Example 129 |
| 8 | | 1-[4-(6-Amino-8-vinylpurin-9-yl)phenyl]-3-(4-chloro-3-(trifluoromethyl)phenyl)urea | Example 130 |
| 9 | | 1-{4-[6-Amino-8-(1,2-dihydroxyethyl)purin-9-yl]phenyl}-3-(4-chloro-3-(trifluoromethyl)-phenyl)urea | Example 131 |
| 10 | | 1-[4-(6-Amino-8-(hydroxymethyl)-purin-9-yl)phenyl]-3-(4-chloro-3-(trifluoromethyl)phenyl)urea | Example 132 |

TABLE 2-continued

| Structural formula | Name of Compound | Example No. |
|---|---|---|
| 11 | 1-(4-Chloro-3-(trifluoromethyl)-phenyl)-3-{4-[6-(2-morpholin-4-yl-ethylamino)purin-9-yl]-phenyl}urea | Example 133 |
| 12 | 1-[4-(6-Amino-8-dimethylamino-methyl-purin-9-yl)phenyl]-3-(4-chloro-3-(trifluoromethyl)-phenyl)urea | Example 134 |
| 13 | 1-(9-{4-[3-(4-Chloro-3-(tri-fluoromethyl)phenyl)ureido]-phenyl}-8-vinyl-9H-purin-6-yl)-3-propylurea | Example 135 |
| 14 | 1-[4-(6-Amino-8-methoxypurin-9-yl)phenyl]-3-(4-chloro-3-tri-fluoromethyl)phenyl)urea | Example 136 |
| 15 | 1-[9-{4-[3-(4-Chloro-3-(tri-fluoromethyl)phenyl)ureido]-phenyl}-8-(1,2-dihydroxyethyl)-9H-purin-6-yl]-3-propylurea | Example 137 |
| 16 | 1-[4-(6-Aminopurin-9-yl)phenyl]-2-bromophenyl]-3-(4-chloro-3-(trifluoromethyl)phenyl)urea | Example 138 |

TABLE 2-continued

| Structural formula | Name of Compound | Example No. |
|---|---|---|
| 17 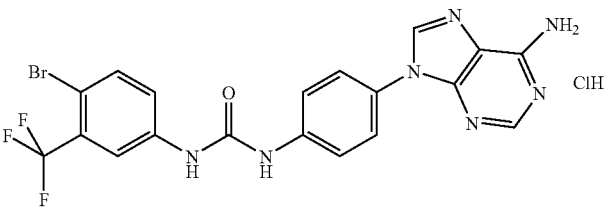 [SMILES: Nc1ncnc2c1ncn2-c1ccc(NC(=O)Nc2ccc(Br)c(C(F)(F)F)c2)cc1 ; Cl] | 1-[4-(6-Aminopurin-9-yl)phenyl]-3-(4-bromo-3-(3-(trifluoromethyl)phenyl)urea hydrochloride | Example 139 |
| 18 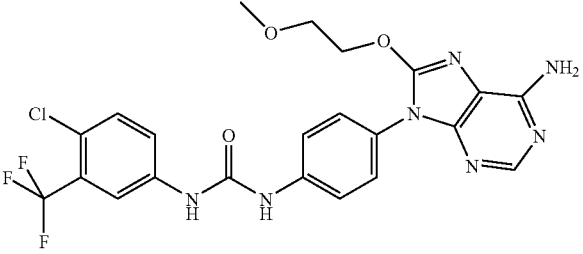 [SMILES: COCCOc1nc2c(N)ncnc2n1-c1ccc(NC(=O)Nc2ccc(Cl)c(C(F)(F)F)c2)cc1] | 1-{4-[6-Amino-8-(2-methoxyethyl)-purin-9-yl]-phenyl}-3-(4-chloro-3-(trifluoromethyl)phenyl)urea | Example 140 |
| 19 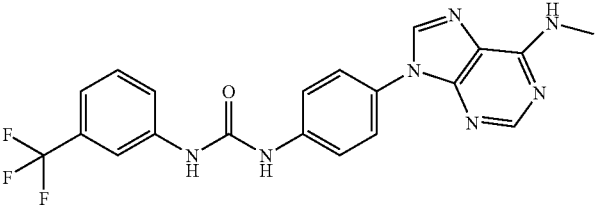 [SMILES: CNc1ncnc2c1ncn2-c1ccc(NC(=O)Nc2cccc(C(F)(F)F)c2)cc1] | 1-[4-(6-(Methylamino)purin-9-yl)phenyl]-3-(3-(trifluoromethyl)phenyl)urea | Example 141 |
| 20 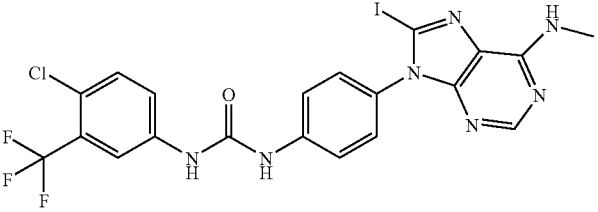 [SMILES: CNc1ncnc2c1nc(I)n2-c1ccc(NC(=O)Nc2ccc(Cl)c(C(F)(F)F)c2)cc1] | 1-(4-Chloro-3-(trifluoromethyl)-phenyl)-3-[4-(8-iodo-6-(methylamino)purin-9-yl)phenyl]urea | Example 142 |
| 21 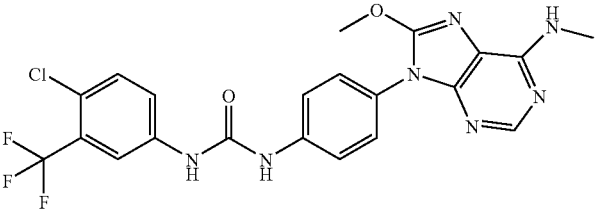 [SMILES: CNc1ncnc2c1nc(OC)n2-c1ccc(NC(=O)Nc2ccc(Cl)c(C(F)(F)F)c2)cc1] | 1-(4-Chloro-3-(trifluoromethyl)-phenyl)-3-[4-(8-methoxy-6-(methylamino)purin-9-yl)phenyl]-urea | Example 143 |
| 22 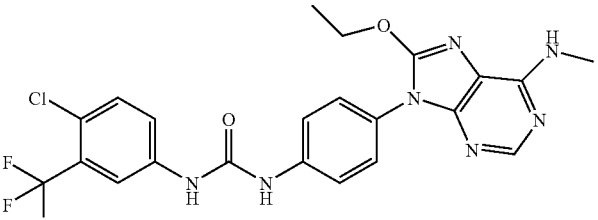 | 1-(4-Chloro-3-(trifluoromethyl)-phenyl)-3-[4-(8-ethoxy-6-(methylamino)purin-9-yl)phenyl]-urea | Example 144 |

TABLE 2-continued

| Structural formula | Name of Compound | Example No. |
|---|---|---|
| 23 | 1-(4-Chloro-3-(trifluoromethyl)-phenyl)-3-{4-[8-(2-methoxy-ethoxy)-6-(methylamino)purin-9-yl]phenyl}urea | Example 145 |
| 24 | 1-(4-Chloro-3-(trifluoromethyl)-phenyl)-3-{4-[8-(2-dimethyl-amino-ethoxy)-6-(methylamino)-purin-9-yl]phenyl}urea | Example 146 |
| 25 | 1-[4-(6-(Methylamino)purin-9-yl)phenyl]-3-[3-(4-methyl-piperazin-1-ylmethyl)-5-(tri-fluoromethyl)phenyl]urea | Example 147 |
| 26 | 1-[4-(6-(Aminopurin-9-yl)-phenyl]-3-[3-(4-methyl-piperazin-1-ylmethyl)-5-(tri-fluoromethyl)phenyl]urea | Example 148 |
| 27 | 1-[4-(6-(Amino-8-iodopurin-9-yl)phenyl]-3-[3-(4-methyl-piperazin-1-ylmethyl)-5-(tri-fluoromethyl)phenyl]urea | Example 149 |

TABLE 2-continued

| Structural formula | Name of Compound | Example No. |
|---|---|---|
| 28 | 1-[4-(6-(Amino-8-vinylpurin-9-yl)phenyl]-3-[3-(4-methyl-piperazin-1-ylmethyl)-5-(tri-fluoromethyl)phenyl]urea | Example 150 |
| 29 | 1-[4-(6-(Aminopurin-9-yl)-phenyl]-3-(3-dimethylamino-methyl)-5-(trifluoromethyl)-phenyl)urea | Example 151 |
| 30 | 1-(3-Dimethylaminomethyl-5-(trifluoromethyl)phenyl)-3-[4-(6-(methylamino)purin-9-yl)-phenyl]urea | Example 152 |
| 31 | 1-[4-[4-Cyano-imidazo[4,5-c]-pyridin-1-yl)phenyl]-3-[3-(4-methylpiperazin-1-ylmethyl)-5-(trifluoromethyl)phenyl]urea | Example 153 |
| 32 | 1-[4-(6-(Amino-8-ethylpurin-9-yl)phenyl]-3-[3-(4-methyl-piperazin-1-ylmethyl)-5-(tri-fluoromethyl)phenyl]urea | Example 154 |

TABLE 2-continued

| Structural formula | Name of Compound | Example No. |
|---|---|---|
| 33 | 1-(4-{3-[3-(4-Methylpiperazin-1-ylmethyl)-5-(trifluoromethyl)-phenyl]ureido}-phenyl)-1H-imidazo[4,5-c]pyridine-4-carboxamide | Example 155 |
| 34 | 1-[4-(6-(Methylamino)purin-9-yl)phenyl]-3-[4-(4-methyl-piperazin-1-yl)-3-(trifluoro-methyl)phenyl]urea | Example 156 |
| 35 | 1-[4-(6-Aminopurin-9-yl)phenyl]-3-{4-[(2-dimetylaminoethyl)-methylamino]-3-(trifluoro-methyl)phenyl]urea | Example 157 |
| 36 | 1-[4-(6-Aminopurin-9-yl)phenyl]-3-(4-dimethylamino-3-(trifluoro-methyl)phenyl)urea | Example 158 |
| 37 | 1-[4-(6-Aminopurin-9-yl)phenyl]-3-[3-(4-methylpiperazine-1-carbonyl)-5-(trifluoromethyl)-phenyl]urea | Example 159 |
| 38 | 3-{3-[4-(6-Aminopurin-9-yl)-phenyl]ureido}-N-(2-dimethyl-aminoethyl)-5-(trifluoromethyl)-benzamide | Example 160 |

TABLE 2-continued

| Structural formula | Name of Compound | Example No. |
|---|---|---|
| 39 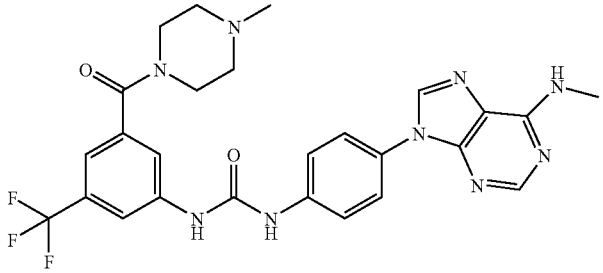 [SMILES: CNc1ncnc2c1ncn2-c1ccc(NC(=O)Nc2cc(C(=O)N3CCN(C)CC3)cc(C(F)(F)F)c2)cc1] | 1-[4-(6-(Methylamino)purin-9-yl)phenyl]-3-[3-(4-methyl-piperazine-1-carbonyl)-5-(trifluoromethyl)phenyl]urea | Example 161 |
| 40 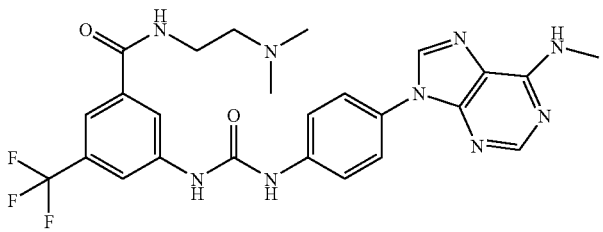 [SMILES: CNc1ncnc2c1ncn2-c1ccc(NC(=O)Nc2cc(C(=O)NCCN(C)C)cc(C(F)(F)F)c2)cc1] | N-(2-Dimethylaminoethyl)-3-{3-[4-(6-(methylamino)purin-9-yl)-phenyl]ureido}-5-(trifluoro-methyl)benzamide | Example 162 |
| 41 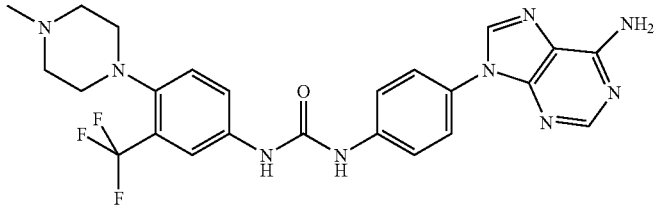 [SMILES: CN1CCN(c2ccc(NC(=O)Nc3ccc(-n4cnc5c(N)ncnc54)cc3)cc2C(F)(F)F)CC1] | 1-[4-(6-Aminopurin-9-yl)phenyl]-3-[4-(4-methyl-piperazin-1-yl)-3-(trifluoromethyl)phenyl]urea | Example 163 |
| 42 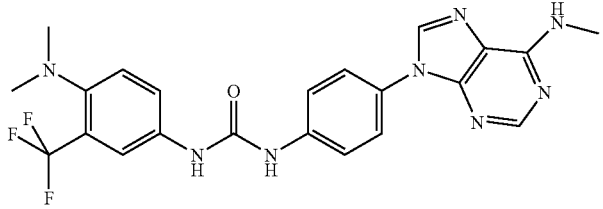 [SMILES: CNc1ncnc2c1ncn2-c1ccc(NC(=O)Nc2ccc(N(C)C)c(C(F)(F)F)c2)cc1] | 1-(4-Dimethylamino-3-(trifluoro-methyl)phenyl)-3-[4-(6-(methyl-amino)pruin-9-yl) phenyl]urea | Example 164 |
| 43 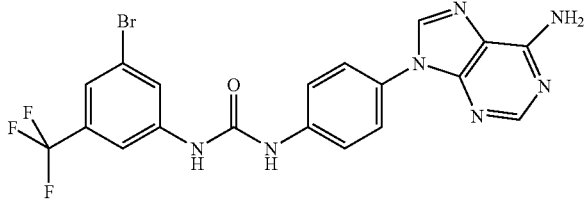 [SMILES: Nc1ncnc2c1ncn2-c1ccc(NC(=O)Nc2cc(Br)cc(C(F)(F)F)c2)cc1] | 1-[4-(6-Aminopurin-9-yl)phenyl]-3-(3-bromo-5-(trifluoromethyl)-phenyl)urea | Example 165 |
| 44 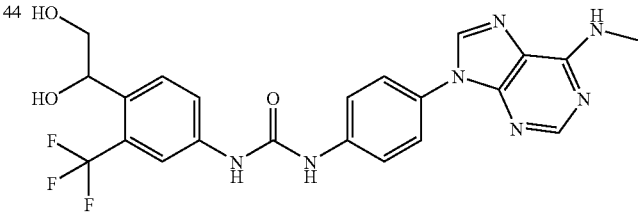 | 1-[4-(1,2-Dihydroxyethyl)-3-(trifluoromethyl)phenyl]-3-[4-(6-(methylamino)purin-9-yl)-phenyl]urea | Example 166 |

TABLE 2-continued

| | Structural formula | Name of Compound | Example No. |
|---|---|---|---|
| 45 | | 1-(4-Hydroxymethyl-3-(trifluoromethyl)phenyl)-3-[4-(6-(methylamino)purin-9-yl)phenyl]urea | Example 167 |
| 46 | | 1-[4-(6-(Methylamino)purin-9-yl)phenyl]-3-[4-(4-methylpiperazin-1-yl)-3-(trifluoromethyl)phenyl]urea | Example 168 |
| 47 | | 1-[4-(6-(Methylamino)purin-9-yl)phenyl]-3-(4-morpholin-4-yl-methyl)-3-(trifluoromethyl)-phenyl]urea | Example 169 |
| 48 | | 1-(3-Dimethylmethyl-5-(trifluoromethyl)phenyl)-3-[4-(6-(methylamino)purin-9-yl)phenyl]-urea | Example 170 |
| 49 | | 1-[4-(6-Aminopurin-9-yl)phenyl]-3-[4-(2-dimethylamino-ethoxy)-3-(trifluoromethyl)phenyl]urea | Example 171 |
| 50 | | 1-[4-(6-Aminopurin-9-yl)phenyl]-3-[4-(2-morpholin-4-yl-ethoxy)-3-(trifluoromethyl)-phenyl]urea | Example 172 |

TABLE 2-continued

| | Structural formula | Name of Compound | Example No. |
|---|---|---|---|
| 51 | | 1-(3-Amino-5-(trifluoromethyl)-phenyl)-3-[4-(6-(methylamino)-purin-9-yl)phenyl]urea | Example 173 |
| 52 | | 1-[4-(2-Dimethylaminoethoxy)-3-(trifluoromethyl)phenyl]-3-[4-(6-(methylamino)purin-9-yl)-phenyl]urea | Example 174 |
| 53 | | 1-[4-(6-Methylamino)purin-9-yl)-phenyl]-3-[4-(2-morpholin-4-yl-ethoxy)-3-(trifluoromethyl)-phenyl]urea | Example 175 |
| 54 | | N-(2-Hydroxy-1-hydroxymethyl-ethyl)-3-{3-[4-(6-(methylamino)-purin-9-yl)phenyl]ureido}-5-(trifluoromethyl)benzamide | Example 176 |
| 55 | | 3-{3-[4-(6-Aminopurin-9-yl)-phenyl]ureido}-N-(2,3-di-hydroxypropyl)-5-(trifluoro-methyl)benzamide | Example 177 |
| 56 | | 3-{3-[4-(6-Aminopurin-9-yl)-phenyl]ureido}-N-(2-hydroxy-1-hydroxylmethyl-ethyl)-5-(tri-fluoromethyl)benzamide | Example 178 |

TABLE 2-continued

| Structural formula | Name of Compound | Example No. |
| --- | --- | --- |
| 57 | N-(2,3-Dihydroxypropyl)-3-{3-[4-(6-(methylamino)purin-9-yl)-phenyl]ureido}-5-(trifluoro-methyl)benzamide | Example 179 |
| 58 | 3-{3-[4-(6-(Methylamino)purin-9-yl)phenyl]ureido}-N-(2-morpholin-4-yl-ethyl)-5-(tri-fluoromethyl)benzamide | Example 180 |
| 59 | 1-(4-Dimethylaminomethyl-3-(tri-fluoromethyl)phenyl)-3-[4-(6-(methylamino)purin-9-yl)-phenyl]urea | Example 181 |
| 60 | 1-{4-[(2-Dimethylamino-ethyl-amino)-methyl]-3-(trifluoro-methyl)phenyl}-3-[4-(6-(methyl-amino)purin-9-yl)phenyl]urea | Example 182 |
| 61 | 1-[4-(6-Aminopurin-9-yl)phenyl]-3-[4-(1-methyl-piperidin-4-yloxy)-3-(trifluoromethyl)-phenyl]urea | Example 183 |

TABLE 2-continued

| Structural formula | Name of Compound | Example No. |
|---|---|---|
| 62 | 1-[4-(6-Methylamino)purin-9-yl)phenyl]-3-[4-(1-methyl-piperidin-4-yloxy)-3-(trifluoro-methyl)phenyl]urea | Example 184 |
| 63 | 1-{4-[(2-Hydroxy-ethylamino)-methyl]-3-(trifluoromethyl)-phenyl]-3-[4-(6-(methylamino)-purin-9-yl)phenyl]urea | |
| 64 | 1-{4-[(2,3-Diydroxy-propyl-amino)-methyl)-3-(trifluoro-methyl)phenyl]-3-[4-(6-(methyl-amino)purin-9-yl)phenyl]urea | |
| 65 | 1-{4-[(2-Hydroxy-1-hydroxy-methyl-ethylamino)-methyl]-3-(trifluoromethyl)phenyl]-3-[4-(6-(methylamino)purin-9-yl)-phenyl]urea | |
| 66 | 1-[4-(6-(Methylamino)purin-9-yl)phenyl]-3-(3-morpholin-4-yl-methyl)-5-(trifluoromethyl)-phenyl]urea | |

TABLE 2-continued

| Structural formula | Name of Compound | Example No. |
|---|---|---|
| 67 | 1-{3-[(2-Dimethylamino-ethyl-amino)-methyl]-5-(trifluoro-methyl)phenyl}-3-[4-(6-(methyl-amino)purin-9-yl)phenyl]urea | |
| 68 | 1-[4-(2-Dimethylamino-ethyl)-3-(trifluoromethyl)phenyl]-3-[4-(6-(methylamino)purin-9-yl)-phenyl]urea | Example 185 |
| 69 | 1-[4-(6-(Methylamino)purin-9-yl)phenyl]-3-{4-[2-(4-methyl-piperazin-1-yl)-ethyl]-3-(tri-fluoromethyl)phenyl}urea | Example 186 |
| 70 | 1-[4-(6-(Methylamino)purin-9-yl)phenyl]-3-[4-(2-morpholin-4-yl)-ethyl]-3-(trifluoromethyl)-phenyl]urea | Example 187 |
| 71 | 1-[3-(2-Dimethylamino-ethyl)-5-(trifluoromethyl)phenyl]-3-[4-(6-(methylamino)purin-9-yl)-phenyl]urea | Example 188 |

TABLE 2-continued

| | Structural formula | Name of Compound | Example No. |
|---|---|---|---|
| 72 | | 1-[4-(6-(Methylamino)purin-9-yl)phenyl]-3-{3-[2-(4-methyl-piperazin-1-yl)-ethyl]-5-(tri-fluoromethyl)phenyl}urea | Example 189 |
| 73 | | 1-[4-(6-(Methylamino)purin-9-yl)phenyl]-3-[3-[2-morpholin-4-yl)-ethyl]-5-(trifluoromethyl)-phenyl]urea | Example 190 |
| 74 | | 1-[4-(3-Dimethylamino-propyl)-3-(trifluoromethyl)phenyl]-3-[4-(6-(methylamino)purin-9-yl)-phenyl]urea | Example 191 |
| 75 | | 1-[4-(6-(Methylamino)purin-9-yl)phenyl]-3-{4-[3-(4-methyl-piperazin-1-yl)-propyl]-3-(tri-fluoromethyl)phenyl}urea | Example 192 |

TABLE 2-continued

| | Structural formula | Name of Compound | Example No. |
|---|---|---|---|
| 76 | 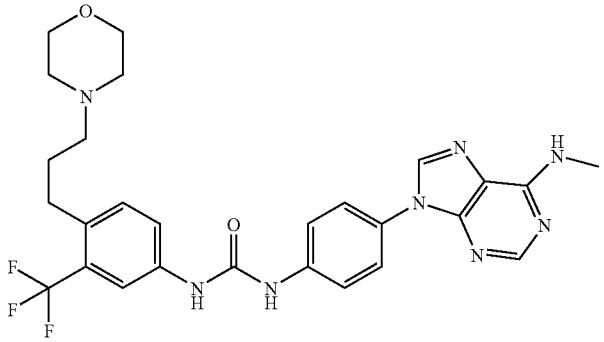 [SMILES: CNc1ncnc2c1ncn2-c1ccc(NC(=O)Nc2ccc(CCCN3CCOCC3)c(C(F)(F)F)c2)cc1] | 1-[4-(6-(Methylamino)purin-9-yl)phenyl]-3-[4-(3-morpholin-4-yl-propyl)-3-(trifluoromethyl)-phenyl]urea | Example 193 |
| 77 | 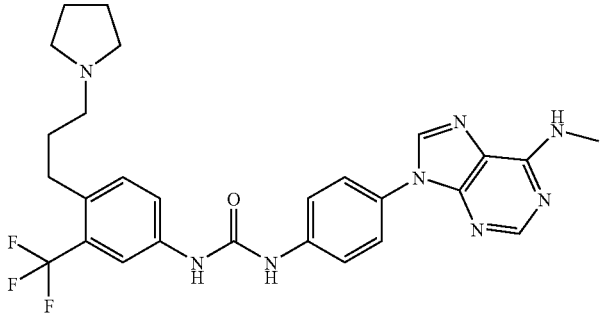 [SMILES: CNc1ncnc2c1ncn2-c1ccc(NC(=O)Nc2ccc(CCCN3CCCC3)c(C(F)(F)F)c2)cc1] | 1-[4-(6-(Methylamino)purin-9-yl)phenyl]-3-[4-(3-pyrrolidin-1-yl-propyl)-3-(trifluoromethyl)-phenyl]urea | Example 194 |
| 78 | 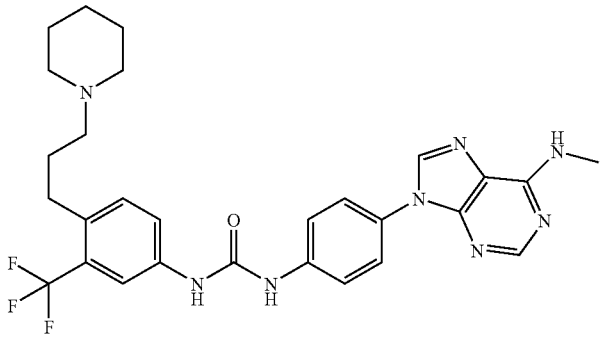 [SMILES: CNc1ncnc2c1ncn2-c1ccc(NC(=O)Nc2ccc(CCCN3CCCCC3)c(C(F)(F)F)c2)cc1] | 1-[4-(6-(Methylamino)purin-9-yl)phenyl]-3-[4-(3-piperidin-1-yl-propyl)-3-(trifluoromethyl)-phenyl]urea | Example 195 |
| 79 | 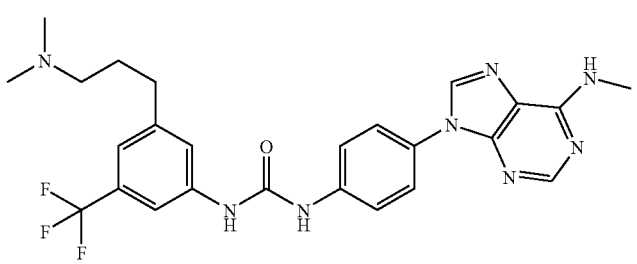 | 1-[3-(3-Dimethylamino-propyl)-5-(trifluoromethyl)phenyl]-3-[4-(6-(methylamino)purin-9-yl)-phenyl]urea | |
| 80 | 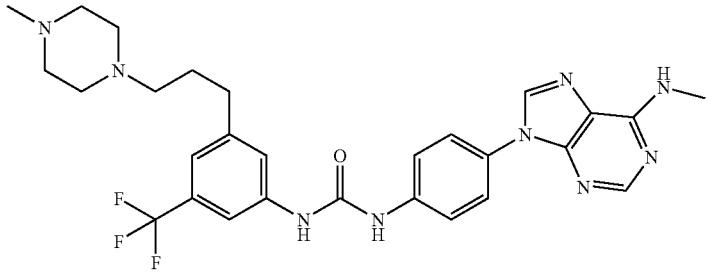 | 1-[4-(6-(Methylamino)purin-9-yl)phenyl]-3-{3-[3-(4-methyl-piperazin-1-yl)-propyl]-5-(tri-fluoromethyl)phenyl}urea | |

TABLE 2-continued

| Structural formula | Name of Compound | Example No. |
|---|---|---|
| 81 | 1-[4-(6-(Methylamino)purin-9-yl)phenyl]-3-[3-(3-morpholin-4-yl-propyl)-5-(trifluoromethyl)phenyl]urea | |
| 82 | 1-[3-(1,2-Dihydroxy-ethyl)-5-(trifluoromethyl)phenyl]-3-[4-(6-(methylamino)purin-9-yl)-phenyl]urea | |
| 83 | 1-(3-Hydroxmethyl-5-(trifluoromethyl)phenyl)-3-[4-(6-(methylamino)purin-9-yl)phenyl]urea | |
| 84 | 1-[4-(2-Hydroxy-ethoxymethyl)-3-(trifluoromethyl)phenyl]-3-[4-(6-(methylamino)purin-9-yl)-phenyl]urea | |
| 85 | 1-[3-(2-Hydroxy-ethoxymethyl)-5-(trifluoromethyl)phenyl]-3-[4-(6-(methylamino)purin-9-yl)-phenyl]urea | |
| 86 | 1-[3-(2-Dimethylamino-ethoxy)-5-(trifluoromethyl)phenyl]-3-[4-(6-(methylamino)purin-9-yl)-phenyl]urea | Example 196 |

TABLE 2-continued

| Structural formula | Name of Compound | Example No. |
|---|---|---|
| 87 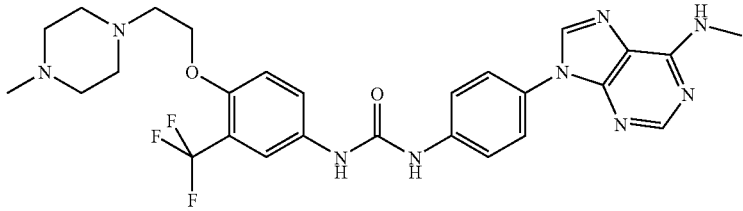 | 1-[4-(6-(Methylamino)purin-9-yl)phenyl]-3-{4-[2-(4-methyl-piperazin-1-yl)ethoxy]-3-(trifluoromethyl)phenyl}urea | |
| 88 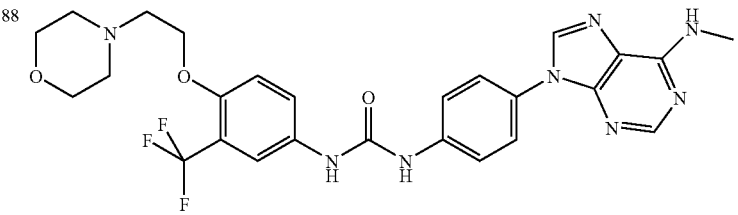 | 1-[4-(6-(Methylamino)purin-9-yl)phenyl]-3-[4-(2-morpholin-4-yl-ethoxy)-3-(trifluoromethyl)-phenyl]urea | |
| 89 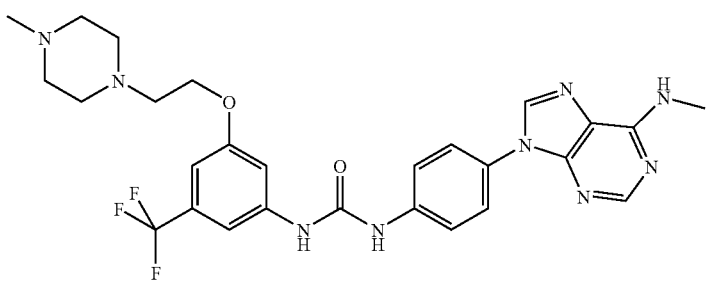 | 1-[4-(6-(Methylamino)purin-9-yl)phenyl]-3-{3-[2-(4-methyl-piperazin-1-yl)-ethoxy]-5-(trifluoromethyl)phenyl]urea | |
| 90 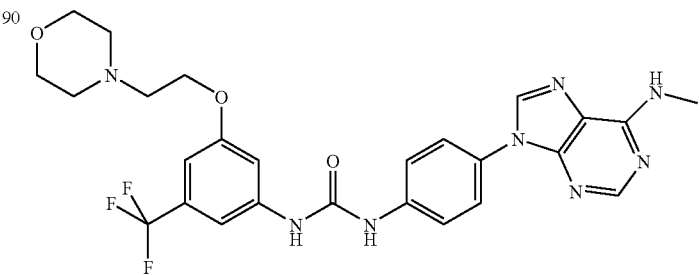 | 1-[4-(6-(Methylamino)purin-9-yl)phenyl]-3-[3-[2-morpholin-4-yl-ethoxy]-5-(trifluoromethyl)-phenyl]urea | |
| 91 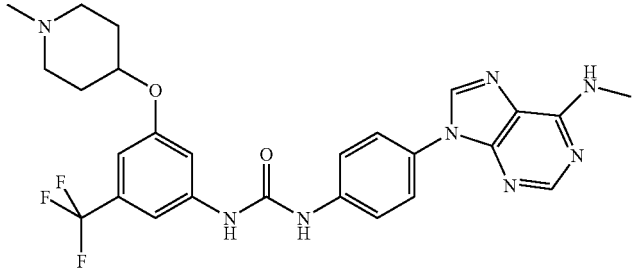 | 1-[4-(6-(Methylamino)purin-9-yl)phenyl]-3-[3-[1-methyl-piperidin-4-yloxy]-5-(tri-fluoromethyl)phenyl]urea | Example 197 |
| 92 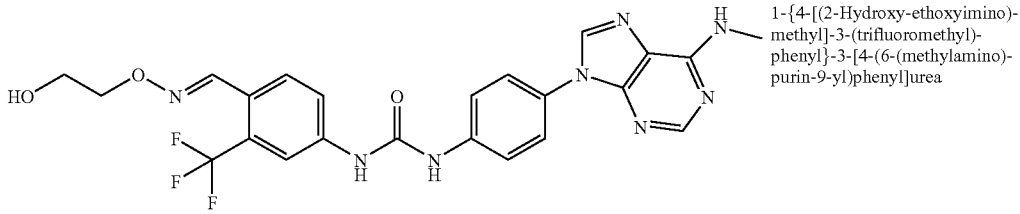 | 1-{4-[(2-Hydroxy-ethoxyimino)-methyl]-3-(trifluoromethyl)-phenyl}-3-[4-(6-(methylamino)-purin-9-yl)phenyl]urea | |

TABLE 2-continued

| Structural formula | Name of Compound | Example No. |
|---|---|---|
| 93 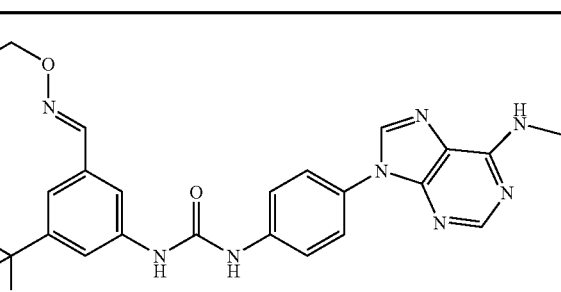 | 1-{3-[(2-Hydroxy-ethoxyimino)-methyl]-5-(trifluoro-methyl)-phenyl}-3-[4-(6-(methylamino)-purin-9-yl)phenyl]urea | |
| 94 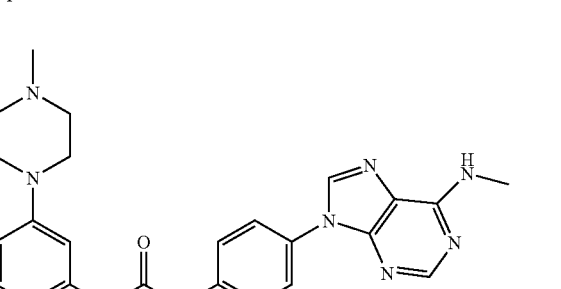 | 1-[4-(6-(Methylamino)purin-9-yl)phenyl]-3-[3-[4-methyl-piperazin-1-yl]-5-(trifluoro-methyl)phenyl]urea | |

TABLE 3

| Structural Formula | Name of Compound | Example No. |
|---|---|---|
| 1 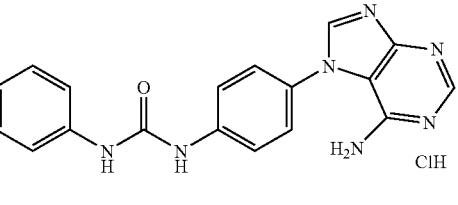 | 1-[4-(6-Aminopurin-7-yl)phenyl]-3-(4-chloro-3-(trifluoromethyl)-phenyl)urea hydrochloride | Example 198 |
| 2 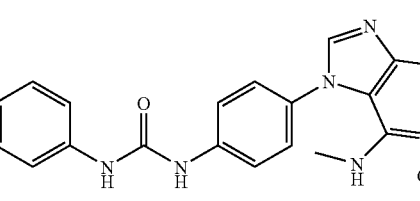 | 1-(4-Chloro-3-(trifluoromethyl)-phenyl-3-[4-(6-(methylamino)-purin-7-yl)phenyl]urea hydrochloride | Example 199 |
| 3 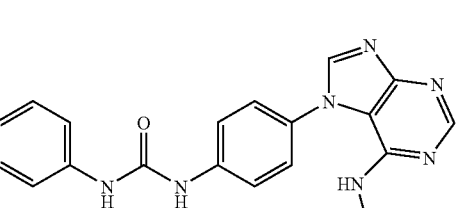 | 1-(7-{4-[3-(4-Chloro-3-(tri-fluoromethyl)phenyl)ureido]-phenyl}-7H-purin-6-yl)-3-propyl-urea | Example 200 |

TABLE 3-continued

| | Structural Formula | Name of Compound | Example No. |
|---|---|---|---|
| 4 | | 1-[4-(6-Aminopurin-7-yl)phenyl]-3-[3-(4-methyl-piperazin-1-yl-methyl)-5-(trifluoromethyl)-phenyl]urea | Example 201 |
| 5 | | 9-{4-[3-(4-Chloro-3-(trifluoro-methyl)phenyl)ureido]phenyl}-9H-purine-6-carboxylic acid methyl ester | Example 202 |
| 6 | | 9-{4-[3-(4-Chloro-3-(trifluoro-methyl)phenyl)ureido]phenyl}-9H-purine-6-carboxylic acid | Example 203 |
| 7 | | 9-{4-[3-(4-Chloro-3-(trifluoro-methyl)phenyl)ureido]phenyl}-9H-purine-6-carboxylic acid methylamide | Example 204 |
| 8 | | 1-[4-(6-Aminopurin-7-yl)phenyl]-3-(3-dimethylaminomethyl-5-tri-fluoromethyl-phenyl)urea | Example 205 |
| 9 | | 3-{3-[4-(6-Aminopurin-7-yl)-phenyl]ureido}-N-(2-dimethyl-amino)ethyl)-5-(trifluoro-methyl)benzamide | Example 206 |

TABLE 3-continued

| Structural Formula | Name of Compound | Example No. |
|---|---|---|
| 10 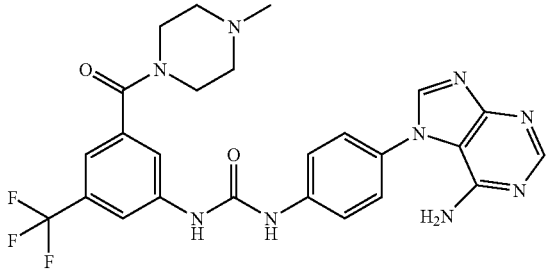 [SMILES: CN1CCN(C(=O)c2cc(NC(=O)Nc3ccc(-n4cnc5ncnc(N)c54)cc3)cc(C(F)(F)F)c2)CC1] | 1-[4-(6-Aminopurin-7-yl)phenyl]-3-[3-(4-methyl-piperazin-1-carbonyl)-5-(trifluoromethyl)-phenyl]urea | Example 207 |
| 11 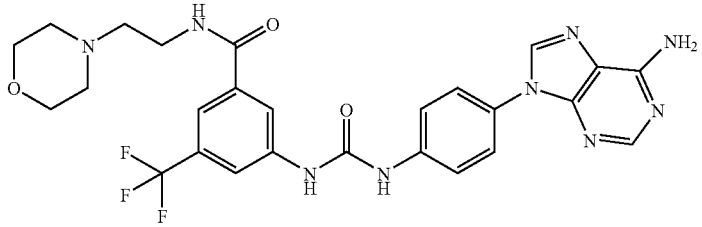 [SMILES: Nc1ncnc2c1ncn2-c1ccc(NC(=O)Nc2cc(C(=O)NCCN3CCOCC3)cc(C(F)(F)F)c2)cc1] | 3-{3-[4-(6-Aminopurin-9-yl)-phenyl]ureido}-N-(2-morpholin-4-yl-ethyl)-5-(trifluoromethyl)-benzamide | Example 208 |
| 12 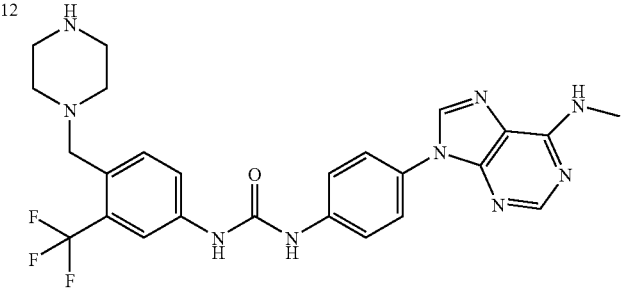 | 1-[4-(6-(Methylamino)purin-9-yl)phenyl]-3-(4-piperazin-1-yl-methyl-3-(trifluoromethyl)-phenyl)urea | Example 209 |
| 13 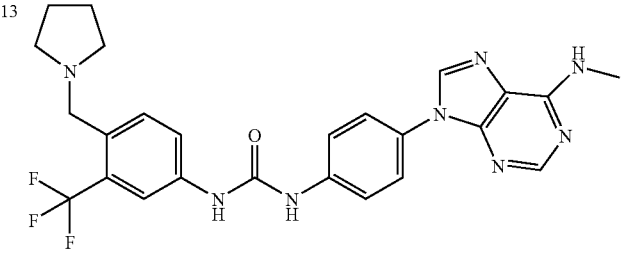 | 1-[4-(6-(Methylamino)purin-9-yl)phenyl]-3-(4-pyrrolidin-1-ylmethyl-3-(trifluoromethyl)-phenyl)urea | Example 210 |
| 14 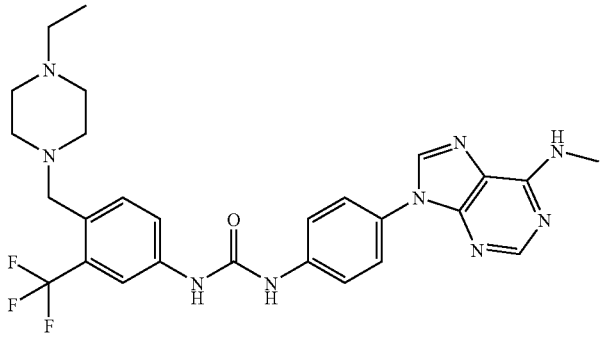 [SMILES: CCN1CCN(Cc2ccc(NC(=O)Nc3ccc(-n4cnc5c(NC)ncnc54)cc3)cc2C(F)(F)F)CC1] | 1-[4-(4-Ethyl-piperazin-1-yl-methyl)-3-(trifluoromethyl)-phenyl]-3-[4-(6-(methylamino)-purin-9-yl)phenyl]urea | Example 211 |

TABLE 3-continued

| Structural Formula | Name of Compound | Example No. |
|---|---|---|
| 15 | 1-[4-(6-(Methylamino)purin-9-yl)phenyl]-3-{4-[(2-pyrrolidin-1-ylethyamino)methyl]-3-(trifluoromethyl)phenyl}urea | Example 212 |
| 16 | 1-[4-(6-(Methylamino)purin-9-yl)phenyl]-3-(4-piperidin-1-ylmethyl-3-(trifluoromethyl)phenyl)urea | Example 213 |
| 17 | 1-(4-(Cyclohexylamino)methyl-3-(trifluoromethyl)phenyl)-3-[4-(6-(methylamino)purin-9-yl)-phenyl]urea | Example 214 |
| 18 | 1-(4-Imidazo[4,5-c]pyridin-1-yl-phenyl)-3-[4-(4-methyl-piperazin-1-ylmethyl)-3-(trifluoromethyl)phenyl]urea | Example 215 |
| 19 | 1-[4-(6-(Methylamino)purin-9-yl)phenyl]-3-{4-(tetrahydropyran-4-ylamino)-methyl]-3-(trifluoromethyl)phenyl}urea | Example 216 |

TABLE 3-continued

| | Structural Formula | Name of Compound | Example No. |
|---|---|---|---|
| 20 | 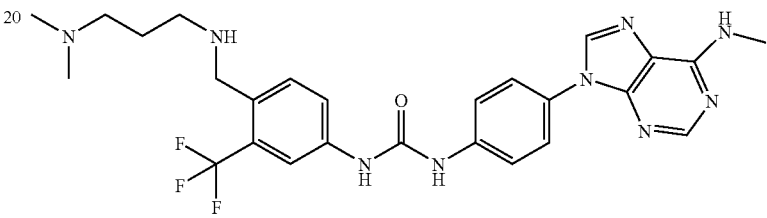 | 1-{4-[(3-(Dimethylamino)propyl-amino)methyl]-3-(trifluoro-methyl)phenyl}-3-[4-(6-(methyl-amino)purin-9-yl)phenyl]urea | Example 217 |
| 21 | 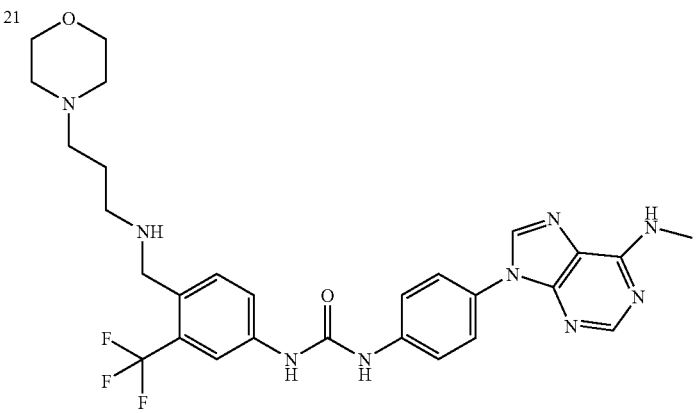 | 1-[4-(6-(Methylamino)purin-9-yl)phenyl]-3-{4-[(3-morpholin-4-yl-propylamino)methyl]-3-(tri-fluoromethyl)phenyl}urea | Example 218 |
| 22 | 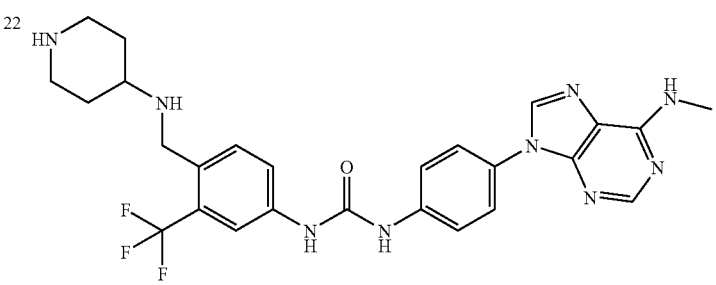 | 1-[4-(6-(Methylamino)purin-9-yl)phenyl]-3-[4-(piperidin-4-yl-aminomethyl)-3-(trifluoro-methyl)phenyl]urea | Example 219 |
| 23 | 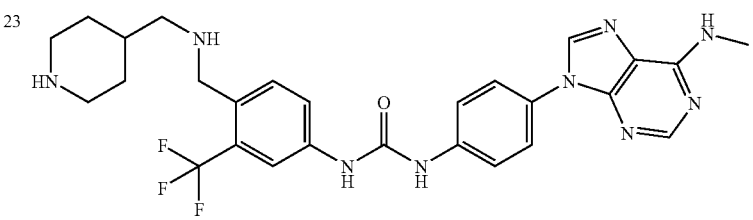 | 1-[4-(6-(Methylamino)purin-9-yl)phenyl]-3-(4-{[(piperidin-4-ylmethyl)amino]methyl}-3-(tri-fluoromethyl)phenyl)urea | Example 220 |
| 24 | 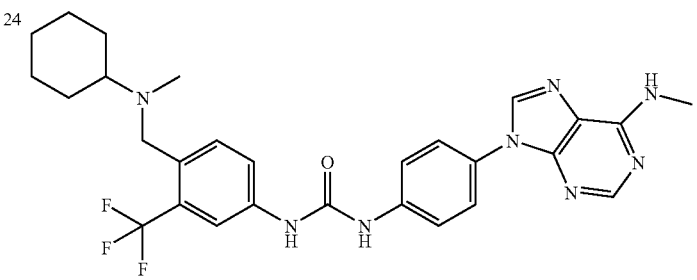 | 1-{4-[(Cyclohexyl-methylamino)-methyl]-3-(trifluoromethyl)-phenyl}-3-[4-(6-(methylamino)-purin-9-yl)phenyl]urea | Example 221 |

TABLE 3-continued

| Structural Formula | Name of Compound | Example No. |
|---|---|---|
| 25 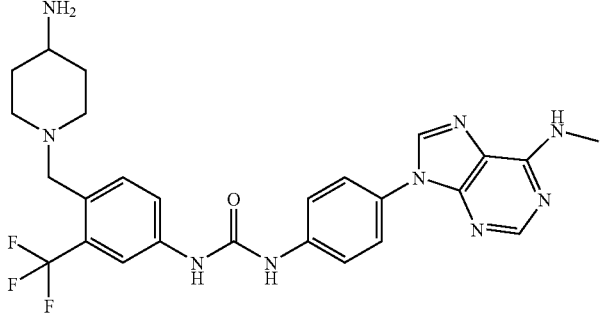 [SMILES: CNc1ncnc2c1ncn2-c1ccc(NC(=O)Nc2ccc(CN3CCC(N)CC3)c(C(F)(F)F)c2)cc1] | 1-[4-(4-Amino-piperidin-1-yl-methyl)-3-(trifluoromethyl)-phenyl]-3-[4-(6-(methylamino)-purin-9-yl)phenyl]urea | Example 222 |
| 26 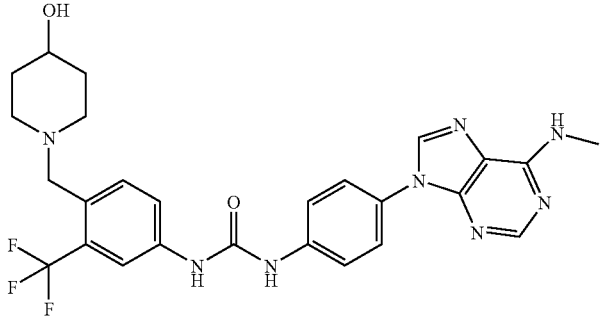 [SMILES: CNc1ncnc2c1ncn2-c1ccc(NC(=O)Nc2ccc(CN3CCC(O)CC3)c(C(F)(F)F)c2)cc1] | 1-[4-(4-Hydroxy-piperidin-1-yl-methyl)-3-(trifluoromethyl)-phenyl]-3-[4-(6-(methylamino)-purin-9-yl)phenyl]urea | Example 223 |
| 27 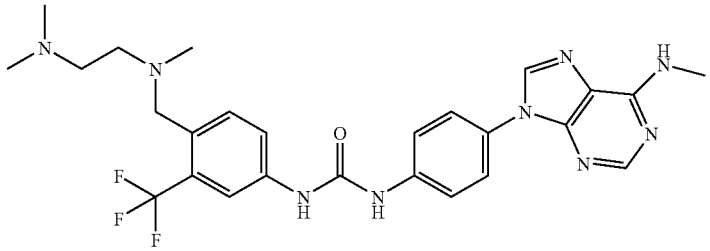 | 1-(4-{[(2-(Dimethylamino)-ethyl)-methylamino]-methyl}-3-(tri-fluoromethyl)phenyl)-3-[4-(6-(methylamino)purin-9-yl)-phenyl]urea | Example 224 |
| 28 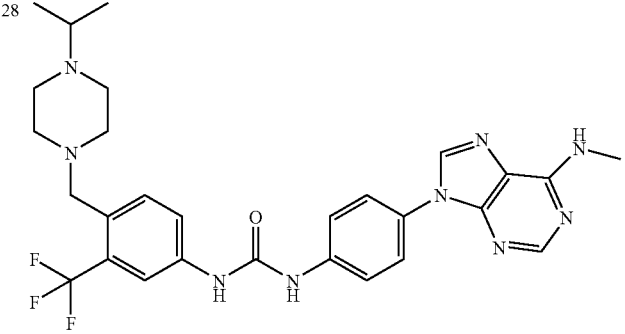 | 1-[4-(4-Isopropyl-piperazin-1-ylmethyl)-3-(trifluoromethyl)-phenyl]-3-[4-(6-(methylamino)-purin-9-yl)phenyl]urea | Example 225 |
| 29 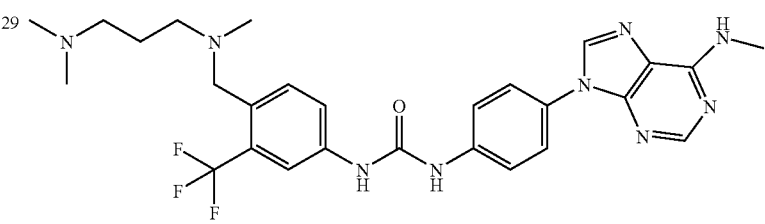 | 1-(4-{[(3-(Dimethylamino)-propyl)-methylamino]methyl}-3-(trifluoromethyl)phenyl)-3-[4-(6-(methylamino)purin-9-yl)-phenyl]urea | Example 226 |

TABLE 3-continued

| Structural Formula | Name of Compound | Example No. |
|---|---|---|
| 30 | 1-[4-(6-(Methylamino)purin-9-yl)-phenyl]-3-[3-(2-piperazin-1-yl-ethyl)-5-(trifluoromethyl)-phenyl]urea | Example 227 |
| 31 | 1-[4-(6-(Methylamino)purin-9-yl)-phenyl]-3-[3-(2-pyrrolidin-1-yl-ethyl)-5-(trifluoromethyl)phenyl]urea | Example 228 |
| 32 | 1-[4-(3-(Dimethylamino)-propoxy)-3-(trifluoromethyl)-phenyl]-3-[4-(6-(methylamino)-purin-9-yl)phenyl]urea | Example 229 |
| 33 | 1-[4-(6-(Methylamino)purin-9-yl)-phenyl]-3-[4-(2-piperidin-1-yl-ethyl)-3-(trifluoromethyl)phenyl]urea | Example 230 |
| 34 | 1-[4-(6-(Methylamino)purin-9-yl)-phenyl]-3-[4-(2-pyrrolidin-1-yl-ethyl)-3-(trifluoromethyl)phenyl]urea | Example 231 |

TABLE 3-continued

| Structural Formula | Name of Compound | Example No. |
|---|---|---|
| 35 | 1-{4-[2-(Cyclohexyl-methyl-amino)ethyl]-3-(trifluoro-methyl)phenyl}-3-[4-(6-(methyl-amino)purin-9-yl)phenyl]urea | Example 232 |
| 36 | 1-(4-{2-[(2-(Dimethylamino)-ethyl)-methylamino]-ethyl}-3-(trifluoromethyl)phenyl)-3-[4-(6-(methylamino)purin-9-yl)-phenyl]urea | Example 233 |
| 37 | 1-{4-[2-(4-Isopropyl-piperazin-1-yl)ethyl]-3-(trifluoro-methyl)phenyl}-3-[4-(6-(methyl-amino)purin-9-yl)phenyl]urea | Example 234 |
| 38 | 1-(4-{2-[(3-(Dimethylamino)-propyl)-methylamino]ethyl}-3-(trifluoromethyl)phenyl)-3-[4-(6-(methylamino)purin-9-yl)-phenyl]urea | Example 235 |
| 39 | 1-{4-[2-(4-Ethyl-piperazin-1-yl)ethyl]-3-(trifluoromethyl)-phenyl}-3-[4-(6-(methylamino)-purin-9-yl)phenyl]urea | Example 236 |

TABLE 3-continued

| Structural Formula | Name of Compound | Example No. |
|---|---|---|
| 40 | 1-[4-(6-(Methylamino)purin-9-yl)-phenyl]-3-[4-(2-piperazin-1-yl-ethyl)-3-(trifluoromethyl)phenyl]urea | Example 237 |
| 41 | 1-[4-(2-Methoxy-ethoxy)-3-(trifluoromethyl)phenyl]-3-[4-(6-(methylamino)purin-9-yl)-phenyl]urea | Example 238 |
| 42 | 1-{4-[2-(2-Methoxy-ethoxy)-ethoxy]-3-(trifluoromethyl)-phenyl}-3-[4-(6-(methylamino)-purin-9-yl)-phenyl]urea | Example 239 |
| 43 | 1-[4-(6-(Methylamino)purin-9-yl)-phenyl]-3-[4-(2-piperidin-4-yl-ethoxy)-3-(trifluoromethyl)phenyl]urea | Example 240 |
| 44 | 1-[4-(6-(Methylamino)purin-9-yl)-phenyl]-3-[4-(piperidin-4-yl-methoxy)-3-(trifluoromethyl)phenyl]urea | Example 241 |

TABLE 3-continued

| Structural Formula | Name of Compound | Example No. |
|---|---|---|
| 45 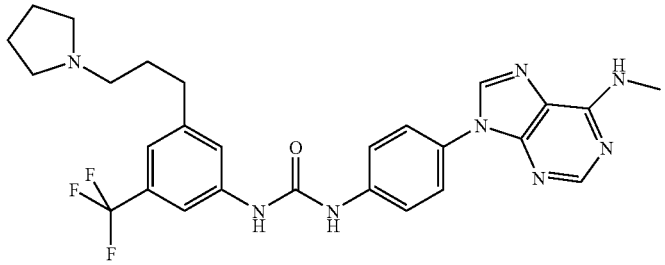 [SMILES: CNc1ncnc2c1ncn2-c1ccc(NC(=O)Nc2cc(CCCN3CCCC3)cc(C(F)(F)F)c2)cc1] | 1-[4-(6-(Methylamino)purin-9-yl)phenyl]-3-[3-(3-pyrrolidin-1-yl-propyl)-5-(trifluoromethyl)phenyl]urea | Example 242 |
| 46 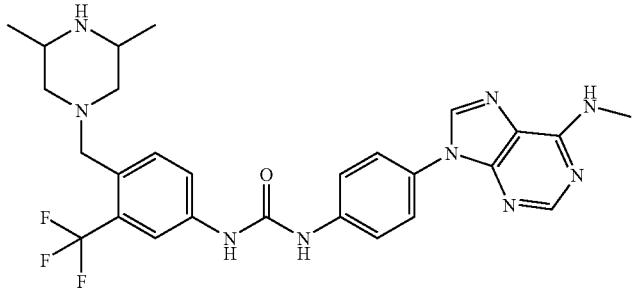 | 1-[4-(3,5-Dimethyl-piperazin-1-ylmethyl)-3-(trifluoromethyl)-phenyl]-3-[4-(6-(methylamino)-purin-9-yl)phenyl]urea | Example 243 |
| 47 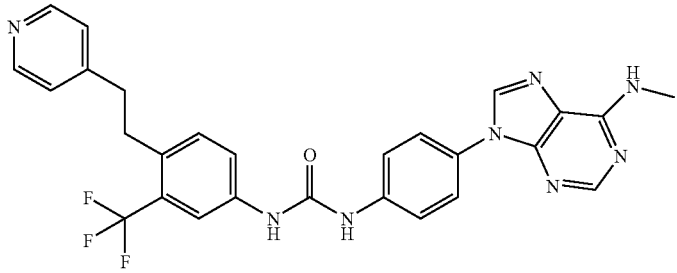 [SMILES: CNc1ncnc2c1ncn2-c1ccc(NC(=O)Nc2ccc(CCc3ccncc3)c(C(F)(F)F)c2)cc1] | 1-[4-(6-Methylamino)purin-9-yl]-phenyl]-3-[4-(2-pyridin-4-yl-ethyl)-3-(trifluoromethyl)-phenyl]urea | Example 244 |
| 48 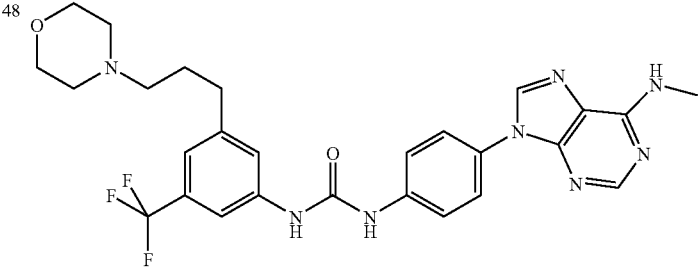 | 1-[4-(6-Methylamino)purin-9-yl]-phenyl]-3-[3-(3-morpholin-4-yl-propyl)-5-(trifluoromethyl)phenyl]urea | Example 245 |
| 49 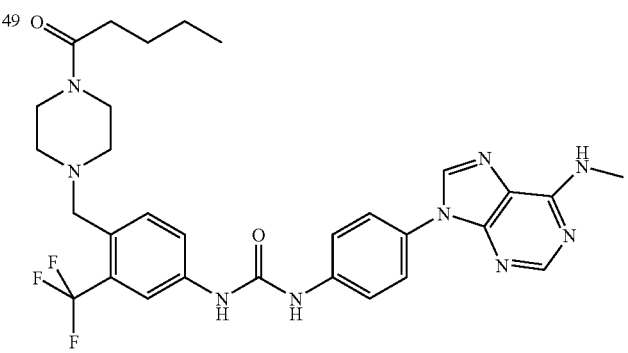 | 1-[4-(6-Methylamino)purin-9-yl]-phenyl]-3-[4-(4-pentanoyl-piperazin-1-ylmethyl)-3-(trifluoromethyl)phenyl]urea | Example 246 |

TABLE 3-continued

| Structural Formula | Name of Compound | Example No. |
|---|---|---|
| 50 | 1-[4-(4-Acetyl-piperazin-1-yl-methyl)-3-(trifluoromethyl)-phenyl]-3-[4-(6-(methylamino)-purin-9-yl)phenyl]urea | Example 247 |
| 51 | 1-{4-[4-(2,2-Dimethyl-propionyl)-piperazin-1-yl-methyl]-3-(trifluoromethyl)-phenyl}-3-[4-(6-(methylamino)-purin-9-yl)phenyl]urea | Example 248 |
| 52 | 1-[4-(6-(Methylamino)purin-9-yl)-phenyl]-3-(4-pyridin-4-ylmethyl-3-(trifluoromethyl)-phenyl)urea | Example 249 |
| 53 | N-Methyl-3-(4-{3-[4-(6-(methyl-amino)purin-9-yl)phenyl]-ureido}-2-(trifluoromethyl)-phenyl)propionamide | Example 250 |

The method for preparing the compound of the present invention will now be explained. Further, when the defined groups undergo an undesirable chemical conversion under the conditions for carrying out the method in the preparation method as shown below, for example, by using means to protect and deprotect the functional groups, the preparation can be performed. Herein, as the selection of a protective group and the operation of deprotection, for example, the method as described in Greene and Wuts, "Protective Groups in Organic Synthesis" (Second Edition, John Wiley & Sons, 1991)" can be mentioned, and this may be suitably used in accordance with reaction conditions. Further, if necessary or required, the order of the reaction step for introducing a substituent and the like may be changed. As the method for preparing the compound represented by formula (1), various methods can be thought and the compound can be synthesized by using the conventional organic synthesis means and, for example, the compound can be prepared by the following method as a representative method.

Representative Preparation Method

Preparation Method 1

The compounds which are represented by formula (1) of the present invention can be prepared, for example, according to the following method but the method for preparing the compounds of the present invention is not limited thereto. The compounds of the present inventions are all novel compounds not described in literature but can be prepared by using known chemical techniques. Further, as the raw material compounds which are used in the preparation, commercially available compounds may be used or the raw material may be prepared according to the conventional method, if necessary. Further, in Reaction Steps 1 to 4 and their explanation, $R^1$ to $R^7$, Q, $Z^1$, $Z^2$, W, Ra, Rb, Ra', Rb', Rc, Rc', Rd and Rd' mean the same as in defined in the above described formula (1). Further, L is an elimination group such as a halogen atom, a methanesulfonyloxy group and a p-toluenesulfonyloxy group, and PG is a protective group such as a $C_1$-$C_6$ alkylcarbonyl group including an acetyl group, a $C_1$-$C_6$ alkoxycarbonyl group including t-butoxycarbonyl group, an aryl $C_1$-$C_6$ alkylcarbonyl group including a benzyloxycarbonyl group and tri($C_1$-$C_6$ alkyl) silyl group including t-butylmethylsilyl group.

1. General Method for Synthesizing Compound (1a) when $Z^1$ and $Z^2$ are Both H Reaction Step 1

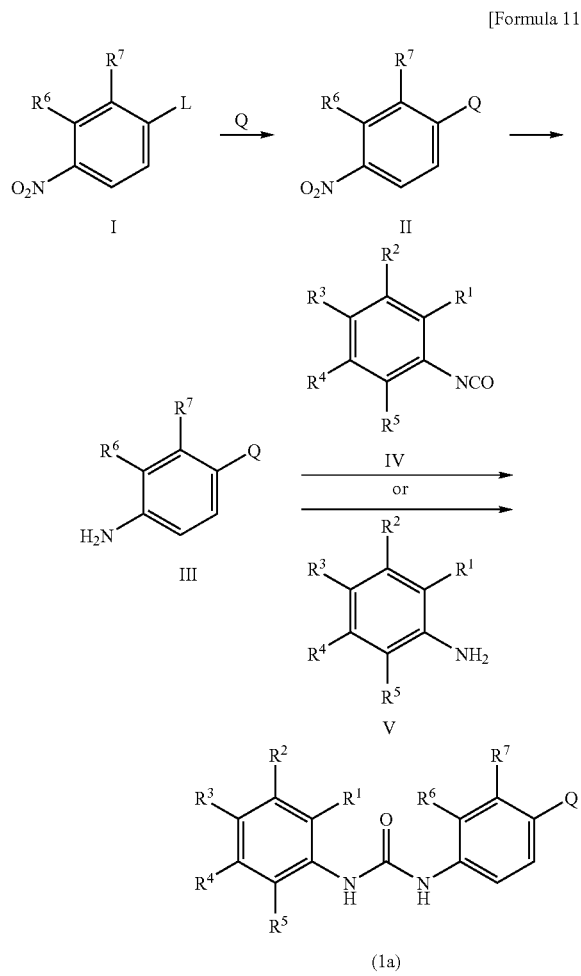

[Formula 11]

A 4-heteroaryl nitrobenzene derivative (II) can be prepared by the method as described in the known document [Ichikawa, J. et al., J. Org. Chem., Vol. 61(8), 2763-2769, 1996] or a similar method. According to this method, a nitrobenzene derivative (I) can is allowed to react with a heteroaryl derivative Q in the presence of a suitable base (for example, sodium hydride, potassium carbonate or potassium butoxide) in a suitable solvent [for example, DMF (dimethylformamide) or DMSO (dimethyl sulfoxide)] to obtain a 4-heteroarylnitrobenzene derivative (II). The obtained 4-heteroarylnitrobenzene (II) is isolated and purified and then is reduced to a 4-heteroarylaniline derivative (III) by a known method (for example, catalytic reduction). By allowing the obtained 4-heteroarylaniline derivative (III) to react with an aryl isocyanate derivative (IV) in a suitable solvent (for example, dichloromethane or THF), a compound represented by formula (1a) can be obtained. The aryl isocyanate derivative (IV) is easily available by utilizing a commercially available reagent or by using the method as described in the known document [Knolker, H. J. et al., Angew. Chem. Int., Ed, Engl., Vol. 34(22), 2497-2500, 1995] or a similar method. The compound (1a) can be prepared by using the method as described in the known documents [Nicolaou, K. C. et al., J. Am. Chem. Soc., Vol. 122(12), 2966-2967, 2000; Macor, J. E. et al., Tetrahedron Lett., Vol. 40(14), 2733-2736, 1999; and Kitterigham, J. et al., Synth. Commun., Vol. 30 (11), 1937-1943, 2000] or a similar method. That is, the compound represented by formula (1a) can be obtained by allowing the 4-heteroarylaniline derivative (III) to react with an aniline derivative (V) in a suitable solvent [for example, dichloromethane, THF (tetrahydrofuran) or the like] in the presence of a urea bonding-forming reagent (for example, carbonyldiimidazole, phosgene, diphosgene, triphosgene or p-nitrophenyl chloroformate) and a base [for example, pyridine, trimethylamine or a Hunig's base (N,N-diisopropylethylamine)]

2. General Method for Synthesizing Compound (1b) when $Z^1$ is H and $Z^2$ is OH Reaction Step 2

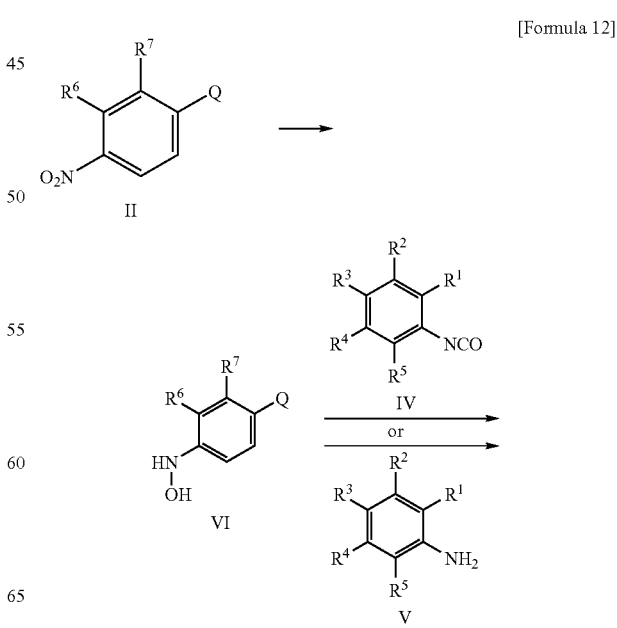

[Formula 12]

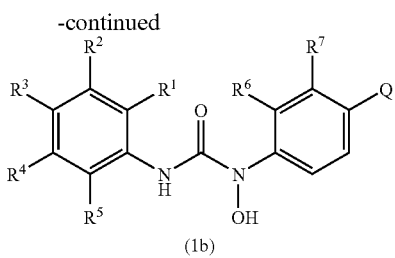

(1b)

In reaction step 2, the 4-heteroarylnitrobenzene derivative (II) obtained in Reaction Step 1 is isolated, purified and then is reduced to a 4-heteroarylphenyl-hydroxylamine derivative (VI) by using the known method as described in the known document (Panetta, C. A. et al., J. Org. Chem., Vol. 34, 2773, 1969) or a similar method. By allowing the obtained 4-heteroarylphenylhydroxylamine derivative (VI) to react with the aryl isocyanate derivative (IV) in the same manner as in Reaction Step 1, a compound represented by formula (1b) can be obtained. Further, the compound represented by formula (1b) can be also prepared from the 4-heteroarylphenylhydroxylamine derivative (VI) and the aniline derivative (V) by using the known method as described in the known documents [Nicolaou, K. C. et al., J. Am. Chem. Soc., Vol. 122 (12), 2966-2967, 2000; Macor, J. E. et al., Tetrahedron Lett., Vol. 40(14), 2733-2736, 1999; and Kitterigham, J. et al., Synth. Commun., Vol. 30(11), 1937-1943, 2000] or a similar method.

3. General Method for Synthesizing Compound (1c) when $Z^1$ is OH and $Z^2$ is H Reaction Step 3

[Formula 13]

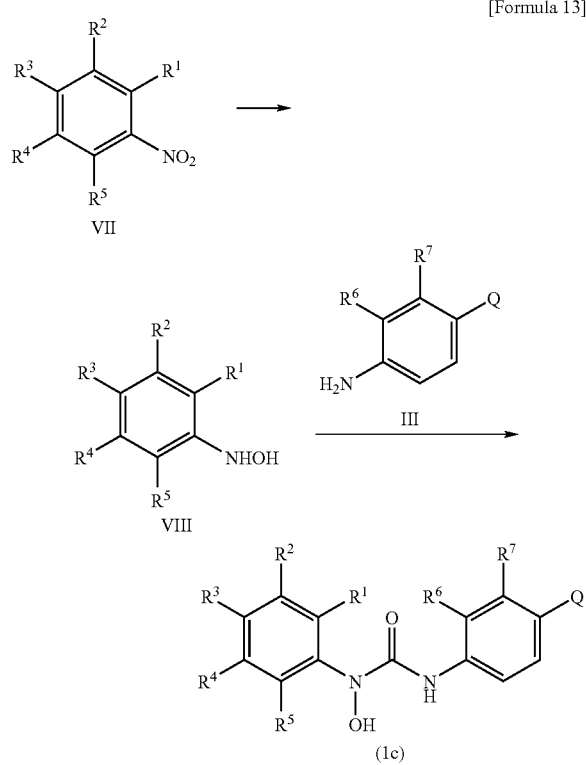

A nitrobenzene derivative (VII) can be easily obtained by utilizing a commercially available reagent or by using the known method (for example, aromatic nitration reaction). The nitrobenzene derivative (VII) is reduced to a phenylhydroxylamine derivative (VIII) in the same manner as in Reaction Step 2. By allowing the obtained phenylhydroxylamine derivative (VIII) to react with the 4-heteroarylaniline derivative (III) obtained in Reaction Process 1 in the same manner as in reaction Step 2, a compound represented by formula (1c) can be prepared.

4. Functional Group Conversion of Substituent W on Heteroaryl Group Q

The compounds (1a) to (1c) in the Reaction Steps 1 to 3 can be further derivatized by the functional group conversion of a functional group W on the heteroaryl group with the use of known techniques of organic chemistry. By converting the same functional group in the starting material Q and in the stage (II) of an intermediate in the Reaction Steps and then further performing the Reaction Steps 1 to 3, a derivative can also be obtained. On conversion of a functional group, if necessary, techniques of protection or deprotection with a suitable protective group (for example, acetyl, t-butoxy-carbonyl, benzyloxycarbonyl or t-butyldimethylsilyl) by the known method can be used.

As the representative example of functional group conversion used in the present invention, Reaction Processes 4-1 to 4-7 are given in a generalized form.

Reaction Step 4-1

[Formula 14]

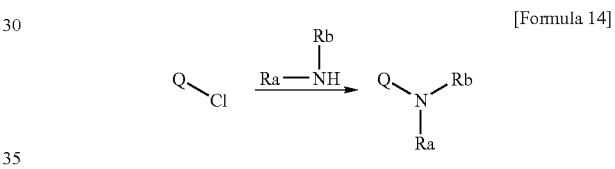

Reaction Step 4-1 is a reaction step of converting a chlorine on a heteroaryl group into an amino group. A target compound can be obtained by allowing a chloro-substituted heteroaryl compound to react with ammonia, a primary amine or a secondary amine in the absence of a solvent or in a suitable solvent (for example, methanol, ethanol or isopropanol).

Reaction Step 4-2

[Formula 15]

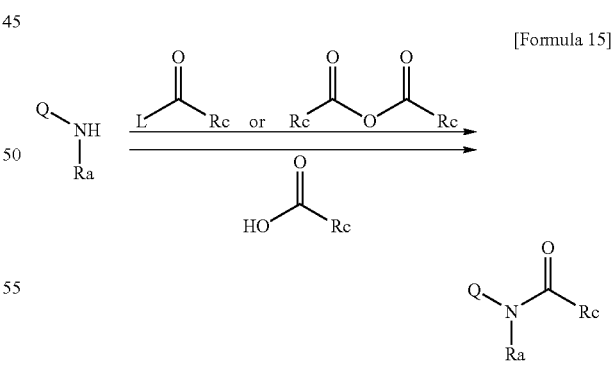

Reaction Step 4-2 is a step of acylating an amino group on the heteroaryl group to obtain an amide derivative. A target compound can be obtained by reacting the amino substituted heteroaryl compound to react with a carboxylic acid halide or a carboxylic anhydride in the presence of a suitable base, for example, Hunig's base [N,N-diisopropylethylamine], triethylamine, pyridine or DMAP (dimethylaminopyridine). The target compound can be also prepared by allowing the amino substituted heteroaryl compound to react with a carboxylic acid together with a dehydration condensation agent and an auxiliary. As the dehydration condensation agent, HATU (O-(7-azabenzotriazol-1-yl)-N,N,N,N-tetra-methyluronium hexafluorophosphate), EEDQ (2-ethoxy-1-ethyoxy-carbonyl-1,2-dihydroquinoline), PyBOP (benzotriazolyloxytripyrrolidino-phosphonium=hexafluorophosphate), PyBrOP [(bromotris(pyrrolidino)-phosphonium=hexafluorophosphate], DDC (dicyclohexyl-carbo-diimide), EDC (1-ethyl-3-(3,3'-dimethylaminopropyl-carbodiimide) and the like can be mentioned. As the auxiliary, HOSu (N-hydroxysuccinimide), HOAt (1-hydroxy-7-aza-benzo-triazole), HOBt (1-hydroxybenzotriazole) can be mentioned. As the base, triethylamine, Hunig's base (N,N-diisopropylethylamine) or the like can be added.

Reaction Step 4-3

[Formula 16]

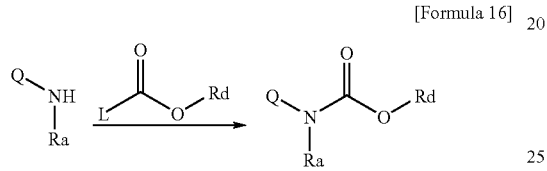

Reaction Step 4-3 is a step of obtaining a carbamate derivative by oxycarbonylating an amino group on the heteroaryl group. A target compound can be obtained by allowing the amino substituted heteroaryl compound to react with an alkyl chloroformate in the presence of a suitable base [for example, Hunig's base (N,N-diisopropylethylamine), triethylamine, pyridine or DMAP (dimethylaminopyridine) or the like].

Reaction Step 4-4

[Formula 17]

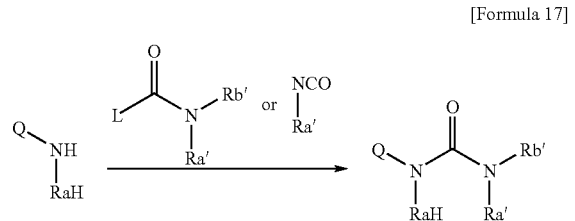

Reaction Step 4-4 is a step of obtaining a urea derivative by carbamoylating an amino group on the heteroaryl group. A target compound can be obtained by allowing the amino substituted heteroaryl compound to react with an carbamoyl chloride or an isocyanate in the presence of a suitable base [for example, Hunig's base (N,N-diisopropylethylamine), triethylamine, pyridine or DMAP (dimethylaminopyridine) or the like].

Reaction Step 4-5

[Formula 18]

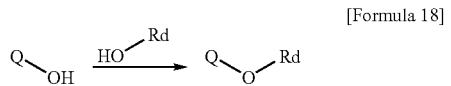

Reaction Step 4-5 is a step of obtaining an alkoxy derivative by alkylating a hydroxyl group on the heteroaryl group. A target compound can be obtained by performing the known Mitsunobu Reaction with the use of a heteroaryl compound substituted with a hydroxyl group and an alcohol corresponding to the hydroxyl group, that is, in any combination of a suitable phosphorus compound (for example, triphenylphosphine or tri-n-butylphosphine) with a suitable azo compound [for example, DEAD (diethyl azodicarboxylate) or TMAD (1,1'-azibis(N,N-dimethylformamide))].

Reaction Step 4-6

[Formula 19]

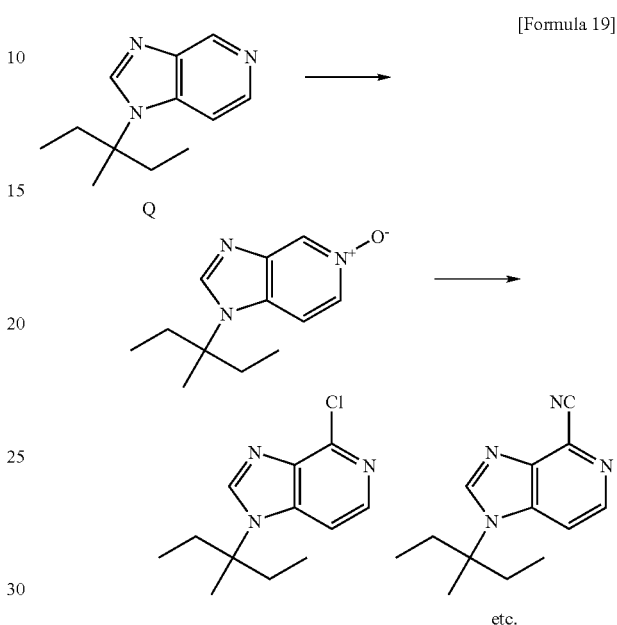

The reaction Step 4-6 is a step of introducing a chlorine atom, a cyano group or the like as a substituent W when the heteroaryl group Q is imidazo[4,5-c]pyridine. Imidazo[4,5-c]pyridine can be oxidized to imidazo[4,5-c]pyridine 5-oxide in a suitable acid solvent (for example, acetic acid) with the use of an suitable oxidizing agent (for example, hydrogen peroxide) in accordance with the method described in the known document (Mizuno, Y. et al., Chem. Pharm. Bull., Vol. 12(8), 866-873, 1964) or a similar method. A nucleophile such as a chlorine atom, a cyano group or the like can be introduced into the imidazo[4,5-c]pyridine 5-oxide by using Reissert method or analogous methods described in the document (Hamana et al., Yakugaku Zasshi, Vol. 120(2), 206-223, 2000) or a similar method.

Reaction Step 4-7

[Formula 20]

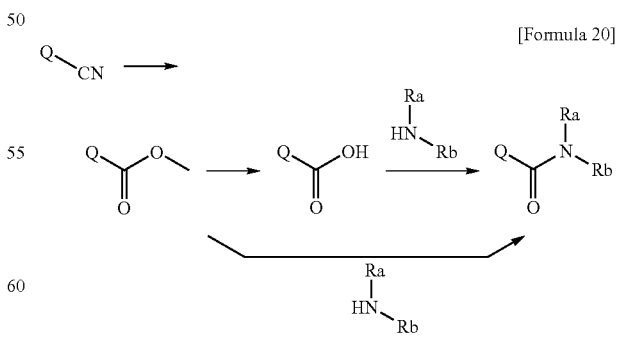

Reaction Step 4-7 is a step of converting a cyano group on the heteroaryl group into a carboxamide through a carboxylate. By treating the cyano substituted heteroaryl compound in a suitable solvent (for example, methanol) with a suitable base (for example, sodium methylate) or an acid (for example, methanol hydrochloric acid), the cyano group can be converted to carboxylic acid methyl ester. By leading the carboxylic acid methyl ester to a carboxylic acid by hydrolysis and then allowing the carboxylic acid to react with the corresponding amine together with the dehydration condensation agent and the auxiliary as described in Reaction Step 4-2, the carboxamide can be prepared. The carboxamide derivative can be obtained in one step by the exchange reaction of the carboxylic acid methyl ester derivative with the corresponding amine in a suitable solvent (for example, methanol).

Synthesis of Raw Materials

Part of the raw materials of the compounds of the present invention are novel compounds and these compounds can be easily synthesized in the same manner as in synthesizing known raw materials or using known methods for a person with ordinary skill in the art.

One example of the method for preparing the compounds of formula (1) relating to the present invention is shown above but the isolation/purification of the target compounds as shown in the above described Reaction Steps can be performed by applying normal chemical operations such as extraction, concentration, distillation, crystallization, filtration, recrystallization and various types of chromatographies.

The compounds and their pharmaceutically acceptable salts of the present invention include all stereoisomers [for example, enantiomers and diastereomers (including cis- and trans-geometrical isomers)] of the compounds represented by formula (1), racemic bodies of the above described isomers and other mixtures of the above described isomers.

Further, the compounds and their pharmaceutically acceptable salts of the present invention can exist in several tautomeric forms, for example, enol and imine forms, keto and enamine forms and their mixtures. The tautomers exist as a mixture of a tautomeric set in a solution, and one of the tautomers normally prevails in the form of a solid. The compounds of the present invention include all tautomers.

When the compounds relating to the present invention are obtained in free-forms, they can be converted to salts hydrates or solvates which the compounds are allowed to form according to the conventional methods.

Further, when the compounds relating to the present invention are obtained as the salts, hydrates or solvates of the compounds, they can be converted to the free forms of the compounds according to the conventional methods.

The compounds or their pharmaceutically acceptable salts relating to the present invention have excellent Ras inhibition and angiogenesis inhibition actions and excel in the internal stability and the solubility in water, and are useful as preventive or therapeutic agents (especially therapeutic agents) for the disease selected from cancer, psoriasis, atherosclerosis, chronic rheumatoid arthritis and diabetes. Furthermore, the compounds of the present invention are useful as preventive or therapeutic agents (especially therapeutic agents) for the metastasis/infiltration of a solid cancer.

These methods include a step of administering a pharmaceutically effective amount of a pharmaceutical composition containing the compound or its pharmaceutically acceptable salt disclosed in the present invention to a patient who requires such a treatment or has such a disease or in such a state.

When the pharmaceutical composition of the present invention is used as a therapeutic agent or a preventive for a disease selected from cancer, psoriasis, athero-sclerosis, chronic rheumatoid arthritis and diabetes, as the administration method, oral, rectal, parenteral (intravenous, intramuscular and subcutaneous), intracisternal, vaginal, intraabdominal, intravesical and topical (a drip, a powder, an ointment, a gel or a cream) administrations, inhalation (an oral cavity or nasal spray) and the like can be mentioned. As the administration form, for example, tablets, capsules, granules, powders, pills, aqueous or nonaqueous oral solutions or suspensions and parenteral solutions filled in containers suitable for subdivision into an each dose can be mentioned. Further, the administration form can be adjusted to various administration methods including a releasably adjusted formulation such as subcutaneous implantation.

The above described pharmaceutical preparations can be prepared by the known method with the use of additives such as an excipient, a lubricant (a coating material), a binder, a disintegrator, a stabilizer, a corrective and a diluent.

As the excipient, for example, starch such as starch, potato starch and corn starch, lactose, crystalline cellulose, calcium hydrogenphosphate and the like can be mentioned.

As the coating material, for example, ethyl cellulose, hydroxypropyl cellulose, hydroxypropylmethyl cellulose, shellac, talc, carnauba wax, paraffin and the like can be mentioned.

As the binder, for example, polyvinylpyrrolidone, macrogol and the same compounds as the excipients can be mentioned.

As the disintegrator, for example, the same compounds as the excipients and chemically modified starch/celluloses such as cross calmellose sodium, carboxymethyl starch sodium and crosslinked polyvinylpyrrolidone can be mentioned.

As the stabilizer, for example, p-hydroxybenzoic acid esters such as methylparaben and propylparaben; alcohols such chlorobutanol, benzyl alcohol and phenylethyl alcohol; benzalkonium chloride; phenols such as phenol and cresol; thimerosal; dehydroacetic acid; and sorbic acid.

As the corrective, for example, a sweet taste, an acid taste, a flavor and the like which are conventionally used can be mentioned.

Further, as a solvent for preparing a liquid and a solution, for example, ethanol, phenol, chlorocresol, purified water, distilled water and the like can be used.

As the surface active agent or an emulsifier, for example, polysorbate 80, polyoxyl 40 stearate, lauromacgol and the like can be mentioned.

When the pharmaceutical composition of the present invention is used as a therapeutic or preventive agent for a disease selected from cancer, psoriasis, athero-sclerosis, chronic rheumatoid arthritis and diabetes, the amount of use of the compound or its pharmaceutically acceptable salt of the present invention varies depending on the state of a disease, age, body weight, relative state of health, the presence or absence of other medications, the method of administration and the like. For example, for a patient (a warm-blooded animal, particularly a human), a typical daily effective dose as an active ingredient (the compound represented by formula (1) of the present invention) for an oral medicine is preferably 0.1 to 1,000 mg/kg of body weight, more preferably 1 to 400 mg/kg of body weight. The daily dose for the normal weight of an adult patient is preferably in the range of 10 to 800 mg. For an parenteral medicine, the daily dose is preferably 0.1 to 1,000 mg/kg of body weight, more preferably 10 to 800 mg/kg of body weight. It is preferred that these doses are administered at one time a day or in divisions at several times in according to the state of the disease.

EXAMPLES

The present invention will be explained in more detail by examples but the present invention is not limited to these examples.

Further, the NMR analysis was performed by using JEOL JNM-EX 270 (270 MHz) or JNM GSX 400 (400 MHz), and the NMR data were shown by ppm (parts per million: δ) and the deuterium lock signal for a sample solvent was referred to. The mass spectral data were obtained by using JEOL JMS-DX 300 or JMS-SX/SX 102 or with the use of Finnigan micromass Navigator equipped with Agilent Technologies Agilent 100 gradient HPLC. The specific rotation was measured with the use of sodium D-line at room temperature.

In the organic synthesis reactions, commercially available reagents were used without further purification. The term "room temperature" refers to a range of about 20 to 25° C. All water prohibitive reactions were performed under nitrogen atmosphere. Concentration under reduced pressure and removal of the solvents were carried out with the use of a rotary evaporator unless expressly stated.

In preparing the compounds, if necessary, a functional group was protected with a protective group and after preparation of the protected target compound, the protective group was removed. The selection of protective groups and the operation of deprotection were performed, for example, according to the method described in Greene and Wuts, "Protective Groups in Organic Synthesis" (Second Edition, John Wiley & Sons, 1991)".

Example 1

Synthesis of 1-(4-chloro-3-(trifluoromethyl)phenyl)-3-(4-imidazo[4,5-c]pyridin-1-ylphenyl)urea (Table 1, Compound No. 1)

Step A

Preparation of 3-(4-nitrophenyl)-3H-imidazo[4,5-c]-pyridine and 1-(4-nitrophenyl)1H-imidazo[4,5-c]pyridine

[Formula 21]

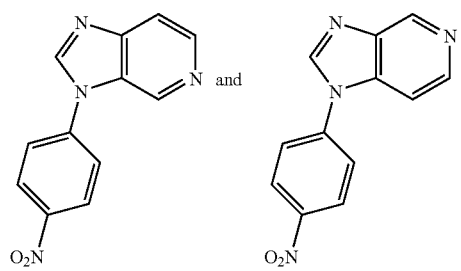

In 3 mL of dimethylformamide, 119 mg (1.00 mmol) of imidazo[4,5-c]pyridine was dissolved, and 138 mg (1.00 mmol) of potassium carbonate and 141 mg (1.00 mmol) of 4-fluoronitrobenzene were added thereto and the mixture solution was stirred at 80° C. for two hours. The solution was diluted with 10 mL of water, and the formed precipitate was collected by filtration, washed with water, and vacuum dried. The obtained crude product was separated by a silica gel column (Si-10, a product of Kusano Co., Ltd., column 30 cm, dichloromethane:methanol=15:1) to obtain 18.9 mg (8%) of 3-(4-nitrophenyl)-3H-imidazo[4,5-c]pyridine and 66.6 mg (28%) of 1-(4-nitrophenyl)-1H-imidazo[4,5-c]pyridine as yellow solids, respectively.

3-(4-Nitrophenyl)-3H-imidazo[4,5-c]pyridine $^1$H-NMR (270 MHz, CDCl$_3$) δ (ppm): 7.77 (2H, d, J=9.9 Hz), 7.82 (1H, dd, J=1.0, 5.6 Hz), 8.30 (1H, s), 8.51 (2H, d, J=9.9 Hz), 8.59 (1H, dd, J=1.0, 5.6 Hz), 9.03 (1H, s)

1-(4-Nitrophenyl)-1H-imidazo[4,5-c]pyridine $^1$H-NMR (270 MHz, CDCl$_3$) δ (ppm): 7.51 (1H, dd, J=1.0, 5.6 Hz), 7.72 (2H, d, J=9.9 Hz), 8.23 (1H, s), 8.50 (2H, d, J=9.9 Hz), 8.59 (1H, dd, J=1.0, 5.6 Hz), 9.24 (1H, s)

Step B

Preparation of 4-(imidazo[4,5-c]pyridin-1-yl)aniline

[Formula 22]

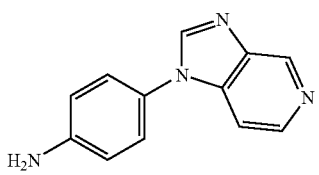

In 20 mL of methanol, 33 mg (0.1237 mmol) of 1-(4-nitrophenyl)-1H-imidazo[4,5-c]pyridine prepared in Step A was dissolved and the solution was stirred on 5 mg of 10% palladium carbon in a hydrogen atmosphere at room temperature at normal pressures for one hour. After removal of the palladium carbon by filtration, the solvent was distilled under reduced pressure, and the obtained product was vacuum dried to obtain 4-(imidazo[4,5-c]-pyridin-1-yl)aniline as a white solid. This product was used in process C without further purification.

Step C

Preparation of 1-(4-chloro-3-(trifluoromethyl)phenyl)-3-(4-imidazo[4,5-c]pyridin-1-ylphenyl)urea (Table 1, Compound No. 1)

[Formula 23]

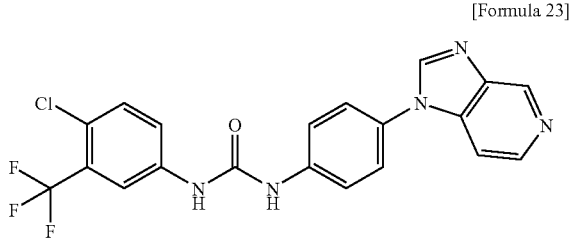 [SMILES: O=C(Nc1ccc(-n2cnc3cnccc32)cc1)Nc1ccc(Cl)c(C(F)(F)F)c1]

The 4-(imidazo[4,5-c]pyridin-1-yl)aniline prepared in Step B was dissolved in 10 mL of dichloromethane, and 30 mg (0.137 mmol) of 4-chloro-3-(trifluoromethyl)phenyl isocyanate was added thereto and the mixture solution was stirred at room temperature for three hours. The solvent was distilled under reduce pressure, and the obtained crude product was recrystallized from ethyl acetate to obtain 35.0 mg (51%) of 1-(4-chloro-3-(trifluoromethyl)-phenyl)-3-(4-imidazo[4,5-c]pyridin-1-ylphenyl)urea (Table 1, Compound No. 1) as a colorless crystal.

$^1$H-NMR (270 MHz, DMSO-$d_6$) δ (ppm): 7.62-7.76 (7H, m), 8.14 (1H, d, J=2.0 Hz), 8.43 (1H, d, J=5.6 Hz), 8.70 (1H, s), 9.09 (1H, s), 9.18 (1H, s), 9.28 (1H, s)

ESI (LC-MS positive mode) m/z 431.9 (M+H)

Example 2

1-(4-Chloro-3-(trifluoromethyl)phenyl)-3-(4-imidazo-[4,5-c]pyridin-3-ylphenyl)urea (Table 1, Compound No. 2)

Step A

Preparation of 4-(imidazo[4,5-c]pyridin-3-yl)aniline

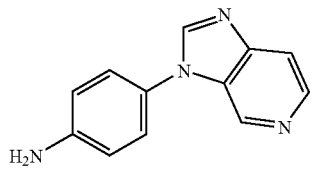

[Formula 24]

In 10 mL of methanol, 15.9 mg (0.066 mmol) of 4-nitrophenyl-3H-imidazo[4,5-c]pyridine prepared in Step A of Example 1 was dissolved and the solution was stirred on 5 mg of 10% palladium carbon in a hydrogen atmosphere at room temperature at normal pressures for one hour. After removal of the palladium carbon by filtration, the solvent was distilled under reduced pressure, and the residue was vacuum dried to obtain 4-(imidazo[4,5-c]pyridin-3-yl)aniline as a white solid. The product was used in Step B without further purification.

Step B

Preparation of 1-(4-chloro-3-(trifluoromethyl)phenyl)-3-(4-imidazo[4,5-c]pyridin-3-ylphenyl)urea (Table 1, Compound No. 2)

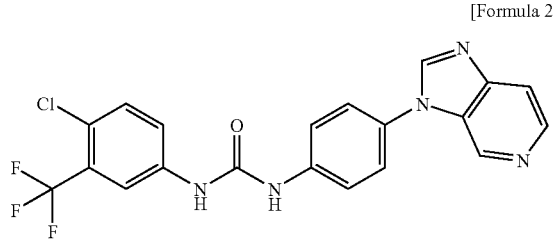

[Formula 25]

The 4-(imidazo[4,5-c]pyridin-3-yl)aniline prepared in Step A was dissolved in 10 mL of dichloromethane, and 14.2 mg (0.064 mmol) of 4-chloro-3-(trifluoromethyl)phenyl isocyanate was added thereto and the mixture solution was stirred at room temperature for three hours. The solvent was distilled under reduced pressure, and the obtained crude product was recrystallized from ethyl acetate to obtain 20.2 mg (73%) of 1-(4-chloro-3-(trifluoromethyl)-phenyl)-3-(4-imidazo[4,5-c]pyridin-3-ylphenyl)urea (Table 1, Compound No. 2) as a colorless crystal.

$^1$H-NMR (270 MHz, DMSO-$d_6$) δ (ppm): 7.63-7.80 (7H, m), 8.14 (1H, d, J=2.0 Hz), 8.43 (1H, d, J=5.6 Hz), 8.77 (1H, s), 8.98 (1H, s), 9.18 (1H, s), 9.28 (1H, s), 9.29 (1H, s)

ESI (LC-MS positive mode) m/z 431.9 (M+H)

Example 3

Preparation of 1-(4-chloro-3-(trifluoromethyl)phenyl)-3-(4-indol-1-ylphenyl)urea (Table 1, Compound No. 3)

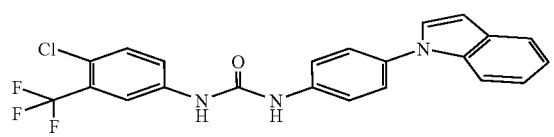

[Formula 26]

The titled compound can be synthesized from indole, 4-fluoronitrobenzene and 4-chloro-3-(trifluoromethyl)-phenyl isocyanate by using the same techniques as in Example 1.

$^1$H-NMR (270 MHz, DMSO-$d_6$) δ (ppm): 6.68 (1H, d, J=3.3 Hz), 7.03-7.20 (7H, m), 7.50 (2H, d, J=8.6 Hz), 7.60-7.70 (7H, m), 8.14 (1H, d, J=1.0 Hz), 9.06 (1H, s), 9.24 (1H, s)

ESI (LC-MS positive mode) m/z 431.9 (M+H)

Example 4

Preparation of 1-(4-chloro-3-(trifluoromethyl)phenyl)-3-(4-purin-7-ylphenyl)urea (Table 1, Compound No. 4)

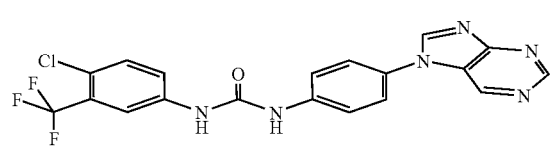

[Formula 27]

The title compound can be synthesized from purine, 4-fluoronitrobenzene and 4-chloro-3-(trifluoromethyl)phenyl isocyanate by using the same techniques as in Example 1.

$^1$H-NMR (270 MHz, DMSO-$d_6$) δ (ppm): 7.62-7.67 (3H, m), 7.73 (3H, s), 8.12 (1H, m), 9.08 (2H, d, J=5.3 Hz), 9.21 (1H, s), 9.36 (1H, s), 9.50 (1H, s)

ESI (LC-MS positive mode) m/z 433 (M+H)

Example 5

Preparation of 1-(4-chloro-3-(trifluoromethyl)phenyl)-3-(4-purin-9-ylphenyl)urea (Table 1, Compound No. 5)

[Formula 28]

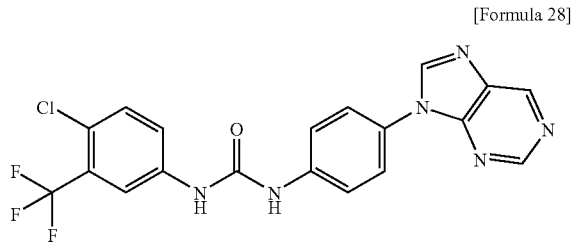

The title compound can be synthesized from purine, 4-fluoronitrobenzene and 4-chloro-3-(trifluoromethyl)phenyl isocyanate by using the same techniques as in Example 1.

$^1$H-NMR (270 MHz, DMSO-$d_6$) δ (ppm): 7.63 (2H, m), 7.85 (4H, dd, J=23.8, 11.8 Hz), 8.08 (1H, d, J=3.7 Hz), 8.39 (1H, s), 9.02 (1H, s), 9.17 (1H, s), 9.28 (1H, s), 9.30 (1H, s)

ESI (LC-MS positive mode) m/z 433 (M+H)

Example 6

1-(4-Chloro-3-(trifluoromethyl)phenyl)-3-(4-pyrrolo-[2,3-b]pyridin-1-ylphenyl)urea (Table 1, Compound No. 6)

[Formula 29]

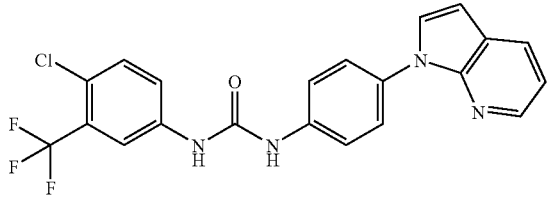

The title compound can be synthesized from pyrrolo[2,3-b]pyridine, 4-fluoronitrobenzene and 4-chloro-3-(trifluoromethyl)phenyl isocyanate by using the same techniques as in Example 1.

$^1$H-NMR (270 MHz, DMSO-$d_6$) δ (ppm): 6.70 (1H, d, J=3.6 Hz), 7.19 (1H, dd, J=7.9, 4.8 Hz), 7.58-7.66 (4H, m), 7.80 (2H, d, J=8.9 Hz), 7.89 (1H, d, J=3.7 Hz), 8.04-8.13 (2H, m), 8.30 (1H, s), 9.02 (1H, s), 9.22 (1H, s)

ESI (LC-MS positive mode) m/z 431 (M+H)

Example 7

1-(4-Chloro-3-(trifluoromethyl)phenyl)-3-(4-imidazo-[4,5-b]pyridin-1-ylphenyl)urea (Table 1, Compound No. 7)

[Formula 30]

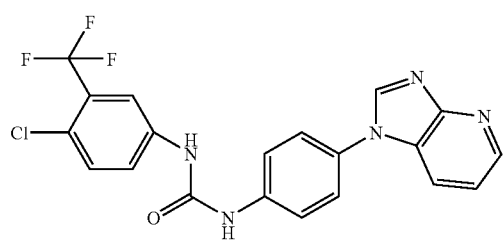

The title compound can be synthesized from imidazo[4,5-b]pyridine, 4-fluoronitrobenzene and 4-chloro-3-(trifluoromethyl)phenyl isocyanate by using the same techniques as in Example 1.

$^1$H-NMR (270 MHz, DMSO-$d_6$) δ (ppm): 7.39 (1H, dd, J=4.6, 7.9 Hz), 7.60-7.70 (4H, m), 7.85 (2H, d, J=8.9 Hz), 8.13 (1H, m), 8.20 (1H, m), 8.43 (2H, m), 8.85 (1H, s), 9.11 (1H, s), 9.25 (1H, s)

ESI (LC-MS positive mode) m/z 432 (M+H)

Example 8

1-(4-Chloro-3-(trifluoromethyl)phenyl)-3-(4-imidazo-[4,5-b]pyridin-3-ylphenyl)urea (Table 1, Compound No. 8)

[Formula 31]

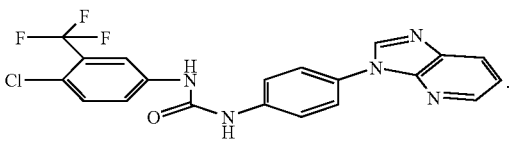

The title compound can be synthesized from imidazo[4,5-b]pyridine, 4-fluoronitrobenzene and 4-chloro-3-(trifluoromethyl)phenyl isocyanate by using the same techniques as in Example 1.

$^1$H-NMR (270 MHz, DMSO-$d_6$) δ (ppm): 7.37 (1H, dd, J=4.9, 8.2 Hz), 7.60-7.75 (6H, m), 8.05 (1H, dd, J=1.3, 7.9 Hz), 8.14 (1H, d, J=2.3 Hz), 8.51 (1H, dd, J=1.7, 5.0 Hz), 8.81 (1H, s), 9.17 (1H, s), 9.28 (1H, s)

ESI (LC-MS positive mode) m/z 432 (M+H)

Example 9

1-(4-Chloro-3-(trifluoromethyl)phenyl)-3-[4-(5-cyanoindol-1-yl)phenyl]urea (Table 1, Compound No. 9)

[Formula 32]

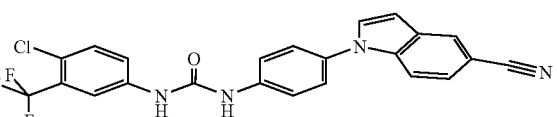

The title compound can be synthesized from 5-cyanoindole, 4-fluoronitrobenzene and 4-chloro-3-(trifluoromethyl) phenyl isocyanate by using the same techniques as in Example 1.

$^1$H-NMR (270 MHz, DMSO-$d_6$) δ (ppm): 6.85 (1H, d, J=3.3 Hz), 7.50-7.56 (3H, m), 7.60-7.72 (5H, m), 7.83 (1H, d, J=3.3 Hz), 8.13 (1H, d, J=2.3 Hz), 8.21 (1H, d, J=0.7 Hz), 9.12 (1H, s), 9.24 (1H, s)

ESI (LC-MS positive mode) m/z 455 (M+H)

Example 10

1-(4-Benzimdazol-1-ylphenyl)-3-(4-chloro-3-(trifluoromethyl)phenyl)urea (Table 1, Compound No. 10)

[Formula 33]

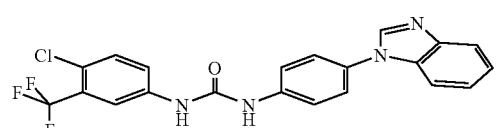

The title compound can be synthesized from benzimidazole, 4-fluoronitrobenzene and 4-chloro-3-(trifluoromethyl)phenyl isocyanate by using the same techniques as in Example 1.

$^1$H-NMR (270 MHz, DMSO-d$_6$) δ (ppm): 7.28-7.33 (2H, m), 7.55-7.80 (8H, m), 8.14 (1H, d, J=0.8 Hz), 8.51 (1H, s), 9.14 (1H, s), 9.28 (1H, s)

ESI (LC-MS positive mode) m/z 431 (M+H)

Example 11

1-{4-[3-(4-Chloro-3-(trifluoromethyl)phenyl)ureido]-phenyl}-1H-indole-5-carboxylic acid methylamide (Table 1, Compound No. 11)

Step A

Preparation of 1H-indole-5-carboxylic acid methylamide

[Formula 34]

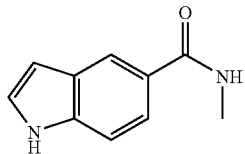

In 5 mL of N,N-dimethylformamide, 500 mg (3.1 mmol) of 1H-indole-5-carboxylic acid, 750 mg (9.3 mmol) of 40% methylamine, 477 mg (3.1 mmol) of benzotriazole-1-ol hydrate and 713 mg (3.8 mmol) of (3-dimethylaminopropyl)ethylcarbodiimide hydrochloride were dissolved and the solution was stirred at room temperature for three hours, and then the solvent was distilled under reduced pressure. The obtained residue was dissolved in ethyl acetate and washed with a saturated sodium hydrogencarbonate solution (50 mL, twice) and a saturated saline (50 mL) in the order named. The organic layer was dried and then concentrated to obtain 397 mg (73%) of a crude product of 1H-indole-5-carboxylic acid methylamide. The product was used in the next reaction without further purification.

$^1$H-NMR (270 MHz, DMSO-d$_6$) δ (ppm): 3.01 (3H, d, J=4.9 Hz), 6.20 (1H, br.s), 6.59 (1H, br.s), 7.20-7.22 (2H, m), 7.37 (1H, d, J=8.6 Hz), 7.60 (1H, d, J=8.6 Hz), 8.07 (1H, s), 8.64 (1H, br.s)

ESI (LC-MS positive mode) m/z 175 (M+H)

Step B

Preparation of 1-(4-nitrophenyl)-1H-indole-5-carboxylic acid methylamide

[Formula 35]

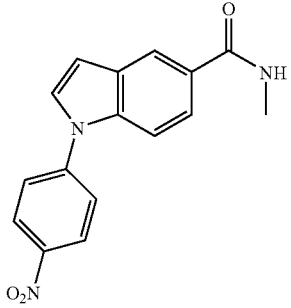

The title compound can be synthesized from 1H-indole-5-carboxylic acid methylamide and 4-fluoronitrobenzene in the same manner as in Step A of Example 1.

$^1$H-NMR (270 MHz, DMSO-d$_6$) δ (ppm): 2.84 (3H, d, J=4.8 Hz), 6.93 (1H, d, J=3.3 Hz), 7.80 (2H, s), 7.90-8.00 (3H, m), 8.24 (1H, s), 8.42-8.50 (3H, m)

Step C

Preparation of 1-(4-aminophenyl)-1H-indole-5-carboxylic acid methylamide

[Formula 36]

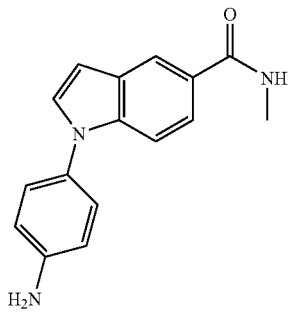

The title compound can be synthesized from 1-(4-nitrophenyl)-1H-indole-5-carboxylic acid methylamide in the same manner as in Step B of Example 1.

$^1$H-NMR (270 MHz, CD$_3$OD) δ (ppm): 2.95 (3H, d, J=4.8 Hz), 6.78 (1H, d, J=3.3 Hz), 6.86 (2H, d, J=9.6 Hz), 7.21 (2H, d, J=9.6 Hz), 7.38-7.41 (2H, m), 7.62 (1H, dd, J=1.6, 8.5 Hz), 8.13 (1H, d, J=1.3 Hz), 8.34 (1H, br.s), ESI (LC-MS positive mode) m/z 266 (M+H)

Step D

Preparation of 1-{4-[3-(4-chloro-3-(trifluoromethyl)phenyl)ureido]phenyl}-1H-indole-5-carboxylic acid methylamide (Table 1, Compound No. 11)

[Formula 37]

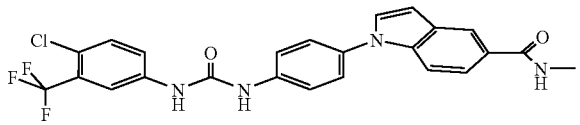

The title compound can be synthesized from 1-(4-aminophenyl)-1H-indole-5-carboxylic acid methylamide and 4-chloro-3-(trifluoromethyl)phenyl isocyanate in the same manner as in Step C in Example 1.

$^1$H-NMR (270 MHz, DMSO-d$_6$) δ (ppm): 2.81 (3H, d, J=4.3 Hz), 6.79 (1H, d, J=3.3 Hz), 7.50-7.55 (3H, m), 7.63-7.75 (6H, m), 8.14 (1H, d, J=2.0 Hz), 8.20 (1H, d, J=0.7 Hz), 8.38 (1H, q, J=4.3 Hz), 9.09 (1H, s), 9.24 (1H, s)

ESI (LC-MS positive mode) m/z 487 (M+H)

Example 12

1-{4-[3-(4-Chloro-3-(trifluoromethyl)phenyl)ureido]-phenyl}-1H-indole-4-carboxylic acid methylamide (Table 1, Compound No. 12)

[Formula 38]

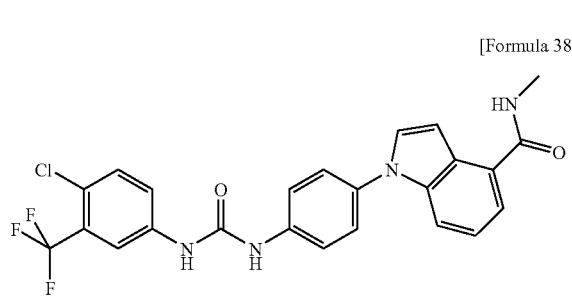

The title compound can be synthesized from 1H-indole-4-carboxylic acid, 4-fluoronitrobenzene and 4-chloro-3-(trifluoromethyl)phenyl isocyanate by using the same techniques as in Example 11.

$^1$H-NMR (270 MHz, DMSO-$d_6$) δ (ppm): 2.84 (3H, d, J=4.3 Hz), 7.09 (1H, d, J=3.3 Hz), 7.23 (1H, dd, J=8.3, 7.6 Hz), 7.47-7.53 (3H, m), 7.60-7.75 (6H, m), 8.14 (1H, d, J=2.0 Hz), 8.29 (1H, t, J=4.3 Hz), 9.08 (1H, s), 9.24 (1H, s)

ESI (LC-MS positive mode) m/z 487.2 (M+H)

Example 13

1-(4-[3-(4-Chloro-3-(trifluoromethyl)phenyl)ureido]-phenyl)-1H-indole-6-carboxylic acid methylamide (Table 1, Compound No. 13)

[Formula 39]

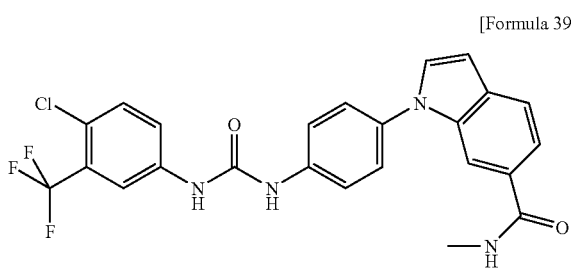

The title compound can be synthesized from 1H-indole-6-carboxylic acid, 4-fluoronitrobenzene and 4-chloro-3-(trifluoromethyl)phenyl isocyanate by using the same techniques as in Example 11.

$^1$H-NMR (270 MHz, DMSO-$d_6$) δ (ppm): 2.88 (3H, d, J=4.3 Hz), 6.73 (1H, d, J=3.0 Hz), 7.55 (2H, d, J=8.9 Hz), 7.60-7.76 (7H, m), 8.00 (1H, s), 8.14 (1H, d, J=2.3 Hz), 8.40 (1H, t, J=4.3 Hz), 9.10 (1H, s), 9.26 (1H, s)

ESI (LC-MS positive mode) m/z 487.0 (M+H)

Example 14

1-{4-[3-(4-Chloro-3-(trifluoromethyl)phenyl)ureido]-phenyl}-1H-indole-5-carboxylic acid thiazol-2-ylamide (Table 1, Compound No. 14)

[Formula 40]

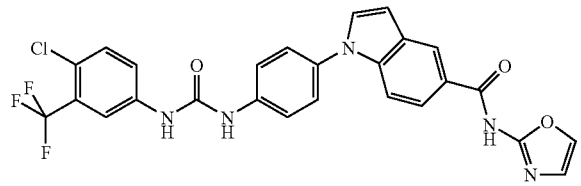

The title compound can be synthesized from 1H-indole-4-carboxylic acid, 4-fluoronitrobenzene, 2-aminothiazole and 4-chloro-3-(trifluoromethyl)phenyl isocyanate by using the same techniques as in Example 11.

$^1$H-NMR (270 MHz, DMSO-$d_6$) δ (ppm): 6.52 (1H, s), 7.12 (1H, d, J=4.3 Hz), 7.39-7.40 (2H, m), 7.60-7.75 (7H, m), 7.85 (1H, d, J=8.6 Hz), 8.16 (1H, s), 8.31 (1H, s), 9.23 (1H, s), 9.39 (1H, s), 11.30 (1H, s)

ESI (LC-MS positive mode) m/z 556 (M+H)

Example 15

1-{4-[3-(4-Chloro-3-(trifluoromethyl)phenyl)ureido]-phenyl}-1H-benzimidazole-5-carboxylic acid methylamide (Table 1, Compound No. 15)

[Formula 41]

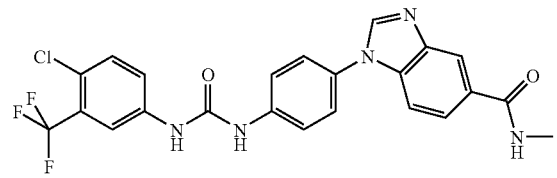

The title compound can be synthesized from 1H-benzimidazole-5-carboxylic acid, 4-fluoronitrobenzene and 4-chloro-3-(trifluoromethyl)phenyl isocyanate by using the same techniques as in Example 11.

$^1$H-NMR (270 MHz, DMSO-$d_6$) δ (ppm): 2.82 (3H, d, J=2.7 Hz), 7.76-7.90 (8H, m), 8.17 (1H, br.d, J=1.0 Hz), 8.30 (1H, s), 8.50 (1H, br.s), 8.61 (1H, s), 9.45 (1H, br.s), 9.60 (1H, br.s)

ESI (LC-MS positive mode) m/z 488 (M+H)

Example 16

(1-{4-[3-(4-Chloro-3-(trifluoromethyl)phenyl)ureido]-2-fluorophenyl}-1H-indol-5-yl)carbamic acid tert-butyl ester (Table 1, Compound No. 16)

Step A

Preparation of (1H-indole-5-yl)carbamic acid tert-Butyl ester

[Formula 42]

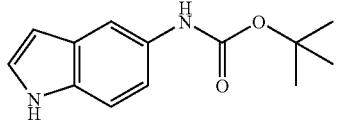

In 100 mL of methanol, 2.64 g (20 mmol) of 5-aminoindole was dissolved, and 4.15 mL (30 mmol) of triethylamine and 5.23 g (24 mmol) of Boc2O were added thereto and the mixture solution was stirred at room temperature for six hours. The reaction solution was concentrated under reduced pressure, and the residue was partitioned with ethyl acetate (200 mL) and water (100 mL), and the organic layer was washed with a saturated sodium chloride solution. The organic layer was dried and then concentrated under reduced pressure, and the residue was partitioned between ethyl acetate (200 mL) and water (100 mL) and the organic layer was washed with a saturated sodium chloride solution. The organic layer was dried and then concentrated under reduced pressure, and the residue was purified by a silica gel column (Wako Gel C200: 300 g, n-hexane:ethyl acetate=4:1) to obtain 4.38 g (94%) of (1H-indol-5-yl)carbamic acid tert-butyl ester as a white solid.

$^1$H-NMR (270 MHz, CDCl$_3$) δ (ppm): 1.43 (9H, s), 6.38 (1H, br.s), 6.29-6.33 (1H, m), 7.04 (1H, dd, J=2.3, 8.9 Hz), 7.19 (1H, s), 7.23 (1H, d, J=8.9 Hz), 7.61 (1H, br.s)

Step B

Preparation of [1-(2-fluoro-4-nitrophenyl)-1H-indol-5-yl]carbamic acid tert-butyl ester

[Formula 43]

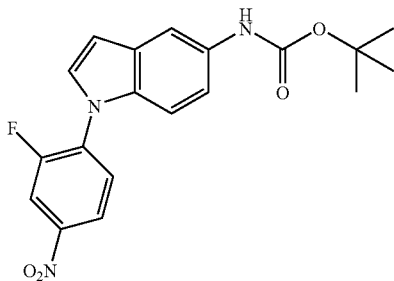

The title compound can be synthesized from (1H-indol-5-yl)carbamic acid tert-butyl ester and 3,4-difluoronitrobenzene in the same manner as in Step A of Example 1.

$^1$H-NMR (270 MHz, DMSO-d$_6$) δ (ppm): 1.49 (9H, s), 6.74 (1H, d, J=3.3 Hz), 7.29 (2H, s), 7.62 (1H, t, J=3.3 Hz), 7.82 (1H, br.s), 7.96 (1H, dd, J=8.6, 8.7 Hz), 8.23-8.29 (1H, m), 9.23 (1H, s), 9.26 (1H, br.s)

Step C

Preparation of [1-(4-amino-2-fluorophenyl)-1H-indol-5-yl]carbamic acid tert-butyl ester

[Formula 44]

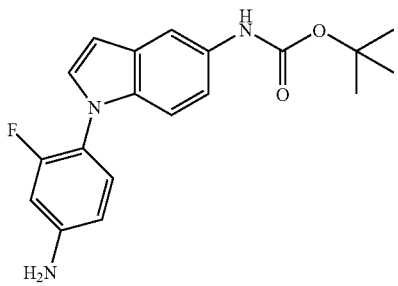

The title compound can be synthesized from [1-(2-fluoro-4-nitrophenyl)-1H-indol-5-yl]carbamic acid tert-butyl ester in the same manner as in step B of Example 1.

$^1$H-NMR (270 MHz, CDCl$_3$) δ (ppm): 1.49 (9H, s), 6.40-6.58 (4H, m), 7.04-7.20 (4H, m), 7.69 (1H, br.s)

Step D

Preparation of 1-{4-[3-(4-Chloro-3-(trifluoromethylphenyl)ureido)-2-fluorophenyl]-1H-indol-5-yl}carbamic acid tert-butyl ester (Table 1, Compound No. 16)

[Formula 45]

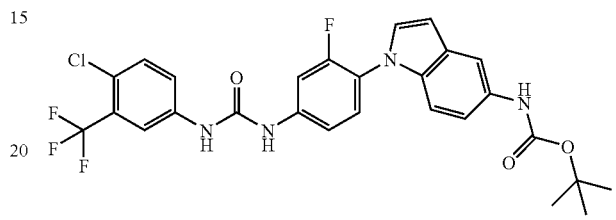

The title compound can be synthesized from [1-(4-amino-2-fluorophenyl)-1H-indol-5-yl]carbamic acid tert-butyl ester and 4-chloro-3-(trifluoromethyl)phenyl isocyanate in the same manner as in Step C of Example 1.

$^1$H-NMR (270 MHz, DMSO-d$_6$) δ (ppm): 1.58 (9H, s), 6.60 (1H, d, J=3.3 Hz), 7.60 (1H, d, J=8.9 Hz), 7.21 (1H, d, J=0.8 Hz), 7.34 (1H, dd, J=0.8, 9.2 Hz), 7.42-7.54 (2H, m), 7.62-7.78 (4H, m), 8.12 (1H, d, J=1.3 Hz), 9.18 (1H, s), 9.28 (1H, s), 9.33 (1H, s)

ESI (LC-MS positive mode) m/z 563.0 (M+H)

Example 17

1-[4-(5-Aminoindol-1-yl)-3-fluorophenyl]-3-(4-chloro-3-(trifluoromethyl)phenyl)urea hydrochloride (Table 1, Compound No. 17)

[Formula 46]

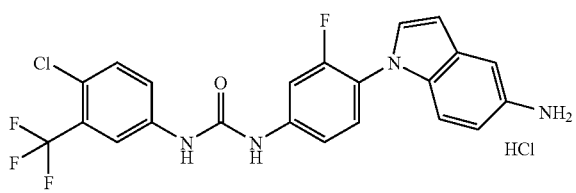

In 2 mL of ethyl acetate, 104 mg (0.18 mmol) of (1-{4-[3-(4-chloro-3-(trifluoromethyl)phenyl)ureido]-2-fluorophenyl}-1H-indol-5-yl)carbamic acid tert-butyl ester was dissolved, and 2 mL of a 4N hydrogen chloride ethyl acetate solution was added thereto and the mixture solution was stirred at room temperature for one hour. The reaction solution was concentrated and the obtained product was triturated with ethyl acetate to obtain 80 mg (86%) of 1-[4-(5-aminoindol-1-yl)-3-fluorophenyl]-3-(4-chloro-3-(trifluoromethyl)phenyl)urea hydrochloride (Table 1, Compound No. 17).

$^1$H-NMR (270 MHz, DMSO-d$_6$) δ (ppm): 6.80 (1H, d, J=2.6 Hz), 7.17 (1H, d, J=8.9 Hz), 7.29 (1H, d, J=8.9 Hz), 7.34 (1H, d, J=9.2 Hz), 7.55 (1H, t, J=8.9 Hz), 7.67 (4H, m), 7.78 (1H, d, J=13.2 Hz), 8.14 (1H, s), 9.74 (1H, br.s), 9.78 (1H, br.s), 10.00 (2H, br.s)

ESI (LC-MS positive mode) m/z 463.2 (M+H)

Example 18

Acetic acid 1-{4-[3-(4-chloro-3-(trifluoromethyl)phenyl)ureido]phenyl}-1H-indol-4-yl ester (Table 1, Compound No. 18)

Step A

Preparation of 1-(4-nitrophenyl)-1H-indole-4-ol

[Formula 47]

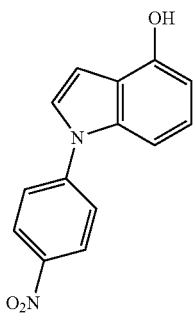

The title compound can be synthesized from 1H-indole-4-ol and 4-fluoronitrobenze in the same manner as in Step A of Example 1.

$^1$H-NMR (270 MHz, DMSO-d$_6$) δ (ppm): 6.11-6.14 (1H, m), 6.82 (1H, dd, J=0.7, 7.6 Hz), 6.59 (1H, br.s), 7.06-7.10 (2H, m), 7.16 (1H, t, J=7.9 Hz), 7.34-7.38 (2H, m), 8.20-8.28 (2H, m), 11.45 (1H, br.s)

Step B

Preparation of Acetic acid 1-(4-nitrophenyl)-1H-indol-4-yl ester

[Formula 48]

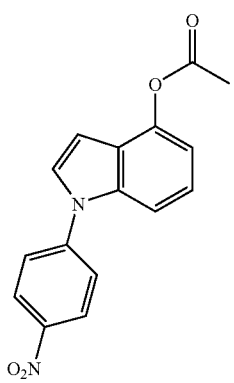

In 8 mL of methylene chloride, 387 mg (1.52 mmol) of 1-(4-nitrophenyl)-1H-indole-4-ol was dissolved, and 0.186 mL (2.00 mmol) of acetic anhydride and 0.318 mL (2.28 mmol) of triethylamine were added thereto and the mixture solution was stirred at room temperature for 14 hours. The reaction solution was partitioned between methylene chloride (50 mL) and a saturated ammonium chloride aqueous solution (20 mL) and washed with a saturated sodium chloride solution, and the organic layer was dried and then concentrated under reduced pressure to obtain acetic acid 1-(4-nitrophenyl)-1H-indol-4-yl ester. The product was used in the next reaction without further purification.

$^1$H-NMR (270 MHz, CDCl$_3$) δ (ppm): 2.66 (3H, s), 6.47-6.49 (1H, m), 6.97-7.07 (3H, m), 7.16-7.41 (3H, m), 8.12-8.22 (2H, m), 8.37 (1H, d, J=8.6 Hz)

Step C

Preparation of acetic acid 1-(4-aminophenyl)-1H-indol-4-yl ester

[Formula 49]

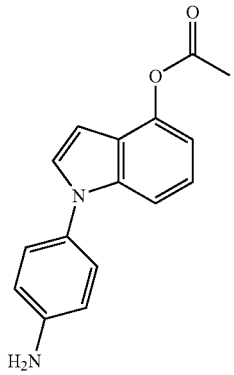

The title compound can be synthesized from acetic acid 1-(4-nitrophenyl)-1H-indol-4-yl ester in the same manner as in Step B of Example 1.

$^1$H-NMR (270 MHz, CDCl$_3$) δ (ppm): 2.65 (3H, s), 3.59 (2H, s), 6.65-6.71 (5H, m), 7.05-7.16 (1H, m), 7.20 (1H, d, J=3.2 Hz), 7.35 (1H, d, J=2.7 Hz), 8.12 (1H, d, J=5.5 Hz)

Step D

Preparation of acetic acid 1-(4-[3-(4-chloro-3-(trifluoromethyl)phenyl)ureido]phenyl)-1H-indol-4-yl ester

[Formula 50]

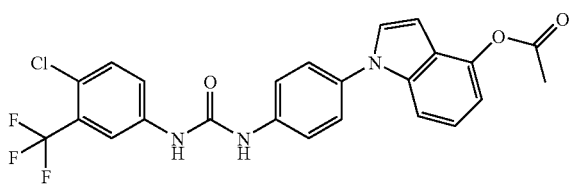

The title compound can be synthesized from acetic acid 1-(4-aminophenyl)-1H-indol-4-yl ester and 4-chloro-3-(trifluoromethyl)phenyl isocyanate in the same manner as in Step C of Example 1.

$^1$H-NMR (270 MHz, DMSO-d$_6$) δ (ppm): 2.66 (3H, s), 6.60 (1H, d, J=3.5 Hz), 6.75 (1H, d, J=8.1 Hz), 6.99 (2H, d, J=8.9 Hz), 7.28 (1H, t, J=8.3 Hz), 7.45 (2H, d, J=8.9 Hz), 7.60 (2H, m), 7.82 (1H, d, J=4.1 Hz), 8.11 (2H, m), 8.82 (1H, s), 9.12 (1H, s)

ESI (LC-MS positive mode) m/z 488 (M+H)

Example 19

1-(4-Chloro-3-(trifluoromethyl)phenyl)-3-[4-(4-hydroxyindol-1-yl)phenyl]urea (Table 1, Compound No. 19)

[Formula 51]

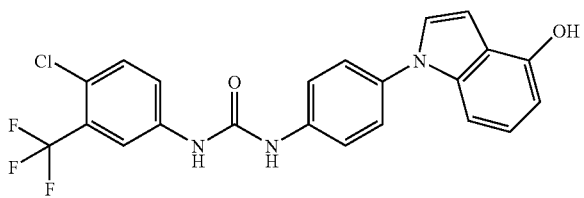

In 3 mL of tetrahydrofuran, 60 mg (0.12 mmol) of acetic acid 1-(4-[3-(4-chloro-3-(trifluoromethyl)phenyl)-ureido]phenyl)-1H-indol-4-yl ester was dissolved, and 1 mL of a 1N sodium hydroxide aqueous solution was added thereto and the mixture solution was stirred at room temperature for two hours. The reaction solution was neutralized with 1N hydrochloric acid, and extracted with ethyl acetate. The organic layer was washed with a saturated sodium chloride solution, dried and then concentrated under reduced pressure, and the obtained residue was recrystallized from ethyl acetate to obtain 17 mg (31%) of 1-(4-chloro-3-(trifluoromethyl)phenyl)-3-[4-(4-hydroxyindol-1-yl)phenyl]urea (Table 1, Compound No. 19) as a white solid.

$^1$H-NMR (270 MHz, DMSO-d$_6$) δ (ppm): 6.21 (1H, br), 6.48 (1H, d, J=8.1 Hz), 6.63 (1H, s), 6.89 (4H, s), 6.95-7.02 (2H, m), 7.05 (1H, d, J=8.0 Hz), 7.19 (1H, d, J=8.9 Hz), 7.25 (1H, t, J=3.0 Hz), 7.43 (2H, d, J=8.6 Hz), 8.11 (1H, s), 9.12 (1H, s), 11.24 (1H, s)

ESI (LC-MS positive mode) m/z 446 (M+H)

trated, and then partitioned between ethyl acetate and a saturated ammonium chloride aqueous solution. The organic layer was washed with a saturated sodium chloride solution, dried and concentrated, and the obtained residue was purified by a silica gel column (50 g, n-hexane:ethyl acetate=2:1) to obtain 433 mg (99%) of [2-(1H-indol-4-yloxy)ethyl]-methyl-carbamic acid tert-butyl ester as a viscous oily substance.

$^1$H-NMR (270 MHz, CDCl$_3$) δ (ppm): 1.48 (9H, s), 3.06 (3H, s), 3.70 (2H, br.s), 4.52 (2H, br.s), 6.50 (1H, d, J=7.3 Hz), 6.63 (1H, t, J=2.1 Hz), 7.02-7.15 (3H, m), 8.19 (1H, br.s)

ESI (LC-MS positive mode) m/z 291 (M+H)

Step B

[2-(1-{4-[3-(4-Chloro-3-(trifluoromethyl)phenyl)ureido]phenyl}-1H-indol-4-yloxy)ethyl]-methylcarbamic acid tert-butyl ester (Table 1, Compound No. 20)

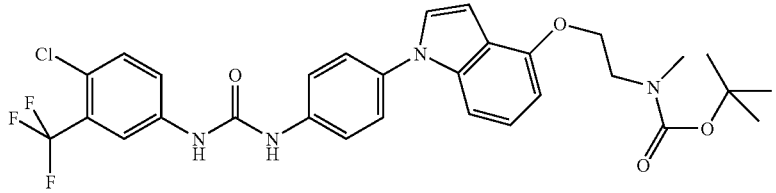

[Formula 53]

Example 20

[2-(1-{4-[3-(4-Chloro-3-(trifluoromethyl)phenyl)ureido]phenyl}-1H-indol-4-yloxy)ethyl]-methylcarbamic acid tert-butyl ester (Table 1, Compound No. 20)

Step A

Preparation of [2-(1H-indol-4-yloxy)ethyl]-methylcarbamic acid tert-butyl ester

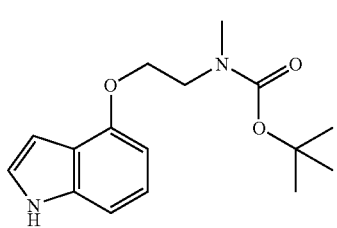

[Formula 52]

In 50 mL of tetrahydrofuran, 200 mg (1.51 mmol) of 1H-indole-4-ol and 527 mg (3.00 mmol) of 2-hydroxyethyl-methylcarbamic acid tert-butyl ester were dissolved, and 1.51 mL (3.00 mmol) of a diethyl azodicarboxylate 40% toluene solution and 788 mg (3.00 mmol) of triphenylphosphine were added thereto and the mixture solution was stirred at room temperature for 14 hours. The reaction solution was concen- The title compound can be synthesized from [2-(1H-indol-4-yloxy)ethyl]-methylcarbamic acid tert-butyl ester, 4-fluoronitrobenzene and 4-chloro-3-(trifluoromethyl)-phenyl isocyanate by using the same techniques as in Example 1.

$^1$H-NMR (270 MHz, DMSO-d$_6$) δ (ppm): 1.38 (9H, d, J=11.3 Hz), 2.94 (2H, d, J=6.8 Hz), 3.63 (2H, t, J=5.4 Hz), 4.22 (2H, br), 6.63 (1H, d, J=3.0 Hz), 6.65 (1H, br), 7.10 (2H, d, J=4.5 Hz), 7.48 (3H, m), 7.63-7.70 (4H, m), 8.13 (1H, d, J=2.7 Hz), 9.12 (1H, br), 9.30 (1H, br)

ESI (LC-MS positive mode) m/z 603 (M+H)

Example 21

1-(4-Chloro-3-(trifluoromethyl)phenyl)-3-{4-[4-(2-methylamino-ethoxy)-indol-1-yl]phenyl}urea hydrochloride (Table 1, Compound No. 21)

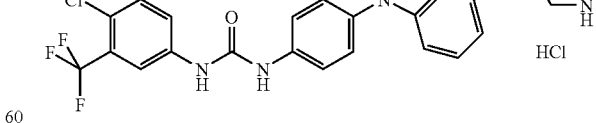

[Formula 54]

In 5 ml of a 4N hydrogen chloride ethyl acetate solution, 200 mg (0.33 mmol) of [2-(1-{4-[3-(4-chloro-3-(trifluoromethyl)phenyl)ureido]phenyl}-1H-indol-4-yloxy)ethyl]-methylcarbamic acid tert-butyl ester was dissolved and the solution was stirred at room temperature for 14 hours. The reaction solution was concentrated under reduced pressure, and then the obtained residue was triturated with ethyl acetate to obtain 110 mg (66%) of 1-(4-chloro-3-(tri-fluoromethyl)phenyl)-3-{4-[4-(2-methylamino-ethoxy)-indol-1-yl]phenyl}urea hydrochloride.

$^1$H-NMR (270 MHz, DMSO-d$_6$) δ (ppm): 2.71 (3H, t, J=5.4 Hz), 3.42 (2H, br.s), 4.39 (2H, t, J=4.8 Hz), 6.68 (1H, dd, J=6.8, 1.6 Hz), 6.85 (1H, d, J=3.5 Hz), 7.08-7.17 (2H, m), 7.48 (2H, d, J=8.7 Hz), 7.53 (1H, d, J=2.9 Hz), 7.65-7.70 (4H, m), 8.14 (1H, d, J=2.1 Hz), 9.48 (1H, s), 9.74 (1H, s)

ESI (LC-MS positive mode) m/z 503 (M+H)

Example 22

1-(4-Chloro-3-(trifluoromethyl)phenyl)-3-{4-[4-(2-morpholin-4-yl-ethoxy)indol-1-yl]phenyl}urea (Table 1, Compound No. 22)

[Formula 55]

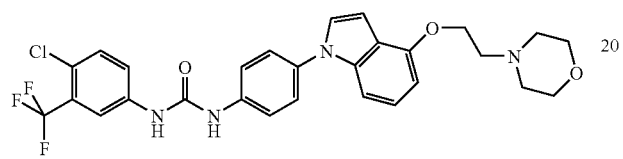

The title compound can be synthesized from 1H-indole-4-ol, 2-morpholin-4-ylethanol, 4-fluoronitrobenzene and 4-chloro-3-(trifluoromethyl)phenyl isocyanate in the same manner as in Example 20.

$^1$H-NMR (270 MHz, CDCl$_3$) δ (ppm): 2.68 (4H, t, J=4.6 Hz), 2.94 (2H, t, J=5.4 Hz), 3.76 (4H, t, J=4.6 Hz), 4.32 (2H, t, J=5.4 Hz), 6.58 (1H, t, J=4.1 Hz), 6.70 (1H, s), 6.77 (1H, d, J=3.2 Hz), 6.81 (1H, s), 7.12 (2H, d, J=4.9 Hz), 7.19 (1H, d, J=3.2 Hz), 7.43-7.51 (5H, m), 7.63 (1H, d, J=7.3 Hz), 7.73 (1H, d, J=2.4 Hz)

ESI (LC-MS positive mode) m/z 559 (M+H)

Example 23

1-(4-Chloro-3-(trifluoromethyl)phenyl)-3-{4-[4-(2-piperazin-1-yl-ethoxy)-indol-1-yl]phenyl}urea (Table 1, Compound No. 23)

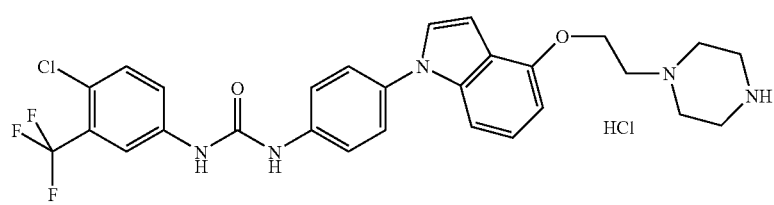

The title compound can be synthesized from 1H-indole-4-ol, 4-(2-hydroxyethyl)piperazine-1-carboxylic acid tert-butyl ester, 4-fluoronitrobenzene and 4-chloro-3-(trifluoromethyl)phenyl isocyanate in the same manner as in Example 20 and Example 21.

$^1$H-NMR (270 MHz, DMSO-d$_6$) δ (ppm): 3.10-3.80 (10H, br.s), 4.53 (2H, br.s), 6.68 (1H, dd, J=6.8, 1.6 Hz), 6.80 (1H, d, J=3.5 Hz), 7.08-7.18 (2H, m), 7.48 (2H, d, J=8.7 Hz), 7.53 (1H, d, J=2.9 Hz), 7.65-7.70 (4H, m), 8.14 (1H, d, J=2.1 Hz), 9.42 (1H, s), 9.66 (1H, s)

ESI (LC-MS positive mode) m/z 558 (M+H)

Example 24

1-{4-[3-(4-Chloro-3-(trifluoromethyl)phenyl)ureido]-phenyl}-N-hydroxy-1H-indole-5-carboxamidine (Table 1, Compound No. 24)

[Formula 57]

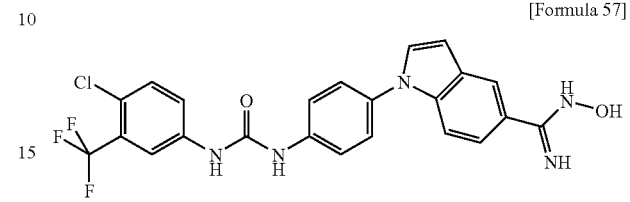

In 10 mL of ethanol, 91 mg (0.20 mmol) of 1-(4-chloro-3-(trifluoromethyl)phenyl)-3-[4-(5-cycanoindol-1-yl)phenyl]urea was dissolved, and 109 μL (0.79 mmol) of triethylamine and 55 mg (0.79 mmol) of hydroxylamine hydrochloride were added thereto, and the mixture solution was heated and refluxed for 5 hours. The reaction solution was concentrated under reduced pressure, and the obtained residue was partitioned between ethyl acetate and water, and the organic layer was washed with a saturated sodium chloride solution. The organic layer was dried and then concentrated under reduced pressure, and the obtained residue was recrystallized from methanol to obtain 51.6 mg (53%) of 1-{4-[3-(4-chloro-3-(trifluoromethyl)phenyl)ureido]phenyl}-N-hydroxy-1H-indole-5-carboxamidine (Table 1, Compound No. 24).

$^1$H-NMR (270 MHz, DMSO-d$_6$) δ (ppm): 5.78 (2H, br.s), 6.72 (1H, d, J=3.3 Hz), 7.45-7.68 (10H, m), 7.96 (1H, s), 8.14 (1H, d, J=2.0 Hz), 9.08 (1H, s), 9.23 (1H, s), 9.47 (1H, s)

ESI (LC-MS positive mode) m/z 488.5 (M+H)

[Formula 56]

Example 25

1-{4-[3-(3-(Trifluoromethyl)phenyl)ureido]phenyl}-1H-indole-5-carboxamidine (Table 1, Compound No. 25)

[Formula 58]

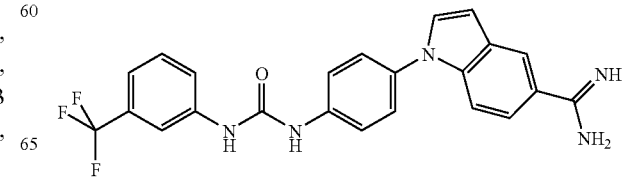

In 10 mL of methanol, 12 mg (0.025 mmol) of 1-{4-[3-(4-chloro-3-(trifluoromethyl)phenyl)ureido]phenyl}-N-hydroxy-1H-indole-5-carboxamidine was dissolved and the solution was subjected to hydrogenation catalytic reduction on 10% palladium carbon in a hydrogen atmosphere at room temperature for 14 hours. After removal of the palladium carbon by a membrane filter, the filtrate was concentrated under reduced pressure, and the obtained product was triturated from diethyl ether to obtain 3 mg (25%) of 1-{4-[3-(3-(trifluoromethyl)phenyl)-ureido]phenyl}-1H-indole-5-carboxamidine (Table 1, Compound No. 25).

$^1$H-NMR (270 MHz, DMSO-$d_6$) δ (ppm): 6.90-6.98 (1H, m), 7.25-7.35 (2H, m), 7.45-7.85 (8H, m), 8.03 (1H, d, J=4.9 Hz), 8.24 (1H, s), 8.49 (1H, s), 8.62 (0.5H, s), 8.79 (0.5H, s), 8.93 (0.5H, s), 9.09 (0.5H, s), 9.24 (0.5H, s), 9.34 (0.5H, s), 9.38 (0.5H, s), 9.47 (0.5H, s)

ESI (LC-MS positive mode) m/z 438 (M+H)

Example 26

1-(4-Chloro-3-(trifluoromethyl)phenyl)-3-{4-[5-(5-methyl-[1,2,4]oxadiazol-3-yl)indol-1-yl]phenyl}urea (Table 1, Compound No. 26)

[Formula 59]

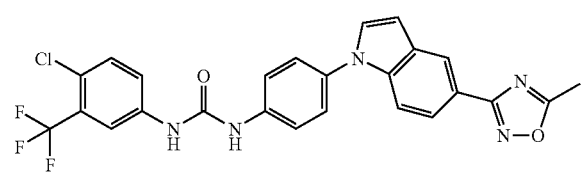

In 0.2 mL of pyridine, 10.5 mg (0.022 mmol) of 1-{4-[3-(4-chloro-3-(trifluoromethyl)phenyl)ureido]phenyl}-N-hydroxy-1H-indole-5-carboxamidine was dissolved, and 10 mg (0.098 mmol) of acetic anhydride was added thereto, and the mixture solution was stirred at 80° C. for 14 hours. The reaction solution was concentrated under reduced pressure, and then the obtained residue was purified by Megabond Elute Silica Gel (a product of Varian, 1 g, methylene chloride: methanol=20:1) to obtain 4.1 mg (37%) of 1-(4-chloro-3-(trifluoromethyl)phenyl)-3-{4-[5-(5-methyl-[1,2,4]oxadiazol-3-yl)indol-1-yl]phenyl}urea (Table 1, Compound No. 26).

$^1$H-NMR (270 MHz, CD$_3$OD) δ (ppm): 2.68 (3H, s), 6.78 (1H, d, J=3.3 Hz), 7.45-7.53 (3H, m), 7.55-7.68 (5H, m), 7.87 (1H, dd, J=1.7, 8.6 Hz), 7.96 (1H, d, J=2.3 Hz), 8.37 (1H, d, J=1.3 Hz), ESI (LC-MS positive mode) m/z 512.0 (M+H)

Example 27

1-{4-[5-(5-tert-Butyl-[1,2,4]oxadiazol-3-yl)indol-1-yl]phenyl}-3-(4-chloro-3-(trifluoromethyl)phenyl)urea (Table 1, Compound No. 27)

[Formula 60]

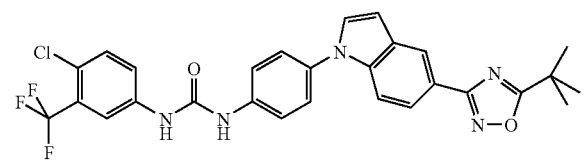

The title compound can be synthesized from 1-{4-[3-(4-chloro-3-(trifluoromethyl)phenyl)ureido]phenyl}-N-hydroxy-1H-indole-5-carboxamidine and pivalic anhydride by using the same techniques as in Example 26.

$^1$H-NMR (270 MHz, CDCl$_3$) δ (ppm): 1.44 (9H, s), 6.63 (1H, d, J=3.3 Hz), 7.13 (1H, d, J=3.0 Hz), 7.20-7.40 (7H, m), 7.50 (1H, dd, J=2.3, 8.5 Hz), 7.58 (1H, d, J=2.3 Hz), 7.62 (1H, br.s), 7.78 (1H, dd, J=1.7, 8.6 Hz), 8.36 (1H, d, J=1.3 Hz)

ESI (LC-MS positive mode) m/z 554 (M+H)

Example 28

1-(4-Chloro-3-trifluoromethyl)phenyl)-3-{4-[5-(5-oxo-4,5-dihydro-[1,2,4]oxadiazol-3-yl)indol-1-yl]-phenyl}urea (Table 1, Compound No. 28)

[Formula 61]

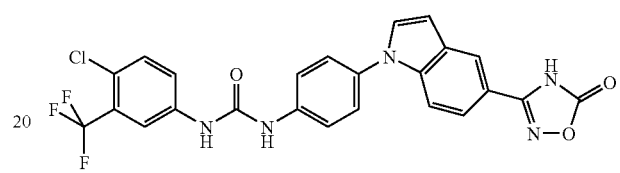

The title compound can be synthesized from 1-{4-[3-(4-chloro-3-(trifluoromethyl)phenyl)ureido]phenyl}-N-hydroxy-1H-indole-5-carboxamidine and ethyl chloroformate by using the same techniques as in Example 26.

$^1$H-NMR (270 MHz, DMSO-$d_6$) δ (ppm): 6.84 (1H, d, J=3.2 Hz), 7.55 (1H, d, J=8.4 Hz), 7.65-7.71 (6H, m), 7.77 (1H, d, J=3.2 Hz), 8.14-8.16 (2H, m), 9.13 (1H, s), 9.26 (1H, s)

ESI (LC-MS positive mode) m/z 514.0 (M+H)

Example 29

1-(4-Chloro-3-(trifluoromethyl)phenyl)-3-{4-[6-(di-tert-butoxycarbonylamino)purin-9-yl]phenyl}urea (Table 1, Compound No. 29)

Step A

Preparation of 6-di-tert-butoxycarbonylamino-9-(4-nitrophenyl)-9H-purine

[Formula 62]

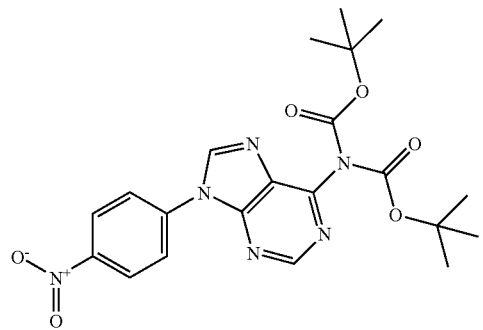

In 100 mL of dimethyl sulfoxide, 4.05 g (30.0 mmol) of adenine was dissolved, and 3.5 g (31.0 mmol) of potassium tert-butoxide and 5.0 g (35.0 mmol) of 4-fluoronitrobenzene were added thereto and the mixture solution was stirred at 80° C. for three hours. The solution was diluted with 200 mL of water, and the formed precipitate was collected by filtration, washed with water, and vacuum dried. The obtained product (6.66 g) dissolved in 20 mL of dimethyl sulfoxide, and 17.1 g (78.0 mmol) and 0.35 g (2.86 mmol) of 4-dimethylaminopyridine were added thereto, and the mixture solution was stirred at room temperature for six hours. The reaction solution was partitioned between ethyl acetate and a saturated sodium chloride solution, and the organic layer was further washed with a saturated sodium chloride solution, dried and concentrated under reduced pressure. The residue was separated by a silica gel column (Wako Gel C-200: 300 g, n-hexane:ethyl acetate=2:1) to obtain 7.86 g (57%) of 6-di-tert-butoxycarbonylamino-9-(4-nitrophenyl)-9H-purine as a white solid.

$^1$H-NMR (270 MHz, CDCl$_3$) δ (ppm): 1.50 (9H, s), 1.56 (9H, s), 8.09 (2H, d, J=8.4 Hz), 8.45-8.52 (3H, m), 8.98 (1H, s)

ESI (LC-MS positive mode) m/z 457 (M+H)

Step B

Preparation of 9-(4-aminophenyl)6-di-tert-butoxycarbonylamino-9H-purine

[Formula 63]

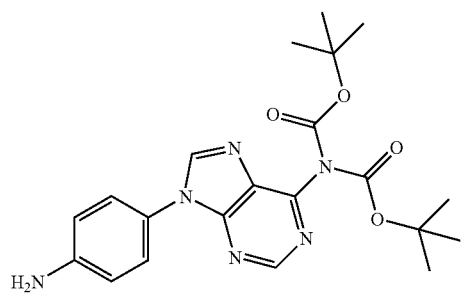

The title compound can be synthesized from 6-di-tert-butoxycarbonylamino-9-(4-nitrophenyl)-9H-prine by using the same techniques as in Step B of Example 1.

ESI (LC-MS positive mode) m/z 427 (M+H)

Step C

Preparation of 1-(4-chloro-3-(trifluoromethyl)phenyl)-3-{4-[6-(di-tert-butoxycarbonylamino)purin-9-yl]phenyl}urea (Table 1, Compound No. 29)

[Formula 64]

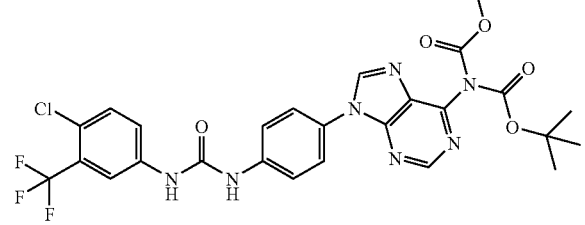

The title compound can be synthesized from 9-(4-aminophenyl)-6-di-tert-butoxycarbonylamino-9H-purine and 4-chloro-3-(trifluoromethyl)phenyl isocyanate by using the same techniques as in Step C of Example 1.

$^1$H-NMR (270 MHz, DMSO-d$_6$) δ (ppm): 1.41 (18H, s), 7.65-7.86 (6H, m), 8.14 (1H, d, J=2.0 Hz), 8.91 (1H, s), 9.02 (1H, s), 9.18 (1H, s), 9.28 (1H, s)

ESI (LC-MS positive mode) m/z 648 (M+H)

Example 30

1-[4-(6-Aminopurin-9-yl)phenyl]-3-(4-chloro-3-(trifluoromethyl)phenyl)urea hydrochloride (Table 1, Compound No. 30)

[Formula 65]

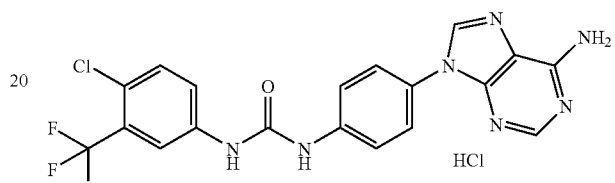

In a 3 mL of a 4N hydrogen chloride ethyl acetate solution, 32 mg (0.049 mmol) of 1-(4-chloro-3-(trifluoromethyl)-3-{4-[6-(di-tert-butoxycarbonyl amino)purin-9-yl] phenyl}urea was dissolved, and the solution was stirred at room temperature for three hours. After concentrating the reaction solution, the residue was triturated with diethyl ether to obtain 22 mg (quantitative) of 1-[4-(6-aminopurin-9-yl) phenyl]-3-(4-chloro-3-(trifluoromethyl)phenyl)urea hydrochloride (Table 1, Compound No. 30) as a white solid.

$^1$H-NMR (270 MHz, DMSO-d$_6$) δ (ppm): 7.65 (2H, s), 7.71 (4H, s), 8.14 (1H, s), 8.51 (1H, s), 8.82 (1H, s), 9.57 (1H, s), 9.76 (1H, s)

ESI (LC-MS positive mode) m/z 448 (M+H)

Example 31

1-[4-(6-Aminopurin-9-yl)phenyl]-3-(3,5-bis-(trifluoromethyl)phenyl)urea hydrochloride (Table 1, Compound No. 31)

[Formula 66]

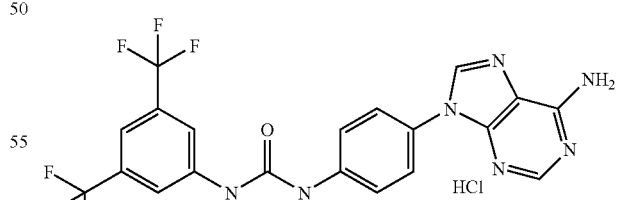

The title compound can be synthesized from 3,5-bis-(trifluoromethyl)phenyl isocyanate by the same methods as in Examples 29 and 30.

$^1$H-NMR (270 MHz, DMSO-d$_6$) δ (ppm): 7.65 (2H, s), 7.70-7.77 (3H, m), 8.14 (2H, s), 8.54 (1H, s), 8.88 (1H, s), 9.57 (1H, s), 9.88 (1H, s)

ESI (LC-MS positive mode) m/z 482 (M+H)

Example 32

1-[4-(6-Aminopurin-9-yl)phenyl]-3-(2-chloro-5-(trifluoromethyl)phenyl)urea hydrochloride (Table 1, Compound No. 32)

[Formula 67]

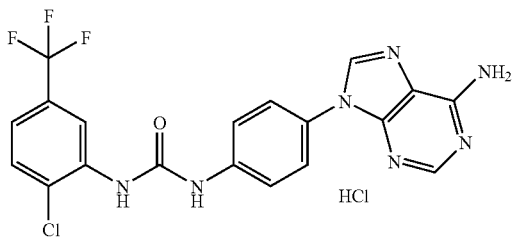

The title compound can be synthesized from 2-chloro-5-(trifluoromethyl)phenyl isocyanate by the same methods as in Examples 29 and 30.

$^1$H-NMR (270 MHz, DMSO-$d_6$) δ (ppm): 7.29 (1H, dd, J=2.0, 8.3 Hz), 7.70-7.77 (5H, m), 8.48 (1H, s), 8.64 (1H, d, J=2.0 Hz), 8.80 (1H, s), 8.86 (1H, s), 10.19 (1H, s)

ESI (LC-MS positive mode) m/z 448 (M+H)

Example 33

1-[4-(6-Aminopurin-9-yl)-2-fluorophenyl]-3-(4-chloro-3-(trifluoromethyl)phenyl)urea hydrochloride (Table 1, Compound No. 33)

[Formula 68]

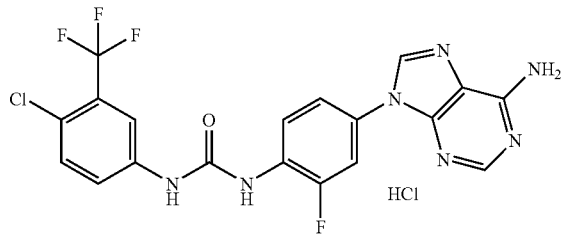

The title compound can be synthesized from adenine, 2,4-difluoronitrobenzene and 4-chloro-3-(trifluoromethyl)phenyl isocyanate by the same method as in Examples 29 and 30.

$^1$H-NMR (270 MHz, DMSO-$d_6$) δ (ppm): 7.43-7.60 (4H, m), 7.96 (1H, d, J=2.0 Hz), 8.14 (1H, dd, J=5.6, 8.0 Hz), 8.43 (2H, s), 8.62 (1H, s), 9.95 (1H, s)

ESI (LC-MS positive mode) m/z 466 (M+H)

Example 34

1-[4-(2-Aminopurin-9-yl)phenyl]-3-(4-chloro-3-(trifluoromethyl)phenyl)urea hydrochloride (Table 1, Compound No. 34)

[Formula 69]

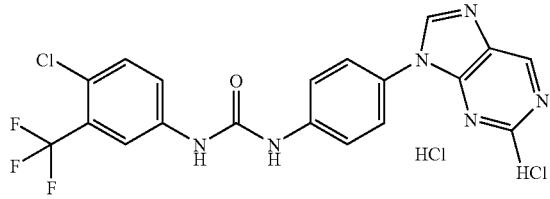

The title compound can be synthesized from 2-aminopurine, 4-fluoronitrobenzene and 4-chloro-3-(trifluoromethyl)phenyl isocyanate by the same methods as in Examples 29 and 30.

$^1$H-NMR (270 MHz, DMSO-$d_6$) δ (ppm): 7.65-7.73 (6H, m), 8.12 (1H, d, J=2.0 Hz), 8.73 (1H, s), 8.96 (1H, s), 9.46 (1H, s), 9.65 (1H, s)

ESI (LC-MS positive mode) m/z 448 (M+H)

Example 35

1-(4-Chloro-3-(trifluoromethyl)phenyl)-3-{4-[6-(2-methoxy-ethylamino)purin-9-yl]phenyl}urea hydrochloride (Table 1, Compound No. 35)

Step A

Preparation of 6-chloro-9-(4-nitrophenyl)-9H-purine

[Formula 70]

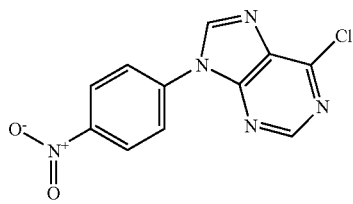

The title compound can be synthesized from 2-chloropurine and 4-fluoronitrobenzene by the same method as in Step A of Example 1.

$^1$H-NMR (270 MHz, DMSO-$d_6$) δ (ppm): 8.27-8.33 (2H, m), 8.51-8.56 (2H, m), 8.95 (1H, s), 9.32 (1H, s)

ESI (LC-MS positive mode) m/z 276 (M+H)

Step B

Preparation of (2-methoxyethyl)-[9-(4-nitrophenyl)-9H-purin-6-yl]carbamic acid tert-butyl ester

[Formula 71]

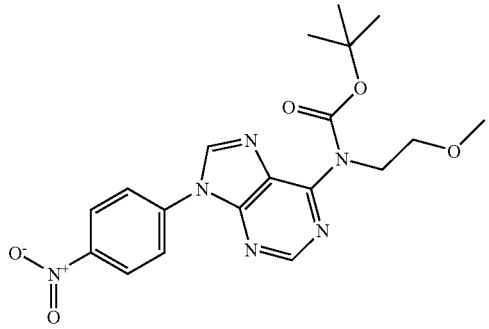

In 1 mL of isopropanol, 100 mg (0.36 mmol) of 6-chloro-9-(4-nitrophenyl)-9H-purine was dissolved, and 400 mg (5.3 mmol) of 2-methoxyethylamine was added thereto, and the mixture solution was stirred at 80° C. for four hours. The reaction solution was concentrated under reduced pressure and then partitioned between ethyl acetate and a saturated sodium chloride solution. The organic layer was further washed with a saturated sodium chloride solution, dried and then concentrated under reduced pressure. The obtained residue was dissolved in 1 mL of dimethylformamide, and 114 mg (0.525 mmol) of dibutyl dicarbonate and the 4 mg (0.035 mmol) of 4-dimethylaminopyridine were added thereto, and the mixture solution was stirred at room temperature. The reaction solution was concentrated under reduced pressure, and the residue was purified by Megabond Elute Silica Gel (5 g, n-hexane:ethyl acetate=1:1) to obtain 118 mg (72%) of (2-methoxyethyl)-[9-(4-nitrophenyl)-9H-purin-6-yl]-carbamic acid tert-butyl ester.

$^1$H-NMR (270 MHz, DMSO-$d_6$) δ (ppm): 2.50 (9H, s), 3.25 (3H, s), 3.65 (2H, t, J=5.7 Hz), 3.70 (2H, br.s), 7.96 (1H, s), 8.27-8.33 (2H, m), 8.49-8.52 (2H, m), 8.85 (1H, s)

ESI (LC-MS positive mode) m/z 315 (M+H)

Step C

Preparation of 1-(4-chloro-3-(trifluoromethyl)phenyl)-3-{4-[6-(2-methoxy-ethylamino)purin-9-yl]-phenyl}urea hydrochloride (Table 1, Compound No. 35)

[Formula 72]

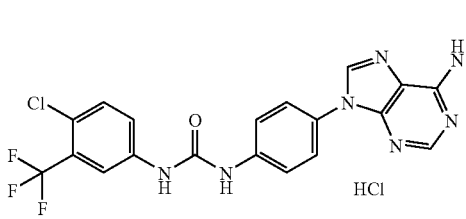

The title compound can be synthesized from (2-methoxyethyl)-[9-(4-nitrophenyl)-9H-purin-6-yl]carbamic acid tert-butyl ester and 4-chloro-3-(trifluoromethyl)phenyl isocyanate by the methods of Steps B and C of Example 1 and Example 30.

$^1$H-NMR (270 MHz, DMSO-$d_6$) δ (ppm): 3.29 (3H, s), 3.59 (2H, br.s), 3.73 (2H, br.s), 7.60-7.80 (7H, m), 8.13 (1H, s), 8.40 (1H, br.s), 8.72 (1H, br.s), 9.50 (1H, br.s), 9.70 (1H, br.s)

ESI (LC-MS positive mode) m/z 506 (M+H)

Example 36

1-(4-Chloro-3-(trifluoromethyl)phenyl)-3-[4-(6-(methylamino)purin-9-yl)phenyl]urea hydrochloride (Table 1, Compound No. 36)

[Formula 73]

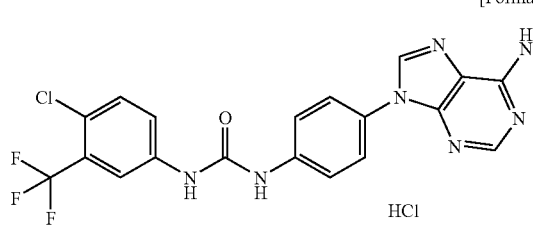

The title compound can be synthesized from 6-chloropurine, methylamine, 4-fluoronitrobenzene and 4-chloro-3-(trifluoromethyl)phenyl isocyanate by the same method as in Example 35.

$^1$H-NMR (270 MHz, DMSO-$d_6$) δ (ppm): 3.54 (3H, s), 7.60-7.80 (7H, m), 8.13 (1H, s), 8.46 (1H, s), 8.73 (1H, s), 9.52 (1H, s), 9.72 (1H, s)

ESI (LC-MS positive mode) m/z 462 (M+H)

Example 37

3-{4-[3-(4-Chloro-3-(trifluoromethyl)phenyl)ureido]-phenyl}-3H-benzimidazol-5-yl)carbamic acid tert-butyl ester (Table 1, Compound No. 37)

[Formula 74]

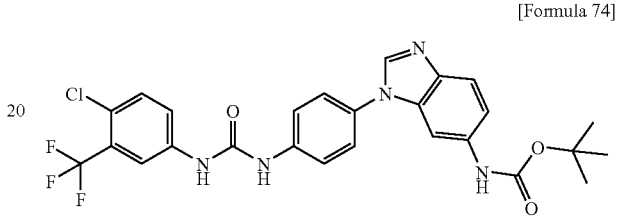

The title compound can be synthesized from 6-amino-1H-benzimidazole, di-tert-butyl dicarbonate, 4-fluoronitrobenzene and 4-chloro-3-(trifluoromethyl)phenyl isocyanate by the same method as in Example 16.

$^1$H-NMR (270 MHz, CDCl$_3$) δ (ppm): 1.50 (9H, s), 6.87 (1H, s), 6.98 (1H, dd, J=1.9, 8.6 Hz), 7.34-7.50 (7H, m), 7.65 (1H, s), 7.70 (1H, d, J=8.9 Hz), 7.85 (1H, s), 7.97 (1H, s)

ESI (LC-MS positive mode) m/z 546 (M+H)

Example 38

(1-{4-[3-(4-Chloro-3-(trifluoromethyl)phenyl)ureido-phenyl]-1H-benzimidazol-5-yl}carbamic acid tert-butyl ester (Table 1, Compound No. 38)

[Formula 75]

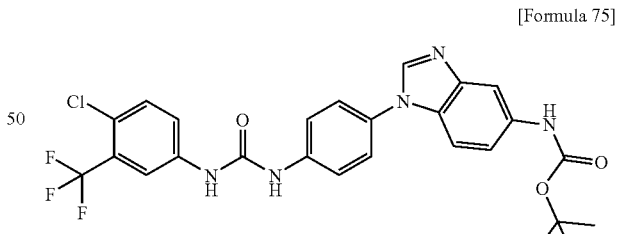

The title compound can be synthesized from 6-amino-1H-benzimidazole, di-tert-butyl dicarbonate, 4-fluoro-nitrobenzene and 4-chloro-3-(trifluoromethyl)phenyl isocyanate by the same method as in Example 16.

$^1$H-NMR (270 MHz, DMSO-$d_6$) δ (ppm): 1.50 (9H, s), 7.37-7.50 (2H, m), 7.55-7.70 (6H, m), 7.88 (1H, s), 8.12 (1H, d, J=2.0 Hz), 8.42 (1H, s), 9.11 (1H, s), 9.25 (1H, s), 9.34 (1H, s)

ESI (LC-MS positive mode) m/z 546 (M+H)

Example 39

1-[4-(6-Aminobenzimidazol-1-yl)phenyl]-3-(4-chloro-3-(trifluoromethyl)phenyl)urea hydrochloride (Table 1, Compound No. 39)

[Formula 76]

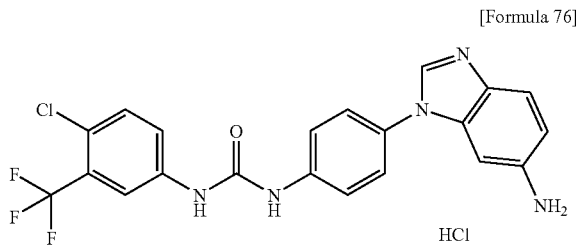 [SMILES: Nc1ccc2ncn(-c3ccc(NC(=O)Nc4ccc(Cl)c(C(F)(F)F)c4)cc3)c2c1 ; Cl]

The title compound can be synthesized from (3-{4-[3-(4-chloro-3-(trifluoromethyl)phenyl)ureido]phenyl}-3H-benzimidazol-5-yl)carbamic acid tert-butyl ester by the same method as in Example 17.

$^1$H-NMR (270 MHz, DMSO-$d_6$) δ (ppm): 4.79 (2H, br.s), 7.20-7.27 (2H, m), 7.60-7.82 (7H, m), 8.14 (1H, s), 9.39 (1H, s), 9.96 (1H, s), 10.11 (1H, s)

ESI (LC-MS positive mode) m/z 446 (M+H)

Example 40

1-[4-(5-Aminobenzimidazol-1-yl)phenyl]-3-(4-chloro-3-(trifluoromethyl)phenyl)urea hydrochloride (Table 1, Compound No. 40)

[Formula 77]

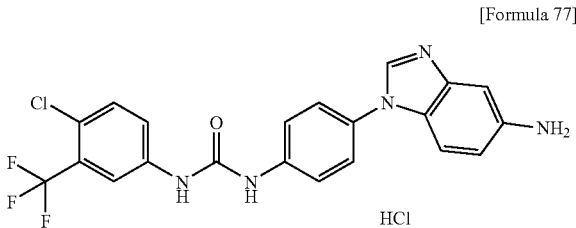 [SMILES: Nc1ccc2c(c1)ncn2-c1ccc(NC(=O)Nc2ccc(Cl)c(C(F)(F)F)c2)cc1 ; Cl]

The title compound can be synthesized from (1-{4-[3-(4-chloro-3-(trifluoromethyl)phenyl)ureido]phenyl}-1H-benzimidazol-5-yl)carbamic acid tert-butyl ester by the same method as in Example 17.

$^1$H-NMR (270 MHz, DMSO-$d_6$) δ (ppm): 7.23 (1H, d, J=9.5 Hz), 7.52 (1H, s), 7.63-7.77 (7H, m), 8.13 (1H, s), 9.32 (1H, s), 9.85 (1H, s), 10.00 (1H, s)

ESI (LC-MS positive mode) m/z 446 (M+H)

Example 41

N-(3-{4-[3-(4-Chloro-3-(trifluoromethyl)phenyl)ureido]phenyl}-3H-benzimidazol-5-yl)acetamide (Table 1, Compound No. 41)

[Formula 78]

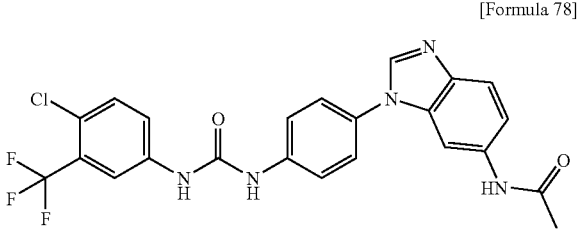 [SMILES: CC(=O)Nc1ccc2ncn(-c3ccc(NC(=O)Nc4ccc(Cl)c(C(F)(F)F)c4)cc3)c2c1]

In a mixed solution of 2 mL of methylene chloride and 1 mL of pyridine, 40 mg (0.083 mmol) of 1-[4-(6-amino-benzimidazol-yl)phenyl]-3-(4-chloro-3-(trifluoromethyl-phenyl)urea hydrochloride was dissolved, and 0.016 mL (0.16 mmol) of acetic anhydride was added thereto and the mixture solution was stirred at room temperature for 14 hours. The reaction solution was concentrated under reduced pressure, and the residue was partitioned between ethyl acetate and a saturated ammonium chloride aqueous solution. The organic layer was washed with a saturated sodium chloride solution, dried and concentrated under reduced pressure. The residue was triturated with n-hexane:ethyl acetate=1:2 to obtain 28 mg (70%) of N-(3-{4-[3-(4-chloro-3-(trifluoromethyl)phenyl)ureido]phenyl}-3H-benzimidazol-5-yl)acetamide (Table 1, Compound No. 41) as a white solid.

$^1$H-NMR (270 MHz, DMSO-$d_6$) δ (ppm): 2.04 (3H, s), 7.32 (1H, dd, J=1.6, 8.9 Hz), 7.55 (2H, d, J=8.9 Hz), 7.62-7.70 (5H, m), 8.11 (2H, dd, J=2.0, 8.9 Hz), 9.15 (1H, s), 9.28 (1H, s), 10.05 (1H, s)

ESI (LC-MS positive mode) m/z 488 (M+H)

Example 42

N-(1-{4-[3-(4-Chloro-3-(trifluoromethyl)phenyl)ureido]phenyl}-1H-benzimidazol-5-yl)acetamide (Table 1, Compound No. 42)

[Formula 79]

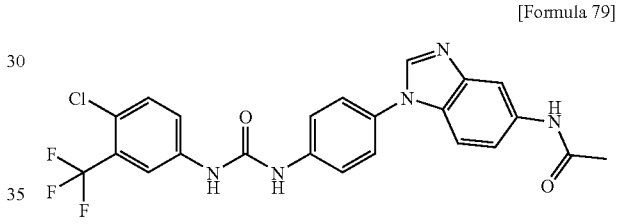

The title compound can be synthesized from 1-[4-[5-aminobenzimidazol-1-yl]phenyl]-3-(4-chloro-3-(trifluoromethyl)phenyl)urea hydrochloride and acetic anhydride by the same method as in Example 41.

$^1$H-NMR (270 MHz, DMSO-$d_6$) δ (ppm): 2.07 (3H, s), 7.41-7.55 (2H, m), 7.62-7.70 (6H, m), 8.12 (2H, dd, J=2.0, 5.9 Hz), 8.45 (1H, s), 9.13 (1H, s), 9.26 (1H, s), 9.98 (1H, s)

ESI (LC-MS positive mode) m/z 488 (M+H)

Example 43

(1-{4-[3-(4-chloro-3-(trifluoromethyl)phenyl)ureido]phenyl}-1H-benzimidazol-5-yl)carbamic acid ethyl ester (Table 1, Compound No. 43)

[Formula 80]

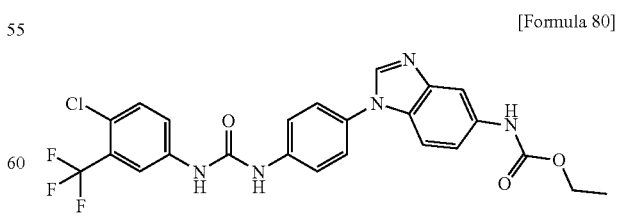

The title compound can be synthesized from 1-[4-[5-aminobenzimidazol-1-yl]phenyl]-3-(4-chloro-3-(trifluoro-methyl)phenyl)urea hydrochloride and ethyl chloroformate by the same method as in Example 41.

¹H-NMR (270 MHz, DMSO-d₆) δ (ppm): 1.27 (3H, t, J=7.0 Hz), 4.15 (2H, q, J=7.0 Hz), 7.41-7.70 (7H, m), 7.91 (1H, s), 8.11-8.13 (2H, m), 8.45 (1H, d, J=3.5 Hz), 9.13 (1H, s), 9.25 (1H, s), 9.63 (0.5H, s), 9.99 (0.5H, s)

ESI (LC-MS positive mode) m/z 518 (M+H)

Example 44

(1-{4-[3-(4-Chloro-3-(trifluoromethyl)phenyl)ureido]phenyl}-1H-benzimidazol-5-yl)carbamic acid 2-methoxyethyl ester (Table 1, Compound No. 44)

[Formula 81]

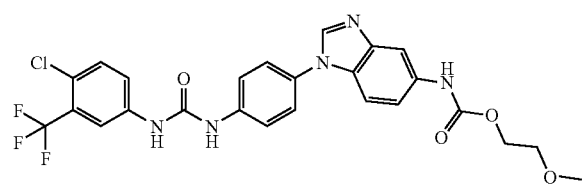

The title compound can be synthesized from 1-[4-(5-aminobenzimdazol-1-yl)phenyl]-3-(4-chloro-3-(trifluoro-methyl)phenyl)urea hydrochloride and methoxyethyl chloroformate by the same method as in Example 41.

¹H-NMR (270 MHz, DMSO-d₆) δ (ppm): 3.27 (3H, s), 3.57 (2H, m), 4.22 (2H, m), 7.41-7.70 (7H, m), 7.92 (1H, s), 8.11-8.13 (2H, m), 8.45 (1H, d, J=3.5 Hz), 9.13 (1H, s), 9.26 (1H, s), 9.76 (0.5H, s), 9.99 (0.5H, s)

ESI (LC-MS positive mode) m/z 548 (M+H)

Example 45

1-(4-Chloro-3-(trifluoromethyl)phenyl)-3-hydroxy-3-(4-imidazo[4,5-c]pyridin-1-ylphenyl)urea (Table 1, Compound No. 45)

Step A

Preparation of N-(4-imidazo[4,5-c]pyridin-1-ylphenyl)hydroxylamine

[Formula 82]

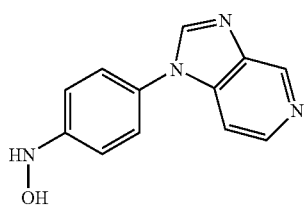

In 3 mL of dioxane, 40 mg (0.167 mmol) of 1-(4-nitrophenyl)-1H-imidazo[4,5-c]pyridine obtained in Step A of Example 1 was dissolved, and 40 mg of zinc powder and 1 mL of a saturated ammonium chloride aqueous solution were added thereto and the mixture solution was vigorously stirred at room temperature for one hour. The reaction solution was partitioned between ethyl acetate and water. The organic layer was washed with a sodium chloride solution, dried and then concentrated under reduced pressure to obtain a crude product of N-(4-imidazo[4,5-c]pyridine-1-ylphenyl)-hydroxylamine. The product was used in the next reaction without further purification.

ESI (LC-MS positive mode) m/z 227 (M+H)

Step B

Preparation of 1-(4-chloro-3-(trifluoromethyl)phenyl)-3-hydroxy-3-(4-imidazo[4,5-c]pyridin-1ylphenyl)urea (Table 1, Compound No. 45)

[Formula 83]

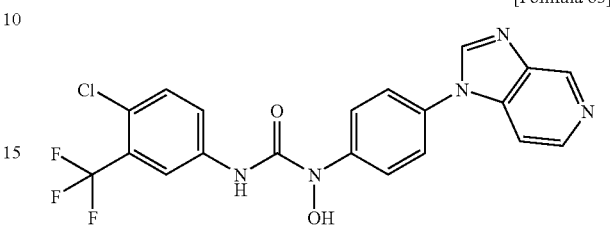

In 5 mL of methylene chloride, 37 mg of N-(4-imidazo[4,5-c]pyridin-1-yl-phenyl)hydroxylamine obtained in Step A was dissolved, and 41 mg (1.84 mmol) of 4-chloro-3-(trifluoromethyl)phenyl isocyanate was added thereto and the mixture solution was stirred at room temperature for three hours. The reaction solution was concentrated, and then the residue was partitioned between ethyl acetate and a saturated ammonium chloride aqueous solution. The organic layer was washed with a saturated sodium chloride solution, dried and concentrated under reduced pressure. The residue was triturated with n-hexane:ethyl acetate=1:1 to obtain 12 mg (16%) of 1-(4-chloro-3-(trifluoromethyl)phenyl)-3-hydroxy-3-(4-imidazo-[4,5-c]pyridin-1-ylphenyl)urea (Table 1, Compound No. 45) as a white solid.

¹H-NMR (270 MHz, DMSO-d₆) δ (ppm): 7.62-7.76 (7H, m), 8.14-8.43 (2H, m), 8.55 (1H, m), 8.98 (1H, m), 10.00 (1H, s), 11.10 (1H, s)

ESI (LC-MS positive mode) m/z 448 (M+H)

Example 46

1-(4-Chloro-3-(trifluoromethyl)phenyl)-3-hydroxy-3-(4-purin-7-ylphenyl)urea (Table 1, Compound No. 46)

[Formula 84]

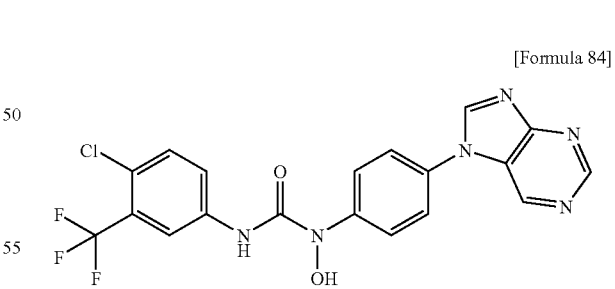

The title compound can be synthesized from purine, 4-fluoronitrobenzene and 4-chloro-3-(trifluoromethyl)phenyl isocyanate by using the same techniques as in Example 45.

¹H-NMR (270 MHz, DMSO-d₆) δ (ppm): 7.65 (1H, d, J=10.9 Hz), 7.82 (4H, dd, J=25.3, 13.0 Hz), 8.04 (1H, dd, J=9.2, 3.7 Hz), 8.33 (1H, d, J=2.3 Hz), 9.08 (2H, d, J=6.8 Hz), 9.24 (1H, s), 10.0 (1H, s), 11.06 (1H, s)

ESI (LC-MS positive mode) m/z 449 (M+H)

Example 47

1-(4-Chloro-3-(trifluoromethyl)phenyl)-3-hydroxy-3-(4-purin-9-ylphenyl)urea (Table 1, Compound No. 47)

[Formula 85]

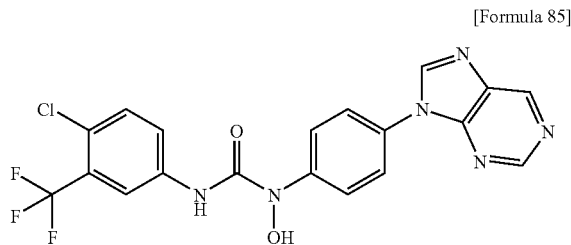 [SMILES: O=C(Nc1ccc(Cl)c(C(F)(F)F)c1)N(O)c1ccc(-n2cnc3cncnc32)cc1]

The title compound can be synthesized from purine, 4-fluoronitrobenzene and 4-chloro-3-(trifluoromethyl)phenyl isocyanate by using the same techniques as in Example 45.

$^1$H-NMR (270 MHz, DMSO-$d_6$) δ (ppm): 7.66 (1H, d, J=8.9 Hz), 7.88 (4H, dd, J=20.3, 12.8 Hz), 8.05 (1H, dd, J=8.9, 2.3 Hz), 8.33 (1H, d, J=2.3 Hz), 9.02 (2H, d, J=1.3 Hz), 9.29 (1H, s), 9.96 (1H, s), 11.0 (1H, s)

ESI (LC-MS positive mode) m/z 449 (M+H)

Example 48

1-(4-Chloro-3-(trifluoromethyl)phenyl)-3-{4-[6-(di-tert-butoxycarbonylamino)purin-9-yl]phenyl}-3-hydroxyurea (Table 1, Compound No. 48)

[Formula 86]

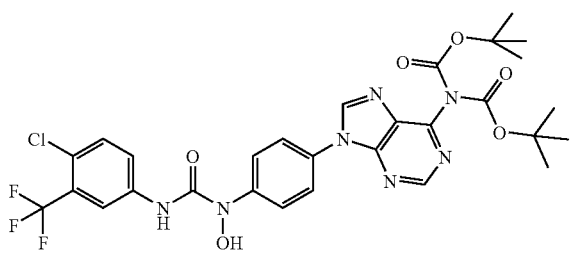

The title compound can be synthesized from 6-di-tert-butoxycarbonylamino-9-(4-nitrophenyl)-9H-purine and 4-chloro-3-(trifluoromethyl)phenyl isocyanate by using the same techniques as in Example 45.

$^1$H-NMR (270 MHz, CDCl$_3$) δ (ppm): 1.50 (9H, s), 7.44 (1H, d, J=8.6 Hz), 7.62 (2H, d, J=7.0 Hz), 7.77 (1H, dd, J=8.9, 3.0 Hz), 7.86 (2H, d, J=7.2 Hz), 7.97 (1H, d, J=2.7 Hz), 8.2 (1H, s), 8.48 (1H, d, J=4.3 Hz), 8.83 (1H, s), 9.43 (1H, br)

ESI (LC-MS positive mode) m/z 664 (M+H)

Example 49

1-[4-(6-Aminopurin-9-yl)phenyl]-3-(4-chloro-3-(trifluoromethyl)phenyl)-1-hydroxyurea hydrochloride (Table 1, Compound No. 49)

[Formula 87]

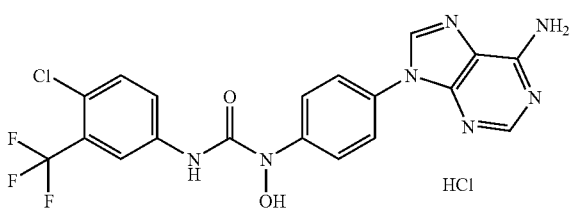

The title compound can be synthesized from 1-(4-chloro-3-(trifluoromethyl)phenyl-3-{4-[6-(di-tert-butoxycarbonylamino)purin-9-yl]phenyl}-3-hydroxyurea by using the same techniques as in Example 30.

$^1$H-NMR (270 MHz, DMSO-$d_6$) δ (ppm): 7.65 (1H, d, J=8.9 Hz), 7.80 (4H, dd, J=15.9, 9.3 Hz), 8.04 (1H, dd, J=8.9, 2.3 Hz), 8.34 (1H, d, J=3.6 Hz), 8.43 (1H, s), 8.79 (1H, s), 9.98 (1H, s), 11.05 (1H, s)

ESI (LC-MS positive mode) m/z 464 (M+H)

Example 50

3-(4-Chloro-3-(trifluoromethyl)phenyl)-1-hydroxy-1-[4-(6-methylpurin-9-yl)phenyl]urea (Table 1, Compound No. 50)

[Formula 88]

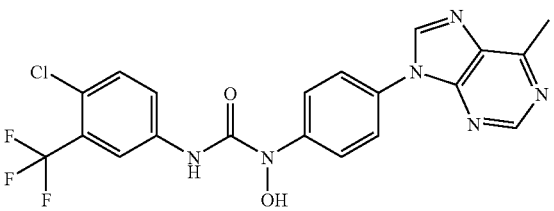

The title compound can be synthesized from 6-methylpurine, 4-fluoronitrobenzene and 4-chloro-3-(trifluoromethyl)phenyl isocyanate by using the same techniques as in Example 45.

$^1$H-NMR (270 MHz, DMSO-$d_6$) δ (ppm): 2.80 (3H, s), 7.65 (1H, d, J=8.9 Hz), 7.87 (4H, dd, J=8.5, 7.6 Hz), 8.05 (1H, dd, J=8.6, 2.6 Hz), 8.34 (1H, d, J=2.6 Hz), 8.85 (1H, s), 8.98 (1H, s), 9.98 (1H, s), 11.01 (1H, s)

ESI (LC-MS positive mode) m/z 463 (M+H)

Example 51

3-(4-Chloro-3-trifluoromethyl)phenyl)-1-hydroxy-1-(4-imidazo[4,5-b]pyridin-1-ylphenyl)urea (Table 1, Compound No. 51)

[Formula 89]

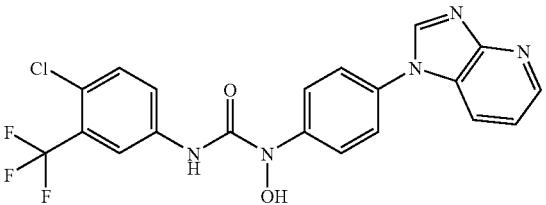

The title compound can be synthesized from imidazo-[4,5-b]pyridine, 4-fluoronitrobenzene and 4-chloro-3-(trifluoromethyl)phenyl isocyanate by using the same techniques as in Example 45.

$^1$H-NMR (400 MHz, DMSO-$d_6$) δ (ppm): 7.40 (1H, dd, J=3.2, 4.8 Hz), 7.66 (1H, d, J=9.2 Hz), 7.83 (2H, d, J=8.8 Hz), 7.93 (2H, d, J=8.8 Hz), 8.06 (1H, d, J=7.6 Hz), 8.22 (1H, d, J=8.0 Hz), 8.35 (1H, d, J=2.4 Hz), 8.45 (1H, d, J=4.8 Hz), 8.90 (1H, s), 9.98 (1H, s), 10.99 (1H, s)

ESI (LC-MS positive mode) m/z 448 (M+H)

Example 52

1-[4-(6-Chloropurin-9-yl)phenyl]-3-(4-chloro-3-(trifluoromethyl)phenyl)-1-hydroxyurea (Table 1, Compound No. 52)

[Formula 90]

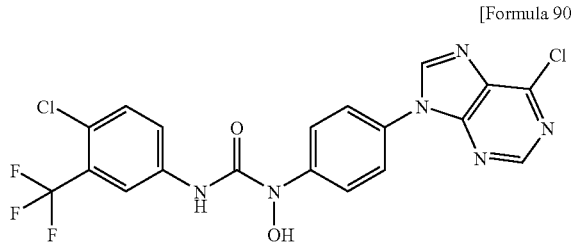 [SMILES: Cc1ncnc2c1ncn2-c1ccc(N(O)C(=O)Nc2ccc(Cl)c(C(F)(F)F)c2)cc1]

The title compound can be synthesized from 6-chloropurine, 4-fluoronitrobenzene and 4-chloro-3-(trifluoromethyl)phenyl isocyanate by using the same techniques as in Example 45.

$^1$H-NMR (270 MHz, DMSO-$d_6$) δ (ppm): 7.65 (1H, d, J=8.5 Hz), 7.88 (4H, s), 8.04 (1H, dd, J=8.5, 2.3 Hz), 8.32 (1H, d, J=2.5 Hz), 8.85 (1H, s), 9.12 (1H, s), 10.01 (1H, s), 11.03 (1H, s)

ESI (LC-MS positive mode) m/z 483 (M+H)

Example 53

3-(4-Chloro-3-(trifluoromethyl)phenyl)-1-hydroxy-1-[4-(6-(methylamino)pruin-9-yl)phenyl]urea (Table 1, Compound No. 53)

[Formula 91]

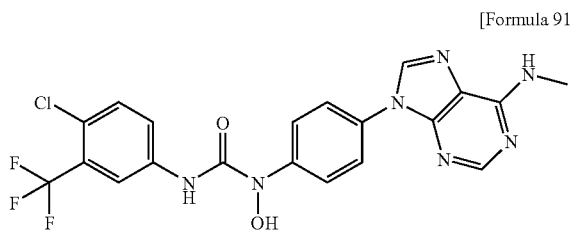

In 2 mL of a 40% methylamine methanol solution, 30 mg (0.062 mmol) of 1-[4-(6-chloropurin-9-yl)phenyl]-3-(4-chloro-3-(trifluoromethyl)phenyl)-1-hydroxyurea was dissolved and the solution stirred at room temperature for 18 hours. The reaction solution was concentrated under reduced pressure, and then the residue was purified by Megabond Elute Silica Gel (1 g, ethyl acetate:methanol=10:1) to obtain 3.21 mg (11%) of 3-(4-chloro-3-(trifluoromethyl)phenyl)-1-hydroxy-1-[4-(6-(methylamino)pruin-9-yl)phenyl]urea (Table 1, Compound No. 53).

$^1$H-NMR (270 MHz, DMSO-$d_6$) δ (ppm): 3.51 (3H, br.s), 7.67 (1H, d, J=8.1 Hz), 7.82 (4H, m), 8.06 (1H, dd, J=8.2, 2.5 Hz), 8.28 (1H, s), 8.35 (1H, d, J=2.6 Hz), 8.56 (1H, s), 9.96 (1H, s), 10.98 (1H, s)

ESI (LC-MS positive mode) m/z 478 (M+H)

Example 54

1-{4-[6-(Benzyl-methylamino)purin-9-yl]phenyl}-3-(4-chloro-3-(trifluoromethyl)phenyl)-1-hydroxyurea (Table 1, Compound No. 54)

[Formula 92]

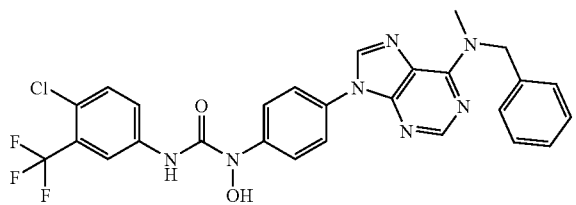

The title compound can be synthesized from 1-[4-(6-chloropurin-9-yl)phenyl]-3-(4-chloro-3-(trifluoro-methylphenyl)-1-hydroxyurea and benzylmethylamine by using the same techniques as in Example 53.

$^1$H-NMR (270 MHz, CDCl$_3$) δ (ppm): 1.27 (3H, s), 7.26-7.32 (5H, m), 7.38 (1H, d, J=13.4 Hz), 7.42 (2H, d, J=12.8 Hz), 7.54 (1H, dd, J=13.4, 2.6 Hz), 7.65 (2H, d, J=12.3 Hz), 7.80 (1H, d, J=2.7 Hz), 7.89 (1H, s), 8.15 (1H, s), 8.39 (1H, s)

ESI (LC-MS positive mode) m/z 568 (M+H)

Example 55

1-(4-Chloro-3-(trifluoromethyl)phenyl)-3-hydroxy-3-[4-(6-(morpholin-4-yl)purin-9-yl)phenyl]urea (Table 1, Compound No. 55)

[Formula 93]

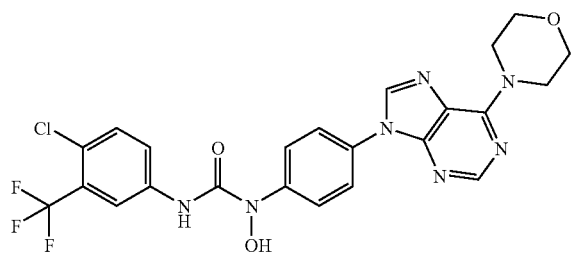

The title compound can be synthesized from 1-[4-(6-chloropurin-9-yl)phenyl]-3-(4-chloro-3-(trifluoromethyl)-phenyl)-1-hydroxyurea and morpholine by using the same techniques as in Example 53.

$^1$H-NMR (270 MHz, DMSO-$d_6$) δ (ppm): 3.77 (4H, t, J=4.8 Hz), 4.27 (4H, br), 7.65 (1H, d, J=8.9 Hz), 7.82 (4H, s), 8.03 (1H, dd, J=8.9, 2.6 Hz), 8.32 (2H, d, J=2.5 Hz), 8.61 (1H, s), 9.97 (1H, s), 10.98 (1H, s)

ESI (LC-MS positive mode) m/z 534 (M+H)

Example 56

3-(4-Chloro-3-(trifluoromethyl)phenyl)-1-[4-(6-dimethylamino-purin-9-yl)phenyl]-1-hydroxyurea (Table 1, Compound No. 56)

[Formula 94]

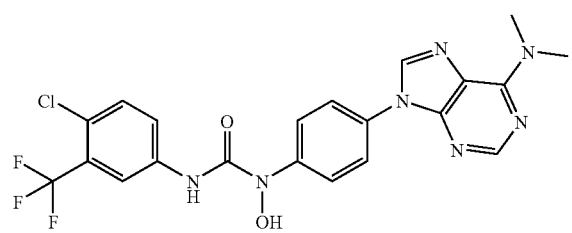

The title compound can be synthesized from 1-[4-(6-chloropurin-9-yl)phenyl]-3-(4-chloro-3-(trifluoromethyl-phenyl)-1-hydroxyurea and dimethylamine by using the same techniques as in Example 53.

¹H-NMR (270 MHz, DMSO-d₆) δ (ppm): 3.51 (6H, br), 7.67 (1H, d, J=8.1 Hz), 7.82 (4H, m), 8.06 (1H, dd, J=8.2, 2.5 Hz), 8.28 (1H, s), 8.35 (1H, d, J=2.6 Hz), 8.56 (1H, s), 9.96 (1H, s), 10.98 (1H, s)

ESI (LC-MS positive mode) m/z 492 (M+H)

Example 57

1-(4-Chloro-3-(trifluoromethyl)phenyl)-3-hydroxy-3-(4-{6-[(2-hydroxyethyl)-methylamino]purin-9-yl}-phenyl)urea (Table 1, Compound No. 57)

[Formula 95]

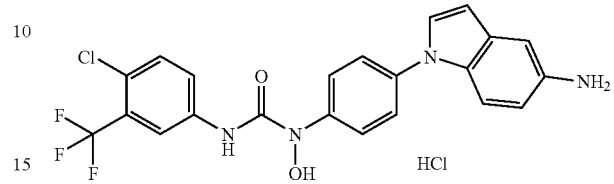

The title compound can be synthesized from 1-[4-(6-chloropurin-9-yl)phenyl]-3-(4-chloro-3-(trifluoromethyl)phenyl)-1-hydroxyurea and 2-methylamino-ethanol by using the same techniques as in Example 53.

¹H-NMR (270 MHz, DMSO-d₆) δ (ppm): 3.71 (2H, br), 4.80 (2H, br), 7.66 (1H, d, J=8.9 Hz), 7.82 (4H, m), 8.05 (1H, dd, J=8.9, 2.6 Hz), 8.27 (1H, s), 8.33 (1H, d, J=2.3 Hz), 8.56 (1H, s), 9.97 (1H, s), 10.99 (1H, s)

ESI (LC-MS positive mode) m/z 522 (M+H)

Example 58

1-{4-[3-(4-Chloro-3-(trifluoromethyl)phenyl)-1-hydroxyureido]phenyl}-1H-indol-5-yl)carbamic acid tert-butyl ester (Table 1, Compound No. 58)

[Formula 96]

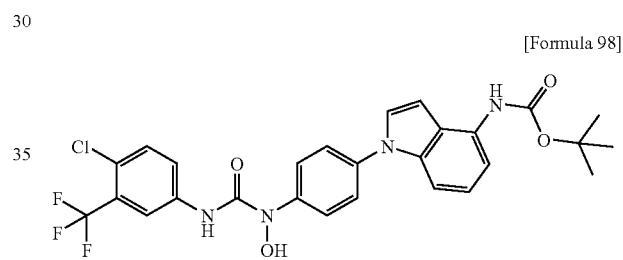

The title compound can be synthesized from (1H-indol-5-yl)-carbamic acid tert-butyl ester, 4-fluoronitrobenzene and 4-chloro-3-(trifluoromethyl)phenyl isocyanate by using the same techniques as in Example 53.

¹H-NMR (270 MHz, CDCl₃) δ (ppm): 1.56 (9H, s), 6.57 (2H, d, J=2.7 Hz), 6.88-7.01 (2H, br), 7.15-7.70 (9H, m), 7.83 (1H, d, J=2.6 Hz), 8.18 (1H, s), 8.37 (1H, s)

ESI (LC-MS positive mode) m/z 561 (M+H)

Example 59

1-[4-(5-Aminoindol-1-yl)phenyl]-3-(4-chloro-3-(trifluoromethyl)phenyl)1-hydroxyurea hydrochloride (Table 1, Compound No. 59)

[Formula 97]

The title compound can be synthesized from (1-{4-[3-(4-chloro-3-(trifluoromethyl)phenyl)-1-hydroxyureido]-phenyl}-1H-indol-5-yl)carbamic acid tert-butyl ester by using the same techniques as in Example 17.

ESI (LC-MS positive mode) m/z 461 (M+H)

Example 60

(1-{4-[3-(4-Chloro-3-(trifluoromethyl)phenyl)-1-hydroxyureido]phenyl}-1H-indol-4-yl)carbamic acid tert-butyl ester (Table 1, Compound No. 60)

[Formula 98]

The title compound can be synthesized from 4-aminoindole, di-tert-butyl dicarbonate, 4-fluoronitrobenzene and 4-chloro-3-(trifluoromethyl)phenyl isocyanate by using the same techniques as in Example 45.

¹H-NMR (270 MHz, CDCl₃) δ (ppm): 1.55 (9H, s), 6.52 (1H, br), 6.71 (1H, s), 7.04-7.56 (6H, m), 7.65 (1H, m), 7.88 (1H, s), 8.17 (1H, s), 8.30 (1H, br)

ESI (LC-MS positive mode) m/z 505 (M+H)

Example 61

1-[4-(4-Aminoindol-1-yl)phenyl]-3-(4-chloro-3-(trifluoromethyl)phenyl)-1-hydroxyurea hydrochloride (Table 1, Compound No. 61)

[Formula 99]

The title compound can be synthesized from (1-{4-[3-(4-chloro-3-(trifluoromethyl)phenyl)-1-hydroxyureido]-phenyl}-1H-indol-4-yl)carbamic acid tert-butyl ester by using the same techniques as in Example 17.

$^1$H-NMR (270 MHz, DMSO-d$_6$) δ (ppm): 6.85 (1H, d, J=3.2 Hz), 7.10 (1H, d, J=7.6 Hz), 7.21 (1H, t, J=8.3 Hz), 7.48 (1H, d, J=8.6 Hz), 7.56 (2H, d, J=8.5 Hz), 7.65 (1H, d, J=8.2 Hz), 7.75 (1H, d, J=3.3 Hz), 7.80 (2H, d, J=8.5 Hz), 8.14 (1H, dd, J=9.0, 2.8 Hz), 9.95 (1H, s), 11.02 (1H, br)

ESI (LC-MS positive mode) m/z 461 (M+H)

Example 62

1-(4-Chloro-3-(trifluoromethyl)phenyl)-3-{4-[6-(di-tert-butoxycarbonylamino)purin-9-yl]phenyl}-1-hydroxyurea (Table 1, Compound No. 62)

Step A

Preparation of N-(4-chloro-3-(trifluoromethyl)phenyl)hydroxylamine hydrochloride

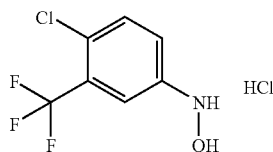

[Formula 100]

In 21 mL of ethanol, 4.51 g (20 mmol) of 2-chloro-5-nitrobenzotrifluoride was dissolved, and a solution obtained by dissolving 3.8 g of zinc powder and 420 mg of ammonium chloride in 5 mL of water was added thereto, and the mixture solution was stirred at 70° C. for one hour. The reaction solution after removal of insolubles by filtration was concentrated, and the residue was partitioned between water and ethyl acetate, and the organic layer was washed with a saturated sodium chloride solution. The organic layer was dried, and then concentrated under reduced pressure, and to the obtained residue, 30 mL of a 4N hydrogen chloride ethyl acetate solution was added, and the formed white precipitate was collected by filtration, washed with ethyl acetate and vacuum dried to obtain 3.08 g (63%) of N-(4-chloro-3-(trifluoromethyl)phenyl)hydroxylamine hydrochloride.

$^1$H-NMR (270 MHz, DMSO-d$_6$) δ (ppm): 7.10 (1H, dd, J=2.6, 8.5 Hz), 7.29 (1H, d, J=2.6 Hz), 7.48 (1H, d, J=8.5 Hz) 7.55 (3H, br.s)

ESI (LC-MS positive mode) m/z 249 (M+H)

Step B

Preparation of 1-(4-chloro-3-(trifluoromethyl)phenyl)-3-{4-[6-(di-tert-butoxycarbonylamino)purin-9-yl]phenyl}-1-hydroxyurea (Table 1, Compound No. 62)

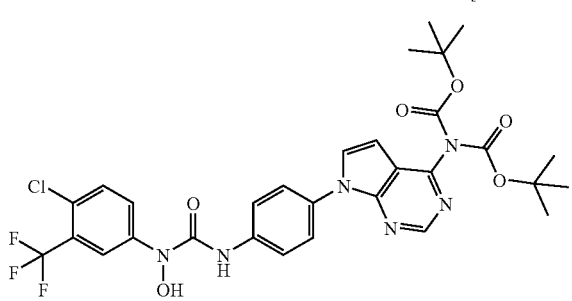

[Formula 101]

In 6 mL of methylene chloride, 100 mg (2.35 mmol) of 9-(4-aminophenyl)-6-di-tert-butoxycarbonylamino-9H-purine prepared in Step B of Example 29 was dissolved, and 28 mg (0.94 mmol) of triphosgene was added thereto at one time. Successively, 0.042 mL (2.42 mmol) of Hunig's base was added thereto and the resulting solution was stirred at room temperature for five minutes. To the formed slurry, 64 mg (2.59 mmol) of N-(4-chloro-3-(trifluoromethyl)phenyl)hydroxylamine hydrochloride dissolved in 0.123 mL (7.05 mmol) of Hunig's base and 4 mL of methylene chloride was added dropwise and the resulting solution was stirred at room temperature for one hour. The reaction solution was concentrated under reduced pressure, and then the residue was partitioned between ethyl acetate (100 mL) and water (100 mL), and the organic layer was washed with a saturated sodium chloride solution. The organic layer was dried and then concentrated under reduced pressure, and the residue was purified by Megabond Elute Silica Gel (5 g, n-hexane:ethyl acetate=1:1) to obtain 57 mg (37%) of 1-(4-chloro-3-(trifluoromethyl)phenyl)-3-{4-[6-(di-tert-butoxycarbonyl-amino)purin-9-yl]phenyl}-1-hydroxyurea (Table 1, Compound No. 62) as a white solid.

$^1$H-NMR (270 MHz, CDCl$_3$) δ (ppm): 1.50 (18H, s), 6.80 (1H, m), 7.39 (1H, d, J=9.0 Hz), 7.48 (1H, d, J=9.2 Hz), 7.62 (4H, dd, J=26.1, 8.9 Hz), 7.82 (1H, m), 8.03 (1H, m), 8.15 (1H, s), 8.22 (1H, s), 8.28 (1H, s), 8.74 (1H, br), 8.88 (1H, s)

ESI (LC-MS positive mode) m/z 664 (M+H)

Example 63

1-[4-(6-Aminopurin-9-yl)phenyl]-3-(4-chloro-3-(trifluoromethyl)phenyl)-3-hydroxyurea hydrochloride (Table 1, Compound No. 63)

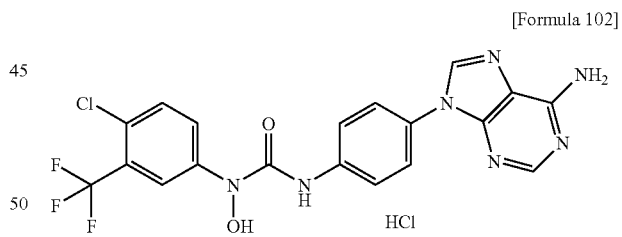

[Formula 102]

The title compound can be synthesized from (1-(4-chloro-3-(trifluoromethyl)phenyl)-3-{4-[6-(di-tert-butoxy-carbonylamino)purin-9-yl]phenyl}-1-hydroxyurea by using the same techniques as in Example 30.

$^1$H-NMR (270 MHz, DMSO-d$_6$) δ (ppm): 7.38 (1H, d, J=8.6 Hz), 7.66-7.78 (4H, m), 7.95 (3H, d, J=6.9 Hz), 8.20 (1H, d, J=2.7 Hz), 8.55 (1H, d, J=2.6 Hz), 8.83 (1H, d, J=4.3 Hz), 9.86 (1H, s)

ESI (LC-MS positive mode) m/z 464 (M+H)

Example 64

1-{4-[3-(4-Chloro-3-(trifluoromethyl)phenyl)-3-hydroxyureido]-2-fluorophenyl}-1H-indol-5-yl)carbamic acid tert-butyl ester (Table 1, Compound No. 64)

[Formula 103]

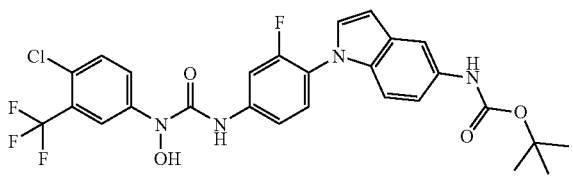

The title compound can be synthesized from N-(4-chloro-3-(trifluoromethyl)phenyl)hydroxylamine hydrochloride and [1-(4-amino-2-fluorophenyl)-1H-indol-5-yl]carbamic acid tert-butyl ester by using the same techniques as in Example 62.

$^1$H-NMR (270 MHz, DMSO-d$_6$) δ (ppm): 1.52 (9H, s), 6.60 (1H, d, J=3.6 Hz), 7.08 (1H, d, J=8.9 Hz), 7.22 (1H, d, J=8.9 Hz), 7.44 (1H, d, J=1.0 Hz), 7.55 (1H, t, J=8.9 Hz), 7.68-7.78 (3H, m), 7.85-7.95 (2H, m) 8.18 (1H, d, J=2.3 Hz), 9.19 (1H, s), 10.00 (1H, s), 11.19 (1H, s)

ESI (LC-MS positive mode) m/z 523.03 (M+H-t-Bu)

Example 65

3-[4-(5-Aminoindol-1-yl)-3-fluorophenyl]-1-(4-chloro-3-(trifluoromethyl)phenyl)-1-hydroxyurea (Table 1, Compound No. 65)

[Formula 104]

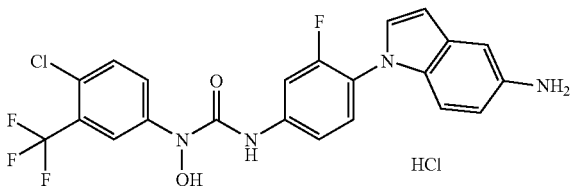

The title compound can be synthesized from (1-{4-[3-(4-chloro-3-(trifluoromethyl)phenyl)-3-hydroxy-ureido]-2-fluorophenyl}-1H-indol-5-yl)carbamic acid tert-butyl ester by using the same techniques as in Example 30.

$^1$H-NMR (400 MHz, DMSO-d$_6$) δ (ppm): 6.81 (1H, d, J=2.8 Hz), 7.16 (1H, dd, J=2.4, 8.8 Hz), 7.32 (1H, d, J=9.6 Hz), 7.55 (1H, t, J=8.8 Hz), 7.67 (2H, d, J=2.0 Hz), 7.73-7.76 (2H, m), 7.93 (2H, d, J=11.2 Hz), 8.19 (1H, d, J=2.4 Hz), 10.04 (1H, s), 10.09 (2H, br.s), 11.27 (1H, s)

ESI (LC-MS positive mode) m/z 463.2 (M+H)

Example 66

3-(4-Chloro-3-(trifluoromethyl)phenyl)-3-hydroxy-1-[4-(6-methylpurin-9-yl)phenyl]urea (Table 1, Compound No. 66)

[Formula 105]

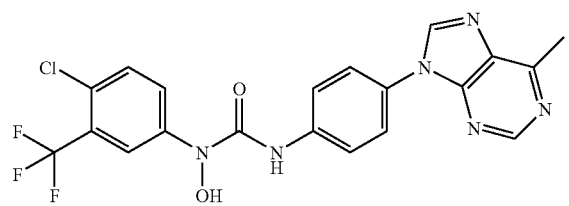

The title compound can be synthesized from N-(4-chloro-3-(trifluoromethyl)phenyl)hydroxylamine hydrochloride, 6-methylpurine and 4-fluoronitrobenzene by using the same techniques as in Example 62.

$^1$H-NMR (270 MHz, DMSO-d$_6$) δ (ppm): 2.79 (3H, s), 7.70 (1H, d, J=8.9 Hz), 7.81-7.98 (5H, m), 8.19 (1H, d, J=2.7 Hz), 8.83 (1H, s), 8.90 (1H, s), 9.86 (1H, s), 11.12 (1H, s)

ESI (LC-MS positive mode) m/z 463 (M+H)

Example 67

1-(4-Chloro-3-(trifluoromethyl)phenyl)-3-[4-(5-cyano-indol-1-yl)phenyl]-1-hydroxyurea (Table 1, Compound No. 67)

[Formula 106]

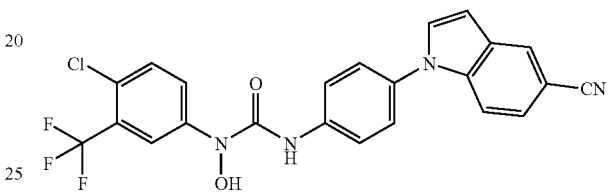

The title compound can be synthesized from N-(4-chloro-3-(trifluoromethyl)phenyl)hydroxylamine hydrochloride, 5-cyanoindole and 4-fluoronitrobenzene by using the same techniques as in Example 62.

$^1$H-NMR (270 MHz, DMSO-d$_6$) δ (ppm): 6.84 (1H, d, J=3.3 Hz), 7.52-7.59 (3H, m), 7.64 (1H, d, J=8.9 Hz), 7.73 (1H, d, J=8.9 Hz), 7.86 (1H, d, J=3.3 Hz), 7.89-7.96 (3H, m), 8.20 (2H, m), 9.96 (1H, s), 11.11 (1H, s)

ESI (LC-MS positive mode) m/z 471.1 (M+H)

Example 68

3-(4-Chloro-3-(trifluoromethyl)phenyl)-1-[4-(6-dimethylaminopurin-9-yl)phenyl]-3-hydroxyurea (Table 1, Compound No. 68)

[Formula 107]

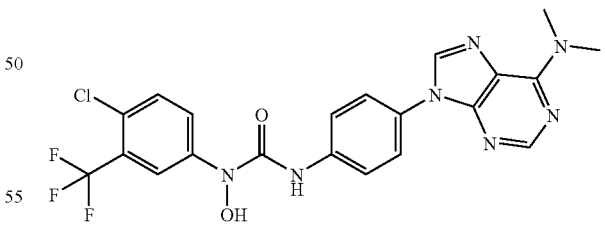

The title compound can be synthesized from N-(4-chloro-3-(trifluoromethyl)phenyl)hydroxylamine hydrochloride and [9-(4-aminophenyl)-9H-purin-6-yl]-dimethylamine by using the same techniques as in Example 62.

$^1$H-NMR (270 MHz, DMSO-d$_6$) δ (ppm): 7.70 (1H, d, J=9.2 Hz), 7.80 (4H, dd, J=30.0, 8.9 Hz), 7.91 (1H, dd, J=8.9, 2.6 Hz), 8.19 (1H, d, J=2.7 Hz), 8.27 (1H, s), 8.52 (1H, s), 9.83 (1H, s), 11.12 (1H, s)

ESI (LC-MS positive mode) m/z 492 (M+H)

Example 69

(1-{4-[3-(4-Chloro-3-(trifluoromethyl)phenyl)-3-hydroxyureido]phenyl}-1H-indol-5-yl)carbamic acid tert-butyl ester (Table 1, Compound No. 69)

[Formula 108]

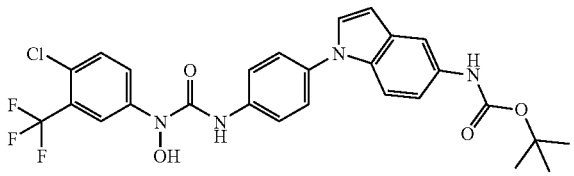

The title compound can be synthesized from N-(4-chloro-3-(trifluoromethyl)phenyl)hydroxylamine hydrochloride, (1H-indol-5-yl)-carbamic acid tert-butyl ester and 4-fluoronitrobenzene by using the same techniques as in Example 62.

$^1$H-NMR (270 MHz, CDCl$_3$) δ (ppm): 1.53 (9H, s), 6.59 (1H, d, J=3.3 Hz), 7.11 (1H, dd, J=8.9, 2.3 Hz), 7.30 (1H, d, J=3.3 Hz), 7.35-7.48 (4H, m), 7.64 (2H, d, J=6.6 Hz), 7.70 (1H, br), 7.87 (1H, dd, J=8.9, 2.7 Hz), 8.08 (1H, d, J=2.7 Hz), 8.55 (1H, s)

ESI (LC-MS positive mode) m/z 561 (M+H)

Example 70

(1-[4-(5-Aminoindol-1-yl)phenyl]-3-(4-chloro-3-(trifluoromethyl)phenyl)-3-hydroxyurea hydrochloride (Table 1, Compound No. 70)

[Formula 109]

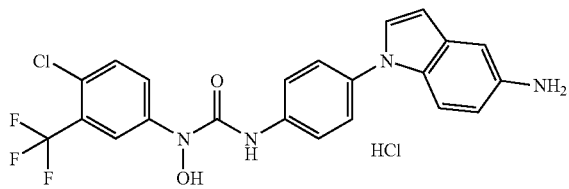

The title compound can be synthesized from (1-{4-[3-(4-chloro-3-(trifluoromethyl)phenyl)-3-hydroxyureido]phenyl}-1H-indol-5-yl)carbamic acid tert-butyl ester by using the same techniques as in Example 30.

$^1$H-NMR (270 MHz, DMSO-d$_6$) δ (ppm): 6.78 (1H, d, J=3.3 Hz), 7.18 (1H, dd, J=8.9, 2.4 Hz), 7.53 (2H, d, J=8.9 Hz), 7.55-7.80 (3H, m), 7.88 (1H, d, J=9.8 Hz), 8.20 (1H, d, J=2.7 Hz), 9.80 (1H, s), 10.11 (1H, br), 11.16 (1H, s)

ESI (LC-MS positive mode) m/z 461 (M+H)

Example 71

1-[4-(4-Aminoindol-1-yl)phenyl]-3-(4-chloro-3-(trifluoromethyl)phenyl)-3-hydroxyurea hydrochloride (Table 1, Compound No. 71)

[Formula 110]

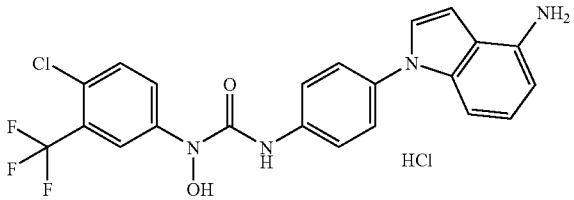

The titled compound can be synthesized from N-(4-chloro-3-(trifluoromethyl)phenyl)hydroxylamine hydrochloride, 4-aminoindol, di-tert-butyl dicarbonate and 4-fluoronitrobenzene by using the same techniques as in Example 70.

$^1$H-NMR (270 MHz, DMSO-d$_6$) δ (ppm): 6.84 (1H, d, J=3.3 Hz), 7.02 (1H, d, J=7.5 Hz), 7.19 (1H, t, J=7.6 Hz), 7.42 (1H, d, J=7.9 Hz), 7.51 (2H, d, J=8.9 Hz), 7.77-7.84 (2H, m), 7.89 (2H, d, J=8.9 Hz), 8.20 (1H, d, J=2.6 Hz), 9.80 (1H, s), 11.12 (1H, s)

ESI (LC-MS positive mode) m/z 461 (M+H)

Example 72

1-{4-[3-(4-Chloro-3-(trifluoromethyl)phenyl)-3-hydroxyureido]phenyl}-1H-indole-5-carboxylic acid methylamide (Table 1, Compound No. 72)

[Formula 111]

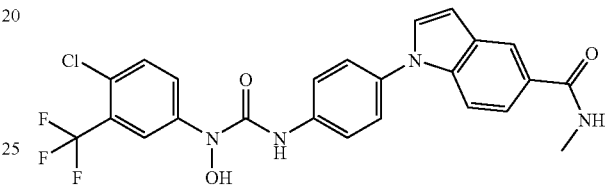

The title compound can be synthesized from N-(4-chloro-3-(trifluoromethyl)phenyl)hydroxylamine hydrochloride, 1-(4-aminophenyl)-1H-indole-5-carboxylic acid methylamide by using the same techniques as in Example 62.

$^1$H-NMR (270 MHz, DMSO-d$_6$) δ (ppm): 2.82 (3H, d, J=4.3 Hz), 6.80 (1H, d, J=3.3 Hz), 7.53-7.58 (3H, m), 7.68-7.74 (3H, m), 7.85-7.93 (3H, m), 8.20 (2H, m), 8.37 (1H, q, J=4.3 Hz), 9.83 (1H, s), 11.12 (1H, s)

ESI (LC-MS positive mode) m/z 503.5 (M+H)

Example 73

N-(1-{4-[3-(4-Chloro-3-(trifluoromethyl)phenyl)-3-hydroxyureido]phenyl}-1H-indol-5-yl)-2,2-dimethylpropion-amide (Table 1, Compound No. 73)

[Formula 112]

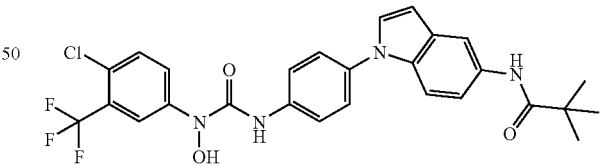

The title compound can be synthesized from 1-[4-(5-aminoindol-1-yl)phenyl]-3-(4-chloro-3-(trifluoromethyl)phenyl)-3-hydroxyurea hydrochloride and pivalic anhydride by using the same techniques as in Example 41.

$^1$H-NMR (270 MHz, DMSO-d$_6$) δ (ppm): 1.23 (9H, s), 6.62 (1H, d, J=3.3 Hz), 7.34 (1H, d, J=8.9 Hz), 7.46 (1H, d, J=8.9 Hz), 7.50 (2H, d, J=8.9 Hz), 7.56 (1H, d, J=3.3 Hz), 7.72 (1H, d, J=8.9 Hz), 7.87 (2H, d, J=8.9 Hz), 7.90-7.96 (2H, m), 8.20 (1H, d, J=2.3 Hz), 9.12 (1H, s), 9.78 (1H, s), 11.09 (1H, s)

ESI (LC-MS positive mode) m/z 545 (M+H)

Example 74

N-(1-{4-[3-(4-Chloro-3-(trifluoromethyl)phenyl)-3-hydroxyureido]phenyl}-1H-indol-5-yl)acetamide (Table 1, Compound No. 74)

[Formula 113]

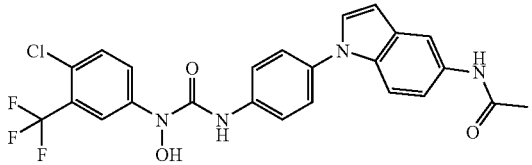

The title compound can be synthesized from 1-[4-(5-aminoindol-1-yl)phenyl]-3-(4-chloro-3-(trifluoromethyl)phenyl)-3-hydroxyurea hydrochloride and acetic anhydride by using the same techniques as in Example 41.

$^1$H-NMR (270 MHz, DMSO-d$_6$) δ (ppm): 2.04 (3H, s), 6.62 (1H, d, J=4.3 Hz), 7.27 (1H, dd, J=9.3, 2.0 Hz), 7.35-7.65 (4H, m), 7.70 (1H, d, J=8.9 Hz), 7.83 (2H, d, J=9.0 Hz), 7.94 (1H, dd, J=9.2, 2.7 Hz), 7.97 (1H, s), 8.20 (1H, d, J=2.7 Hz), 9.78 (1H, s), 9.86 (1H, s), 11.09 (1H, s)

ESI (LC-MS positive mode) m/z 503 (M+H)

Example 75

N-(1-{4-[3-(4-Chloro-3-(trifluoromethyl)phenyl)-3-hydroxyureido]phenyl}-1H-indol-5-yl)pentanamide (Table 1, Compound No. 75)

[Formula 114]

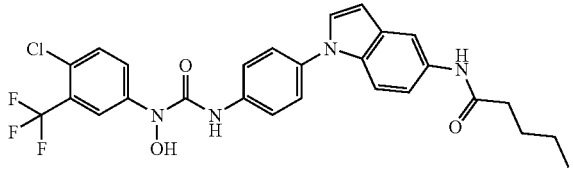

The title compound can be synthesized from 1-[4-(5-aminoindol-1-yl)phenyl]-3-(4-chloro-3-(trifluoromethyl)phenyl)-3-hydroxyurea hydrochloride and n-valeroyl chloride by using the same techniques as in Example 41.

$^1$H-NMR (270 MHz, DMSO-d$_6$) δ (ppm): 0.90 (3H, q, J=5.1 Hz), 1.31 (2H, m), 1.61 (2H, m), 2.31 (1H, t, J=6.5 Hz), 2.76 (1H, t, J=5.5 Hz), 6.62 (1H, d, J=3.3 Hz), 7.29 (1H, dd, J=8.9, 2.0 Hz), 7.46 (1H, d, J=8.9 Hz), 7.55 (2H, d, J=8.9 Hz), 7.58 (1H, d, J=3.3 Hz), 7.70 (2H, d, J=8.9 Hz), 7.74 (1H, d, J=2.1 Hz), 7.78 (1H, d, J=8.9 Hz), 7.94 (1H, d, J=2.6 Hz), 8.00 (1H, d, J=2.6 Hz), 9.65 (1H, s), 9.77 (1H, s)

ESI (LC-MS positive mode) m/z 545 (M+H)

Example 76

N-(1-{4-[3-(4-Chloro-3-(trifluoromethyl)phenyl)-3-hydroxyureido]phenyl}-1H-indol-5-yl)decanamide (Table 1, Compound No. 76)

[Formula 115]

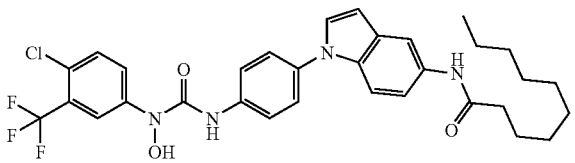

The title compound can be synthesized from 1-[4-(5-aminoindol-1-yl)phenyl]-3-(4-chloro-3-(trifluoromethyl)phenyl)-3-hydroxyurea hydrochloride and n-decanoyl chloride by using the same techniques as in Example 41.

$^1$H-NMR (270 MHz, CDCl$_3$) δ (ppm): 0.89 (3H, t, J=6.3 Hz), 1.27 (14H, br), 2.32 (2H, t, J=8.0 Hz), 6.61 (1H, d, J=3.3 Hz), 7.06-7.31 (5H, m), 7.35-7.50 (3H, m), 7.71 (1H, d, J=2.3 Hz), 7.75 (1H, s), 7.78 (1H, d, J=2.7 Hz), 9.81 (1H, br)

ESI (LC-MS positive mode) m/z 615 (M+H)

Example 77

1-{4-[3-(4-Chloro-3-(trifluoromethyl)phenyl)-3-hydroxyureido]phenyl}-1H-indol-5-yl)carbamic acid methyl ester (Table 1, Compound No. 77)

[Formula 116]

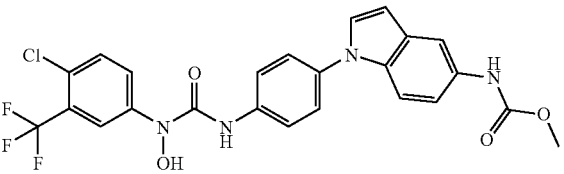

The title compound can be synthesized from 1-[4-(5-aminoindol-1-yl)phenyl]-3-(4-chloro-3-(trifluoromethyl)phenyl)-3-hydroxyurea hydrochloride and methyl chloroformate by using the same techniques as in Example 41.

$^1$H-NMR (270 MHz, CDCl$_3$) δ (ppm): 3.71 (3H, s), 6.60 (1H, d, J=3.0 Hz), 6.75 (1H, s), 7.04 (1H, d, J=8.9 Hz), 7.15-7.30 (5H, m), 7.36 (1H, d, J=8.9 Hz), 7.51 (1H, s), 7.68-7.72 (2H, m), 7.93 (1H, d, J=2.6 Hz), 8.93 (1H, br)

ESI (LC-MS positive mode) m/z 519 (M+H)

Example 78

(1-{4-[3-(4-Chloro-3-(trifluoromethyl)phenyl)-3-hydroxyureido]phenyl}-1H-indol-5-yl)carbamic acid ethyl ester (Table 1, Compound No. 78)

[Formula 117]

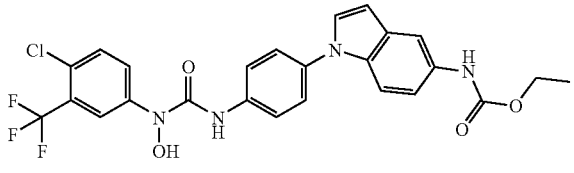

The title compound can be synthesized from 1-[4-(5-aminoindol-1-yl)phenyl]-3-(4-chloro-3-(trifluoromethyl)phenyl)-3-hydroxyurea hydrochloride and ethyl chloroformate by using the same techniques as in Example 41.

$^1$H-NMR (270 MHz, CDCl$_3$) δ (ppm): 1.23 (3H, t, J=7.1 Hz), 4.14 (2H, q, J=7.2 Hz), 6.62 (1H, d, J=2.6 Hz), 6.63 (1H, s), 7.09 (1H, dd, J=8.9, 2.0 Hz), 7.25-7.45 (6H, m), 7.53 (1H, d, J=2.0 Hz), 7.75 (1H, dd, J=8.2, 2.3 Hz), 7.95 (1H, d, J=2.6 Hz)

ESI (LC-MS positive mode) m/z 533 (M+H)

Example 79

1-{4-[3-(4-Chloro-3-(trifluoromethyl)phenyl)-3-hydroxyureido]phenyl}-1H-indol-5-yl)carbamic acid pentyl ester (Table 1, Compound No. 79)

[Formula 118]

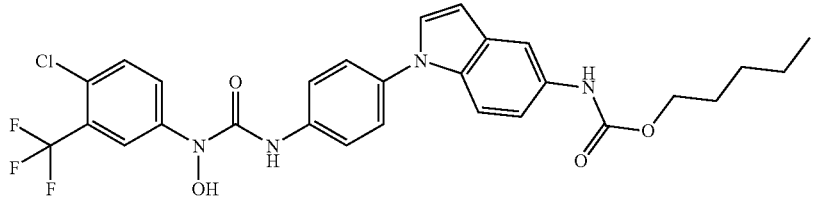

The title compound can be synthesized from 1-[4-(5-aminoindol-1-yl)phenyl]-3-(4-chloro-3-(trifluoromethyl)phenyl)-3-hydroxyurea hydrochloride and n-pentyl chloroformate by using the same techniques as in Example 41.

$^1$H-NMR (270 MHz, CDCl$_3$) δ (ppm): 0.91 (3H, t, J=6.6 Hz), 1.32 (4H, m), 1.62 (2H, m), 4.03 (2H, t, J=6.6 Hz), 6.61 (1H, d, J=2.6 Hz), 6.70 (1H, s), 7.07 (1H, dd, J=8.5, 2.0 Hz), 7.16-7.35 (6H, m), 7.37 (1H, d, J=8.9 Hz), 7.51 (1H, d, J=2.0 Hz), 7.72 (1H, br), 7.75 (1H, br), 7.95 (1H, s)

ESI (LC-MS positive mode) m/z 575 (M+H)

Example 80

(1-{4-[3-(4-Chloro-3-(trifluoromethyl)phenyl)-3-hydroxyureido]phenyl}-1H-indol-5-yl)carbamic acid decyl ester (Table 1, Compound No. 80)

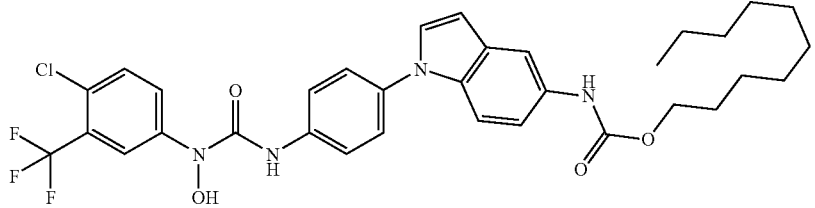

The title compound can be synthesized from 1-[4-(5-aminoindol-1-yl)phenyl]-3-(4-chloro-3-(trifluoromethyl)phenyl)-3-hydroxyurea hydrochloride and n-decyl chloroformate by using the same techniques as in Example 41.

$^1$H-NMR (270 MHz, CDCl$_3$) δ (ppm): 0.89 (3H, m), 1.30 (14H, br), 1.61 (2H, m), 4.03 (2H, t, J=7.0 Hz), 6.60 (1H, d, J=3.3 Hz), 6.68 (1H, s), 6.76 (1H, d, J=8.9 Hz), 7.07 (1H, dd, J=9.0, 2.0 Hz), 7.17-7.36 (6H, m), 7.38 (1H, d, J=8.8 Hz), 7.52 (1H, d, J=2.0 Hz), 7.66-7.75 (2H, m), 7.95 (1H, d, J=2.7 Hz), 8.92 (1H, br)

ESI (LC-MS positive mode) m/z 645 (M+H)

Example 81

N-(1-{4-[3-(4-Chloro-3-(trifluoromethyl)phenyl)-3-hydroxyureido]phenyl}-1H-indol-5-yl)-3-methylbutylamide (Table 1, Compound No. 81)

[Formula 120]

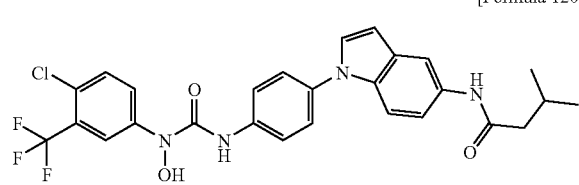

The titled compound can be synthesized from 1-[4-(5-aminoindol-1-yl)phenyl]-3-(4-chloro-3-(trifluoromethyl)phenyl)-3-hydroxyurea hydrochloride and isovaleroyl chloride by using the same techniques as in Example 41.

$^1$H-NMR (270 MHz, DMSO-d$_6$) δ (ppm): 0.95 (6H, d, J=6.3 Hz), 2.12 (1H, m), 2.21 (2H, m), 6.62 (1H, d, J=2.3 Hz), 7.29 (1H, d, J=8.9 Hz), 7.45-7.95 (7H, m), 8.00 (1H, d, J=2.0 Hz), 8.19 (1H, d, J=2.7 Hz), 9.75 (2H, d, J=5.9 Hz), 11.08 (1H, s), ESI (LC-MS positive mode) m/z 545 (M+H)

[Formula 119]

Example 82

N-(1-{4-[3-(4-Chloro-3-(trifluoromethyl)phenyl)-3-hydroxyureido]phenyl}-1H-indol-5-yl)-3,3-dimethyl-butylamide (Table 1, Compound No. 82)

[Formula 121]

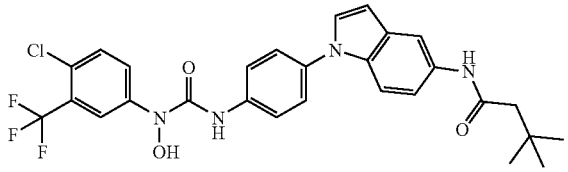

The title compound can be synthesized from 1-[4-(5-aminoindol-1-yl)phenyl]-3-(4-chloro-3-(trifluoromethyl)phenyl)-3-hydroxyurea hydrochloride and tert-butylacetyl chloride by using the same techniques as in Example 41.

$^1$H-NMR (270 MHz, DMSO-d$_6$) δ (ppm): 1.03 (9H, s), 2.20 (2H, s), 6.62 (1H, d, J=3.2 Hz), 7.27 (1H, d, J=10.8 Hz), 7.45 (1H, d, J=8.9 Hz), 7.51 (2H, d, J=8.9 Hz), 7.59 (1H, d, J=3.2 Hz), 7.72 (1H, d, J=9.2 Hz), 7.85 (2H, d, J=8.9 Hz), 7.93 (1H, d, J=11.3 Hz), 8.00 (1H, s), 8.19 (1H, d, J=2.4 Hz), 9.69 (1H, s), 9.78 (1H, s), 11.09 (1H, s), ESI (LC-MS positive mode) m/z 559 (M+H)

Example 83

(1-{4-[3-(4-Chloro-3-(trifluoromethyl)phenyl)-3-hydroxyureido]phenyl}-1H-indol-5-yl)carbamic acid 2-methoxyethyl ester (Table 1, Compound No. 83)

[Formula 122]

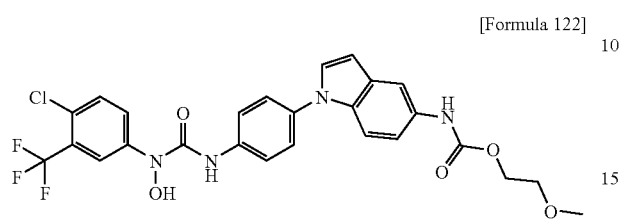

The title compound can be synthesized from 1-[4-(5-aminoindol-1-yl)phenyl]-3-(4-chloro-3-(trifluoromethyl)phenyl)-3-hydroxyurea hydrochloride and 2-methoxyethyl chloroformate by using the same techniques as in Example 41.

¹H-NMR (270 MHz, DMSO-d₆) δ (ppm): 3.28 (3H, s), 3.57 (2H, t, J=5.0 Hz), 4.21 (2H, t, J=5.0 Hz), 6.60 (1H, d, J=3.3 Hz), 7.25 (1H, d, J=8.6 Hz), 7.45 (1H, d, J=8.9 Hz), 7.52 (2H, d, J=8.9 Hz), 7.58 (1H, d, J=3.3 Hz), 7.70 (1H, d, J=8.6 Hz), 7.78 (1H, br), 7.85 (2H, d, J=8.9 Hz), 7.91 (1H, dd, J=8.9, 2.3 Hz), 8.20 (1H, d, J=2.6 Hz), 9.58 (1H, br), 9.75 (1H, s), 11.10 (1H, s), ESI (LC-MS positive mode) m/z 563 (M+H)

Example 84

3-(1-{4-[3-(4-Chloro-3-(trifluoromethyl)phenyl)-3-hydroxyureido]phenyl}-1H-indol-5-yl)-1,1-dimethylurea (Table 1, Compound No. 84)

[Formula 123]

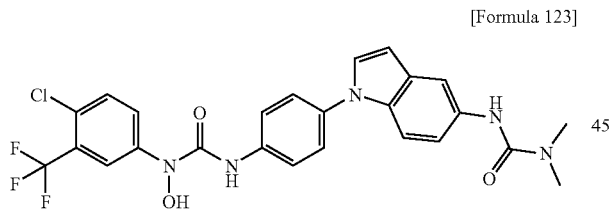

The title compound can be synthesized from 1-[4-(5-aminoindol-1-yl)phenyl]-3-(4-chloro-3-(trifluoromethyl)phenyl)-3-hydroxyurea hydrochloride and N,N-dimethyl-carbamic acid chloride by using the same techniques as in Example 41.

¹H-NMR (270 MHz, DMSO-d₆) δ (ppm): 2.92 (3H, s), 3.16 (3H, s), 4.66 (1H, br), 6.38 (1H, d, J=3.0 Hz), 6.56 (1H, dd, J=8.6, 2.0 Hz), 6.76 (1H, d, J=2.0 Hz), 7.26 (1H, d, J=8.6 Hz), 7.43 (1H, d, J=3.3 Hz), 7.50 (2H, d, J=8.9 Hz), 7.65 (2H, d, J=8.9 Hz), 7.75 (1H, d, J=8.9 Hz), 7.99 (1H, d, J=2.3 Hz), 9.55 (1H, s)

ESI (LC-MS positive mode) m/z 532 (M+H)

Example 85

Morpholine-4-carboxylic acid (1-{4-[3-(4-chloro-3-(trifluoromethyl)phenyl)-3-hydroxyureido]phenyl}-1H-indol-5-yl)amide (Table 1, Compound No. 85)

[Formula 124]

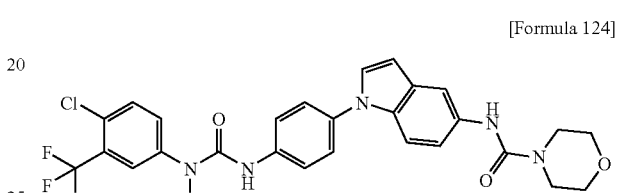

The title compound can be synthesized from 1-[4-(5-aminoindol-1-yl)phenyl]-3-(4-chloro-3-(trifluoromethyl)-phenyl)-3-hydroxyurea hydrochloride and 4-morpholinyl-carbamic acid chloride by using the same techniques as in Example 41.

¹H-NMR (270 MHz, DMSO-d₆) δ (ppm): 3.41 (4H, m), 3.63 (4H, m), 6.58 (1H, d, J=2.1 Hz), 7.22 (1H, d, J=8.9 Hz), 7.40-7.78 (6H, m), 7.85 (2H, d, J=8.9 Hz), 7.96 (1H, d, J=8.9 Hz), 8.19 (1H, d, J=2.0 Hz), 8.45 (1H, s), 9.78 (1H, s), 11.08 (1H, s)

ESI (LC-MS positive mode) m/z 574 (M+H)

Example 86

(2S,3S)-2-Amino-3-methylpentanoic acid (1-{4-[3-(4-chloro-3-(trifluoromethyl)phenyl)-3-hydroxyureido]-phenyl}-1H-indol-5-yl)amide (Table 1, Compound No. 86)

Step A

Preparation of [1-(1-{4-[3-(4-chloro-3-(trifluoromethyl)phenyl)-3-hydroxyureido]phenyl}-1H-indol-5-ylcarbamoyl)-(2S,3S)-2-methylbutyl]carbamic acid tert-butyl ester

[Formula 125]

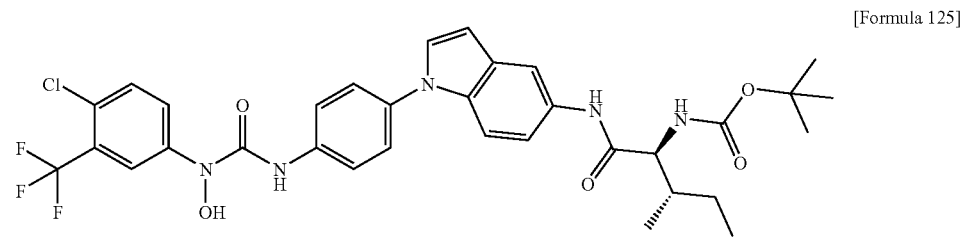 [SMILES: CC[C@H](C)[C@H](NC(=O)OC(C)(C)C)C(=O)Nc1ccc2c(ccn2-c2ccc(NC(=O)N(O)c3ccc(Cl)c(C(F)(F)F)c3)cc2)c1]

In a mixed solution of 0.2 mL of methanol and 2.0 mL of methylene chloride, 80 mg (0.16 mmol) of 1-[4-(5-amino-indol-1-yl)phenyl]-3-(4-chloro-3-(trifluoromethyl)phenyl)-3-hydroxyurea hydrochloride was dissolved, and 59 mg (0.18 mmol) of tert-butyoxycarbonyl-L-isoleucine N-hydroxysuccinimide ester and 0.5 mL of pyridine were added thereto and the mixture solution was stirred at room temperature for 15 hours. The reaction solution was concentrated under reduced pressure, and then the residue was partitioned between ethyl acetate and water, and the organic layer was washed with a saturated sodium chloride solution. The organic layer was dried and then concentrated under reduced pressure, and the residue was purified by Megabond Elute Silica Gel (2 g, n-hexane:ethyl acetate=1:1) to obtain 15.0 mg (14%) of [1-(1-{4-[3-(4-chloro-3-(trifluoromethyl)phenyl)-3-hydroxyureido]-phenyl}-1H-indol-5-ylcarbamoyl)-(2S,3S)-2-methylbutyl]-carbamic acid tert-butyl ester as a white solid.

ESI (LC-MS positive mode) m/z 674 (M+H)

Step B

Preparation of (2S,3S)-2-amino-3-methylpentanoic acid (1-{4-[3-(4-chloro-3-(trifluoromethyl)phenyl)-3-hydroxyureido]phenyl}-1H-indol-5-yl)amide (Table 1, Compound No. 86)

[Formula 126]

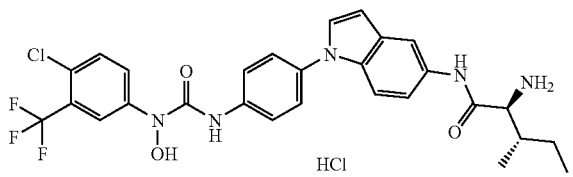

In 2 mL of a 4N hydrogen chloride ethyl acetate solution, 15.0 mg (14%) of [1-(1-{4-[3-(4-chloro-3-(trifluoromethyl)phenyl)-3-hydroxyureido]phenyl}-1H-indol-5-ylcarbamoyl)-(2S,3S)-2-methylbutyl]carbamic acid tert-butyl ester was dissolved and the solution was stirred under cooling with ice for one hour. The reaction solution was concentrated under reduced pressure, and then the residue was triturated with diethyl ether to obtain 7.0 mg (17%) of (2S,3S)-2-amino-3-methylpentanic acid (1-{4-[3-(4-chloro-3-(trifluoromethyl)phenyl)-3-hydroxy-ureido]phenyl}-1H-indol-5-yl)amide (Table 1, Compound No. 86) as a white solid.

$^1$H-NMR (270 MHz, DMSO-$d_6$) δ (ppm): 0.85-1.03 (6H, m), 1.63 (1H, m), 1.95 (1H, br), 3.85 (1H, br), 6.68 (1H, d, J=3.3 Hz), 7.32-7.95 (8H, m), 8.21 (1H, m), 9.73 (1H, d, J=6.9 Hz), 10.53 (1H, br), 11.19 (1H, d, J=3.3 Hz)

ESI (LC-MS positive mode) m/z 574 (M+H)

Example 87

(S)-2-Amino-N-(1-{4-[3-(4-chloro-3-(trifluoromethyl)phenyl)-3-hydroxyureido]phenyl}-1H-indol-5-yl)-3-methylbutylamide (Table 1, Compound No. 87)

[Formula 127]

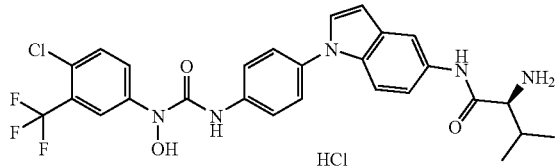

The title compound can be synthesized from 1-[4-(5-amonoindol-1-yl)phenyl]-3-(4-chloro-3-(trifluoromethyl)phenyl)-3-hydroxyurea hydrochloride and tert-butoxycarbonyl-L-valine N-hydroxysuccinimide ester by using the same techniques as in Example 86.

$^1$H-NMR (270 MHz, DMSO-$d_6$) δ (ppm): 1.02 (6H, d, J=7.0 Hz), 2.22 (1H, m), 3.83 (1H, br), 6.69 (1H, d, J=3.3 Hz), 7.40 (1H, dd, J=8.9, 2.0 Hz), 7.68 (1H, d, J=8.9 Hz), 7.75-7.95 (7H, m), 8.20 (1H, s), 8.27 (2H, br), 9.75 (1H, br), 10.55 (1H, br), 11.17 (1H, br)

ESI (LC-MS positive mode) m/z 560 (M+H)

Example 88

1-(4-Chloro-3-(trifluoromethyl)phenyl)-1-hydroxy-3-{4-[4-(2-(morpholin-4-yl)ethoxy)indol-1-yl]phenyl}-urea (Table 1, compound No. 88)

[Formula 128]

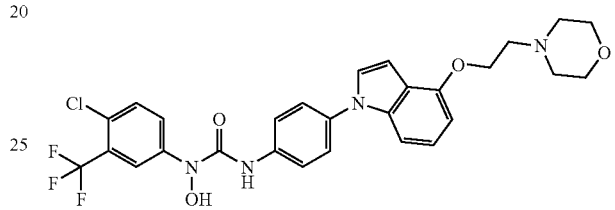

The title compound can be synthesized from N-(4-chloro-3-(trifluoromethyl)phenyl)hydroxylamine hydrochloride, 1H-indole-4-ol, 2-(morpholin-4-yl)ethanol and 4-fluoronitrobenzene in the same manner as in Example 62.

$^1$H-NMR (270 MHz, DMSO-$d_6$) δ (ppm): 2.55 (4H, br), 2.80 (2H, t, J=5.4 Hz), 3.60 (4H, t, J=4.6 Hz), 4.25 (2H, t, J=5.7 Hz), 6.66 (2H, m), 7.11 (2H, m), 7.50 (3H, m), 7.70 (1H, d, J=8.9 Hz), 7.86 (2H, d, J=8.9 Hz), 8.20 (1H, d, J=2.7 Hz), 9.79 (1H, s), 11.10 (1H, s)

ESI (LC-MS positive mode) m/z 575 (M+H)

Example 89

Synthesis of 1-(4-chloro-3-(trifluoromethyl)phenyl)-3-[4-(5-oxy-imidazo[4,5-c]pyridin-1-yl)phenyl]urea (Table 1, Compound No. 89)

[Formula 129]

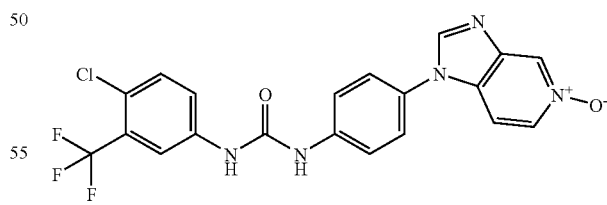

In 10 mL of acetic acid, 540 mg (1.25 mmol) of 1-(4-chloro-3-(trifluoromethyl)phenyl)-3-(4-imidazo[4,5-c]-pyridin-1-ylphenyl)urea prepared in Example 1 was dissolved, and 3 mL of a 30% hydrogen peroxide aqueous solution was added thereto and the mixture solution was stirred at 50° C. for one day. The solvent was distilled under reduced pressure, and the residue was separated by a silica gel column (Si-10, a product of Kusano Co., Ltd., column 30 cm, dichloromethane:methanol=9:1 to 4:1) to obtain 282 mg (53%) of 1-(4-chloro-3-(trifluoromethyl)phenyl)-3-[4-(5-oxy-imidazo[4,5-c]pyridin-1-yl)phenyl]urea (Table 1, Compound No. 89) as a white solid.

$^1$H-NMR (270 MHz, DMSO-d$_6$) δ (ppm): 7.60-7.78 (7H, m), 8.13-8.15 (2H, m), 8.77 (1H, s), 8.83 (1H, d, J=1.3 Hz), 9.20 (1H, s), 9.29 (1H, s)

ESI (LC-MS positive mode) m/z 448 (M+H)

Example 90

Synthesis of 1-[4-(4-chloro-imidazo[4,5-c]pyridin-1-yl)phenyl]-3-(4-chloro-3-(trifluoromethyl)phenyl)urea (Table 1, Compound No. 90)

Step A

Preparation of 1-(4-nitrophenyl)-1H-imidazo[4,5-c]-pyridine 5-oxide

[Formula 130]

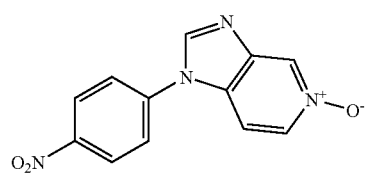

In 15 mL of acetic acid, 483 mg (2.01 mmol) of 1-(4-nitrophenyl)-1H-imidazo[4,5-c]pyridine prepared in Step A of Example 1 was dissolved, and 2 mL of a 30% hydrogen peroxide aqueous solution was added thereto and the mixture solution was stirred at 50° C. for 14 hours. The solvent was distilled under reduced pressure, and the obtained residue was separated by a silica gel column (Si-10, a product of Kusano Co., Ltd., column 30 cm, dichloromethane:methanol=9:1) to obtain 298 mg (57%) of 1-(4-nitrophenyl)-1H-imidazo[4,5-c]pyridine 5-oxide as a pale yellow solid.

$^1$H-NMR (270 MHz, DMSO-d$_6$) δ (ppm): 7.80 (1H, dd, J=0.6, 7.2 Hz), 8.05 (2H, m), 8.20 (1H, dd, J=1.7, 7.0 Hz), 8.45 (2H, m), 8.87 (1H, s), 8.97 (1H, s)

Step B

Preparation of 4-chloro-1-(4-nitrophenyl)-1H-imidazo-[4,5-c]pyridine

[Formula 131]

In 5 mL of phosphorus oxychloride, 42 mg (0.164 mmol) of 1-(4-nitrophenyl)-1H-imidazo[4,5-c]pyridine 5-oxide was dissolved and the solution was stirred at 80° C. for 14 hours. Excess reagent was distilled under reduced pressure, and the residue was partitioned between ethyl acetate (10 mL×2) and a sodium hydrogencarbonate aqueous solution (10 mL). The combined organic layers were washed with a saturated sodium chloride solution, dried on anhydrous sodium sulfate and then concentrated under reduced pressure. The residue was separated by a silica gel column (Si-10, a product of Kusano Co., Ltd., column 30 cm, dichloromethane:methanol=19:1) to obtain 45 mg (quantitative) of 4-chloro-1-(4-nitrophenyl)-1H-imidazo-[4,5-c]pyridine as a pale yellow solid.

$^1$H-NMR (270 MHz, CDCl$_3$) δ (ppm): 7.48 (1H, d, J=5.6 Hz), 7.70-7.80 (3H, m), 8.30 (1H, s), 8.36 (1H, d, J=5.6 Hz), 8.56 (2H, m)

ESI (LC-MS positive mode) m/z 275 (M+H)

Step C

Preparation of 1-[4-(4-chloro-imidazo[4,5-c]pyridin-1-yl)phenyl]-3-(4-chloro-3-(trifluoromethyl)phenyl)urea (Table 1, Compound No. 90)

[Formula 132]

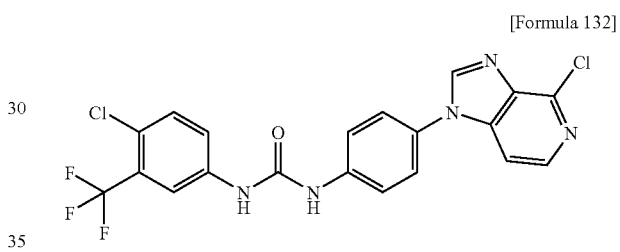

In 50% acetic acid, 41 mg (0.150 mmol) of 4-chloro-1-(4-nitrophenyl)-1H-imidazo[4,5-c]pyridine prepared in Step B was dissolved, and 42 mg (0.75 mmol) of iron powder was added thereto, and the mixture solution was stirred at 50° C. for one hour. The solvent was distilled, and the obtained residue was partitioned between ethyl acetate (10 mL×2) and a sodium hydrogencarbonate aqueous solution (10 mL). The combined organic layers were washed with a saturated sodium chloride solution, dried on anhydrous sodium sulfate, and then concentrated under reduced pressure to obtain 1-(4-aminophenyl)-4-chloroimdazo-1H-[4,5-c]pyridine as a crude product. In 10 mL of dichloromethane, the crude product without further purification was dissolved, and 31 mg (0.15 mmol) of 4-chloro-3-trifluoromethyl)phenyl isocyanate was added thereto and the mixture solution was stirred at room temperature for two hours. The solvent was distilled under reduced pressure, and the obtained residue was separated by a silica gel column (Si-10, a product of Kusano Co., Ltd., column 30 cm, dichloromethane:methanol=19:1), and the obtained crude product was recrystallized from methanol to obtain 44 mg (63%) of 1-[4-(4-chloro-imidazo[4,5-c]pyridin-1-yl)phenyl]-3-(4-chloro-3-(trifluoromethyl)phenyl)urea (Table 1, Compound No. 90) as a colorless crystal.

$^1$H-NMR (270 MHz, DMSO-d$_6$) δ (ppm): 7.60-7.67 (5H, m), 7.70-7.75 (2H, m), 8.14 (1H, d, J=2.0 Hz), 8.23 (1H, d, J=5.6 Hz), 8.79 (1H, s), 9.19 (1H, s), 9.29 (1H, s)

ESI (LC-MS positive mode) m/z 467 (M+H)

Example 91

1-(4-Chloro-3-(trifluoromethyl)phenyl)-3-[4-(4-cyanoimidazo[4,5-c]pyridin-1-yl)phenyl]urea (Table 1, Compound No. 91)

[Formula 133]

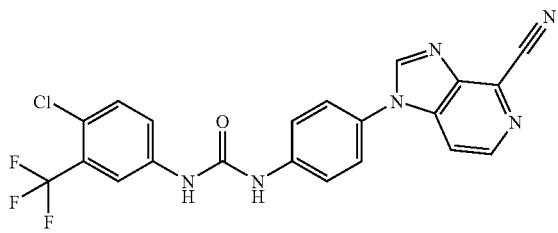

In 10 mL of acetonitrile, 112 mg (0.25 mmol) of 1-(4-chloro-3-(trifluoromethyl)phenyl)-3-[4-(5-oxy-imidazo-[4,5-c]pyridin-1-yl)phenyl]urea prepared in Example 89 was dissolved, and 104 µL (0.75 mmol) of trimethylsilylcyanide and 20 µl (0.75 mmol) of 1,8-diazabicyclo[5.4.0]undecene were added thereto and the mixture solution was stirred at 80° C. for six hours. The solvent was distilled under reduced pressure, and the residue was separated by a silica gel column (Si-10, a product of Kusano Co., Ltd., column 30 cm, dichloromethane:methanol=9:1 to 4:1) to obtain 15 mg (15%) of 1-(4-chloro-3-(trifluoromethyl)-phenyl)-3-[4-(4-cyanoimidazo[4,5-c]pyridin-1-yl)phenyl]-urea (Table 1, Compound No. 91) as a white solid.

$^1$H-NMR (270 MHz, DMSO-d$_6$) δ (ppm): 7.62-7.67 (4H, m), 7.70-7.75 (2H, m), 7.98 (1H, d, J=7.3 Hz), 8.13 (1H, d, J=2.3 Hz), 8.59 (1H, d, J=5.6 Hz), 8.99 (1H, s), 9.19 (1H, s), 9.29 (1H, s)

ESI (LC-MS positive mode) m/z 457 (M+H)

Example 92

1-{4-[3-(4-Chloro-3-(trifluoromethyl)phenyl)ureido]-phenyl}-1H-imidazo[4,5-c]pyridine-4-carboxylic acid (2-(dimethylamino)ethyl)amide (Table 1, Compound No. 92)

Step A

Preparation of 1-(4-nitrophenyl)-1H-imidazo[4,5-c]-pyridine-4-carbonitrile

[Formula 134]

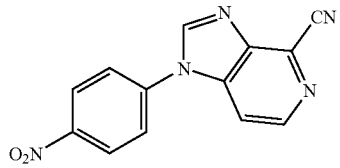

In a mixed solvent of 1 mL of dimethylformamide and 2 mL of dioxane, 100 mg (0.39 mmol) of 1-(4-nitrophenyl)-1H-imidazo[4,5-c]pyridine 5-oxide prepared in Step A of Example 90 was dissolved, and 310 µL (0.78 mmol) of trimethylsilylcyanide and 144 µL (0.78 mmol) of N,N-dimethylcarbamoyl chloride were added thereto and the mixture solution was stirred at 90° C. for 14 hours. The solvent was distilled, and the residue was partitioned between ethyl acetate (10 mL×2) and a sodium hydrogencarbonate aqueous solution (10 mL). The combined organic layers was washed with a saturated sodium chloride solution, dried on anhydrous sodium sulfate and then concentrated under reduced pressure. The residue was triturated with ethyl acetate to obtain 78 mg (75%) of 1-(4-nitrophenyl)-1H-imidazo[4,5-c]pyridine-4-carbonitrile as a pale yellow solid.

$^1$H-NMR (270 MHz, DMSO-d$_6$) δ (ppm): 8.07-8.13 (2H, m), 8.14-8.16 (1H, m), 8.47-8.53 (2H, m), 8.67 (1H, d, J=5.5 Hz), 9.20 (1H, s)

ESI (LC-MS positive mode) m/z 266 (M+H)

Step B

Preparation of 1-(4-nitrophenyl)-1H-imidazo[4,5-c]-pyridine-4-carboxylic acid methyl ester

[Formula 135]

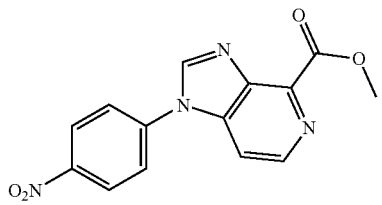

In 10 mL of methanol, 74 mg (0.28 mmol) of 1-(4-nitrophenyl)-1H-imidazo[4,5-c]pyridine-4-carbonitrile prepared in Step A was dissolved, and 2 mL of a 4N hydrogen chloride dioxane solution was added thereto, and the mixture solution was refluxed under heating with stirring for four hours. The solvent was distilled under reduced pressure, and the residue was partitioned between ethyl acetate (10 mL×2) and a sodium hydrogencarbonate aqueous solution (10 mL). The combined organic layers was washed with a saturated sodium chloride solution, dried on anhydrous sodium sulfate and then concentrated under reduced pressure. The solvent was distilled and the residue was separated by Megabond Elute Silica Gel (2 g, dichloromethane:methanol=30:1) to obtain 34 mg (41%) of 1-(4-nitrophenyl)-1H-imidazo[4,5-c]pyridine-4-carboxylic acid methyl ester as a white solid.

$^1$H-NMR (270 MHz, DMSO-d$_6$) δ (ppm): 4.17 (3H, s), 7.70-7.80 (3H, m), 8.40 (1H, s), 8.52-8.57 (2H, m), 8.72-8.74 (1H, d, J=6.3 Hz)

ESI (LC-MS positive mode) m/z 299 (M+H)

Step C

Preparation of 1-(4-nitrophenyl)-1H-imidazo[4,5-c]-pyridine-4-carboxylic acid (2-(dimethylamino)ethyl) amide

[Formula 136]

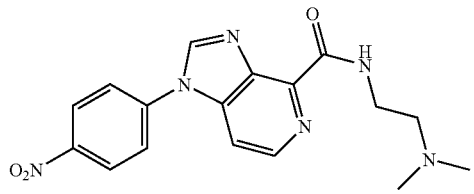

In 5 mL of methanol, 11 mg (0.037 mmol) of 1-(4-nitrophenyl)-1H-imidazo[4,5-c]pyridine-4-carboxylic acid methyl ester prepared in Step B was dissolved, and 100 µL of N,N-dimethylethylenediamine was added thereto and the solution was refluxed under heating with stirring for two hours. The solvent was distilled under reduced pressure, and the residue was separated by Megabond Elute Silica Gel (1 g, dichloromethane:methanol=30:1 to 4:1) to obtain 7.3 mg (51%) of 1-(4-nitrophenyl)-1H-imidazo[4,5-c]pyridine-4-carboxylic acid (2-(dimethylamino)ethyl)amide as a white solid.

¹H-NMR (270 MHz, CDCl₃) δ (ppm): 2.30 (6H, s), 2.65 (2H, t, J=6.3 Hz), 3.73 (2H, t, J=5.9 Hz), 7.62 (1H, d, J=5.3 Hz), 7.73-7.77 (2H, m), 8.39 (1H, s), 8.50-8.54 (2H, m), 8.64 (1H, d, J=5.6 Hz), 8.90 (1H, br.s)

ESI (LC-MS positive mode) m/z 355 (M+H)

Step D

Preparation of 1-{4-[3-(4-chloro-3-(trifluoromethyl) phenyl)ureido]phenyl}-1H-imidazo[4,5-c]pyridine-4-carboxylic acid (2-(dimethylamino)ethyl)amide (Table 1, Compound No. 92)

[Formula 137]

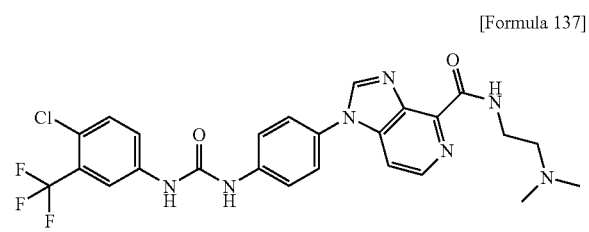 [SMILES: CN(C)CCNC(=O)c1nccc2c1ncn2-c1ccc(NC(=O)Nc2ccc(Cl)c(C(F)(F)F)c2)cc1]

The title compound can be synthesized from 1-(4-nitrophenyl)-1H-imidazo[4,5-c]pyridine-4-carboxylic acid (2-(dimethylamino)ethyl)amide and 4-chloro-3-(trifluoromethyl) phenyl isocyanate in the same manner as in Steps B and C of Example 1.

¹H-NMR (270 MHz, CD₃OD) δ (ppm): 2.39 (6H, s), 2.73 (2H, t, J=6.6 Hz), 3.73 (2H, t, J=6.6 Hz), 7.50-7.70 (4H, m), 7.73-7.77 (3H, m), 8.04 (1H, m), 8.54 (1H, m), 8.66 (1H, s)

ESI (LC-MS positive mode) m/z 546 (M+H)

Example 93

1-{4-[3-(4-Chloro-3-(trifluoromethyl)phenyl)ureido]-phenyl}-1H-imidazo[4,5-c]pyridine-4-carboxylic acid methylamide (Table 1, Compound No. 93)

[Formula 138]

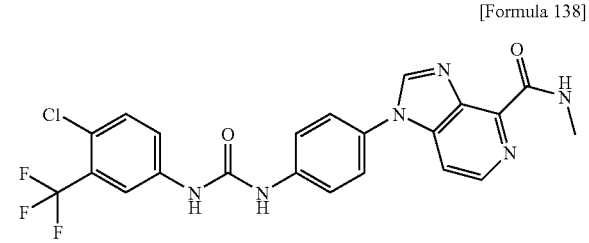 [SMILES: CNC(=O)c1nccc2c1ncn2-c1ccc(NC(=O)Nc2ccc(Cl)c(C(F)(F)F)c2)cc1]

The title compound can be synthesized from 1-(4-nitrophenyl)-1H-imidazo[4,5-c]pyridine-4-carboxylic acid methyl ester, methylamine and 4-chloro-3-(trifluoromethyl)phenyl isocyanate in the same manner as in Steps C and D of Example 92.

¹H-NMR (270 MHz, DMSO-d₆) δ (ppm): 2.93 (3H, d, J=4.6 Hz), 7.62-7.80 (7H, m), 8.14 (1H, d, J=2.0 Hz), 8.49 (1H, d, J=5.6 Hz), 8.83 (1H, s), 9.02 (1H, br.q, J=4.6 Hz), 9.21 (1H, s), 9.30 (1H, s)

ESI (LC-MS positive mode) m/z 489 (M+H)

Example 94

1-{4-[3-(4-Chloro-3-(trifluoromethyl)phenyl)ureido]-phenyl}-N-methyl-1H-imidazo[4,5-c]pyridine-4-carboxamidine hydrochloride (Table 1, Compound No. 94)

[Formula 139]

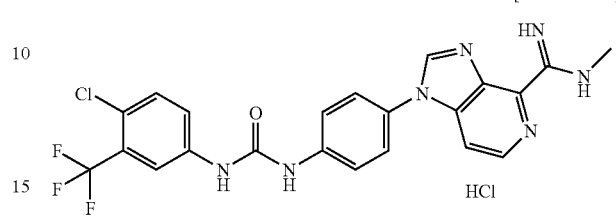

In 5 mL of methanol, 12 mg (0.026 mmol) of 1-(4-chloro-3-(trifluoromethyl)phenyl)-3-[4-(4-cyanoimidazo-[4,5-c] pyridin-1-yl)phenyl]urea prepared in Example 91 was dissolved, and one drop (a catalytic amount) of a 28% methanol solution of sodium methylate was added thereto and the solution was stirred at room temperature for six hours. The reaction solution was neutralized with one drop of acetic acid, and then 50 μL of a dimethylamine 40% methanol solution was added thereto and the mixture solution was further stirred at room temperature for 14 hours. The solvent was distilled under reduced pressure, and the residue was separated by reversed phase high-pressure liquid chromatography (C18 Column, acetonitrile:water=55:45, 0.05% trifluoroacetic acid). The fraction containing a target product was concentrated, and then trifluoroacetic acid was replaced with hydrochloric acid to obtain 4.2 mg (30%) of 1-{4-[3-(4-chloro-3-(trifluoromethyl)phenyl)ureido]phenyl}-N-methyl-1H-imidazo[4,5-c]pyridine-4-carboxamidine hydrochloride (Table 1, Compound No. 94) as a white solid.

¹H-NMR (270 MHz, DMSO-d₆) δ (ppm): 3.20 (3H, d, J=5.2 Hz), 7.63-7.8 (6H, m), 8.05 (1H, d, J=5.6 Hz), 8.13 (1H, s), 8.68 (1H, d, J=5.6 Hz), 9.16 (1H, s), 9.68 (1H, s), 9.73 (1H, s), 9.86 (1H, s), 9.89 (1H, s), 10.34 (1H, s)

ESI (LC-MS positive mode) m/z 457 (M+H)

Example 95

N'-(9-(4-[3-(4-Chloro-3-(trifluoromethyl)phenyl) ureido]phenyl)-9H-purin-6-yl)-N,N-dimethylformamidine hydrochloride (Table 1, Compound No. 95)

[Formula 140]

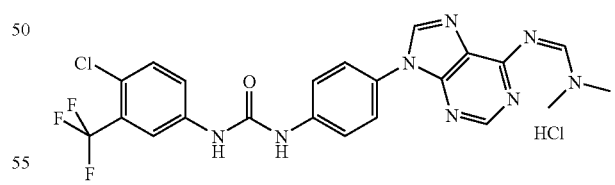

In 10 mL of pyridine, 463 mg (0.957 mmol) of 1-[4-(6-amino-purin-9-yl)phenyl]-3-(4-chloro-3-(trifluoromethyl) phenyl)urea hydrochloride was dissolved, and 455 mg (3.83 mmol) of dimethylformamide dimethylacetal was added thereto and the mixture solution was stirred at room temperature for 16 hours. The reaction solution was concentrated under reduced pressure, and then the residue was triturated with ethyl acetate and collected by filtration, and vacuum dried. The white solid was dissolved in 10 mL of methanol and 4N hydrochloric acid and concentrated under reduced pressure. The residue was triturated with ethyl acetate, collected by filtration, and then vacuum dried to obtain 580 mg (quantitative) of N'-(9-{4-[3-(4-chloro-3-(trifluoromethyl)phenyl)ureido]phenyl}-9H-purin-6-yl)-N,N-dimethylformamidine hydrochloride (Table 1, Compound No. 95) as a white solid.

$^1$H-NMR (270 MHz, DMSO-d$_6$) δ (ppm): 3.30 (3H, s), 3.45 (3H, s), 4.30 (1H, br.s), 7.60-7.80 (6H, q, J=7.2 Hz), 8.14 (1H, m), 8.75 (1H, s), 9.02 (1H, s), 9.63 (1H, s), 10.09 (1H, s), 10.38 (1H, s)

ESI (LC-MS positive mode) m/z 503 (M+H)

Example 96

(S)-2-Amino-4-methyl-pentanoic acid (9-{4-[3-(4-chloro-3-(trifluoromethyl)phenyl)ureido]phenyl}-9H-purin-6-yl)amide hydrochloride (Table 1, Compound No. 96)

Step A

Preparation of [1-(9-{4-[3-(4-chloro-3-(trifluoromethyl)phenyl)ureido]phenyl}-9H-purin-6-ylcarbonyl)-3-methylbutyl]carbamic acid tert-butyl ester

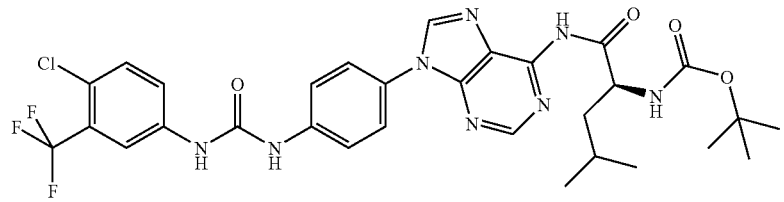

In 15 ml of tetrahydrofuran, 300 mg (0.620 mmol) of 1-[4-(6-aminopurin-9-yl)phenyl]-3-(4-chloro-3-(trifluoromethyl)phenyl)urea hydrochloride was dissolved, and 771 mg (3.10 mmol) of tert-butoxycarbonyl-L-leucine, 1.60 g (3.10 mmol) of (benzotriazolyloxy)tripyrrolidino-phosphonium hexa-fluorophosphate (PyBOP) and 0.54 mL (3.10 mmol) of Hunig's base were added thereto and the mixture solution was stirred at room temperature for three days. The reaction solution was concentrated under reduced pressure, and then the residue was partitioned between ethyl acetate and water. The organic phase was washed with a saturated sodium chloride solution, dried, and then concentrated under reduced pressure. The residue was purified by Megabond Elute Silica Gel (10 g, ethyl acetate), to obtain 320 mg (78%) of [1-(9-{4-[3-(4-chloro-3-(trifluoromethyl)phenyl)ureido]phenyl}-9H-purin-6-ylcarbonyl)-3-methyl-butyl]carbamic acid tert-butyl ester as a white solid.

ESI (LC-MS positive mode) m/z 661 (M+H)

Step B

Preparation of (S)-2-amino-4-methyl-pentanoic acid (9-(4-[3-(4-chloro-3-(trifluoromethyl)phenyl)ureido]-phenyl)-9H-purin-6-yl)amide hydrochloride (Table 1, Compound No. 96)

[Formula 142]

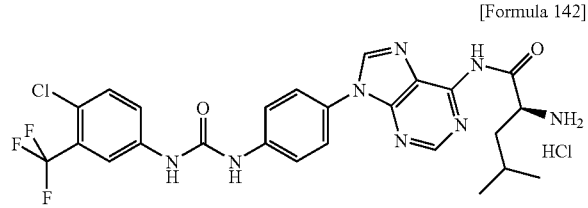 [SMILES: CC(C)C[C@H](N)C(=O)Nc1ncnc2c1ncn2-c1ccc(NC(=O)Nc2ccc(Cl)c(C(F)(F)F)c2)cc1 ; "HCl"]

In 5 mL of a 4N hydrogen chloride ethyl acetate solution, 310 mg (0.47 mmol) of [1-(9-{4-[3-(4-chloro-3-(trifluoromethyl)phenyl)ureido]phenyl}-9H-purin-6-ylcarbonyl)-3-methylbutyl]carbamic acid tert-butyl ester was dissolved and the solution was stirred at room temperature for two hours. The reaction solution was concentrated under reduced pressure, and the residue was triturated with ethyl acetate, collected by filtration, and then vacuum dried to obtain 280 mg (quantitative) of (S)-2-amino-4-methyl-pentanoic acid (9-{4-[3-(4-chloro-3-(trifluoromethyl)phenyl)ureido]phenyl}-9H-purin-6-yl)amide hydrochloride (Table 1, Compound No. 96).

$^1$H-NMR (270 MHz, DMSO-d$_6$) δ (ppm): 0.90 (3H, d, J=4.6 Hz), 0.96 (3H, d, J=4.0 Hz), 1.60-1.65 (1H, m), 1.70-1.80 (2H, m), 4.40 (1H, br.s), 7.65-7.83 (6H, m), 8.14 (1H, d, J=2.3 Hz), 8.30-8.37 (3H, m), 8.75 (1H, s), 8.93 (1H, br.s), 9.38 (1H, br.s), 9.55 (1H, br.s)

ESI (LC-MS positive mode) m/z 561 (M+H)

[Formula 141]

Example 97

2-Amino-N-(9-{4-[3-(4-chloro-3-(trifluoromethyl)phenyl)ureido]phenyl}-9H-purin-6-yl)acetamide hydrochloride (Table 1, Compound No. 97)

[Formula 143]

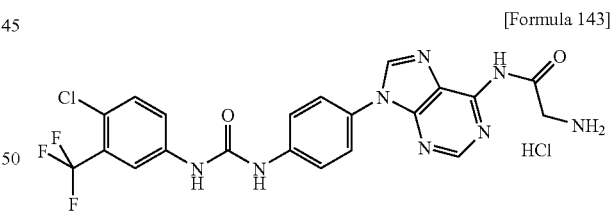

The title compound can be synthesized from 1-[4-(6-aminopurin-9-yl)phenyl]-3-(4-chloro-3-(trifluoromethyl)-phenyl)urea hydrochloride and tert-butoxycarbonyl-glycine by using the same method as in Example 96.

$^1$H-NMR (270 MHz, DMSO-d$_6$) δ (ppm): 4.17 (2H, m), 7.65-7.84 (6H, m), 8.14 (1H, d, J=2.0 Hz), 8.20-8.25 (3H, m), 8.75 (1H, s), 8.92 (1H, s)

ESI (LC-MS positive mode) m/z 505 (M+H)

Example 98

N-(9-{4-[3-(4-Chloro-3-(trifluoromethyl)phenyl)ureido]phenyl}-9H-purin-6-yl)-2-methylaminoacetamide hydrochloride (Table 1, Compound No. 98)

[Formula 144]

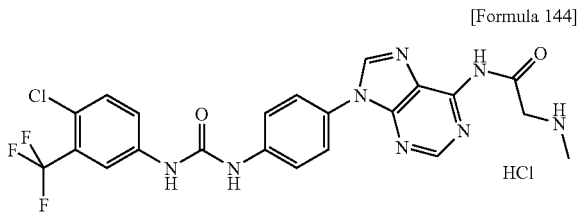 [SMILES: CNCC(=O)Nc1ncnc2c1ncn2-c1ccc(NC(=O)Nc2ccc(Cl)c(C(F)(F)F)c2)cc1 ; Cl]

The titled compound can be synthesized from 1-[4-(6-aminopurin-9-yl)phenyl]-3-(4-chloro-3-(trifluoromethyl)phenyl)urea hydrochloride and tert-butoxycarbonyl-sarcosine by using the same method as in Example 96.

$^1$H-NMR (270 MHz, DMSO-d$_6$) δ (ppm): 3.30 (3H, br.s), 4.87 (2H, br.s), 7.65-7.84 (6H, m), 8.14 (1H, d, J=2.3 Hz), 8.87 (1H, s), 8.93 (1H, s), 9.48 (1H, br.s), 9.53 (1H, br.s), 9.67 (1H, br.s)

ESI (LC-MS positive mode) m/z 519 (M+H)

Example 99

(S)-Pyrrolidine-2-carboxylic acid (9-{4-[3-(4-chloro-3-(trifluoromethyl)phenyl)ureido]phenyl}-9H-purin-6-yl)amide hydrochloride (Table 1, compound No. 99)

[Formula 145]

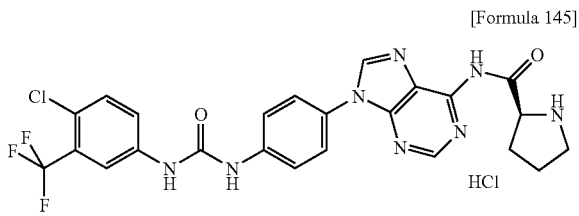 [SMILES: O=C(Nc1ccc(-n2cnc3c(NC(=O)[C@@H]4CCCN4)ncnc32)cc1)Nc1ccc(Cl)c(C(F)(F)F)c1 ; Cl]

The title compound can be synthesized from 1-[4-(6-aminopurin-9-yl)phenyl]-3-(4-chloro-3-(trifluoromethyl)phenyl)urea hydrochloride and tert-butoxycarbonyl-L-proline by using the same method as in Example 96.

$^1$H-NMR (270 MHz, DMSO-d$_6$) δ (ppm): 2.53-2.58 (2H, m), 2.62-2.68 (2H, m), 3.83-3.85 (1H, m), 4.34-4.36 (2H, m), 7.64-7.84 (6H, m), 8.14 (1H, d, J=2.3 Hz), 8.77 (1H, s), 8.93 (1H, s), 8.95 (1H, br.s), 9.55 (1H, br.s), 9.77 (1H, br.s)

ESI (LC-MS positive mode) m/z 545 (M+H)

Example 100

(S)-2-Amino-N-(9-{4-[3-(4-chloro-3-(trifluoromethylphenyl)ureido)phenyl]-9H-purin-6-yl}propionamide hydrochloride (Table 1, Compound No. 100)

[Formula 146]

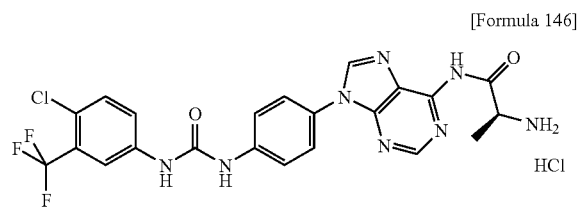 [SMILES: C[C@H](N)C(=O)Nc1ncnc2c1ncn2-c1ccc(NC(=O)Nc2ccc(Cl)c(C(F)(F)F)c2)cc1 ; Cl]

The title compound can be synthesized from 1-[4-(6-aminopurin-9-yl)phenyl]-3-(4-chloro-3-(trifluoromethyl)phenyl)urea hydrochloride and tert-butoxycarbonyl-L-alanine by using the same method as in Example 96.

$^1$H-NMR (270 MHz, DMSO-d$_6$) δ (ppm): 1.54 (3H, d, J=6.9 Hz), 4.4 (1H, br.s), 7.65-7.83 (6H, m), 8.14 (1H, d, J=2.3 Hz), 8.30-8.37 (3H, m), 8.79 (1H, s), 8.93 (1H, s), 8.95 (1H, br.s), 9.52 (1H, br.s), 9.72 (1H, br.s)

ESI (LC-MS positive mode) m/z 519 (M+H)

Example 101

(S)-2-Amino-N-(9-{4-[3-(4-chloro-3-(trifluoromethyl)phenyl)ureido]phenyl}-9H-purin-6-yl)-3,3-dimethylbutylamide hydrochloride (Table 1, Compound No. 101)

[Formula 147]

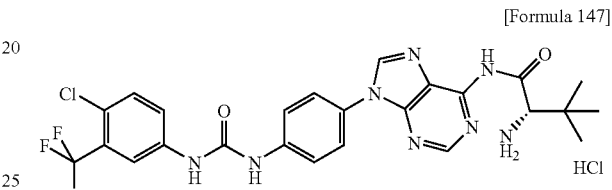

The title compound can be synthesized from 1-[4-(6-aminopurin-9-yl)phenyl]-3-(4-chloro-3-(trifluoromethyl)phenyl)urea hydrochloride and tert-butoxycarbonyl-L-tert-butylglycine by using the same method as in Example 96.

$^1$H-NMR (270 MHz, DMSO-d$_6$) δ (ppm): 1.00 (9H, s), 4.40 (1H, br.s), 7.65-7.80 (6H, m), 8.14 (1H, d, J=2.0 Hz), 8.30-8.37 (3H, m), 8.80 (1H, s), 8.92 (1H, s)

ESI (LC-MS positive mode) m/z 561 (M+H)

Example 102

(R)-2-Amino-N-(9-{4-[3-(4-chloro-3-(trifluoromethyl)phenyl)ureido]phenyl}-9H-purin-6-yl)-3-methylbutylamide hydrochloride (Table 1, Compound No. 102)

[Formula 148]

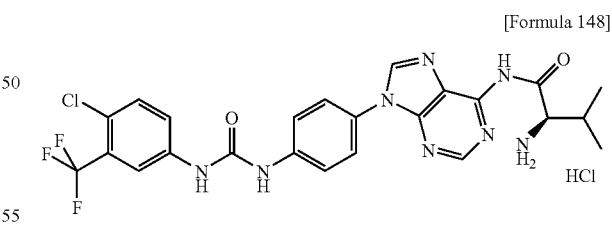

The titled compound can be synthesized from 1-[4-(6-amino-purin-9-yl)phenyl]-3-(4-chloro-3-(trifluoromethyl)phenyl)urea hydrochloride and tert-butoxycarbonyl-D-valine by using the same method as in Example 96.

$^1$H-NMR (270 MHz, DMSO-d$_6$) δ (ppm): 1.07 (3H, d, J=6.9 Hz), 1.13 (3H, d, J=6.9 Hz), 2.30-2.35 (1H, m), 4.15-4.20 (1H, m), 7.66-7.84 (6H, m), 8.14 (1H, d, J=2.3 Hz), 8.30-8.40 (3H, m), 8.79 (1H, s), 8.92 (1H, s), 9.51 (1H, br.s), 9.70 (1H, br.s), 11.48 (1H, br.s)

ESI (LC-MS positive mode) m/z 547 (M+H)

Example 103

(S)-4-Amino-4-(9-{4-[3-(4-chloro-3-(trifluoromethyl)phenyl)ureido]phenyl}-9H-purin-6-ylcarbamoyl)butanoic acid hydrochloride (Table 1, Compound No. 103)

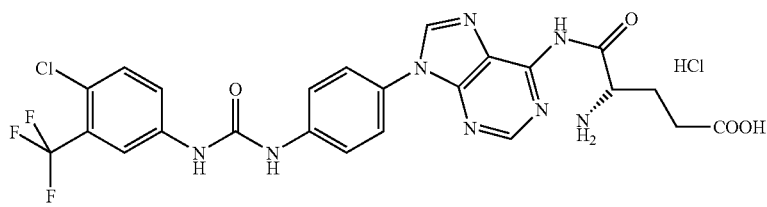

[Formula 149]

The title compound can be synthesized from 1-[4-(6-aminopurin-9-yl)phenyl]-3-(4-chloro-3-(trifluoromethyl)phenyl)urea hydrochloride and tert-butoxycarbonyl-L-glutamic acid 5-tert-butyl ester by using the same method as in Example 96.

$^1$H-NMR (270 MHz, DMSO-d$_6$) δ (ppm): 2.53-2.58 (2H, m), 2.62-2.68 (2H, m), 3.83-3.85 (1H, m), 4.34-4.36 (2H, m), 7.64-7.84 (6H, m), 8.14 (1H, d, J=2.3 Hz), 8.79 (1H, s), 8.92 (1H, s), 9.33 (1H, br.s), 9.47 (1H, br.s)

ESI (LC-MS positive mode) m/z 577 (M+H)

Example 104

(S)-2-Amino-4-(9-{4-[3-(4-chloro-3-(trifluoromethyl)phenyl)ureido]phenyl}-9H-purin-6-ylcarbamoyl)butanoic acid hydrochloride (Table 1, Compound No. 104)

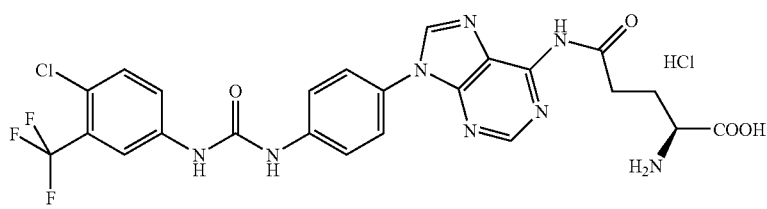

[Formula 150]

The title compound can be synthesized from 1-[4-(6-aminopurin-9-yl)phenyl]-3-(4-chloro-3-(trifluoromethyl)phenyl)urea hydrochloride and tert-butoxycarbonyl-L-glutamic acid 1-tert-butyl ester by using the same method as in Example 96.

ESI (LC-MS positive mode) m/z 577 (M+H)

Example 105

(S)-2,6-Diaminohexanoic acid (9-{4-[3-(4-chloro-3-(trifluoromethyl)phenyl)ureido]phenyl}-9H-purin-6-yl)amide hydrochloride (Table 1, Compound No. 105)

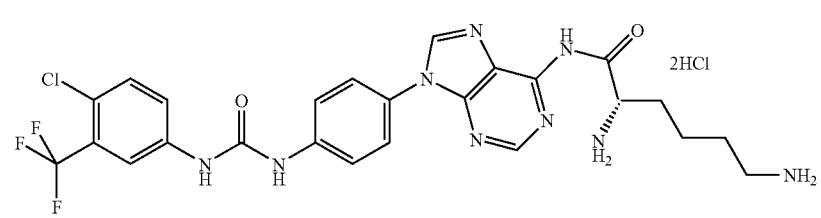

[Formula 151]

The title compound can be synthesized from 1-[4-(6-aminopurin-9-yl)phenyl]-3-(4-chloro-3-(trifluoromethyl)phenyl)urea hydrochloride and di-tert-butoxycarbonyl-L-lysine by using the same method as in Example 96.

ESI (LC-MS positive mode) m/z 576 (M+H)

Example 106

(S)-4-Methyl-2-(methylamino)pentanoic acid (9-(4-[3-(4-chloro-3-(trifluoromethyl)phenyl)ureido]phenyl)-9H-purin-6-yl)amide hydrochloride (Table 1, Compound No. 106)

[Formula 152]

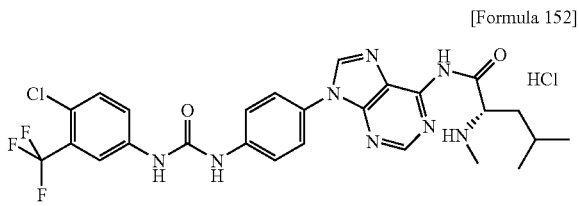 [SMILES: CN[C@@H](CC(C)C)C(=O)Nc1ncnc2c1ncn2-c1ccc(NC(=O)Nc2ccc(Cl)c(C(F)(F)F)c2)cc1 ; Cl]

The title compound can be synthesized from 1-[4-(6-aminopurin-9-yl)phenyl]-3-(4-chloro-3-(trifluoromethyl)phenyl)urea hydrochloride and N-methyl-tert-butoxycarbonyl-L-leucine by using the same method as in Example 96.

ESI (LC-MS positive mode) m/z 575 (M+H)

Example 107

Pentanoic acid (9-{4-[3-(4-chloro-3-(trifluoromethyl)phenyl)ureido]phenyl}-9H-purin-6-yl)amide (Table 1, Compound No. 107)

[Formula 153]

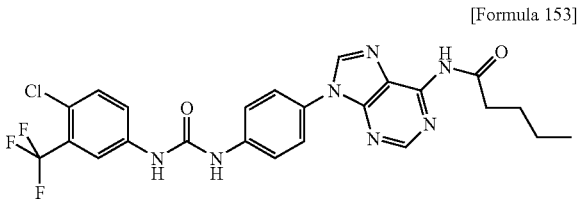 [SMILES: CCCCC(=O)Nc1ncnc2c1ncn2-c1ccc(NC(=O)Nc2ccc(Cl)c(C(F)(F)F)c2)cc1]

In 3 mL of pyridine, 30 mg (0.062 mmol) of 1-[4-(6-aminopurin-9-yl)phenyl]-3-(4-chloro-3-(trifluoromethyl)phenyl)urea hydrochloride was dissolved, and 35 mg (0.186 mmol) of valeric anhydride and 8 mg (0.062 mmol) of 4-(N,N-dimethylamino)pyridine were added thereto, and the mixture solution was stirred at room temperature for 14 hours. The reaction solution was concentrated under reduced pressure, and then the residue was partitioned between ethyl acetate and water, and the organic layer was washed with a saturated sodium chloride solution, dried and concentrated. The residues was purified by Megabond Elute Silica Gel (1 g, ethyl acetate) to obtain 22.2 mg (56%) of pentanoic acid (9-{4-[3-(4-chloro-3-(trifluoromethyl)phenyl)ureido]phenyl}-9H-purin-6-yl)amide (Table 1, Compound No. 107) as a white solid.

$^1$H-NMR (270 MHz, DMSO-$d_6$) δ (ppm): 0.93 (3H, t, J=7.0 Hz), 1.37 (2H, m), 1.61 (2H, m), 2.59 (2H, m), 7.64-7.83 (6H, m), 8.14 (1H, d, J=2.3 Hz), 8.68 (1H, s), 8.83 (1H, s), 9.16 (1H, s), 9.27 (1H, s), 10.73 (1H, br.s)

ESI (LC-MS positive mode) m/z 532 (M+H)

Example 108

N-(9-{4-[3-(4-Chloro-3-(trifluoromethyl)phenyl)ureido]phenyl}-9H-purin-6-yl)-2,2-dimethylpropionamide (Table 1, Compound No. 108)

[Formula 154]

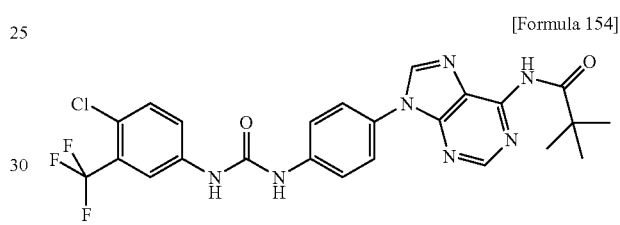

The title compound can be synthesized from 1-[4-(6-aminopurin-9-yl)phenyl]-3-(4-chloro-3-(trifluoromethyl)phenyl)urea hydrochloride and pivalic anhydride by using the same method as in Example 107.

$^1$H-NMR (270 MHz, DMSO-$d_6$) δ (ppm): 1.30 (9H, s), 7.60-7.82 (6H, m), 8.14 (1H, d, J=2.3 Hz), 8.76 (1H, s), 8.81 (1H, s), 9.17 (1H, s), 9.28 (1H, s), 10.24 (1H, br.s)

ESI (LC-MS positive mode) m/z 532 (M+H)

Example 109

N-(9-{4-[3-(4-Chloro-3-(trifluoromethyl)phenyl)ureido]phenyl}-9H-purin-6-yl)-2-[2-(2-methoxyethoxy)ethoxy]acetamide (Table 1, Compound No. 109)

[Formula 155]

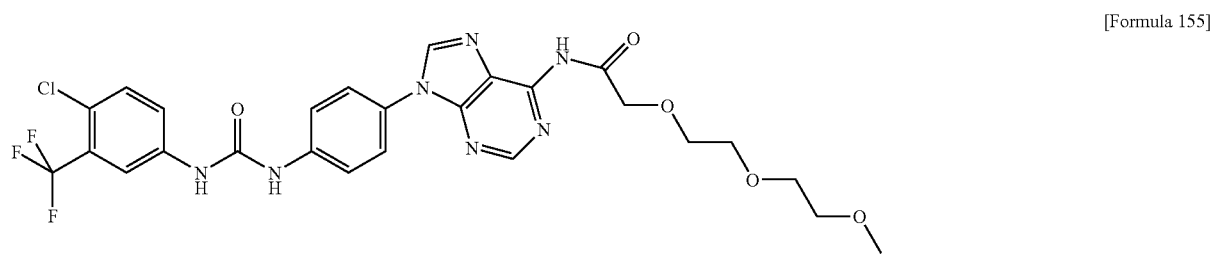 [SMILES: COCCOCCOCC(=O)Nc1ncnc2c1ncn2-c1ccc(NC(=O)Nc2ccc(Cl)c(C(F)(F)F)c2)cc1]

The title compound can be synthesized from 1-[4-(6-aminopurin-9-yl)phenyl]-3-(4-chloro-3-(trifluoromethyl)phenyl)urea hydrochloride and 2-[2-(2-methoxyethoxy)ethoxy]acetyl chloride by using the same method as in Example 107.

¹H-NMR (270 MHz, DMSO-d₆) δ (ppm): 3.20 (2H, s), 3.41-3.45 (2H, m), 3.55-3.65 (4H, m), 4.69-4.75 (2H, m), 4.37 (3H, s), 7.64-7.84 (6H, m), 8.14 (1H, d, J=2.3 Hz), 8.73 (1H, s), 8.88 (1H, s), 9.25 (1H, br.s), 9.39 (1H, br.s), 10.45 (1H, br.s)

ESI (LC-MS positive mode) m/z 608 (M+H)

Example 110

1-(4-Chloro-3-(trifluoromethyl)phenyl)-3-{4-[6-(dimethanesulfonylamino)-purin-9-yl]phenyl}urea (Table 1, Compound No. 110)

[Formula 156]

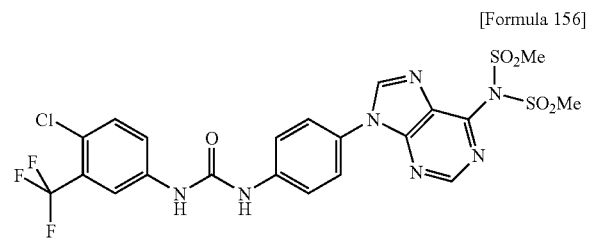 [SMILES: CS(=O)(=O)N(c1ncnc2c1ncn2-c1ccc(NC(=O)Nc2ccc(Cl)c(C(F)(F)F)c2)cc1)S(C)(=O)=O]

The title compound can be synthesized from 1-[4-(6-aminopurin-9-yl)phenyl]-3-(4-chloro-3-(trifluoromethyl)phenyl)urea hydrochloride and methanesulfonyl chloride by using the same method as in Example 107.

¹H-NMR (270 MHz, DMSO-d₆) δ (ppm): 3.93 (6H, s), 7.62-7.91 (6H, m), 8.14 (1H, br.s), 8.40 (1H, t, J=7.9 Hz), 8.83-8.86 (2H, m), 9.05 (1H, s), 9.16 (1H, s), 9.32 (1H, br.s), 9.45 (1H, br.s)

ESI (LC-MS positive mode) m/z 604 (M+H)

Example 111

(9-{4-[3-(4-Chloro-3-(trifluoromethyl)phenyl)ureido]-phenyl}-9H-purin-6-yl)carbamic acid pentyl ester (Table 1, Compound No. 111)

[Formula 157]

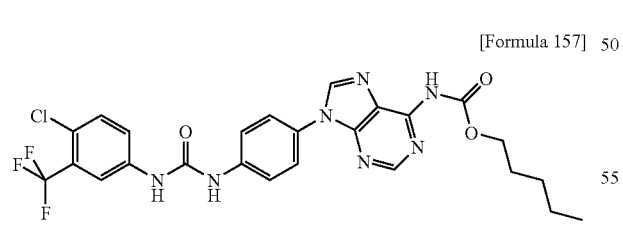

The title compound can be synthesized from 1-[4-(6-aminopurin-9-yl)phenyl]-3-(4-chloro-3-(trifluoromethyl)-phenyl)urea hydrochloride and pentyl chloroformate by using the same method as in Example 107.

¹H-NMR (270 MHz, DMSO-d₆) δ (ppm): 0.90 (3H, t, J=6.9 Hz), 1.32-1.36 (4H, m), 1.66 (2H, dd, J=6.6, 7.3 Hz), 4.14 (2H, t, J=6.6 Hz), 7.60-7.80 (6H, m), 8.16 (1H, d, J=2.7 Hz), 8.67 (1H, s), 8.81 (1H, s), 9.38 (1H, br.s), 9.49 (1H, br.s), 10.58 (1H, br.s)

ESI (LC-MS positive mode) m/z 562 (M+H)

Example 112

(9-{4-[3-(4-Chloro-3-(trifluoromethyl)phenyl)ureido]-phenyl}-9H-purin-6-yl)carbamic acid ethyl ester (Table 1, Compound No. 112)

[Formula 158]

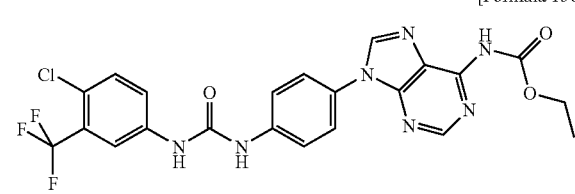

The title compound can be synthesized from 1-[4-(6-aminopurin-9-yl)phenyl]-3-(4-chloro-3-(trifluoromethyl)phenyl)urea hydrochloride and ethyl chloroformate by using the same method as in Example 107.

¹H-NMR (270 MHz, DMSO-d₆) δ (ppm): 1.28 (3H, t, J=6.9 Hz), 4.19 (2H, t, J=6.9 Hz), 7.62-7.82 (6H, m), 8.15 (1H, d, J=2.3 Hz), 8.68 (1H, s), 8.82 (1H, s), 9.32 (1H, br.s), 9.45 (1H, br.s), 10.58 (1H, br.s)

ESI (LC-MS positive mode) m/z 520 (M+H)

Example 113

(9-{4-[3-(4-Chloro-3-(trifluoromethyl)phenyl)ureido]-phenyl}-9H-purin-6-yl)carbamic acid isobutyl ester (Table 1, Compound No. 113)

[Formula 159]

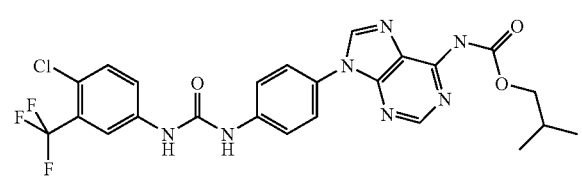

The title compound can be synthesized from 1-[4-(6-aminopurin-9-yl)phenyl]-3-(4-chloro-3-(trifluoromethyl)phenyl)urea hydrochloride and isobutyl chloroformate by using the same method as in Example 107.

¹H-NMR (270 MHz, DMSO-d₆) δ (ppm): 0.97 (6H, d, J=6.6 Hz), 1.95 (1H, m), 3.95 (2H, d, J=6.6 Hz), 7.62-7.82 (6H, m), 8.18 (1H, br.s), 8.67 (1H, s), 8.80 (1H, s), 9.17 (1H, br.s), 9.29 (1H, br.s)

ESI (LC-MS positive mode) m/z 548 (M+H)

Example 114

(9-{4-[3-(4-Chloro-3-(trifluoromethyl)phenyl)ureido]-phenyl}-9H-purin-6-yl)carbamic acid allyl ester (Table 1, Compound No. 114)

[Formula 160]

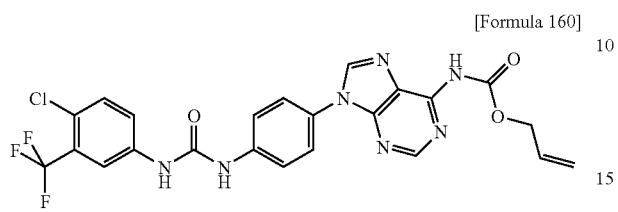

The title compound can be synthesized from 1-[4-(6-aminopurin-9-yl)phenyl]-3-(4-chloro-3-(trifluoromethyl)phenyl)urea hydrochloride and allyl chloroformate by using the same method as in Example 107.

$^1$H-NMR (270 MHz, DMSO-$d_6$) δ (ppm): 4.69 (2H, d, J=5.3 Hz), 5.27 (1H, dd, J=2.0, 10.5 Hz), 5.44 (1H, dd, J=2.0, 15.5 Hz), 6.00 (1H, m), 7.62-7.82 (6H, m), 8.17 (1H, d, J=2.3 Hz), 8.68 (1H, s), 8.83 (1H, s), 9.49 (1H, br.s), 9.60 (1H, br.s), 10.84 (1H, br.s)

ESI (LC-MS positive mode) m/z 532 (M+H)

Example 115

(9-{4-[3-(4-Chloro-3-(trifluoromethyl)phenyl)ureido]-phenyl}-9H-purin-6-yl)carbamic acid 2-methoxyethyl ester (Table 1, Compound No. 115)

[Formula 161]

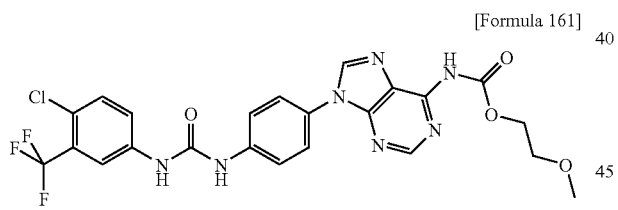

The title compound can be synthesized from 1-[4-(6-aminopurin-9-yl)phenyl]-3-(4-chloro-3-(trifluoromethyl)phenyl)urea hydrochloride and 2-methoxyethyl chloroformate by using the same method as in Example 107.

$^1$H-NMR (270 MHz, DMSO-$d_6$) δ (ppm): 3.29 (3H, s), 3.60 (2H, d, J=4.6 Hz), 4.28 (2H, d, J=4.6 Hz), 7.65-7.82 (6H, m), 8.13 (1H, d, J=2.0 Hz), 8.68 (1H, s), 8.80 (1H, s), 9.15 (1H, br.s), 9.25 (1H, br.s), 10.78 (1H, br.s)

ESI (LC-MS positive mode) m/z 550 (M+H)

Example 116

1-(4-Chloro-3-(trifluoromethyl)phenyl)-3-{4-[6-(2-oxo-oxazolidin-3-yl)purin-9-yl]phenyl}urea (Table 1, Compound No. 116)

[Formula 162]

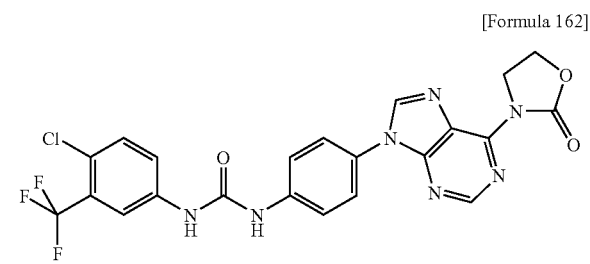 [SMILES: O=C(Nc1ccc(-n2cnc3c(N4CCOC4=O)ncnc32)cc1)Nc1ccc(Cl)c(C(F)(F)F)c1]

The title compound can be synthesized from 1-[4-(6-aminopurin-9-yl)phenyl]-3-(4-chloro-3-(trifluoromethyl)phenyl)urea hydrochloride and 2-chloroethyl chloroformate by using the same method as in Example 107.

$^1$H-NMR (270 MHz, DMSO-$d_6$) δ (ppm): 3.90 (2H, t, J=5.3 Hz), 4.43 (2H, t, J=5.3 Hz), 7.62-7.82 (6H, m), 8.14 (1H, d, J=2.0 Hz), 8.69 (1H, s), 8.83 (1H, s), 9.17 (1H, br.s), 9.29 (1H, br.s)

ESI (LC-MS positive mode) m/z 518 (M+H)

Example 117

(9-{4-[3-(4-Chloro-3-(trifluoromethyl)phenyl)ureido]-phenyl}-9H-purin-6-yl)carbamic acid 2-(methylamino)ethyl ester hydrochloride (Table 1, Compound No. 117)

Step A

Preparation of (9-{4-[3-(4-chloro-3-(trifluoromethyl)phenyl)ureido]phenyl}-9H-purin-6-yl)carbamic acid 2-(tert-butoxycarbonylamino)ethyl ester

[Formula 163]

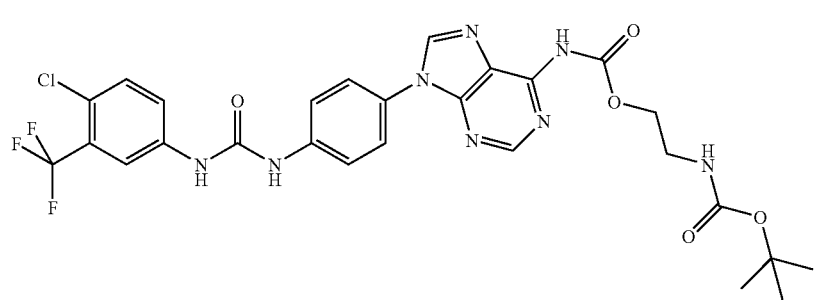

In 3 mL of methylene chloride, 110 mg (0.62 mmol) of (2-hydroxyethyl)-methylcarbamic acid tert-butyl ester and 108 μL (0.62 mol) of Hunig's base were dissolved, and 74 mg (0.248 mmol) of triphosgene was added thereto at one time, and the mixture solution was stirred for 15 minutes. To the obtained solution, a solution obtained by dissolving 30 mg (0.062 mmol) of 1-[4-(6-aminopurin-9-yl)phenyl]-3-(4-chloro-3-(trifluoromethyl)phenyl)urea hydrochloride in 3 mL of pyridine was added and the mixture solution was stirred at room temperature for three hours. The reaction solution was concentrated under reduced pressure, and then the residue was partitioned between ethyl acetate and water, and the organic layer was washed with a saturated sodium chloride solution, dried and concentrated. The residue was purified by Megabond Elute Silica Gel (1 g, methanol:ethyl acetate=1:30) to obtain 13 mg (33%) of (9-{4-[3-(4-chloro-3-(trifluoromethyl)phenyl)ureido]phenyl}-9H-purin-6-yl]carbamic acid 2-(tert-butoxycarbonylamino)ethyl ester as a white solid.

ESI (LC-MS positive mode) m/z 649 (M+H)

Step B

Preparation of (9-{4-[3-(4-Chloro-3-(trifluoromethyl)phenyl)ureido]phenyl}-9H-purin-6-yl)carbamic acid 2-(methylamino)ethyl ester hydrochloride (Table 1, Compound No. 117)

[Formula 164]

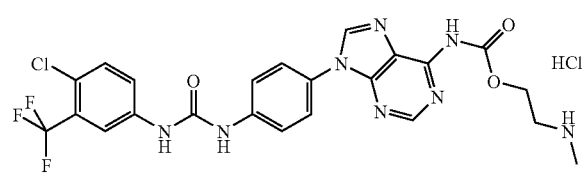

In 2 mL of a 4N hydrogen chloride ethyl acetate solution, 13 mg (0.02 mmol) of (9-{4-[3-(4-chloro-3-(trifluoromethyl)phenyl)ureido]phenyl}-9H-purin-6-yl]carbamic acid 2-(tert-butoxycarbonylamino)ethyl ester was dissolved and the solution was stirred at room temperature for two hours. The reaction solution was concentrated under reduced pressure, and then the residue was triturated with n-hexane:ethyl acetate=1:1, collected by filtration and vacuum dried to obtain 1.7 mg (16%) of (9-{4-[3-(4-chloro-3-(trifluoromethyl)phenyl)ureido]phenyl}-9H-purin-6-ylcarbamic acid 2-(methylamino)ethyl ester hydrochloride as a white solid.

$^1$H-NMR (270 MHz, DMSO-d$_6$) δ (ppm): 3.85 (3H, br.s), 4.37 (2H, t, J=5.3 Hz), 7.62-7.81 (6H, m), 8.08 (1H, br.s), 8.14 (1H, s), 8.71 (1H, s), 8.88 (1H, s), 9.60 (1H, br.s), 9.82 (1H, br.s)

ESI (LC-MS positive mode) m/z 549 (M+H)

Example 118

(9-{4-[3-(4-Chloro-3-(trifluoromethyl)phenyl)ureido]-phenyl}-9H-purin-6-yl)carbamic acid 2-aminoethyl ester hydrochloride (Table 1, Compound No. 118)

[Formula 165]

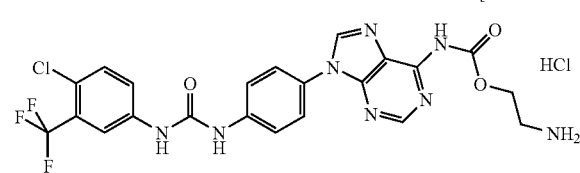

The title compound can be synthesized from 1-[4-(6-aminopurin-9-yl)phenyl]-3-(4-chloro-3-(trifluoromethyl)phenyl)urea hydrochloride and (2-hydroxyethyl)carbamic acid tert-butyl ester by using the same techniques as in Example 117.

$^1$H-NMR (270 MHz, DMSO-d$_6$) δ (ppm): 3.19 (2H, m), 3.85 (3H, br.s), 4.37 (2H, t, J=5.3 Hz), 7.62-7.81 (6H, m), 8.08 (1H, br.s), 8.14 (1H, s), 8.71 (1H, s), 8.88 (1H, s), 9.60 (1H, br.s), 9.82 (1H, br.s)

ESI (LC-MS positive mode) m/z 535 (M+H)

Example 119

1-(9-{4-[3-(4-Chloro-3-(trifluoromethyl)phenyl)ureido]phenyl}-9H-purin-6-yl)-3-propylurea (Table 1, Compound No. 119)

[Formula 166]

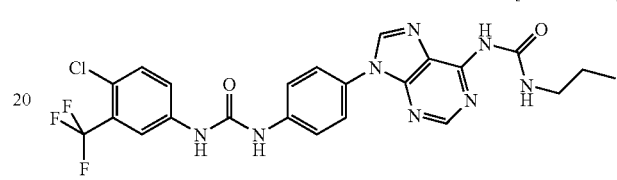

In 10 mL of pyridine, 300 mg (0.62 mmol) of 1-[4-(6-aminopurin-9-yl)phenyl]-3-(4-chloro-3-(trifluoromethyl)phenyl)urea hydrochloride was dissolved, and 1.58 g (18.6 mmol) of propyl isocyanate was added thereto and the mixture solution was stirred at 50° C. for eight hours. The reaction solution was concentrated under reduced pressure, and then the residue was partitioned between ethyl acetate and water, and the organic layer was washed with a saturated sodium chloride solution, dried and concentrated. The residue was triturated with n-hexane:ethyl acetate=1:1, collected by filtration and vacuum dried to obtain 210 mg (64%) of 1-(9-(4-[3-(4-chloro-3-(trifluoromethyl)phenyl)ureido]phenyl)-9H-purin-6-yl)-3-propylurea (Table 1, Compound No. 119) as a white solid.

$^1$H-NMR (270 MHz, DMSO-d$_6$) δ (ppm): 0.96 (3H, t, J=7.2 Hz), 1.56 (2H, q, J=7.3 Hz), 3.25 (2H, m), 7.62-7.79 (6H, m), 8.16 (1H, d, J=2.3 Hz), 8.59 (1H, s), 8.79 (1H, s), 9.45 (1H, br.s), 9.59 (1H, br.s), 9.68 (1H, br.s), 9.72 (1H, br.s)

ESI (LC-MS positive mode) m/z 533 (M+H)

Example 120

1-(9-{4-[3-(4-Chloro-3-(trifluoromethyl)phenyl)ureido]phenyl}-9H-purin-6-yl)-3-cyclohexylurea (Table 1, Compound No. 120)

[Formula 167]

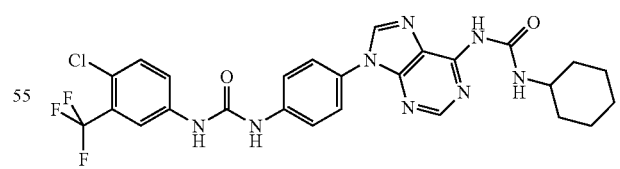

The title compound can be synthesized from 1-[4-(6-aminopurin-9-yl)phenyl]-3-(4-chloro-3-(trifluoromethyl)phenyl)urea hydrochloride and cyclohexyl isocyanate by using the same techniques as in Example 119.

$^1$H-NMR (270 MHz, DMSO-d$_6$) δ (ppm): 1.35 (6H, m), 1.70 (2H, m), 1.90 (2H, m), 3.67 (1H, m), 7.65-7.83 (6H, m), 8.13 (1H, d, J=2.0 Hz), 8.59 (1H, s), 8.79 (1H, s), 9.16 (1H, s), 9.26 (1H, s), 9.47 (1H, br.s), 9.61 (1H, s)

ESI (LC-MS positive mode) m/z 573 (M+H)

Example 121

1-(9-{4-[3-(4-Chloro-3-(trifluoromethyl)phenyl)ureido]phenyl}-9H-purin-6-yl)-3-ethylurea (Table 1, Compound No. 121)

[Formula 168]

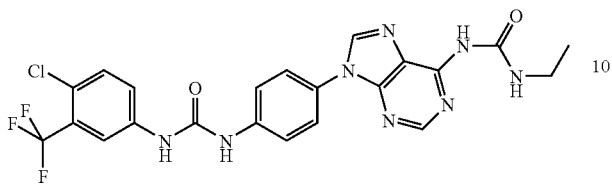

The title compound can be synthesized from 1-[4-(6-aminopurin-9-yl)phenyl]-3-(4-chloro-3-(trifluoromethyl)phenyl)urea hydrochloride and ethyl isocyanate by using the same techniques as in Example 119.

$^1$H-NMR (270 MHz, DMSO-$d_6$) δ (ppm): 1.17 (3H, t, J=7.1 Hz), 3.30 (2H, m), 7.62-7.80 (6H, m), 8.13 (1H, d, J=2.3 Hz), 8.59 (1H, s), 8.79 (1H, s), 9.15 (1H, br.s), 9.26 (1H, br.s), 9.39 (1H, br.s), 9.66 (1H, br.s)

ESI (LC-MS positive mode) m/z 519 (M+H)

Example 122

1-Allyl-3-(9-{4-[3-(4-chloro-3-(trifluoromethyl)phenyl)ureido]phenyl}-9H-purin-6-yl)urea (Table 1, Compound No. 122)

[Formula 169]

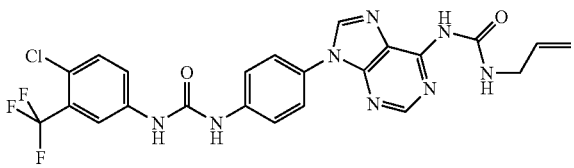

The title compound can be synthesized from 1-[4-(6-aminopurin-9-yl)phenyl]-3-(4-chloro-3-(trifluoromethyl)phenyl)urea hydrochloride and allyl isocyanate by using the same techniques as in Example 119.

$^1$H-NMR (400 MHz, DMSO-$d_6$) δ (ppm): 3.95 (2H, m), 5.13 (1H, d, J=10.0 Hz), 5.24 (1H, d, J=17.2 Hz), 6.95 (1H, m), 7.62-7.80 (6H, m), 8.12 (1H, d, J=2.4 Hz), 8.59 (1H, s), 8.79 (1H, s), 9.15 (1H, br.s), 9.25 (1H, br.s), 9.55 (1H, br.s), 9.78 (1H, br.s)

ESI (LC-MS positive mode) m/z 531 (M+H)

Example 123

1-(9-{4-[3-(4-Chloro-3-(trifluoromethyl)phenyl)ureido]phenyl}-9H-purin-6-yl)-1-methyl-3-propylurea (Table 2, Compound No. 1)

[Formula 170]

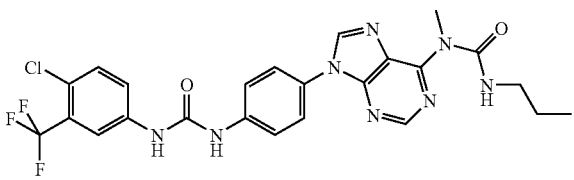

The title compound can be synthesized from 1-(4-chloro-3-(trifluoromethyl)phenyl)-3-[4-(6-(methylamino)purin-9-yl)phenyl]urea hydrochloride and propyl isocyanate by using the same techniques as in Example 119.

$^1$H-NMR (270 MHz, DMSO-$d_6$) δ (ppm): 0.93 (3H, t, J=7.3 Hz), 1.54 (2H, m), 3.22 (2H, q, J=7.9 Hz), 3.84 (3H, s), 7.60-7.80 (6H, m), 8.14 (1H, d, J=2.3 Hz), 8.61 (1H, s), 8.79 (1H, s), 9.18 (1H, s), 9.30 (1H, s), 10.01 (1H, t, J=5.6 Hz)

ESI (LC-MS positive mode) m/z 547 (M+H)

Example 124

1-(9-{4-[3-(4-Chloro-3-(trifluoromethyl)phenyl)ureido]phenyl}-9H-purin-6-yl)-3-(2-hydroxyethyl)urea (Table 2, Compound No. 2)

[Formula 171]

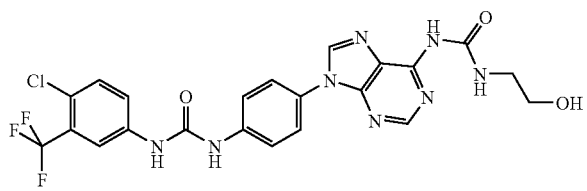

In a mixed solution of 3 mL of tetrahydrofuran and 1 mL of water, 50 mg (0.09 mmol) of 1-allyl-3-(9-{4-[3-(4-chloro-3-(trifluoromethyl)phenyl)ureido]phenyl}-9H-purin-6-yl)urea was dissolved, and 19 μL of a 0.1 M osmium tetraoxide aqueous solution and 81 mg (0.19 mmol) of sodium periodate were added thereto and the mixture solution was stirred at room temperature for three hours. The reaction solution was concentrated under reduced pressure and partitioned between ethyl acetate and water. The organic layer was washed with a saturated sodium chloride solution and concentrated under reduced pressure. The residue was dissolved in 2 mL of ethanol, and 5 mg (0.13 mmol) of sodium borohydride was added thereto and the mixture solution was stirred at room temperature for one hour. The reaction solution was concentrated, and purified by a silica gel column (dichloromethane:methanol=9:1) to obtain 5 mg (13%) of a target product as a white solid.

$^1$H-NMR (270 MHz, DMSO-$d_6$) δ (ppm): 3.30 (2H, m), 3.54 (2H, m), 4.86 (1H, t, J=4.9 Hz), 7.60-7.80 (6H, m), 8.14 (1H, d, J=2.0 Hz), 8.58 (1H, s), 8.79 (1H, s), 9.30 (1H, s), 9.44 (1H, s), 9.52 (1H, m), 9.69 (1H, s)

ESI (LC-MS positive mode) m/z 535 (M+H)

Example 125

1-(4-Chloro-3-(trifluoromethyl)phenyl)-3-(4-{6-[(2-hydroxyethyl)-methylamino]purin-9-yl}phenyl)urea (Table 2, Compound No. 3)

[Formula 172]

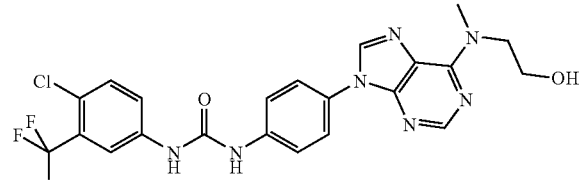

The title compound can be synthesized from 6-chloropurine, 2-(methylamino)ethanol, 4-fluoronitrobenzene and 4-chloro-3-(trifluoromethyl)phenyl isocyanate by using the same techniques as in Example 35.

$^1$H-NMR (270 MHz, DMSO-d$_6$) δ (ppm): 3.30 (5H, m), 3.78 (2H, m), 4.78 (1H, t, J=5.3 Hz), 7.60-7.80 (6H, m), 8.13 (1H, s), 8.28 (1H, s), 8.52 (1H, s), 9.16 (1H, m), 9.29 (1H, s)

ESI (LC-MS positive mode) m/z 506 (M+H)

Example 126

1-(4-Chloro-3-(trifluoromethyl)phenyl)-3-[4-(6-morpholin-4-yl-purin-9-yl)phenyl]urea (Table 2, Compound No. 4)

[Formula 173]

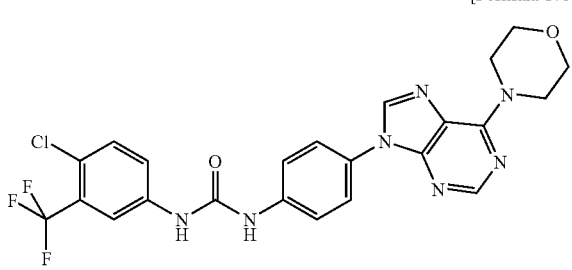

The title compound can be synthesized from 6-chloropurine, morpholine, 4-fluoronitrobenzene and 4-chloro-3-(trifluoromethyl)phenyl isocyanate by using the same techniques as in Example 35.

$^1$H-NMR (270 MHz, DMSO-d$_6$) δ (ppm): 3.74 (4H, m), 4.28 (4H, m), 7.60-7.80 (6H, m), 8.13 (1H, d, J=2.0 Hz), 8.32 (1H, s), 8.57 (1H, s), 9.18 (1H, m), 9.29 (1H, s)

ESI (LC-MS positive mode) m/z 517 (M+H)

Example 127

1-(4-Chloro-3-(trifluoromethyl)phenyl)-3-[4-(6-pentylamino)purin-9-yl]phenyl]urea (Table 2, Compound No. 5)

[Formula 174]

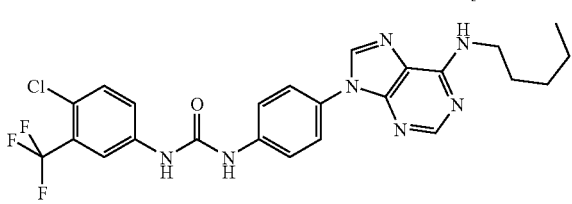

The title compound can be synthesized from 6-chloropurine, n-pentylamine, 4-fluoronitrobenzene and 4-chloro-3-(trifluoromethyl)phenyl isocyanate by using the same techniques as in Example 35.

$^1$H-NMR (270 MHz, DMSO-d$_6$) δ (ppm): 0.88 (3H, t, J=6.9 Hz), 1.32 (4H, m), 1.61 (2H, m), 3.49 (2H, m), 7.60-7.80 (6H, m), 7.98 (1H, br.s), 8.13 (1H, d, J=2.0 Hz), 8.28 (1H, s), 8.52 (1H, s), 9.16 (1H, m), 9.29 (1H, s)

ESI (LC-MS positive mode) m/z 518 (M+H)

Example 128

1-(4-Chloro-3-(trifluoromethyl)phenyl)-3-[4-(6-piperazin-1-yl-purin-9-yl)phenyl]urea hydrochloride (Table 2, Compound No. 6)

[Formula 175]

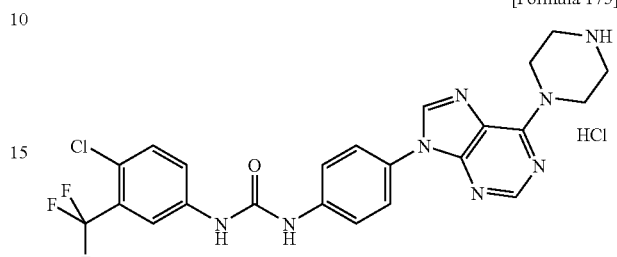

The title compound can be synthesized from 6-chloropurine, piperazine, 4-fluoronitrobenzene and 4-chloro-3-(trifluoromethyl)phenyl isocyanate by using the same techniques as in Example 35.

$^1$H-NMR (270 MHz, DMSO-d$_6$) δ (ppm): 4.50 (4H, m), 5.16 (4H, m), 7.60-7.78 (6H, m), 8.14 (1H, d, J=2.0 Hz), 8.66 (1H, s), 9.28 (1H, br.s), 9.74 (1H, s), 9.89 (1H, s)

ESI (LC-MS positive mode) m/z 517 (M+H)

Example 129

1-[4-(6-Amino-8-iodopurin-9-yl)phenyl]-3-(4-chloro-3-(trifluoromethyl)phenyl)urea (Table 2, Compound No. 7)

[Formula 176]

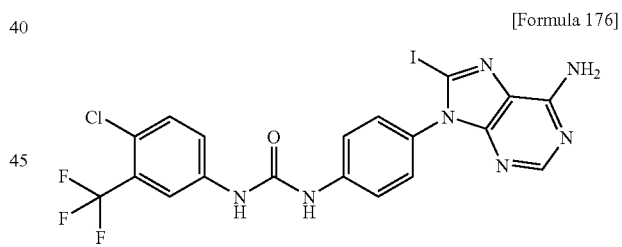

In 18 mL of tetrahydrofuran, 300 mg (0.67 mmol) of 1-[4-(6-aminopurin-9-yl)phenyl]-3-(4-chloro-3-(trifluoromethyl)phenyl)urea was suspended, and the suspension was cooled to −70° C. To the suspension, 3 mL of a tetrahydrofuran solution of lithium diisopropylamide (1.8 M) was added dropwise, and with stirring the temperature of the suspension was raised to 0° C. over two hours. Again, the suspension was cooled to −70° C., and 350 mg (1.38 mmol) of iodine was added thereto, and the suspension was stirred one hour. To the reaction solution, 100 μL of acetic acid was added, and the reaction solution was concentrated, and purified by a silica gel column (dichloromethane:methanol=9:1) to obtain 243 mg (63%) of a target product as a yellow solid.

$^1$H-NMR (270 MHz, DMSO-d$_6$) δ (ppm): 7.37 (2H, d, J=8.9 Hz), 7.45 (2H, s), 7.65-7.70 (4H, m), 8.02 (1H, s), 8.14 (1H, s), 9.19 (1H, s), 9.30 (1H, s)

ESI (LC-MS positive mode) m/z 574 (M+H)

Example 130

1-[4-(6-Amino-8-vinylpurin-9-yl)phenyl]-3-(4-chloro-3-(trifluoromethyl)phenyl]urea (Table 2, Compound No. 8)

[Formula 177]

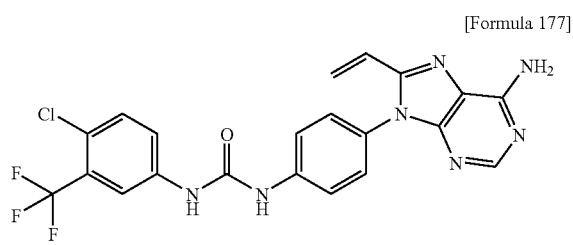 [SMILES: C=Cc1nc2c(N)ncnc2n1-c1ccc(NC(=O)Nc2ccc(Cl)c(C(F)(F)F)c2)cc1]

In 2 mL of dimethylformamide, 158 mg (0.28 mmol) of 1-[4-(6-amino-8-iodopurin-9-yl)phenyl]-3-(4-chloro-3-(trifluoromethyl)phenyl)urea was dissolved, and 262 mg (0.82 mmol) of vinyltributyltin and 20 mg (0.01 mmol) of tetrakistriphenylphosphine palladium was added thereto and the mixture solution was stirred at 95° C. for three hours. The reaction solution was concentrated and purified by a silica gel column (dichloromethane:methanol=9:1) to obtain 122 mg (93%) of a target product as a white solid.

$^1$H-NMR (270 MHz, DMSO-$d_6$) δ (ppm): 5.60 (1H, dd, J=0.1, 11.1 Hz), 6.27 (1H, dd, J=0.1, 17.5 Hz), 6.52 (1H, dd, J=11.1, 17.5 Hz), 7.37 (2H, d, J=8.9 Hz), 7.45 (2H, s), 7.65-7.70 (4H, m), 8.05 (1H, s), 8.14 (1H, s), 9.19 (1H, s), 9.30 (1H, s)

ESI (LC-MS positive mode) m/z 474 (M+H)

Example 131

1-{4-[6-Amino-8-(1,2-dihydroxyethyl)purin-9-yl]-phenyl}-3-(4-chloro-3-(trifluoromethyl)phenyl)urea (Table 2, Compound No. 9)

[Formula 178]

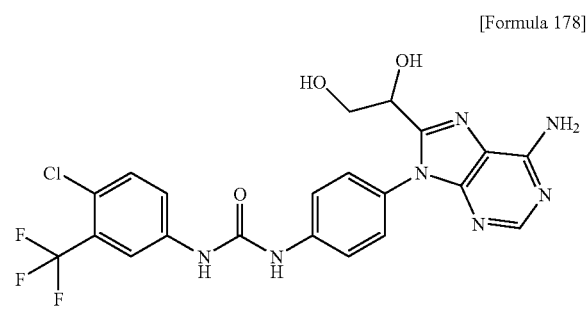 [SMILES: Nc1ncnc2c1nc(C(O)CO)n2-c1ccc(NC(=O)Nc2ccc(Cl)c(C(F)(F)F)c2)cc1]

In 1 mL of tetrahydrofuran, 20 mg (0.04 mmol) of 1-[4-(6-amino-8-vinylpurin-9-yl)phenyl]-3-(4-chloro-3-(trifluoromethyl)phenyl)urea was dissolved, and 20 μL of a 0.1 M osmium tetraoxide aqueous solution and 143 μL of a 3% hydrogen peroxide aqueous solution were added thereto, and the mixture solution was stirred at room temperature for 14 hours. The reaction solution was concentrated under reduced pressure and purified by a silica gel column (dichloromethane:methanol=9:1) to obtain 16.4 mg (77%) of a target product as a white crystal.

$^1$H-NMR (270 MHz, DMSO-$d_6$) δ (ppm): 3.70 (1H, m), 3.80 (1H, m), 4.58 (1H, m), 4.76 (1H, m), 5.58 (1H, m), 7.27 (2H, s), 7.42 (2H, d, J=8.9 Hz), 7.65-7.70 (4H, m), 8.05 (1H, s), 8.15 (1H, s), 9.20 (1H, s), 9.30 (1H, s)

ESI (LC-MS positive mode) m/z 508 (M+H)

Example 132

1-[4-(6-Amino-8-(hydroxymethyl)purin-9-yl)phenyl]-3-(4-chloro-3-(trifluoromethyl)phenyl)urea (Table 2, Compound No. 10)

[Formula 179]

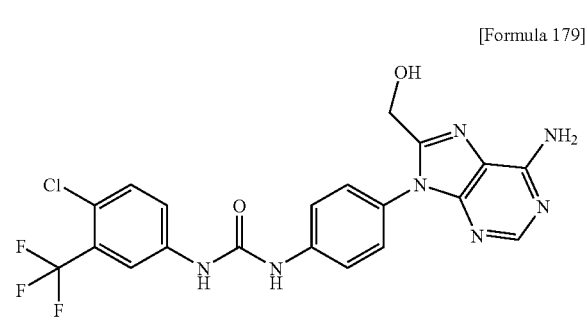 [SMILES: Nc1ncnc2c1nc(CO)n2-c1ccc(NC(=O)Nc2ccc(Cl)c(C(F)(F)F)c2)cc1]

In a mixed solution of 4 mL of tetrahydrofuran and 1 mL of water, 20 mg (0.04 mmol) of 1-[4-(6-amino-8-formyl-purin-9-yl)phenyl]-3-(4-chloro-3-(trifluoromethyl)phenyl-urea was dissolved, and 20 μL of a 0.1 M osmium tetraoxide aqueous solution and 40 mg (0.19 mmol) of a sodium periodate aqueous solution were added thereto and the mixture solution was stirred at room temperature for 14 hours. The reaction solution was concentrated under reduced pressure and partitioned between ethyl acetate and water. The organic layer was washed with a saturated sodium chloride solution, and concentrated under reduced pressure. The residue was dissolved in 2 mL of methanol, and 5 mg (0.13 mmol) of sodium borohydride was added thereto and the mixture solution was stirred at room temperature for one hour. The reaction solution was concentrated and purified by a silica gel column (dichloromethane:methanol=9:1) to obtain 13.4 mg (66%) of a target product as a white crystal.

$^1$H-NMR (270 MHz, DMSO-$d_6$) δ (ppm): 4.53 (2H, d, J=5.2 Hz), 5.48 (1H, t, J=5.2 Hz), 7.29 (2H, s), 7.46 (2H, d, J=8.9 Hz), 7.65-7.70 (4H, m), 8.08 (1H, s), 8.13 (1H, s), 9.19 (1H, s), 9.34 (1H, s)

ESI (LC-MS positive mode) m/z 478 (M+H)

Example 133

1-(4-Chloro-3-(trifluoromethyl)phenyl)-3-{4-[6-(2-morpholin-4-yl-ethylamino)purin-9-yl]phenyl}urea (Table 2, Compound No. 11)

[Formula 180]

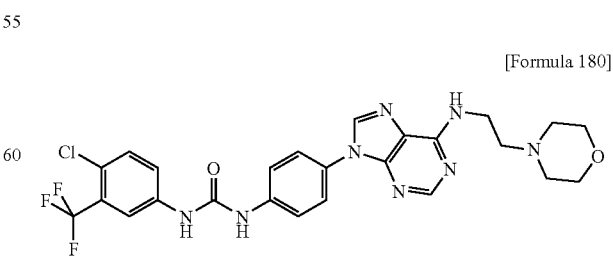

The title compound can be synthesized from 6-chloropurine, 2-morpholin-4-ylethylamine, 4-fluoronitrobenzene and 4-chloro-3-(trifluoromethyl)phenyl isocyanate by using the same techniques as in Example 35.

$^1$H-NMR (270 MHz, DMSO-d$_6$) δ (ppm): 2.44 (4H, m), 2.60 (4H, m), 3.50-3.70 (4H, m), 4.78 (1H, t, J=5.3 Hz), 7.60-7.80 (6H, m), 8.13 (1H, s), 8.28 (1H, s), 8.52 (1H, s), 9.14 (1H, m), 9.29 (1H, s)

ESI (LC-MS positive mode) m/z 561 (M+H)

Example 134

1-[4-(6-Amino-8-dimethylaminomethyl-pruin-9-yl) phenyl]-3-(4-chloro-3-(trifluoromethyl)phenyl)urea (Table 2, Compound No. 12)

Step A

Preparation of 1-[4-(6-amino-8-formylpurin-9-yl) phenyl]-3-(4-chloro-3-(trifluoromethyl)phenyl)urea

[Formula 181]

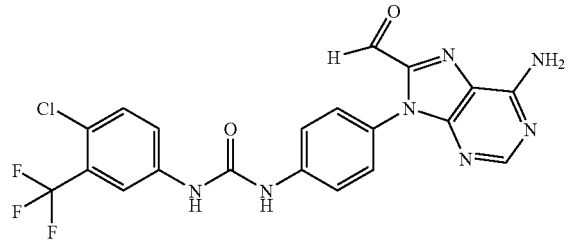

In a mixed solution of 4 mL of tetrahydrofuran and 1 mL of water, 20 mg (0.04 mmol) of 1-[4-(6-amino-8-vinyl-purin-9-yl)phenyl]-3-(4-chloro-3-(trifluoromethyl)phenyl)-urea was dissolved, and 20 µL of a 0.1 M osmium tetraoxide aqueous solution and 40 mg (0.19 mmol) of sodium periodate were added thereto and the mixture solution was stirred at room temperature for 14 hours. The reaction solution was concentrated under reduced pressure and purified by a silica gel column (dichloromethane:methanol=9:1) to obtain 18 mg (90%) of a target product as a white crystal.

ESI (LC-MS positive mode) m/z 476 (M+H)

Step B

Preparation of 1-[4-(6-amino-8-dimethylaminomethyl-pruin-9-yl)phenyl]-3-(4-chloro-3-(trifluoromethyl)phenyl)urea (Table 2, Compound No. 12)

[Formula 182]

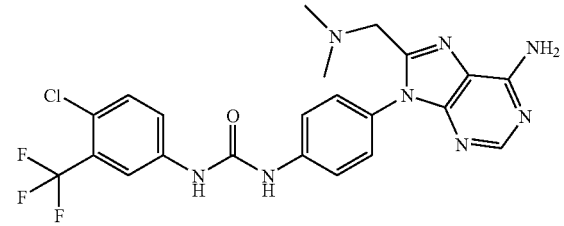

In 1 mL of methanol, 15 mg (0.03 mmol) of 1-[4-(6-amino-8-formylpurin-9-yl)phenyl]-3-(4-chloro-3-(trifluoromethyl) phenyl)urea was dissolved, and 15 µL of acetic acid and 0.1 mL (0.20 mmol) of 2N dimethylamine were added thereto, and the mixture solution was stirred at room temperature for 30 minutes. To the solution, 10 mg (0.26 mmol) of sodium cyanoborohydride was further added thereto and the mixture solution was stirred at room temperature for one hour. The reaction solution was concentrated and partitioned between water and ethyl acetate, and the organic layer was washed with a saturated sodium chloride solution, and concentrated under reduced pressure and purified by a silica gel column (ethyl acetate:methanol=9:1) to obtain 3.45 mg (19%) of a target product as a white solid.

$^1$H-NMR (270 MHz, DMSO-d$_6$) δ (ppm): 2.16 (6H, s), 5.44 (2H, s), 7.45-7.47 (4H, m), 7.61-7.67 (4H, m), 8.11 (1H, s), 8.16 (1H, s), 9.79 (1H, s), 9.96 (1H, s)

ESI (LC-MS positive mode) m/z 505 (M+H)

Example 135

1-(9-{4-[3-(4-Chloro-3-(trifluoromethyl)phenyl) ureido]phenyl}-8-vinyl-9H-purin-6-yl)-3-propylurea (Table 2, Compound No. 13)

[Formula 183]

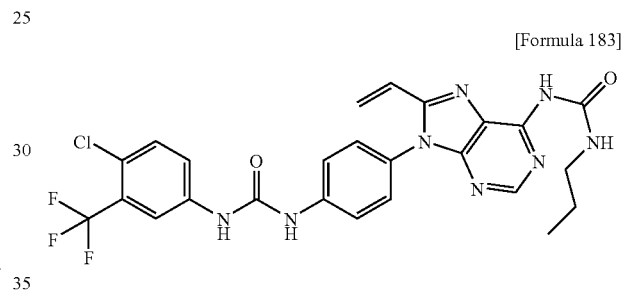

The title compound can be synthesized from 1-[4-(6-amino-8-vinylpruin-9-yl)phenyl]-3-(4-chloro-3-(trifluoromethyl)phenyl)urea and propyl isocyanate by using the same techniques as in Example 119.

$^1$H-NMR (270 MHz, DMSO-d$_6$) δ (ppm): 0.91 (3H, t, J=7.3 Hz), 1.56 (1H, m), 3.24 (2H, m), 5.76 (1H, dd, J=1.8, 12.7 Hz), 6.42 (1H, dd, J=1.8, 15.1 Hz), 6.60 (1H, dd, J=12.7, 15.1 Hz), 7.45 (2H, d, J=8.9 Hz), 7.65-7.70 (4H, m), 8.15 (1H, s), 8.47 (1H, s), 9.30 (1H, s), 9.39 (1H, s)

ESI (LC-MS positive mode) m/z 559 (M+H)

Example 136

1-[4-(6-Amino-8-methoxypurin-9-yl)phenyl]-3-(4-chloro-3-(trifluoromethyl)phenyl)urea (Table 2, Compound No. 14)

[Formula 184]

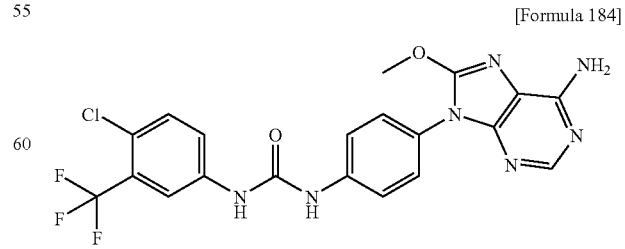

In 2 mL of methanol, 25 mg (0.04 mmol) of 1-[4-(6-amino-8-iodopurin-9-yl)phenyl]-3-(4-chloro-3-(trifluoromethyl)

phenyl)urea was dissolved, and 5.6 mg (0.10 mmol) of sodium methylate was added thereto, and the mixture solution was refluxed with stirring for 14 hours. The reaction solution was concentrated and purified by a silica gel column (dichloromethane:methanol=9:1) to obtain 7 mg (34%) of a target product as a white solid.

$^1$H-NMR (270 MHz, DMSO-$d_6$) δ (ppm): 4.11 (3H, s), 6.90 (2H, s), 7.45 (2H, d, J=8.8 Hz), 7.65-7.74 (4H, m), 8.01 (1H, s), 8.20 (1H, s), 9.11 (1H, s), 9.25 (1H, s)

ESI (LC-MS positive mode) m/z 478 (M+H)

Example 137

1-[9-{4-[3-(4-Chloro-3-(trifluoromethyl)phenyl) ureido]phenyl}-8-(1,2-dihydroxyethyl)-9H-purin-6-yl]-3-propylurea (Table 2, Compound No. 15)

[Formula 185]

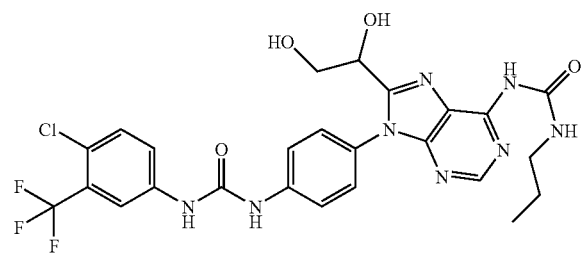

The title compound can be prepared from 1-(9-{4-[3-(4-chloro-3-(trifluoromethyl)phenyl)ureido]phenyl}-8-vinyl-9H-purin-6-yl)-3-propylurea by using the same techniques as in Example 131.

$^1$H-NMR (270 MHz, DMSO-$d_6$) δ (ppm): 0.93 (3H, t, J=7.6 Hz), 1.56 (1H, m), 3.24 (2H, m), 3.72 (1H, m), 3.80 (1H, m), 4.64 (1H, m), 4.84 (1H, t, J=6.0 Hz), 5.70 (1H, d, J=6.0 Hz), 7.45 (2H, d, J=8.9 Hz), 7.65-7.70 (4H, m), 8.18 (1H, d, J=2.4 Hz), 8.46 (1H, s), 9.25 (1H, d, J=6.0 Hz), 9.35-9.45 (2H, m), 9.50 (1H, s)

ESI (LC-MS positive mode) m/z 593 (M+H)

Example 138

1-[4-(6-Aminopurin-9-yl)-2-bromophenyl]-3-(4-chloro-3-(trifluoromethyl)phenyl)urea (Table 2, Compound No. 16)

[Formula 186]

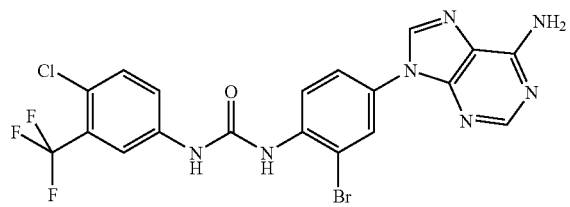

In 30 mL of acetic acid, 1 g (2.23 mmol) of 1-[4-(6-aminopurin-9-yl)phenyl]-3-(4-chloro-3-(trifluoromethyl)phenyl)urea and 0.8 g (9.75 mmol) of sodium acetate were dissolved and to the solution, 0.7 g (4.38 mmol) of bromine was added dropwise and the mixture solution was stirred at 50° C. for one hour. To the reaction solution, 40 mL of water was added, and the deposited product was collected by filtration, and recrystallized from ethanol to obtain 1.095 g (93%) of a target product as a white solid.

$^1$H-NMR (270 MHz, DMSO-$d_6$) δ (ppm): 7.43 (2H, s), 7.65 (1H, d, J=1.3 Hz), 7.91 (1H, dd, J=2.6, 8.9 Hz), 8.13 (1H, s), 8.20-8.23 (2H, m), 8.29 (1H, d, J=2.3 Hz), 8.42 (1H, s), 8.62 (1H, s), 9.96 (1H, s)

ESI (LC-MS positive mode) m/z 529 (M+H)

Example 139

1-[4-(6-Aminopurin-9-yl)phenyl]-3-(4-bromo-3-(trifluoromethyl)phenyl)urea hydrochloride (Table 2, Compound No. 17)

Step A

Preparation of 1-[4-(6-di-(tert-butoxycabonyl)aminopurin-9-yl)phenyl]-3-(4-bromo-3-(trifluoromethyl)phenyl)urea

[Formula 187]

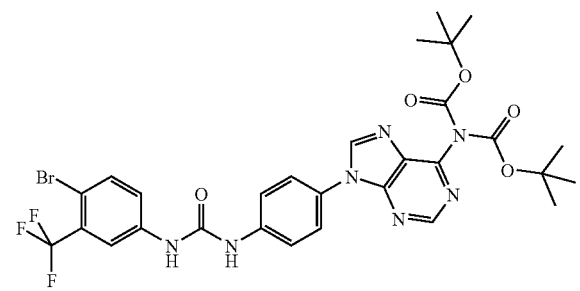

In 0.2 mL of dichloromethane, 73 mg (0.30 mmol) of 4-bromo-3-(trifluoromethyl)aniline was dissolved, and 52 mg (0.32 mmol) of 1,1'-carbonylbis-1H-imidazole was added thereto and the mixture solution was stirred at room temperature for three hours. To the reaction solution, 0.5 mL of a dichloromethane solution of 126 mg (0.30 mmol) of 6-di-tert-butoxycarbonylamino-9-(4-aminophenyl)-1H-purine was added, and the mixture solution was stirred for 24 hours. The reaction solution was concentrated and the residue was partitioned between water and ethyl acetate and the organic layer was washed with a saturated sodium chloride solution and concentrated under reduced pressure. The product was recrystallized from ethyl acetate to obtain a target product as a white crystal.

$^1$H-NMR (270 MHz, DMSO-$d_6$) δ (ppm): 1.41 (18H, s), 7.58 (2H, m), 7.70 (3H, m), 7.82 (2H, m), 8.14 (1H, d, J=2.6 Hz), 8.91 (1H, s), 9.02 (1H, s), 9.18 (1H, s), 9.27 (1H, s)

ESI (LC-MS positive mode) m/z 692, 694 (M+H)

Step B

Preparation of 1-[4-(6-aminopurin-9-yl)phenyl]-3-(4-bromo-3-(trifluoromethyl)phenyl)urea hydrochloride (Table 2, Compound No. 17)

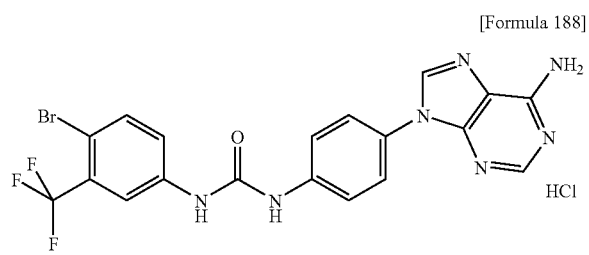 [SMILES: Nc1ncnc2c1ncn2-c1ccc(NC(=O)Nc2ccc(Br)c(C(F)(F)F)c2)cc1 ; Cl]

[Formula 188]

In 1 mL of trifluoroacetic acid, 25 mg of 1-[4-(6-di-(tert-butoxycabonyl)aminopurin-9-yl)phenyl]-3-(4-bromo-3-(trifluoromethyl)phenyl)urea was dissolved, and the solution was stirred at room temperature for two hours. The reaction solution was concentrated under reduced pressure and neutralized with a saturated sodium bicarbonate solution, and the crystal was collected by filtration and a washed with a large amount of water. The crystal was dissolved in a hydrogen chloride methanol solution, concentrated under reduced pressure and then triturated with ethyl acetate to obtain 9.66 mg of a target product as a white solid.

$^1$H-NMR (270 MHz, DMSO-$d_6$) δ (ppm): 7.57 (2H, m), 7.69 (4H, m), 7.79 (2H, m), 8.14 (1H, d, J=2.6 Hz), 8.46 (1H, s), 8.78 (1H, s), 9.53 (1H, s), 9.72 (1H, s)

ESI (LC-MS positive mode) m/z 493 (M+H)

Example 140

1-{4-[6-Amino-8-(2-methoxy-ethoxy)purin-9-yl]phenyl}-3-(4-chloro-3-(trifluoromethyl)phenyl)urea (Table 2, Compound No. 18)

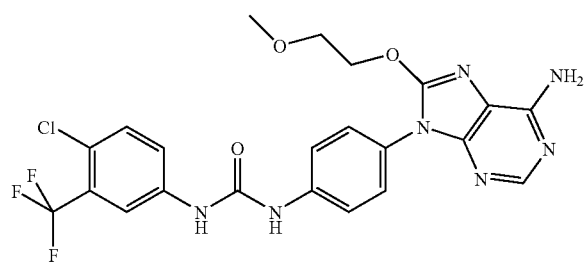

[Formula 189]

The title compound can be prepared from 1-[4-(6-amino-8-iodopurin-9-yl)phenyl]-3-(4-chloro-3-(trifluoromethyl)phenyl)urea and 2-methoxyethanol by using the same techniques as in Example 136.

$^1$H-NMR (270 MHz, DMSO-$d_6$) δ (ppm): 3.28 (3H, s), 3.69 (2H, m) 4.63 (2H, m), 6.93 (2H, s), 7.47 (2H, d, J=8.9 Hz), 7.60-7.70 (4H, m), 8.03 (1H, s), 8.14 (1H, s), 9.10 (1H, s), 9.26 (1H, s)

ESI (LC-MS positive mode) m/z 522 (M+H)

Example 141

1-[4-[6-(Methylamino)purin-9-yl]phenyl]-3-(3-(trifluoromethyl)phenyl)urea (Table 2, Compound No. 19)

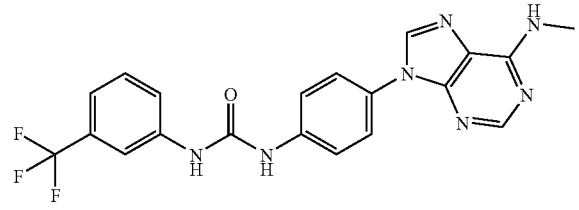

[Formula 190]

The title compound can be synthesized from [9-(4-aminophenyl)-9H-purin-6-yl]-methylcarbamic acid, tert-butyl ester and 3-trifluoromethylaniline by using the same techniques as in Examples 29 and 30.

$^1$H-NMR (270 MHz, DMSO-$d_6$) δ (ppm): 3.00 (3H, s), 7.32 (1H, d, J=7.6 Hz), 7.50-7.62 (2H, m), 7.66 (2H, d, J=8.9 Hz), 7.79 (2H, d, J=8.9 Hz), 7.84 (1H, br.s), 8.03 (1H, s), 8.28 (1H, s), 8.52 (1H, s), 9.05 (1H, s), 9.13 (1H, s)

ESI (LC-MS positive mode) m/z 428 (M+H)

Example 142

1-(4-Chloro-3-(trifluoromethyl)phenyl)-3-[4-(8-iodo-6-(methylamino)purin-9-yl)phenyl]urea (Table 2, Compound 20)

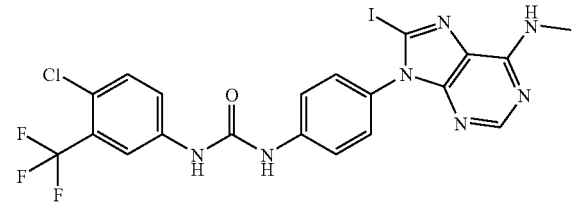

[Formula 191]

The title compound can be prepared from 1-(4-chloro-3-(trifluoromethyl)phenyl)-3-[4-(6-(methylamino)purin-9-yl)phenyl]urea by using the same techniques as in Example 129.

$^1$H-NMR (270 MHz, DMSO-$d_6$) δ (ppm): 2.97 (3H, s), 7.37 (2H, d, J=8.9 Hz), 7.65-7.72 (4H, m), 8.00 (1H, s), 8.09 (1H, s), 8.14 (1H, s), 9.20 (1H, s), 9.31 (1H, s)

ESI (LC-MS positive mode) m/z 588 (M+H)

Example 143

1-(4-Chloro-3-(trifluoromethyl)phenyl)-3-[4-(8-methoxy-6-(methylamino)purin-9-yl)phenyl]urea (Table 2, Compound No. 21)

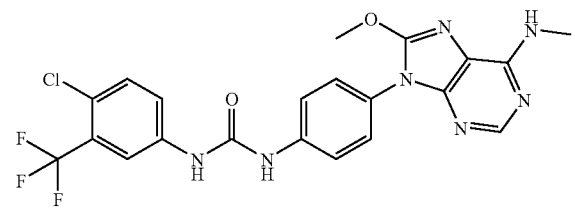

[Formula 192]

The title compound can be prepared from 1-(4-chloro-3-(trifluoromethyl)phenyl)-3-[4-(8-iodo-6-(methylamino)purin-9-yl)phenyl]urea and methanol by using the same technique as in Example 136.

$^1$H-NMR (270 MHz, DMSO-d$_6$) δ (ppm): 2.97 (3H, s), 7.45 (2H, d, J=8.6 Hz), 7.59-7.67 (4H, m), 8.09 (1H, s), 8.10 (1H, s), 8.13 (1H, s), 9.11 (1H, s), 9.25 (1H, s)

ESI (LC-MS positive mode) m/z 492 (M+H)

Example 144

1-(4-Chloro-3-(trifluoromethyl)phenyl)-3-[4-(8-ethoxy-6-(methylamino)purin-9-yl)phenyl]urea (Table 2, Compound 22)

[Formula 193]

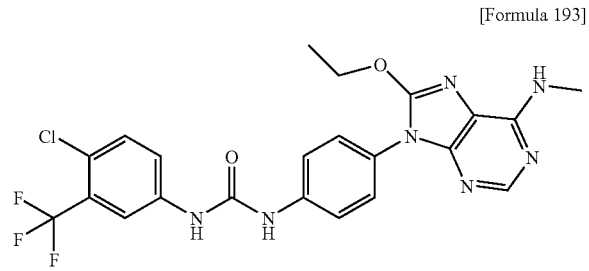 [SMILES: CCOc1nc2c(NC)ncnc2n1-c1ccc(NC(=O)Nc2ccc(Cl)c(C(F)(F)F)c2)cc1]

The title compound can be prepared from 1-(4-chloro-3-(trifluoromethyl)phenyl)-3-[4-(8-iodo-6-(methylamino)purin-9-yl)phenyl]urea and ethanol by using the same techniques as in Example 136.

$^1$H-NMR (270 MHz, DMSO-d$_6$) δ (ppm): 1.38 (3H, t, J=5.3 Hz), 2.97 (3H, s), 4.55 (2H, q, J=5.3 Hz), 7.47 (2H, d, J=8.6 Hz), 7.60-7.70 (4H, m), 8.10 (1H, s), 8.14 (1H, s), 9.10 (1H, s), 9.26 (1H, s)

ESI (LC-MS positive mode) m/z 506 (M+H)

Example 145

1-(4-Chloro-3-(trifluoromethyl)phenyl)-3-[4-[8-(2-methoxy-ethoxy)-6-(methylamino)purin-9-yl]phenyl]urea (Table 2, Compound 23)

[Formula 194]

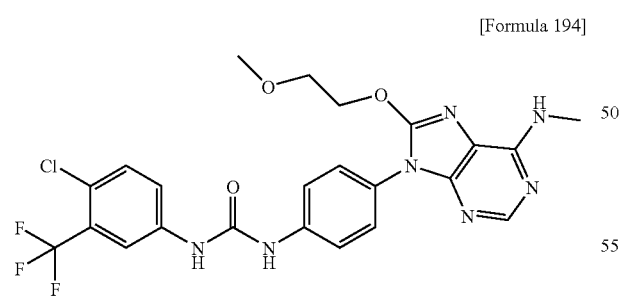

The title compound can be prepared from 1-(4-chloro-3-(trifluoromethyl)phenyl)-3-[4-(8-iodo-6-(methylamino)purin-9-yl)phenyl]urea and 2-methoxyethanol by the same techniques as in Example 136.

$^1$H-NMR (270 MHz, DMSO-d$_6$) δ (ppm): 2.97 (3H, s), 3.26 (3H, s), 3.69 (2H, m), 4.63 (2H, m), 7.32 (1H, s), 7.47 (2H, d, J=8.3 Hz), 7.60-7.70 (4H, m), 8.12 (1H, s), 8.14 (1H, s), 9.11 (1H, s), 9.26 (1H, s)

ESI (LC-MS positive mode) m/z 536 (M+H)

Example 146

1-(4-Chloro-3-(trifluoromethyl)phenyl)-3-{4-[8-(2-dimethylamino-ethoxy)-6-(methylamino)purin-9-yl]-phenyl}urea (Table 2, Compound 24)

[Formula 195]

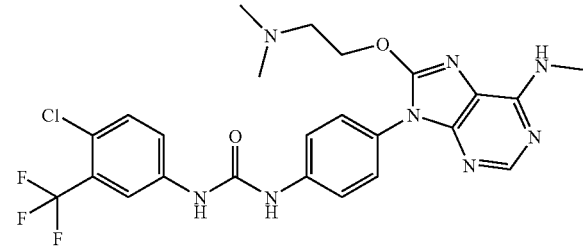

The title compound can be prepared from 1-(4-chloro-3-(trifluoromethyl)phenyl)-3-[4-(8-iodo-6-(methylamino)-purin-9-yl)phenyl]urea and 2-(dimethylamino)ethanol by the same techniques as in Example 136.

$^1$H-NMR (270 MHz, DMSO-d$_6$) δ (ppm): 2.17 (6H, s), 2.64 (2H, t, J=5.6 Hz), 2.98 (3H, s), 4.57 (2H, t, J=5.6 Hz), 7.27 (1H, m), 7.48 (2H, d, J=8.6 Hz), 7.58-7.65 (4H, m), 8.10 (1H, s), 8.12 (1H, s), 9.09 (1H, s), 9.26 (1H, s)

ESI (LC-MS positive mode) m/z 549 (M+H)

Example 147

1-[4-(6-(Methylamino)purin-9-yl)phenyl]-3-[3-(4-methylpiperazin-1-ylmethyl)-5-(trifluoromethyl)phenyl]urea (Table 2, Compound 25)

Step A

Preparation of methyl-(9H-purin-6-yl)amine

[Formula 196]

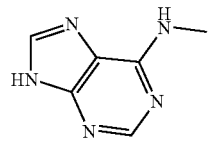

In 20 mL of a 40% methylamine methanol solution and 20 mL of ethanol, 12.5 g (79 mmol) of 6-chloropurin was dissolved and the solution was sealed in a tube and stirred in the tube at 120° C. for four hours. The reaction solution was concentrated, and then triturated with water and collected on a filter, washed with water, and then vacuum dried to obtain 10.78 g (90%) of methyl-(9H-purin-6-yl)amine as a white solid.

$^1$H-NMR (270 MHz, DMSO-d$_6$) δ (ppm): 2.98 (3H, br.s), 7.58 (1H, br.s), 8.06 (1H, s), 8.19 (1H, br.s), 12.89 (1H, br.s)

ESI (LC-MS positive mode) m/z 150 (M+H)

Step B

Preparation of
methyl-[9-(4-nitrophenyl)-9H-purin-6-yl]amine

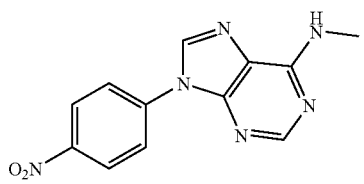

[Formula 197]

In 120 mL of dimethyl sulfoxide, 10.78 g (80 mmol) of methyl-(9H-purin-6-yl)amine was dissolved, and 1.98 g (82.5 mmol) of sodium hydride (60%) after washing with hexane was added thereto and the mixture solution was stirred at room temperature for one hour. To the reaction solution, 13.0 g (92 mmol) of 4-fluoronitrobenzene was added dropwise and the resulting solution was stirred at 80° C. for two hours. The reaction solution was diluted with 300 mL of water, and the crystal deposited was collected on a filter, then washed with 100 mL of water and subsequently with 500 mL of ethanol, and vacuum dried to obtain 16.14 g (83%) of a target product as a yellow solid.

$^1$H-NMR (270 MHz, DMSO-d$_6$) δ (ppm): 2.98 (3H, br.s), 7.98 (1H, br.s), 8.30-8.50 (5H, m), 8.81 (1H, s)

ESI (LC-MS positive mode) m/z 271 (M+H)

Step C

Preparation of
[9-(4-aminophenyl)-9H-purin-6-yl]-methylamine

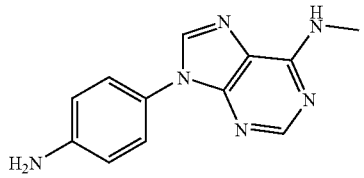

[Formula 198]

In 1,000 mL of methanol, 13.0 g (48 mmol) of methyl-[9-(4-nitrophenyl)-9H-purin-6-yl]amine was suspended, and 1.8 g of 10% palladium carbon was added thereto, and the suspension was stirred in a hydrogen atmosphere at 60° C. for six hours. The palladium carbon was removed by Celite filtration, and the product was concentrated under reduced pressure, and the obtained crude product was purified by a silica gel column (ethyl acetate:methanol=9.1) to obtain 8.2 g (70%) of a target product as a pale yellow solid.

$^1$H-NMR (270 MHz, DMSO-d$_6$) δ (ppm): 2.98 (3H, br.s), 5.38 (2H, s), 6.73 (2H, d, J=8.5 Hz), 7.38 (2H, d, J=8.5 Hz), 7.75 (1H, s), 8.23 (1H, s), 8.31 (1H, s)

ESI (LC-MS positive mode) m/z 241 (M+H)

Step D

Preparation of (3-nitro-5-(trifluoromethyl)phenyl)(4-methylpiperazin-1-yl)methanone

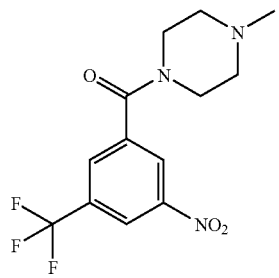

[Formula 199]

In 50 mL of dichloromethane, 5.0 g (21 mmol) of 3-trifluoromethyl-5-nitrobenzoic acid was suspended, and 4.3 g (34 mmol) of oxalyl chloride was added thereto and the mixture solution was stirred at room temperature for three hours. The reaction solution was concentrated under reduced pressure, dissolved in 70 ml of dichloromethane, and added dropwise to 70 mL of a dichloromethane solution of 1-methylpiperazine under cooling with ice. The organic layer was washed with a saturated sodium bicarbonate solution and a saturated sodium chloride solution and concentrated under reduced pressure to obtain 6.77 g (quantitative) of a target product.

$^1$H-NMR (270 MHz, CDCl$_3$) δ (ppm): 2.35 (3H, s), 2.15-2.60 (4H, m), 3.43 (2H, br.s), 3.83 (2H, br.s), 8.02 (1H, s), 8.45 (1H, s), 8.55 (1H, s)

ESI (LC-MS positive mode) m/z 318 (M+H)

Step E

Preparation of (3-amino-5-(trifluoromethyl)phenyl)(4-methylpiperazin-1-yl)methanone

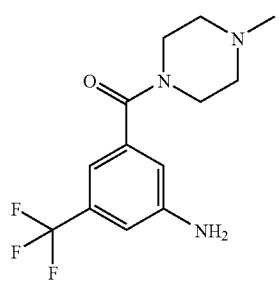

[Formula 200]

In 50 mL of methanol, 6.77 g (21 mmol) of (3-nitro-5-(trifluoromethyl)phenyl)-(4-methylpiperazin-1-yl)methanone was dissolved, and 400 mg of 10% palladium carbon was added thereto and the mixture solution was stirred in an hydrogen atmosphere under normal pressures at room temperature for three hours. The catalyst was removed by filtration and the filtrate was concentrated under reduced pressure and the residue was recrystallized from hexane and diethyl ether to obtain 6.14 g (quantitative) of a target product as a white solid.

$^1$H-NMR (270 MHz, CD$_3$OD) δ (ppm): 2.32 (3H, s), 2.25-2.60 (4H, m), 3.43 (2H, br.s), 3.78 (2H, br.s), 3.98 (2H, br.s), 6.83 (1H, s), 6.91 (1H, s), 6.96 (1H, s)

ESI (LC-MS positive mode) m/z 288 (M+H)

Step F

Preparation of 3-(4-methylpiperazin-1-ylmethyl)-5-(trifluoromethyl)aniline

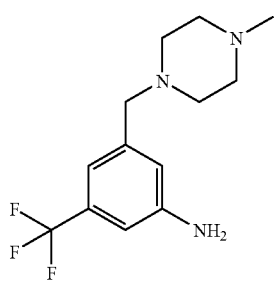

[Formula 201]

In 50 mL of tetrahydrofuran, 6.14 g (21 mmol) of (3-amino-5-(trifluoromethyl)phenyl)-(4-methylpiperazin-1-yl)methanone was dissolved, and 65 mL of a borane tetrahydrofuran complex (a 1N tetrahydrofuran solution) was added thereto and the mixture solution was refluxed with stirring for six hours. To the reaction solution, 60 mL of concentrated hydrochloric acid was added dropwise and the mixture solution was stirred at room temperature for 12 hours. The reaction solution was neutralized with solid sodium carbonate and extracted with diethyl ether. The extract was washed with water and a saturated sodium chloride solution and concentrated under reduced pressure, and the residue was recrystallized from hexane and diethyl ether to obtain 1.76 g (30%) of a target product as a white solid.

$^1$H-NMR (270 MHz, DMSO-$d_6$) δ (ppm): 2.23 (3H, s), 2.35-2.50 (8H, m), 3.43 (2H, s), 3.82 (2H, s), 6.76 (1H, s), 6.82 (1H, s), 6.95 (2H, d, J=8.9 Hz)

ESI (LC-MS positive mode) m/z 274 (M+H)

Step G

Preparation of 1-[4-(6-(methylamino)purin-9-yl)phenyl]-3-[3-(4-methylpiperazin-1-ylmethyl)-5-(trifluoromethyl)phenyl]urea (Table 2, compound No. 25)

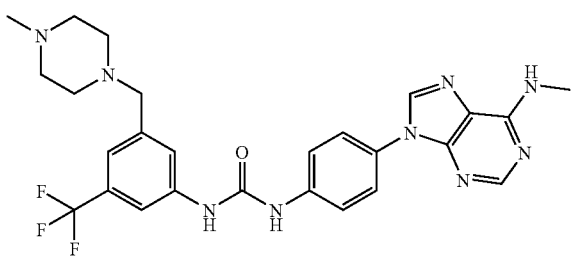

[Formula 202]

In 2 mL of dichloromethane, 608 mg (2.12 mmol) of 3-(methylpiperazin-1-ylmethyl)-5-(trifluoromethyl)aniline was dissolved, and 380 mg (2.34 mmol) of 1,1'-carbonylbis-1H-imidazole was added there to under cooling with ice, and the mixture solution was stirred at room temperature for three hours. To the reaction solution, 520 mg (2.16 mmol) of [9-(4-aminophenyl)-9H-purin-6-yl]-methylamine and 4 ml of dimethylformamide were added, and the mixture solution was further stirred at 40° C. for four hours. The residue obtained by concentrating the reaction solution was partitioned between water and ethyl acetate, and the organic layer was washed with a saturated sodium chloride solution and concentrated under reduced pressure. The product was recrystallized from ethyl acetate to obtain 742 mg (62%) of a target product as a white crystal.

$^1$H-NMR (270 MHz, DMSO-$d_6$) δ (ppm): 2.16 (3H, s), 2.25-2.45 (8H, m), 2.95-3.05 (3H, br.s), 3.53 (2H, s), 7.22 (1H, s), 7.55 (1H, s), 7.66 (2H, d, J=8.9 Hz), 7.79 (2H, d, J=8.9 Hz), 7.81 (1H, br.s), 7.91 (1H, s), 8.29 (1H, s), 8.51 (1H, s), 8.99 (1H, s), 9.15 (1H, s)

ESI (LC-MS positive mode) m/z 540 (M+H)

Example 148

1-[4-(6-Aminopurin-9-yl)phenyl]-3-[3-(4-methylpiperazin-1-ylmethyl)-5-(trifluoromethyl)phenyl]urea (Table 2, Compound No. 26)

Step A

Preparation of [9-(4-nitrophenyl)-9H-purin-6-yl]amine

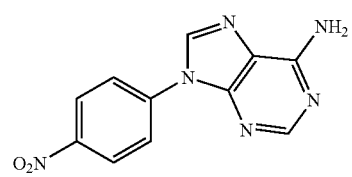

[Formula 203]

In 100 ml of dimethyl sulfoxide, 4.05 g (30.0 mmol) of adenine was dissolved, and 3.5 g (31.0 mmol) of potassium tert-butoxide and 5.0 g (35.0 mmol) of 4-fluoronitrobenzene were added thereto, and the mixture solution was stirred at 80° C. for three hours. The solution was diluted with 200 mL of water and the precipitate formed was collected by filtration, washed with 100 mL of water and 30 mL of methanol in the order named and vacuum dried to obtain 7.2 g (84%) of a target product as a yellow solid.

$^1$H-NMR (270 MHz, DMSO-$d_6$) δ (ppm): 7.53 (2H, br.s), 8.28 (1H, s), 8.32 (2H, d, J=8.4 Hz), 8.48 (2H, d, J=8.4 Hz), 8.84 (1H, s)

Step B

Preparation of [9-(4-aminophenyl)-9H-purin-6-yl]-amine

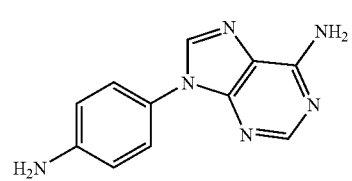

[Formula 204]

In 1,000 mL of methanol, 13.1 g (51 mmol) of [9-(4-nitrophenyl)-9H-purin-6-yl]amine was suspended, and 1.0 g of 10% palladium carbon was added thereto and the mixture suspension was stirred at 60° C. for 22 hours in a hydrogen atmosphere. The palladium carbon was removed by Celite filtration and the filtrate was washed with 3 L of hot methanol. The methanol solution was concentrated under reduced pressure and the formed product was purified by a silica gel column (ethyl acetate:methanol=8:1) to obtain 10.29 g (89%) of a target product as a pale yellow solid.

$^1$H-NMR (270 MHz, DMSO-$d_6$) δ (ppm): 5.45 (2H, s), 6.70 (2H, d, J=8.5 Hz), 7.30 (2H, s), 7.38 (2H, d, J=8.5 Hz), 8.15 (1H, s), 8.34 (1H, s)

ESI (LC-MS positive mode) m/z 227 (M+H)

Step C

Preparation of 1-[4-(6-aminopurin-9-yl)phenyl]-3-[3-(4-methylpiperazin-1-ylmethyl)-5-(trifluoromethyl)phenyl]urea (Table 2, Compound No. 26)

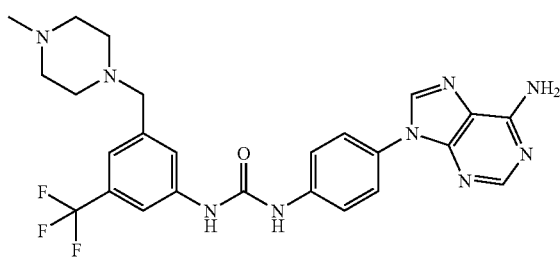

[Formula 205]

The title compound can be prepared from 3-(methylpiperazin-1-ylmethyl)-5-(trifluoromethyl)aniline and [9-(4-aminophenyl)-9H-purin-6-yl]amine by using the same techniques as in Step G of Example 147.

$^1$H-NMR (270 MHz, DMSO-$d_6$) δ (ppm): 2.16 (3H, s), 2.30-2.45 (8H, m), 3.52 (2H, s), 7.22 (1H, s), 7.38 (2H, s), 7.56 (1H, s), 7.66 (2H, d, J=8.9 Hz), 7.79 (2H, d, J=8.9 Hz), 7.93 (1H, s), 8.20 (1H, s), 8.53 (1H, s), 8.99 (1H, s), 9.15 (1H, s)

ESI (LC-MS positive mode) m/z 526 (M+H)

Example 149

1-[4-(6-Amino-8-iodopurin-9-yl)phenyl]-3-[3-(4-methylpiperazin-1-ylmethyl)-5-(trifluoromethyl)phenyl]urea (Table 2, Compound No. 27)

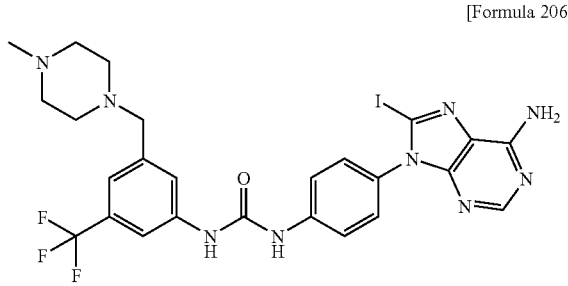

[Formula 206]

The title compound can be prepared from 1-[4-(6-aminopurin-9-yl)phenyl]-3-[3-(4-methylpiperazin-1-ylmethyl)-5-(trifluoromethyl)phenyl]urea by using the same techniques as in Example 129.

$^1$H-NMR (270 MHz, DMSO-$d_6$) δ (ppm): 2.17 (3H, s), 2.30-2.50 (8H, m), 3.53 (2H, s), 7.23 (1H, s), 7.38 (2H, d, J=8.9 Hz), 7.44 (2H, br.s), 7.56 (1H, s), 7.68 (2H, d, J=8.9 Hz), 7.94 (1H, s), 8.01 (1H, s), 9.08 (1H, s), 9.20 (1H, s)

ESI (LC-MS positive mode) m/z 652 (M+H)

Example 150

1-[4-(6-Amino-8-vinylpurin-9-yl)phenyl]-3-[3-(4-methylpiperazin-1-ylmethyl)-5-(trifluoromethylphenyl)urea (Table 2, Compound No. 28)

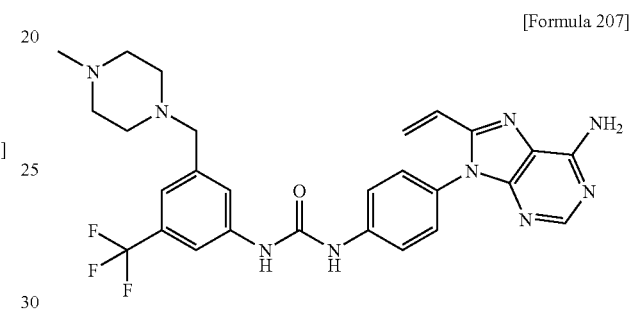

[Formula 207]

The title compound can be prepared from 1-{4-(6-amino-8-iodopurin-9-yl)phenyl}-3-[3-(4-methylpiperazin-1-ylmethyl)-5-(trifluoromethyl)phenyl]urea by using the same techniques as in Example 130.

$^1$H-NMR (270 MHz, DMSO-$d_6$) δ (ppm): 2.16 (3H, s), 2.30-2.50 (8H, m), 3.53 (2H, s), 5.61 (1H, dd, J=0.1, 11.6 Hz), 6.28 (1H, dd, J=0.1, 17.2 Hz), 6.55 (1H, dd, J=11.6, 17.2 Hz), 7.23 (1H, s), 7.35-7.40 (4H, m), 7.57 (1H, s), 7.70 (2H, d, J=7.6 Hz), 7.93 (1H, s), 8.08 (1H, d, J=1.7 Hz), 9.09 (1H, s), 9.20 (1H, s)

ESI (LC-MS positive mode) m/z 552 (M+H)

Example 151

1-[4-(6-Aminopurin-9-yl)phenyl]-3-(3-dimethylaminomethyl-5-(trifluoromethyl)phenyl)urea (Table 2, Compound No. 29)

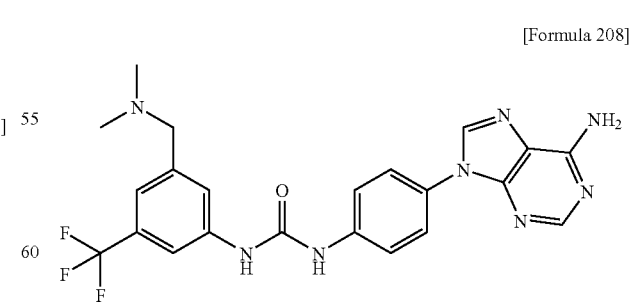

[Formula 208]

The title compound can be prepared from 3-(dimethylamino)methyl-5-(trifluoromethyl)aniline and [9-(4-aminophenyl)-9H-purin-6-yl]amine by using the same techniques as in Step G of Example 147.

¹H-NMR (270 MHz, DMSO-d₆) δ (ppm): 2.19 (6H, s), 3.46 (2H, s), 7.24 (1H, s), 7.36 (2H, s), 7.59 (1H, s), 7.66 (2H, d, J=8.8 Hz), 7.78 (2H, d, J=8.8 Hz), 7.88 (1H, s), 8.20 (1H, s), 8.52 (1H, s), 9.00 (1H, s), 9.13 (1H, s)
ESI (LC-MS positive mode) m/z 471 (M+H)

Example 152

1-(3-Dimethylaminomethyl-5-(trifluoromethyl)phenyl)-3-[4-(6-(methylamino)purin-9-yl)phenyl]urea (Table 2, Compound No. 30)

[Formula 209]

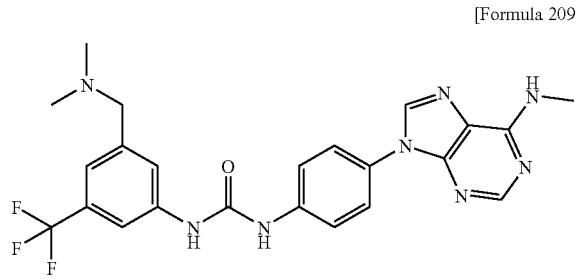 [SMILES: CNc1ncnc2c1ncn2-c1ccc(NC(=O)Nc2cc(CN(C)C)cc(C(F)(F)F)c2)cc1]

The title compound can be prepared from 3-(dimethylamino)methyl-5-(trifluoromethyl)aniline and [9-(4-aminophenyl)-9H-purin-6-yl]methylamine by using the same techniques as in Step G of Example 147.
¹H-NMR (270 MHz, DMSO-d₆) δ (ppm): 2.19 (6H, s), 2.95 (3H, s), 3.46 (2H, s), 7.22 (1H, s), 7.57 (1H, s), 7.66 (2H, d, J=8.9 Hz), 7.79 (2H, d, J=8.9 Hz), 7.81 (1H, br.s), 7.88 (1H, s), 8.28 (1H, s), 8.51 (1H, s), 8.99 (1H, s), 9.13 (1H, s)
ESI (LC-MS positive mode) m/z 471 (M+H)

Example 153

1-[4-(4-Cyano-imidazo[4,5-c]pyridin-1-yl)phenyl]-3-[3-(4-(methylpiperazin-1-ylmethyl)-5-(trifluoromethyl)phenyl]urea (Table 2, Compound No. 31)

Step A

Preparation of 1-(4-Aminophenyl)-1H-imdazo[4,5-c]-pyridine-4-carbonitrile

[Formula 210]

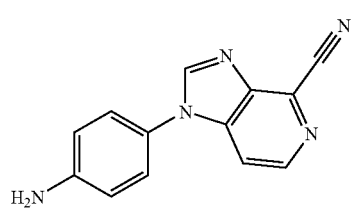

In 100 mL of methanol, 240 mg (0.9 mmol) of 1-(4-nitrophenyl)-1H-imidazo[4,5-c]pyridine-4-carbonitrile was dissolved, and 170 mg of 10% palladium carbon was added thereto and the mixture solution was refluxed with stirring in a hydrogen atmosphere for one hour. The palladium carbon was removed by Celite filtration and the reaction solution was concentrated under reduced pressure, and the obtained crude product was purified by a silica gel column (dichloromethane:methanol=40:1) to obtain 65 mg (30%) of a target product as a pale yellow solid.

¹H-NMR (270 MHz, DMSO-d₆) δ (ppm): 5.57 (2H, s), 6.74 (2H, d, J=8.9 Hz), 7.31 (2H, d, J=8.9 Hz), 7.86 (1H, d, J=5.6 Hz), 8.54 (1H, d, J=5.6 Hz), 8.84 (1H, s)
ESI (LC-MS positive mode) m/z 236 (M+H)

Step B

Preparation of 1-[4-(4-cyano-imidazo[4,5-c]pyridin-1-yl)phenyl]-3-[3-(4-methylpiperazin-1-ylmethyl)-5-(trifluoromethyl)phenyl]urea (Table 2, Compound No. 31)

[Formula 211]

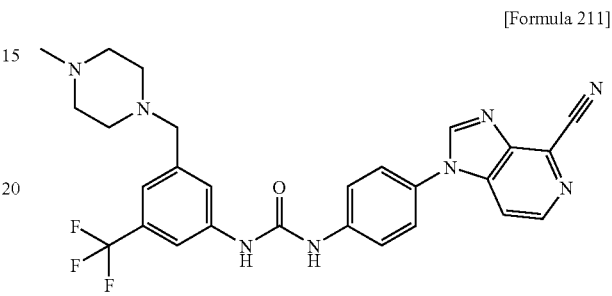

The title compound can be prepared from 3-(methylpiperazin-1-ylmethyl)-5-(trifluoromethyl)aniline and 1-(4-aminophenyl)-1H-imidazo[4,5-c]pyridine-4-carbonitrile by using the same techniques as in Step G of Example 147.
¹H-NMR (270 MHz, DMSO-d₆) δ (ppm): 2.16 (3H, s), 2.30-2.50 (8H, m), 3.53 (2H, s), 7.24 (1H, s), 7.55 (1H, s), 7.66 (2H, d, J=8.9 Hz), 7.76 (2H, d, J=8.9 Hz), 7.93 (1H, s), 7.99 (1H, d, J=5.6 Hz), 8.59 (1H, d, J=5.6 Hz), 8.99 (1H, d, J=3.0 Hz), 9.10 (1H, s), 9.19 (1H, s)
ESI (LC-MS positive mode) m/z 535 (M+H)

Example 154

1-[4-(6-Amino-8-ethylpurin-9-yl)phenyl]-3-[3-(4-methylpiperazin-1-ylmethyl)-5-(trifluoromethyl)phenyl]urea (Table 2, Compound No. 32)

[Formula 212]

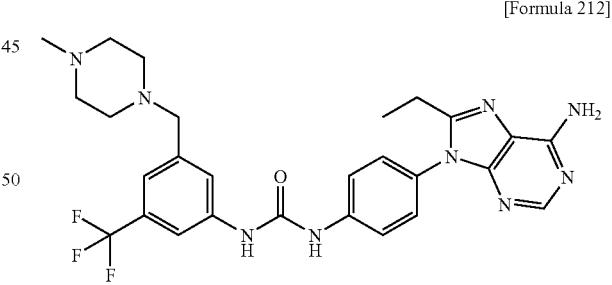

In 3 mL of methanol, 20 mg (0.1 mmol) of 1-[4-(6-amino-8-vinylpurin-9-yl)phenyl]-3-[3-(4-methylpiperazin-1-ylmethyl)-5-(trifluoromethyl)phenyl]urea was dissolved, and 10 mg of 10% palladium carbon was added thereto, and the mixture solution was refluxed with stirring in a hydrogen atmosphere for one hour. The palladium carbon was removed by filtration and the reaction solution was concentrated under reduced pressure, and the obtained crude product was triturated with diethyl ether to obtain 18 mg (90%) of a target product as a pale yellow solid.
¹H-NMR (270 MHz, DMSO-d₆) δ (ppm): 1.21 (3H, t, J=7.3 Hz), 2.16 (3H, s), 2.30-2.50 (8H, m), 2.73 (2H, q, J=7.3

Hz), 3.53 (2H, s), 7.16 (2H, s), 7.23 (1H, s), 7.40 (2H, d, J=8.9 Hz), 7.56 (1H, s), 7.68 (2H, d, J=8.9 Hz), 7.93 (1H, s), 8.03 (1H, s), 9.07 (1H, s), 9.21 (1H, s)

ESI (LC-MS positive mode) m/z 554 (M+H)

Example 155

1-(4-{3-[3-(4-methylpiperazin-1-ylmethyl)-5-(trifluoromethyl)phenyl]ureido}-phenyl)-1H-imidazo[4,5-c]pyridine-4-carboxamide (Table 2, Compound No. 33)

[Formula 213]

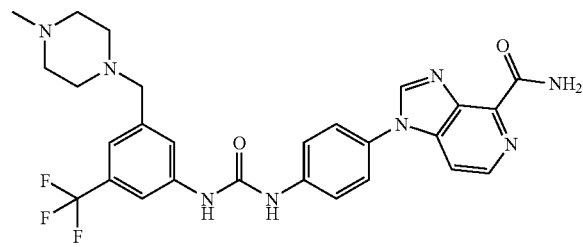

In 1 mL of dimethyl sulfoxide, 40 mg (0.07 mmol) of 1-[4-(4-cyano-imidazo[4,5-c]pyridin-1-yl)phenyl]-3-[3-(4-methylpiperazin-1-ylmethyl)-5-(trifluoromethyl)phenyl]urea was dissolved, and 40 μL (0.35 mmol) of a 30% hydrogen peroxide aqueous solution and 21 mg (0.15 mmol) of potassium carbonate were added thereto and the mixture solution was stirred at 50° C. for one hour. The reaction solution was partitioned between ethyl acetate and water, and the organic layer was washed with water and a saturated sodium chloride solution in the order named and concentrated under reduced pressure. The crude product was purified by a silica gel column (dichloromethane:methanol=10:1) to obtain 19 mg (45%) of a target product as a white solid.

$^1$H-NMR (270 MHz, DMSO-d$_6$) δ (ppm): 2.16 (3H, s), 2.30-2.50 (8H, m), 3.53 (2H, s), 7.24 (1H, s), 7.56 (1H, s), 7.65 (2H, d, J=8.9 Hz), 7.74 (2H, d, J=8.9 Hz), 7.79 (1H, d, J=5.3 Hz), 7.86 (1H, s), 7.93 (1H, s), 8.50 (1H, d, J=5.3 Hz), 8.62 (1H, s), 8.84 (1H, s), 9.10 (1H, s), 9.20 (1H, s)

ESI (LC-MS positive mode) m/z 553 (M+H)

Example 156

1-[4-(6-(Methylamino)purin-9-yl)phenyl]-3-[4-(4-methylpiperazin-1-yl)-3-(trifluoromethyl)phenyl]urea (Table 2, Compound No. 34)

Step A

Preparation of 4-(4-methylpiperazin-1-yl)-3-(trifluoromethyl)aniline

[Formula 214]

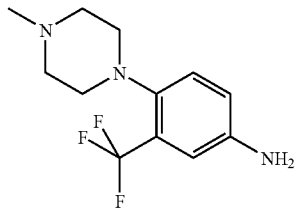

In 10 mL of dimethylformamide, 300 mg (1.44 mmol) of 2-fluoro-5-nitrobenzotrifluoride was dissolved, and 287 mg (2.88 mmol) of 4-methylpiperazine and 792 mg (5.76 mmol) of potassium carbonate were added thereto and the mixture solution was heated at 70° C. for three hours with vigorous stirring. After cooling, the reaction solution was poured into a saturated sodium bicarbonate solution and extracted with ethyl acetate, and the extract was washed with a saturated sodium chloride solution, and the obtained organic layer as such was used as a substrate in the subsequent catalytic reduction. To the organic layer, 10 mg of 10% palladium carbon was added and the mixture was stirred at room temperature for 16 hours in a hydrogen atmosphere at normal pressures. The catalyst was removed by filtration and the filtrate was concentrated and purified by silica gel column chromatography to obtain 350 mg (94%) of a target product as a brown solid.

$^1$H-NMR (270 MHz, CDCl$_3$) δ (ppm): 2.32 (3H, s), 2.51 (2H, br), 2.88 (4H, t, J=4.6 Hz), 3.71 (2H, br), 6.80 (1H, dd, J=8.5, 3.0 Hz), 6.91 (1H, d, J=3.0 Hz), 7.22 (1H, d, J=8.5 Hz)

ESI (LC-MS positive mode) m/z 260 (M+H)

Step B

Preparation of methyl-[9-(4-{3-[4-(4-methylpiperazin-1-yl)-3-(trifluoromethyl)phenyl]ureido}phenyl)-9H-purin-6-yl]carbamic acid tert-butyl ester

[Formula 215]

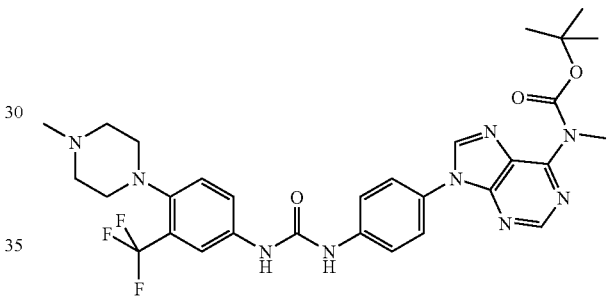

In 1 mL of dichloromethane, 100 mg (0.39 mmol) of 4-(4-methylpiperazin-1-yl)-3-(trifluoromethyl)aniline and 69 mg (4.25 mmol) of 1,1'-carbonylbis-1H-imidazole were dissolved and the mixture solution was stirred at room temperature for 16 hours. To the reaction solution, a solution obtained by dissolving 92 mg (4.25 mmol) of [9-(4-aminophenyl)-9H-purin-6-yl]methylcarbamic acid tert-butyl ester prepared in Example 36 in 2 mL of dichloromethane was added and the mixture solution was stirred at room temperature for 20 hours. The reaction solution was concentrated, and then the residue was purified by silica gel chromatography to obtain 78 mg (72%) of a target product as a white solid.

ESI (LC-MS positive mode) m/z 626 (M+H)

Step C

Preparation of 1-[4-(6-methylamino)purin-9-yl]phenyl]-3-[4-(4-methylpiperazin-1-yl)-3-(trifluoromethyl)phenyl]urea (Table 2, compound No. 34)

[Formula 216]

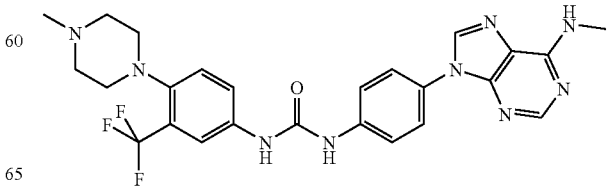

In 1 mL of trifluoroacetic acid, 54 mg (0.086 mmol) of methyl-[9-(4-{3-[4-(4-methylpiperazin-1-yl)-3-trifluoromethylphenyl]ureido}phenyl)-9-purin-6-yl]carbamic acid tert-butyl ester was dissolved and the solution was stirred at room temperature for one hour. The reaction solution was concentrated, and then dissolved in ethyl acetate and washed with a saturated sodium bicarbonate solution, then washed with a saturated sodium chloride solution, dried on anhydrous magnesium sulfate and concentrated, and the obtained residue was solidified with a mixed solvent of ethyl acetate and hexane, and washed with hexane to obtain 38 mg (83%) of a target product as a white solid.

$^1$H-NMR (270 MHz, DMSO-$d_6$) δ (ppm): 2.20 (3H, s), 2.43 (2H, br), 2.80 (4H, t, J=4.5 Hz), 2.98 (2H, br), 7.50 (1H, d, J=8.9 Hz), 7.57 (1H, dd, J=8.9, 2.6 Hz), 7.66 (2H, d, J=8.8 Hz), 7.76 (2H, d, J=8.8 Hz), 7.93 (1H, d, J=2.6 Hz), 8.27 (1H, s), 8.50 (1H, s), 9.02 (1H, s), 9.04 (1H, s)

ESI (LC-MS positive mode) m/z 526 (M+H)

Example 157

1-[4-(6-Aminopurin-9-yl)phenyl]-3-{4-[(2-dimethylaminoethyl)methylamino]-3-(trifluoromethyl)phenyl}-urea (Table 2, Compound No. 35)

Step A

Preparation of N$^1$-(2-(Dimethylamino)ethyl-N$^1$-methyl-2-(trifluoromethyl)benzene-1,4-diamine

[Formula 217]

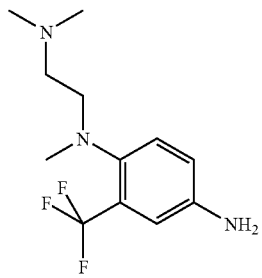

The title compound can be synthesized by obtaining an intermediate from 2-fluoro-5-nitrobenzotrifluoride and N,N,N'-trimethylethylenediamine and successively reducing the nitro group by using the same techniques as in Step A of Example 156.

$^1$H-NMR (270 MHz, CDCl$_3$) δ (ppm): 2.20 (6H, s), 2.26-2.35 (2H, m), 2.59 (3H, s), 2.84-2.98 (2H, m), 6.82 (1H, dd, J=8.0, 2.8 Hz), 6.91 (1H, d, J=2.8 Hz), 7.25 (1H, d, J=8.0 Hz)

ESI (LC-MS positive mode) m/z 262 (M+H)

Step B

Preparation of 1-[4-(6-aminopurin-9-yl)phenyl]-3-{4-[(2-dimethylaminoethyl)-methylamino]-3-(trifluoromethyl)phenyl}urea (Table 2, Compound No. 35)

[Formula 218]

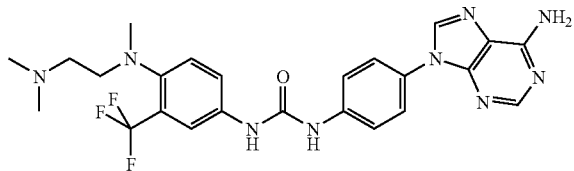

The title compound can be obtained by allowing 6-di-tert-butoxycarbonylamino-9-(4-aminophenyl)-9H-purine and N$^1$-(2-(dimethylamino)ethyl)-N$^1$-methyl-2-(trifluoromethyl)benzene-1,4-diamine to form a urea bonding, and then performing deprotection with trifluoroacetic acid by using the same techniques as in Steps B and C of Example 156.

$^1$H-NMR (270 MHz, DMSO-$d_6$) δ (ppm): 2.17 (6H, s), 2.34 (2H, t, J=7.8 Hz), 2.61 (3H, s), 2.97 (2H, t, J=7.8 Hz), 7.32-8.20 (7H, m), 8.25 (1H, s), 9.00 (1H, s)

ESI (LC-MS positive mode) m/z 514 (M+H)

Example 158

1-[4-(6-(Aminopurin-9-yl)phenyl]-3-(4-dimethylamino-3-(trifluoromethyl)phenyl)urea (Table 2, Compound No. 36)

Step A

Preparation of N$^1$,N$^1$-dimethyl-2-(trifluoromethyl)benzene-1,4-diamine

[Formula 219]

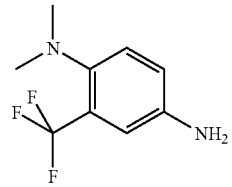

The title compound can be synthesized by obtaining an intermediate from 2-fluoro-5-nitrobenzotrifluoride and dimethylamine and successively reducing the nitro group by using the same techniques as in Step A of Example 156.

$^1$H-NMR (270 MHz, CDCl$_3$) δ (ppm): 2.62 (6H, s), 3.70 (2H, br), 6.80 (1H, dd, J=8.6, 2.8 Hz), 6.90 (1H, d, J=2.8 Hz), 7.27 (1H, d, J=8.6 Hz)

Step B

Preparation of 1-[4-(6-aminopurin-9-yl)phenyl]-3-(4-dimethylamino-3-(trifluoromethyl)phenyl)urea (Table 2, Compound No. 36)

[Formula 220]

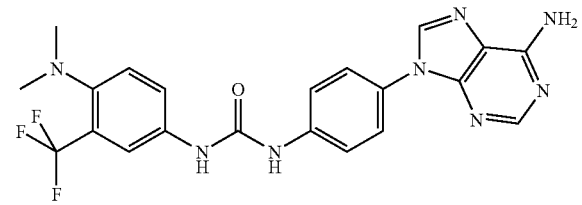

The title compound can be obtained by allowing 6-di-tert-butoxycarbonylamino-9-(4-aminophenyl)-9H-purine and N$^1$,N$^1$-dimethyl-2-(trifluoromethyl)benzene-1,4-diamine to form a urea bonding, and then performing deprotection with trifluoroacetic acid by using the same techniques as in Steps B and C of Example 156.

$^1$H-NMR (270 MHz, DMSO-$d_6$) δ (ppm): 2.61 (6H, s), 7.37 (2H, s), 7.53 (1H, d, J=8.8 Hz), 7.60 (1H, d, J=2.3 Hz), 7.65 (2H, d, J=8.8 Hz), 7.76 (2H, d, J=8.8 Hz), 7.90 (1H, d, J=2.3 Hz), 8.20 (1H, s), 8.51 (1H, s), 8.99 (2H, s)

ESI (LC-MS positive mode) m/z 457 (M+H)

Example 159

1-[4-(6-(Aminopurin-9-yl)phenyl)-3-[3-(4-methylpiperazine-1-carbonyl)-5-(trifluoromethyl)phenyl] urea (Table 2, Compound No. 37)

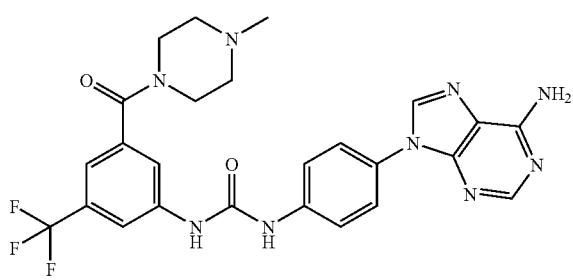

[Formula 221]

The title compound can be obtained by allowing 6-di-tert-butoxycarbonylamino-9-(4-aminophenyl)-9H-purine and (3-amino-5-(trifluoromethyl)phenyl)-(4-methylpiperazin-1-yl)methanone to form a urea bonding, and then performing deprotection with trifluoroacetic acid by using the same techniques as in Steps B and C of Example 156.

$^1$H-NMR (270 MHz, DMSO-d$_6$) δ (ppm): 2.21 (3H, s), 2.31 (2H, br.s), 2.37 (2H, br.s), 3.22-3.34 (2H, m), 3.63 (2H, br.s), 7.30 (1H, s), 7.38 (2H, s), 7.67 (2H, d, J=8.9 Hz), 7.69 (1H, s), 7.79 (2H, d, J=8.9 Hz), 8.02 (1H, s), 8.20 (1H, s), 8.53 (1H, s), 9.24 (1H, s), 9.35 (1H, s)

ESI (LC-MS positive mode) m/z 540 (M+H)

Example 160

3-{3-[4-(6-(Aminopurin-9-yl)phenyl)ureido]-N-(2-dimethylaminoethyl)-5-(trifluoromethyl)benzamide (Table 2, Compound No. 38)

Step A

Preparation of 3-amino-N-(2-(dimethylamino)ethyl)-5-(trifluoromethyl)benzamide

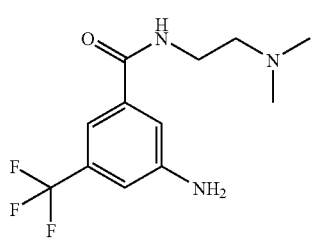

[Formula 222]

The title compound can be obtained by amidating 3-trifluoromethyl-5-nitrobenzoic acid with N,N-dimethylethylenediamine, and then performing catalytic reduction by using the same techniques as in Steps D and E of Example 147.

$^1$H-NMR (270 MHz, CD$_3$OD) δ (ppm): 2.31 (6H, s), 2.57 (2H, t, J=6.8 Hz), 3.50 (2H, t, J=6.8 Hz), 7.04 (1H, s), 7.28 (1H, s), 7.31 (1H, s)

ESI (LC-MS positive mode) m/z 275 (M+H)

Step B

Preparation of 3-{3-[4-(6-Aminopurin-9-yl)phenyl]-ureido}-N-(2-dimethylaminoethyl)-5-(trifluoromethyl)benzamide (Table 2, Compound No. 38)

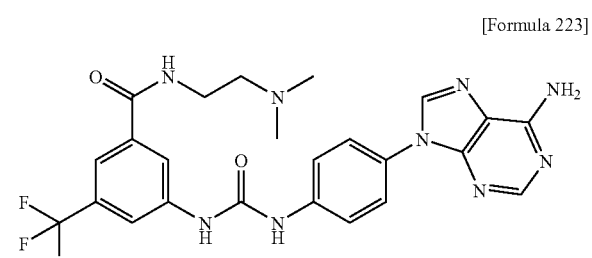

[Formula 223]

The title compound can be obtained by allowing 6-di-tert-butoxycarbonylamino-9-(4-aminophenyl)-9H-purine and 3-amino-N-(2-(dimethylamino)ethyl)-5-(trifluoromethyl) benzamide to form a urea bonding, and then performing deprotection with trifluoroacetic acid by using the same techniques as in Steps B and C of Example 156.

$^1$H-NMR (270 MHz, DMSO-d$_6$) δ (ppm): 2.19 (6H, s), 2.34-2.50 (2H, m), 3.22-3.40 (2H, m), 7.37 (2H, s), 7.68 (2H, d, J=8.9 Hz), 7.79 (1H, s), 7.80 (2H, d, J=8.9 Hz), 8.07 (1H, s), 8.17 (1H, s), 8.20 (1H, s), 8.53 (1H, s), 8.66 (1H, t, J=5.8 Hz), 9.20 (1H, s), 9.41 (1H, s)

ESI (LC-MS positive mode) m/z 524 (M+H)

Example 161

1-[4-(6-(Methylamino)purin-9-yl)phenyl]-3-(4-methylpiperazine-1-carbonyl)-5-(trifluoromethyl)phenyl] urea (Table 2, Compound No. 39)

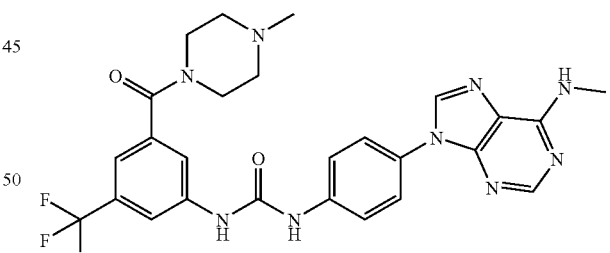

[Formula 224]

The title compound can be obtained by allowing [9-(4-aminophenyl)-9H-purin-6-yl]-methylcarbamic acid tert-butyl ester and (3-amino-5-(trifluoromethyl)phenyl)-(4-methylpiperazin-1-yl)methanone to for a urea bonding, and then performing deprotection with trifluoroacetic acid by using the same techniques as in Steps B and C of Example 156.

$^1$H-NMR (270 MHz, CD$_3$OD) δ (ppm): 2.34 (3H, s), 2.47 (2H, br.s), 2.54 (2H, br.s), 3.14 (3H, br.s), 3.50 (2H, s), 3.79 (2H, br.s), 7.35 (1H, s), 7.66 (2H, d, J=9.2 Hz), 7.71 (2H, d, J=9.2 Hz), 7.80 (1H, s), 7.94 (1H, s), 8.27 (1H, s), 8.30 (1H, s), ESI (LC-MS positive mode) m/z 554 (M+H)

Example 162

N-(2-Dimethylaminoethyl)-3-{3-[4-(6-(methylamino)purin-9-yl)phenyl]ureido}-5-(trifluoromethyl)benzamide (Table 2, Compound No. 40)

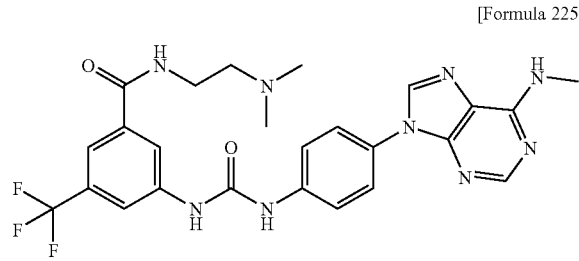 [SMILES: CNc1ncnc2c1ncn2-c1ccc(NC(=O)Nc2cc(C(=O)NCCN(C)C)cc(C(F)(F)F)c2)cc1]

[Formula 225]

The title compound can be obtained by allowing [9-(4-aminophenyl)-9H-purin-6-yl]-methylcarbamic acid tert-butyl ester and 3-amino-N-(2-(dimethylamino)ethyl)-5-(trifluoromethyl)benzamide to form a urea bonding, and then performing deprotection with trifluoroacetic acid by using the same techniques as in Steps B and C of Example 156.

$^1$H-NMR (270 MHz, DMSO-$d_6$) δ (ppm): 2.18 (6H, s), 2.32-2.46 (2H, m), 2.99 (3H, br.s), 3.22-3.42 (2H, m), 7.69 (2H, d, J=8.9 Hz), 7.79 (2H, d, J=8.9 Hz), 7.74-7.89 (2H, m), 8.07 (1H, s), 8.17 (1H, s), 8.29 (1H, s), 8.52 (1H, s), 8.09-8.20 (1H, m), 9.30 (1H, s), 9.50 (1H, s)

ESI (LC-MS positive mode) m/z 542 (M+H)

Example 163

1-[4-(6-Aminopurin-9-yl)phenyl]-3-[4-(4-methylpiperazin-1-yl)-3-(trifluoromethyl)phenyl]urea (Table 2, Compound No. 41)

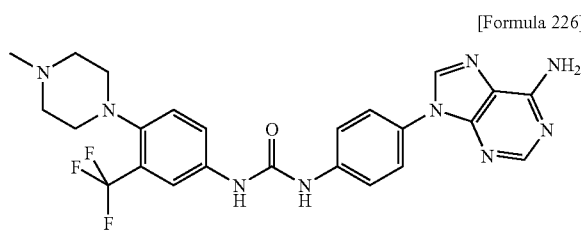 [SMILES: CN1CCN(c2ccc(NC(=O)Nc3ccc(-n4cnc5c(N)ncnc54)cc3)cc2C(F)(F)F)CC1]

[Formula 226]

The title compound can be obtained by allowing 4-(4-methylpiperazin-1-yl)-3-(trifluoromethyl)aniline and 6-di-tert-butoxycarbonylamino-9-(4-aminophenyl)-9H-purine to form a urea bonding, and then performing deprotection with trifluoroacetic acid by using the same techniques as in Steps B and C of Example 156.

$^1$H-NMR (270 MHz, DMSO-$d_6$) δ (ppm): 2.23 (3H, s), 2.83 (4H, t, J=4.5 Hz), 7.35-7.93 (7H, m), 8.18 (1H, s), 8.49 (1H, s), 9.03 (2H, br)

ESI (LC-MS positive mode) m/z 512 (M+H)

Example 164

1-(4-Dimethylamino-3-(trifluoromethyl)phenyl)-3-[4-(6-(methylamino)purin-9-yl)phenyl]urea (Table 2, Compound No. 42)

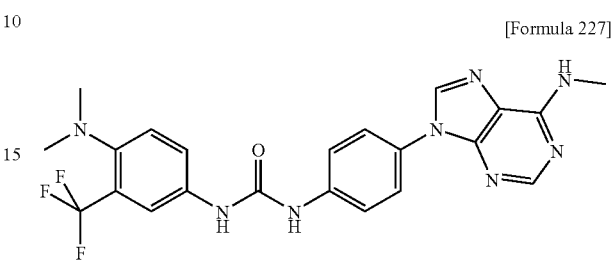

[Formula 227]

The title compound can be obtained by allowing $N^1,N^1$-dimethyl-2-(trifluoromethyl)benzene-1,4-diamine and [9-(4-aminophenyl)-9H-purin-6-yl]-methylcarbamic acid tert-butyl ester to form a urea bonding, and then performing deprotection with trifluoroacetic acid by using the same techniques as in Steps B and C of Example 156.

$^1$H-NMR (270 MHz, DMSO-$d_6$) δ (ppm): 2.61 (6H, s), 2.99 (3H, br), 7.02 (1H, br), 7.50-7.91 (7H, m), 8.28 (1H, br), 8.50 (1H, s), 9.00 (2H, s)

ESI (LC-MS positive mode) m/z 471 (M+H)

Example 165

1-[4-(6-(Aminopurin-9-yl)phenyl)-3-(3-bromo-5-(trifluoromethyl)phenyl)urea (Table 2, Compound No. 43)

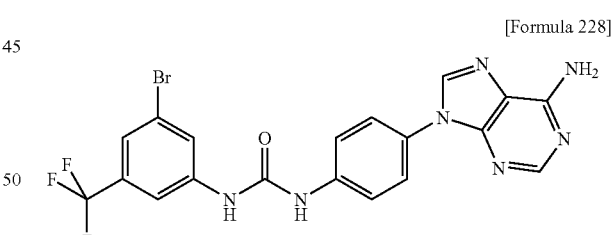

[Formula 228]

The title compound can be obtained by allowing 3-bromo-5-(trifluoromethyl)aniline and 6-di-tert-butoxycarbonylamino-9-(4-aminophenyl)-9H-purine to form a urea bonding, and then performing deprotection with trifluoroacetic acid by using the same techniques as in Steps B and C of Example 156.

$^1$H-NMR (270 MHz, DMSO-$d_6$) δ (ppm): 7.53 (1H, s), 7.70-7.74 (4H, m), 7.89 (1H, s), 7.96 (1H, s), 8.48 (1H, s), 8.80 (1H, s), 9.60 (1H, m), 9.82 (1H, s)

ESI (LC-MS positive mode) m/z 492 (M+H)

Example 166

1-[4-(1,2-Dihydroxyethyl)-3-(trifluoromethyl)phenyl]-3-[4-(6-(methylamino)purin-6-yl)phenyl]urea (Table 2, Compound No. 44)

Step A

Preparation of (9-{4-[3-(4-bromo-3-(trifluoromethyl)phenyl)ureido]phenyl}-9H-purin-6-yl)-methyl-carbamic acid tert-butyl ester

[Formula 229]

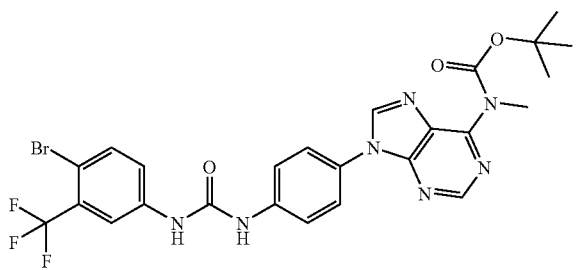

The title compound can be obtained by allowing 4-bromo-3-(trifluoromethyl)aniline and 6-di-tert-butoxycarbonylamino-9-(4-aminophenyl)-9H-purine to form a urea bonding by using the same techniques as in step B of Example 156.

$^1$H-NMR (270 MHz, DMSO-$d_6$) δ (ppm): 1.45 (9H, s), 3.30 (3H, s), 7.65-7.80 (6H, m), 8.14 (1H, d, J=2.6 Hz), 8.79 (1H, s), 8.91 (1H, s), 9.17 (1H, s), 9.27 (1H, s)

ESI (LC-MS positive mode) m/z 606, 608 (M+H)

Step B

Preparation of methyl-(9-{4-[3-(3-trifluoromethyl-4-vinylphenyl)ureido]phenyl}-9H-purin-6-yl)-carbamic acid tert-butyl ester

[Formula 230]

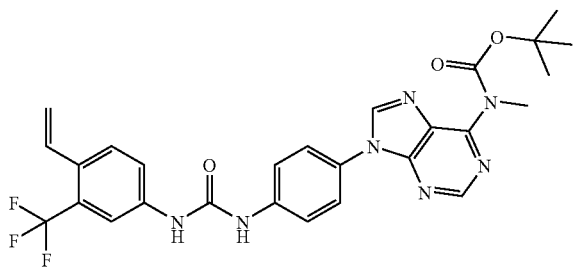

In 10 mL of 1-propanol and 680 µL of diisopropylamine, 900 mg (1.48 mmol) of (9-{4-[3-(4-bromo-3-(trifluoromethyl)phenyl)ureido]phenyl}-9H-purin-6-yl)methyl-carbamic acid tert-butyl ester was dissolved, and 330 mg (2.46 mmol) of potassium (trifluoro)vinylborate and 70 mg (0.09 mmol) of dichlorobistriphenylphosphine palladium were added thereto and the mixture solution was stirred at 80° C. for seven hours in an argon atmosphere. The reaction solution was concentrated, and the residue was partitioned between water and ethyl acetate, and the organic layer was washed with a saturated sodium chloride solution and concentrated under reduced pressure. The product was purified by a silica gel column (ethyl acetate) to obtain 618 mg (75%) of a target product as a white crystal.

$^1$H-NMR (270 MHz, DMSO-$d_6$) δ (ppm): 1.46 (9H, s), 3.40 (3H, s), 5.40 (1H, d, J=11.9 Hz), 5.86 (1H, d, J=17.1 Hz), 6.91 (1H, dd, J=11.9, 17.1 Hz), 7.60-7.80 (6H, m), 8.02 (1H, d, J=2.6 Hz), 8.79 (1H, s), 8.91 (1H, s), 9.12 (1H, s), 9.20 (1H, s)

ESI (LC-MS positive mode) m/z 554 (M+H)

Step C

Preparation of [9-(4-(3-[4-(1,2-dihydroxyethyl)-3-(trifluoromethyl)phenyl]ureido)phenyl)-9H-purin-6-yl]-methyl-carbamic acid tert-butyl ester

[Formula 231]

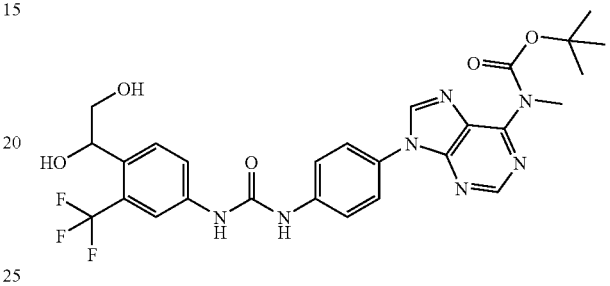

In 2 mL of tetrahydrofuran, 100 mg (0.18 mmol) of methyl-(9-{4-[3-(3-trifluoromethyl-4-vinylphenyl)ureido]phenyl}-9H-purin-6-yl)carbamic acid tert-butyl ester was dissolved, and 200 µL of an 0.1 M osmium tetraoxide aqueous solution and 400 µL of a 30% hydrogen peroxide aqueous solution were added thereto, and the mixture solution was stirred at room temperature for 14 hours. The reaction solution was partitioned between water and ethyl acetate, and the organic layer was washed with a saturated sodium chloride solution and concentrated under reduced pressure. The product was purified by a silica gel column (ethyl acetate) to obtain 39 mg (36%) of a target product as a white crystal.

ESI (LC-MS positive mode) m/z 588 (M+H)

Step D

Preparation of 1-[4-(1,2-dihydroxyethyl)-3-(trifluoromethyl)phenyl]-3-[4-(6-(methylamino)purin-9-yl)phenyl]urea (Table 2, Compound No. 44)

[Formula 232]

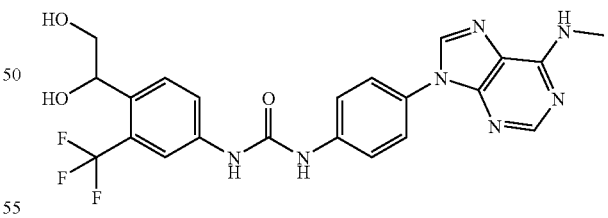

The title compound can be obtained by deprotecting [9-(4-{3-[4-(1,2-dihydroxyethyl)-3-(trifluoromethyl)phenyl]ureido}phenyl)-9H-purin-6-yl]-methyl-carbamic acid tert-butyl ester with trifluoroacetic acid by using the same techniques as in Step C of Example 156.

$^1$H-NMR (270 MHz, DMSO-$d_6$) δ (ppm): 2.99 (3H, s), 3.39 (2H, m), 4.84 (2H, m), 5.44 (1H, d, J=4.3 Hz), 7.55-7.70 (4H, m), 7.78 (2H, d, J=8.9 Hz), 7.85 (1H, br.s), 7.95 (1H, d, J=1.9 Hz), 8.28 (1H, s), 8.51 (1H, s), 9.01 (1H, s), 9.07 (1H, s)

ESI (LC-MS positive mode) m/z 488 (M+H)

Example 167

1-(4-Hydroxymethyl-3-(trifluoromethyl)phenyl)-3-[4-(6-(methylamino)purin-9-yl)phenyl]urea (Table 2, Compound No. 45)

Step A

Preparation of (9-{4-[3-(4-formyl-3-(trifluoromethyl)phenyl)ureido]phenyl}-9H-purin-6-yl)-methylcarbamic acid tert-butyl ester

[Formula 233]

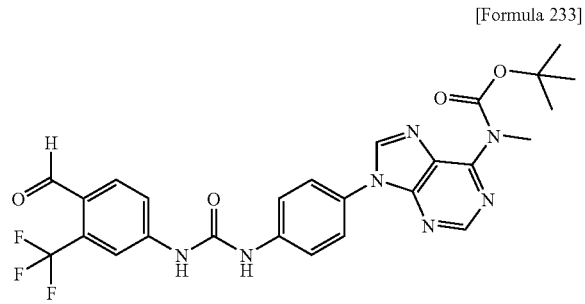 [SMILES: CN(C(=O)OC(C)(C)C)c1ncnc2c1ncn2-c1ccc(NC(=O)Nc2ccc(C=O)c(C(F)(F)F)c2)cc1]

In a mixed solution of 10 mL of tetrahydrofuran and 5 mL of water, 324 mg (0.59 mmol) of methyl-(9-{4-[3-(3-trifluoromethyl-4-vinylphenyl)ureido]phenyl}-9H-purin-6-yl)-carbamic acid tert-butyl ester was dissolved, and 200 µL of a 0.1 M osmium tetraoxide aqueous solution and 510 mg (2.38 mmol) of sodium periodate were added thereto, and the mixture solution was stirred at room temperature for 14 hours. The reaction solution was partitioned between water and ethyl acetate, and the organic layer was washed with a saturated sodium chloride solution and concentrated under reduced pressure. The product was purified by a silica gel column (hexane:ethyl acetate=1:2) to obtain 243 mg (75%) of a target product as a white crystal.

$^1$H-NMR (270 MHz, DMSO-$d_6$) δ (ppm): 1.44 (9H, s), 3.40 (3H, s), 7.70-7.82 (5H, m), 8.08 (1H, d, J=8.2 Hz), 8.20 (1H, d, J=1.6 Hz), 8.79 (1H, s), 8.91 (1H, s), 9.29 (1H, s), 9.68 (1H, s), 10.14 (1H, s)

ESI (LC-MS positive mode) m/z 556 (M+H)

Step B

Preparation of (9-{4-[3-[4-hydroxymethyl-3-(trifluoromethyl)phenyl]ureido]phenyl}-9H-purin-6-yl)methyl-carbamic acid tert-butyl ester

[Formula 234]

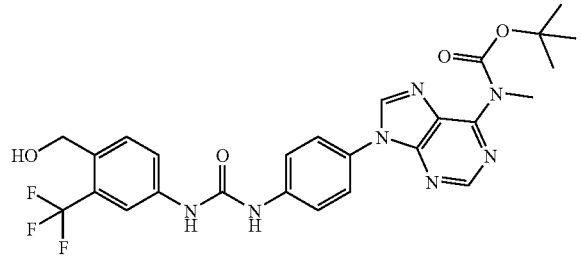

In 2 mL of methanol, 25 mg (0.05 mmol) of (9-{4-[3-(4-formyl-3-(trifluoromethyl)phenyl)ureido]phenyl}-9H-purin-6-yl)-methyl-carbamic acid tert-butyl ester was dissolved, and 10 mg (0.26 mmol) of sodium borohydride was added thereto and the mixture solution was stirred at room temperature for one hour. The reaction solution was concentrated and purified by a silica gel column (ethyl acetate) to obtain 24 mg (96%) of a target product as a white crystal.

ESI (LC-MS positive mode) m/z 558 (M+H)

Step C

Preparation of 1-(4-hydroxymethyl-3-(trifluoromethyl)phenyl)-3-[4-(6-(methylamino)purin-9-yl)phenyl]urea (Table 2, Compound No. 45)

[Formula 235]

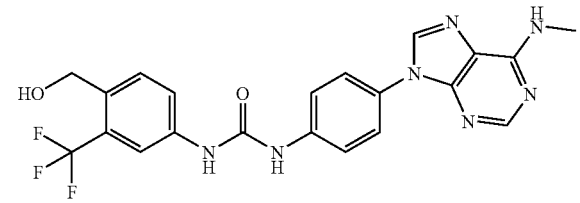

The title compound can be obtained by deprotecting [9-(4-{3-[4-dihydroxymethyl-3-(trifluoromethyl)phenyl)-ureido]phenyl}-9H-purin-6-yl]-methylcarbamic acid tert-butyl ester with trifluoroacetic acid by using the same techniques as in step C of Example 156.

$^1$H-NMR (270 MHz, DMSO-$d_6$) δ (ppm): 2.99 (3H, s), 4.49 (2H, d, J=5.0 Hz), 5.40 (1H, t, J=5.0 Hz), 7.60-7.70 (4H, m), 7.78 (2H, d, J=8.9 Hz), 7.85 (1H, br.s), 7.95 (1H, d, J=1.9 Hz), 8.28 (1H, s), 8.51 (1H, s), 9.01 (1H, s), 9.07 (1H, s)

ESI (LC-MS positive mode) m/z 458 (M+H)

Example 168

1-[4-(6-(Methylamino)purin-9-yl)phenyl]-3-[4-(4-methylpiperazin-1-ylmethyl)-3-(trifluoromethyl)phenyl]urea (Table 2, Compound No. 46)

[Formula 236]

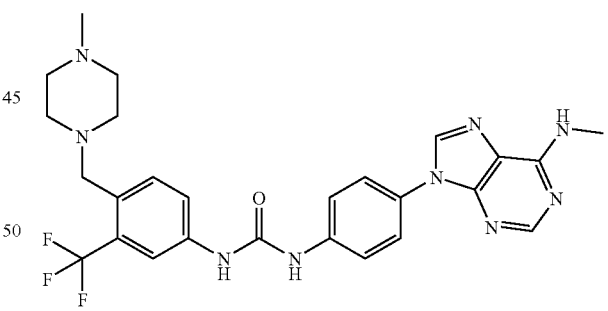

In 2 mL of ethanol, 40 mg (0.07 mmol) of (9-{4-[3-(4-formyl-3-(trifluoromethyl)phenyl)ureido]phenyl}-9H-purin-6-yl)-methyl-carbamic acid tert-butyl ester was dissolved, and 15 µL of acetic acid and 20 mg (0.20 mmol) of 1-methylpiperazine were added thereto, and the mixture solution was stirred at room temperature for 30 minutes. To the reaction solution, 10 mg (0.26 mmol) of sodium cyanoborohydride was further added and the resulting solution was stirred at room temperature for one hour. The reaction solution was concentrated and partitioned between water and ethyl acetate and the organic layer was washed with a saturated sodium chloride solution, concentrated under reduced pressure and purified by a silica gel column (ethyl acetate:

methanol=4:1). The obtained intermediate was dissolved in 1 mL of trifluoroacetic acid and stirred for one hour. The reaction solution was concentrated and partitioned between a saturated sodium bicarbonate solution and ethyl acetate, and the organic layer was washed with a saturated sodium chloride solution, concentrated under reduced pressure, and purified by trituration with ethyl acetate to obtain 27.4 mg (70%) of a target product as a white solid.

$^1$H-NMR (270 MHz, DMSO-$d_6$) δ (ppm): 2.16 (3H, s), 2.30-2.50 (8H, m), 2.99 (3H, s), 3.53 (2H, s), 7.55-7.70 (4H, m), 7.79 (2H, d, J=8.9 Hz), 7.81 (1H, br.s), 7.95 (1H, d, J=1.8 Hz), 8.30 (1H, s), 8.50 (1H, s), 9.03 (1H, s), 9.09 (1H, s)

ESI (LC-MS positive mode) m/z 540 (M+H)

Example 169

1-[4-(6-(Methylamino)purin-9-yl)phenyl]-3-(4-morpholin-4-ylmethyl-3-(trifluoromethyl)phenyl)urea (Table 2, Compound No. 47)

[Formula 237]

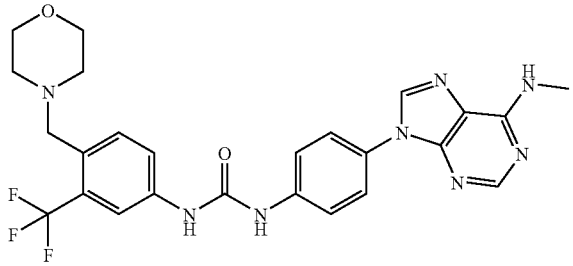

The title compound can be prepared from morpholine and (9-{4-[3-(4-formyl-3-(trifluoromethyl)phenyl)ureido]phenyl}-9H-purin-6-yl)-methyl-carbamic acid tert-butyl ester by the same techniques as in Example 168.

$^1$H-NMR (270 MHz, DMSO-$d_6$) δ (ppm): 2.40 (4H, m), 2.99 (3H, s), 3.53 (2H, s), 3.61 (4H, m), 7.55-7.70 (4H, m), 7.79 (2H, d, J=8.9 Hz), 7.81 (1H, br.s), 7.95 (1H, d, J=1.8 Hz), 8.30 (1H, s), 8.50 (1H, s), 9.03 (1H, s), 9.09 (1H, s)

ESI (LC-MS positive mode) m/z 527 (M+H)

Example 170

1-(3-Dimethylamino-5-(trifluoromethyl)phenyl)-3-[4-(6-(methylamino)purin-9-yl)phenyl]urea (Table 2, Compound No. 48)

Step A

Preparation of 5-(trifluoromethyl)benzene-1,3-diamine

[Formula 238]

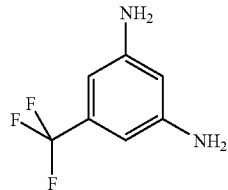

In a mixed solvent of 10 mL of ethyl acetate and 1 mL of methanol, 500 mg (2.12 mmol) of 3,5-dinitrobenzotrifluoride was dissolved, and 20 mg of 10% palladium carbon was added thereto, and the mixture solution was stirred at room temperature for 20 hours in a hydrogen atmosphere at normal pressures. The catalyst was removed by filtration, and the filtrate was concentrated and dried to obtain 380 mg (100%) of a brown oily target product.

ESI (LC-MS positive mode) m/z 177 (M+H)

Step B

Preparation of N-(3-amino-5-(trifluoromethyl)phenyl)-2,2,2-trifluoroacetamide

[Formula 239]

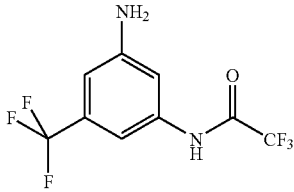

In dichloromethane, 370 mg (2.10 mmol) of 5-(trifluoromethyl)benzene-1,3-diamine and 0.25 ml (3.15 mmol) of pyridine were dissolved and the solution was cooled on an ice bath. To this solution, 0.293 ml (2.10 mmol) of trifluoroacetic anhydride was slowly added, and at that temperature the mixture solution was stirred for one hour. The reaction solution was poured into water and extracted with ethyl acetate and the extract was purified by silica gel column chromatography to obtain 138 mg (25%) of a pale yellow oily target product.

ESI (LC-MS positive mode) m/z 273 (M+H)

Step C

Preparation of N,N-dimethyl-5-(trifluoromethyl) benzene-1,3-diamine

[Formula 240]

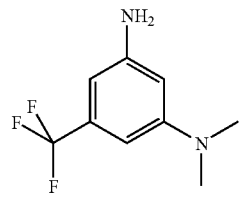

In 3 mL of methanol, 150 mg (0.55 mmol) of N-(3-amino-5-(trifluoromethyl)phenyl)-2,2,2-trifluoroacetamide, 0.076 mL (0.9 mmol) of a 37% formaldehyde aqueous solution and 0.05 mL of acetic acid were dissolved, and 47 mg (0.74 mmol) of sodium cyanoborohydride was added thereto, and the mixture solution was stirred at room temperature for 15 hours. The reaction solution was poured into water and extracted with ethyl acetate, and the extract was washed with a saturated sodium chloride solution and concentrated, and the residue was dissolved in 6 mL of tetrahydrofuran. To this solution, 10 mL of a saturated sodium bicarbonate solution was added and the mixture solution was heated at 50° C. for 20 hours. The reaction solution was poured into water and extracted with ethyl acetate, and the extract was dried on anhydrous magnesium sulfate and concentrated, and the residue was purified by silica gel column chromatography to obtain 100 mg (89%) of a brownish oily target product.

ESI (LC-MS positive mode) m/z 205 (M+H)

Step D

Preparation of 1-(3-dimethylamino-5-(trifluoromethyl)phenyl)-3-[4-(6-(methylamino)purin-9-yl)phenyl]urea (Table 2, Compound No. 48)

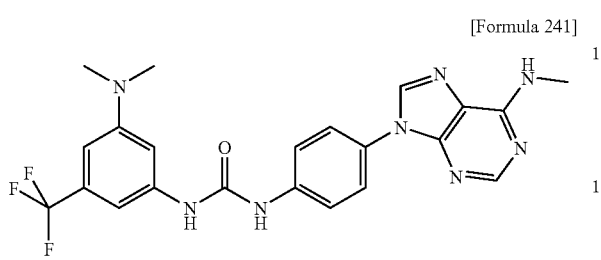

[Formula 241]

The title compound can be obtained by allowing [9-(4-aminophenyl)-9H-purin-6-yl]-methylcarbamic acid tert-butyl ester and N,N-dimethyl-5-(trifluoromethyl)benzene-1,3-diamine to form a urea bonding and then performing deprotection with trifluoroacetic acid by using the same techniques as in Steps B and C of Example 156.

$^1$H-NMR (270 MHz, DMSO-$d_6$) δ (ppm): 2.96 (6H, s), 6.58 (1H, s), 6.97 (1H, s), 7.23 (1H, s), 7.66 (2H, d, J=8.8 Hz), 7.77 (2H, d, J=8.8 Hz), 8.29 (1H, br), 8.51 (1H, s), 8.96 (1H, s), 8.98 (1H, s)

ESI (LC-MS positive mode) m/z 471 (M+H)

Example 171

1-[4-(6-Aminopurin-9-yl)phenyl]-3-[4-(2-dimethylaminoethoxy)-3-(trifluoromethyl)phenyl]urea (Table 2, Compound No. 49)

Step A

Preparation of 4-(2-(dimethylamino)ethoxy)-3-(trifluoromethyl)phenylamine

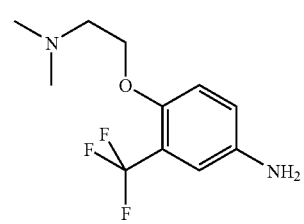

[Formula 242]

In 6 mL of dimethylformamide, 256 mg (2.87 mmol) of 2-dimethylaminoethanol was dissolved, and 42 mg (1.05 mmol) of sodium hydride was added thereto, and the mixture solution was stirred at room temperature for 10 minutes, and then 200 mg (0.96 mmol) of 2-fluoro-5-nitrobenzotrifluoride was added thereto and the mixture solution was heated at 50° C. for two hours. The reaction solution was poured into a saturated ammonium chloride aqueous solution and extracted with ethyl acetate, and the extract was washed with a saturated sodium chloride solution. To the organic layer, 20 mg of 10% palladium carbon and 2 mL of methanol were added, and the mixture solution was stirred at room temperature in a hydrogen atmosphere at normal pressures for 16 hours. After filtration, the filtrate was concentrated and the residue was purified by silica gel column chromatography to obtain 230 mg (97%) of a yellow oily target product.

$^1$H-NMR (270 MHz, CDCl$_3$) δ (ppm): 2.34 (6H, s), 2.74 (2H, t, J=6.0 Hz), 4.07 (2H, t, J=6.0 Hz), 6.70-6.90 (3H, m)

ESI (LC-MS positive mode) m/z 249 (M+H)

Step B

Preparation of 1-[4-(6-aminopurin-9-yl)phenyl]-3-[4-(2-dimethylaminoethoxy)-3-(trifluoromethyl)phenyl]-urea (Table 2, Compound 49)

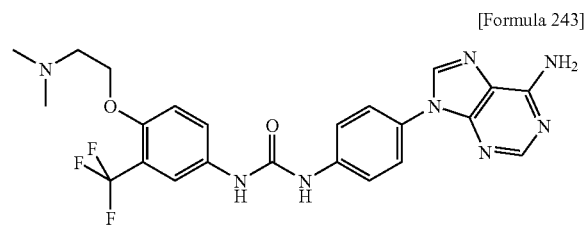 [SMILES: CN(C)CCOc1ccc(NC(=O)Nc2ccc(-n3cnc4c(N)ncnc43)cc2)cc1C(F)(F)F]

[Formula 243]

The title compound can be obtained by allowing 6-di-tert-butylcarbonylamino-9-(4-aminophenyl)-9H-purine and 4-(2-(dimethylamino)ethoxy)-3-(trifluoromethyl)phenylamine to form a urea bonding and then performing deprotection with trifluoroacetic acid by using the same techniques as in Steps B and C of Example 156.

$^1$H-NMR (270 MHz, DMSO-$d_6$) δ (ppm): 2.31 (6H, s), 2.76 (2H, m), 4.18 (2H, m), 7.25 (1H, d, J=9.6 Hz), 7.37 (2H, s), 7.59 (1H, dd, J=9.6, 2.7 Hz), 7.62 (2H, d, J=9.1 Hz), 7.77 (2H, d, J=9.1 Hz), 7.87 (1H, d, J=2.7 Hz), 8.19 (1H, s), 8.51 (1H, s), 8.90 (1H, s), 9.01 (1H, s)

ESI (LC-MS positive mode) m/z 501 (M+H)

Example 172

1-[4-(6-(Aminopurin-9-yl)phenyl)-3-[4-(2-morpholin-4-yl-ethoxy)-3-trifluormethyl]phenyl]urea (Table 2, Compound No. 50)

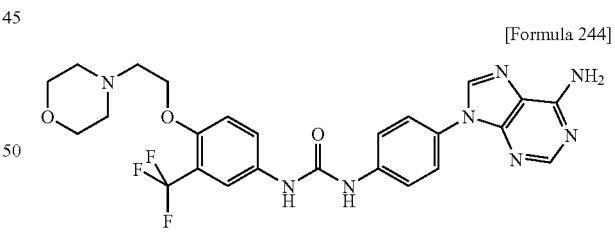

[Formula 244]

The title compound can be obtained by allowing 4-(2-morpholin-4-yl-ethoxy)-3-(trifluoromethyl)aniline prepared from 2-fluoro-5-nitrobenzotrifluoride and 4-(2-hydroxyethyl)-morpholine to form a urea bonding with 6-ditert-butyoxy-carbonylamino-9-(4-aminophenyl)-9H-purine and then performing deprotection with trifluoroacetic acid by using the same techniques as in Example 171.

$^1$H-NMR (270 MHz, DMSO-$d_6$) δ (ppm): 2.76 (2H, br), 3.58 (4H, br), 4.19 (2H, br), 7.15 (1H, d, J=8.8 Hz), 7.37 (2H, s), 7.56 (1H, dd, J=8.8, 2.5 Hz), 7.64 (2H, d, J=8.9 Hz), 7.76 (2H, d, J=8.9 Hz), 7.86 (1H, d, J=2.5 Hz), 8.20 (1H, s), 8.51 (1H, s), 8.85 (1H, s), 8.97 (1H, s)

ESI (LC-MS positive mode) m/z 543 (M+H)

Example 173

1-(3-Amino-5-(trifluoromethyl)phenyl)-3-[4-(6-(methylamino)purin-9-yl)phenyl]urea (Table 2, Compound No. 51)

[Formula 245]

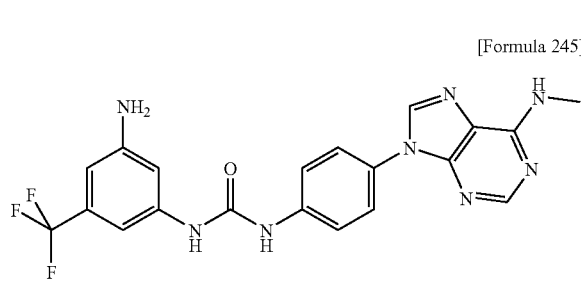 [SMILES: CNc1ncnc2c1ncn2-c1ccc(NC(=O)Nc2cc(N)cc(C(F)(F)F)c2)cc1]

The title compound can be obtained by allowing 5-(trifluoromethyl)benzene-1,3-diamine to form an urea bonding with [9-(4-aminophenyl)-9H-purin-6-yl]methylcarbamic acid tert-butyl ester and then performing deprotection by using the techniques as in Steps B and C of Example 156.

$^1$H-NMR (270 MHz, DMSO-$d_6$) δ (ppm): 2.99 (3H, br), 5.59 (2H, s), 6.49 (1H, s), 6.85 (1H, s), 7.04 (1H, s), 7.65 (2H, d, J=9.0 Hz), 7.77 (2H, d, J=9.0 Hz), 8.29 (1H, s), 8.51 (1H, s), 8.80 (1H, s), 8.88 (1H, s)

ESI (LC-MS positive mode) m/z 443 (M+H)

Example 174

1-[4-(2-Dimethylaminoethoxy)-3-(trifluoromethyl)phenyl]-3-[4-(6-(methylamino)purin-9-yl)phenyl]urea (Table 2, Compound No. 52)

[Formula 246]

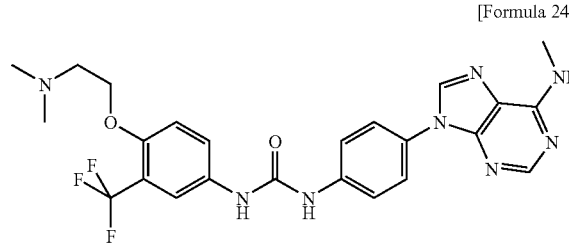

The title compound can be obtained by allowing [9-(4-aminophenyl)-9H-purin-6-yl]methylcarbamic acid tert-butyl ester and 4-(2-(dimethylamino)ethoxy)-3-(trifluoromethyl)phenylamine to form a urea bonding and then performing deprotection with trifluoroacetic acid by using the same techniques as in Steps B and C of Example 156.

$^1$H-NMR (270 MHz, DMSO-$d_6$) δ (ppm): 2.26 (6H, s), 2.69 (2H, m), 2.99 (3H, br), 4.16 (2H, t, J=5.6 Hz), 7.25 (1H, d, J=9.6 Hz), 7.59 (1H, dd, J=9.6, 2.7 Hz), 7.62 (2H, d, J=9.1 Hz), 7.77 (2H, d, J=9.1 Hz), 7.87 (1H, d, J=2.7 Hz), 8.28 (1H, br), 8.50 (1H, s), 8.85 (1H, s), 8.96 (1H, s)

ESI (LC-MS positive mode) m/z 515 (M+H)

Example 175

1-[4-(6-(Methylamino)purin-9-yl)phenyl]-3-[4-(2-morpholin-4-yl-ethoxy)-3-(trifluoromethyl)phenyl]urea (Table 2, Compound No. 53)

[Formula 247]

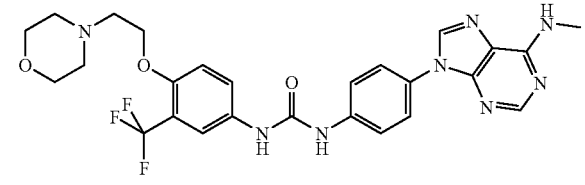

The title compound can be obtained by allowing 4-(2-morpholin-4-yl-ethoxy)-3-(trifluoromethyl)aniline prepared from 2-fluoro-5-nitrobenzotrifluoride and 4-(2-hydroxyethyl)morpholin to form a urea bonding with [9-(4-aminophenyl)-9H-purin-6-yl]methyl-carbamic acid tert-butyl ester and then performing deprotection with trifluoroacetic acid by using the same techniques as in Example 171.

$^1$H-NMR (270 MHz, DMSO-$d_6$) δ (ppm): 2.74 (2H, m), 2.99 (3H, br), 3.54 (4H, t, J=4.3 Hz), 4.19 (2H, t, J=5.6 Hz), 7.25 (1H, d, J=8.9 Hz), 7.60 (1H, dd, J=8.8, 2.8 Hz), 7.64 (2H, d, J=8.9 Hz), 7.76 (2H, d, J=8.9 Hz), 7.85 (1H, d, J=2.8 Hz), 8.29 (1H, s), 8.50 (1H, s), 8.84 (1H, s), 8.96 (1H, s)

ESI (LC-MS positive mode) m/z 557 (M+H)

Example 176

N-(2-Hydroxy-1-hydroxymethyl-ethyl)-3-{3-[4-(6-(methylamino)purin-9-yl)phenyl]ureido}-5-(trifluoromethyl)benzamide (Table 2, Compound No. 54)

Step A

Preparation of 3-(3-{4-[6-(tert-butoxycarbonylmethylamino)purin-9-yl]phenyl}ureido)-5-(trifluoromethyl)benzoic acid benzyl ester

[Formula 248]

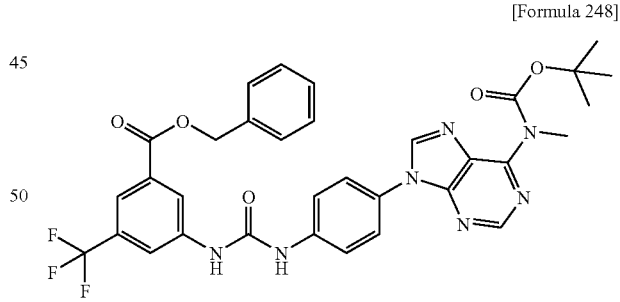

To a 201.7 mg (0.59 mmol) of a dichloromethane (1 mL)/pyridine [95.7 μL (0.59 mmol)] solution, 143 mg (0.71 mmol) of p-nitrophenyl chloroformate was slowly added and the mixture solution was stirred under cooling with ice for 1.5 hours. To this reaction solution, an N,N-dimethylformamide solution (1 mL) of 192.5 mg (0.65 mmol) of 3-amino-5-trifluoromethylbenzoic acid benzyl ester was added and the mixture solution was stirred under refluxing for 24 hours. To the reaction solution, dichloromethane was added and the mixture solution was washed with water and dried on anhydrous sodium sulfate, and then the solvent was distilled under reduced pressure. The obtained residue was purified by silica gel column chromatography (n-hexane:ethyl acetate=1:1 to 1:3) to obtain 229.3 mg (59%) of a target product as a pale yellow amorphous substance.

$^1$H-NMR (270 MHz, CDCl$_3$) δ (ppm): 1.54 (9H, s), 3.59 (3H, s), 5.35 (2H, s), 7.26-7.51 (9H, m), 7.93 (1H, s), 8.05 (1H, s), 8.12 (1H, s), 8.16 (1H, s), 8.19 (1H, s), 8.35 (1H, s), 8.77 (1H, s)

ESI (LC-MS positive mode) m/z 662 (M+H)

Step B

Preparation of 3-(3-{4-[6-(tert-butoxycarbonylmethylamino)-purin-9-yl]phenyl}ureido)-5-(trifluoromethyl)benzoic acid

[Formula 249]

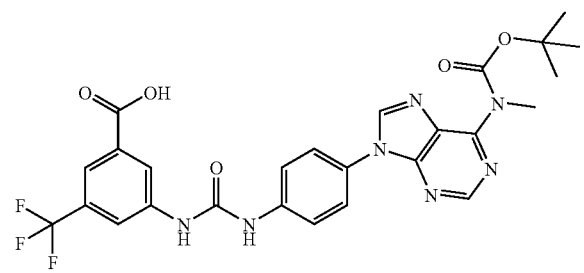

In methanol (2 mL), 229.3 mg (0.349 mmol) of 3-(3-{4-[6-(tert-butoxycarbonyl-methylamino)purin-9-yl]phenyl}ureido)-5-(trifluoromethyl)benzoic acid benzyl ester was dissolved, and 22 mg of 10% palladium carbon was added thereto and the mixture solution was stirred at room temperature in a hydrogen atmosphere for two hours. The catalyst was removed by filtration, and by distilling the solvent under reduced pressure, 188.6 mg (95%) of a target product was obtained as a white solid.

$^1$H-NMR (270 MHz, DMSO-d$_6$) δ (ppm): 1.43 (9H, s), 3.41 (3H, s), 7.73 (2H, d, J=9.1 Hz), 7.79 (1H, s), 7.82 (2H, d, J=9.1 Hz), 8.21 (1H, s), 8.28 (1H, s) 8.79 (1H, s), 8.92 (1H, s), 9.24 (1H, s), 9.46 (1H, s), 13.52 (1H, br.s)

ESI (LC-MS positive mode) m/z 572 (M+H)

Step C

Preparation of [9-(4-{3-[3-(2-hydroxy-1-hydroxymethyl-ethyl-ethylcarbamoyl)-5-trifluoromethyl-phenyl]-ureido}phenyl)-9H-purin-6-yl]-methyl-carbamic acid tert-butyl ester

[Formula 250]

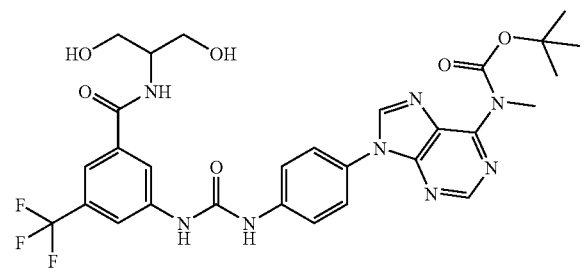

In dichloromethane (3.5 mL), 60 mg (0.105 mmol) of 3-(3-{4-[6-(tert-butoxycarbonyl-methylamino)-purin-9-yl]phenyl}ureido)-5-(trifluoromethyl)benzoic acid was dissolved, and 54.9 µL (0.63 mmol) of oxalyl chloride was slowly added thereto and the mixture solution was stirred under refluxing for 1.5 hours. The solvent was distilled under reduced pressure from the reaction solution and the obtained residue was dissolved in tetrahydrofuran (0.75 mL). The tetrahydrofuran solution thus prepared was added dropwise to a methanol (0.5 mL)/tetrahydrofuran (0.25 mL) solution of 28.7 mg (0.315 mmol) of 2-amino-1,3-propanediol and the resulting solution was stirred at room temperature for 1.5 hours. The solvent was distilled under reduced pressure from the reaction solution and the obtained residue was purified by silica gel column chromatography (dichloromethane:methanol=20:1 to 5:1) to obtain 40.8 mg (60%) of a target product as a white solid.

$^1$H-NMR (270 MHz, CD$_3$OD) δ (ppm): 1.49 (9H, s), 3.49 (3H, s), 3.66-3.85 (4H, m), 4.11-4.27 (1H, m), 7.71 (2H, d, J=9.5 Hz), 7.75 (2H, d, J=9.5 Hz), 7.82 (1H, s), 8.08 (2H, s), 8.67 (1H, s), 8.75 (1H, s), ESI (LC-MS positive mode) m/z 645 (M+H)

Step D

Preparation of N-(2-hydroxy-1-hydroxymethyl-ethyl)-3-{3-[4-(6-(methylamino)purin-9-yl)phenyl]ureido}-5-(trifluoromethyl)benzamide (Table 2, Compound No. 54)

[Formula 251]

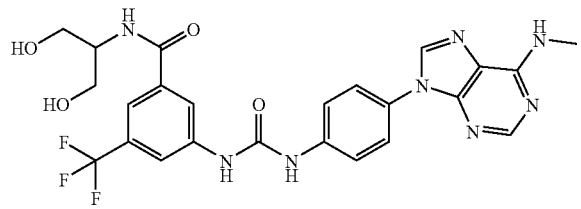

To 40.8 mg (0.063 mmol) of [9-(4-{3-[3-(2-hydroxy-1-hydroxymethyl-ethyl-carbamoyl)-5-trifluoromethylphenyl]ureido}phenyl)-9H-purin-6-yl]-methyl-carbamic acid tert-butyl ester, 1 mL of trifluoroacetic acid was added and the mixture solution was stirred at room temperature for one hour. The solvent was distilled under reduced pressure from the reaction solution and the obtained residue was dissolved in methanol (1 mL) and water (60 µL), and 43.7 mg (0.315 mmol) of potassium carbonate was added thereto, and the mixture solution was stirred at room temperature for 1.5 hours. Water was added to the reaction solution and the obtained solid was collected by filtration and dried under reduced pressure to obtain 32 mg (93%) of a target product as a white solid.

$^1$H-NMR (270 MHz, CD$_3$OD) δ (ppm): 3.14 (3H, br.s), 3.69-3.82 (4H, m), 4.13-4.29 (1H, m), 7.66 (2H, d, J=9.0 Hz), 7.71 (2H, d, J=9.0 Hz), 7.82 (1H, s), 8.08 (2H, s), 8.27 (1H, s), 8.30 (1H, s)

ESI (LC-MS positive mode) m/z 545 (M+H)

Example 177

3-{3-[4-(6-Aminopurin-9-yl)phenyl]ureido}-N-(2,3-dihydroxypropyl)-5-(trifluoromethyl)benzamide (Table 2, Compound No. 55)

[Formula 252]

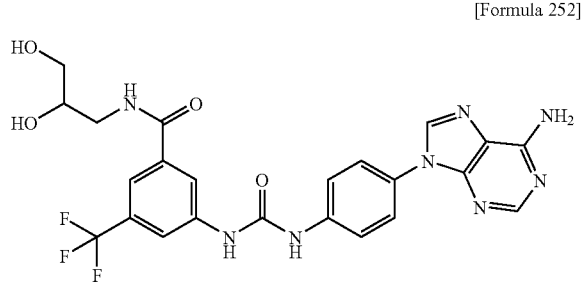 [SMILES: Nc1ncnc2c1ncn2-c1ccc(NC(=O)Nc2cc(C(=O)NCC(O)CO)cc(C(F)(F)F)c2)cc1]

The title compound can be obtained by allowing 3-amino-5-trifluoromethylbenzoic acid benzyl ester and 6-di-tert-butoxycarbonylamino-9-(4-aminophenyl)-9H-purine to form a urea bonding, removing the benzyl group by catalytic reduction, performing amidation with 1-amino-2,3-propanediol, and finally performing deprotection with trifluoroacetic acid by using the same techniques as in Example 176.

$^1$H-NMR (270 MHz, DMSO-d$_6$) δ (ppm): 3.06-3.28 (2H, m), 3.28-3.50 (2H, m), 3.58-3.74 (1H, m), 4.60 (1H, t, J=5.8 Hz), 4.85 (1H, d, J=4.9 Hz), 7.38 (2H, s), 7.68 (2H, d, J=9.0 Hz), 7.79 (2H, d, J=9.0 Hz), 7.83 (1H, s), 8.07 (1H, s), 8.17 (1H, s), 8.20 (1H, s), 8.53 (1H, s), 8.68 (1H, s), 9.19 (1H, s), 9.39 (1H, s)

ESI (LC-MS positive mode) m/z 531 (M+H)

Example 178

3-{3-[4-(6-Aminopurin-9-yl)phenyl]ureido}-N-(2-hydroxyl-1-hydroxymethyl-ethyl)-5-(trifluoromethyl)benzamide (Table 2, Compound No. 56)

[Formula 253]

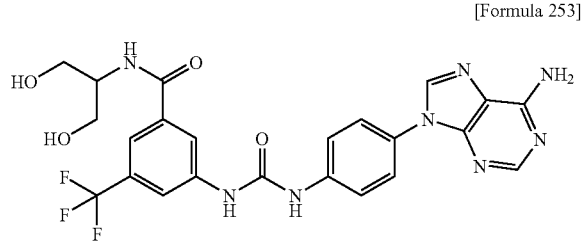 [SMILES: Nc1ncnc2c1ncn2-c1ccc(NC(=O)Nc2cc(C(=O)NC(CO)CO)cc(C(F)(F)F)c2)cc1]

The title compound can be obtained by allowing 3-amino-5-trifluoromethylbenzoic acid benzyl ester and 6-di-tert-butoxycarbonylamino-9-(4-aminophenyl)-9H-purine to form a urea bonding, removing the benzyl group by catalytic reduction, performing amidation with 2-amino-1,3-propanediol and finally performing deprotection with trifluoroacetic acid by using the same techniques as in Example 176.

$^1$H-NMR (270 MHz, CD$_3$OD) δ (ppm): 3.74 (4H, d, J=5.8 Hz), 4.20 (1H, t, J=5.8 Hz), 7.66 (2H, d, J=9.1 Hz), 7.71 (2H, d, J=9.1 Hz), 7.81 (1H, s), 8.08 (2H, s), 8.22 (1H, s), 8.36 (1H, s) ESI (LC-MS positive mode) m/z 531 (M+H)

Example 179

N-(2,3-Dihydroxypropyl)-3-(3-[4-(6-(methylamino-purin-9-yl)phenyl)ureido]-5-(trifluoromethyl)benzamide (Table 2, Compound No. 57)

[Formula 254]

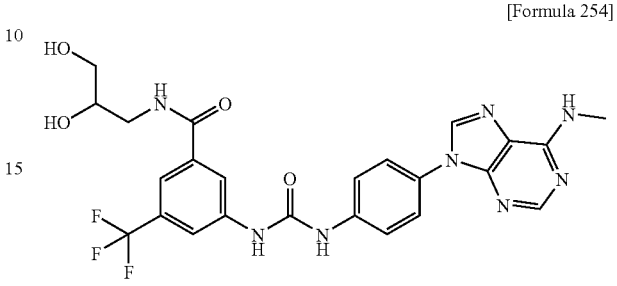

The title compound can be obtained by allowing 3-amino-5-trifluoromethylbenzoic acid benzyl ester and [9-(4-aminophenyl)-9H-purin-6-yl]methylcarbamic acid tert-butyl ester to form a urea bonding, removing the benzyl group by catalytic reduction, performing amidation with 1-amino-2,3-propanediol and finally performing deprotection with trifluoroacetic acid by using the same techniques as in Example 176.

$^1$H-NMR (270 MHz, DMSO-d$_6$) δ (ppm): 2.99 (3H, br.s), 3.11-3.56 (4H, m), 3.60-3.72 (1H, m), 7.34 (2H, d, J=9.0 Hz), 7.79 (2H, d, J=9.0 Hz), 7.84 (1H, s), 7.92 (1H, s), 8.07 (1H, s), 8.17 (1H, s), 8.30 (1H, s), 8.53 (1H, s), 8.68 (1H, t, J=5.7 Hz), 9.12 (1H, s), 9.31 (1H, s)

ESI (LC-MS positive mode) m/z 545 (M+H)

Example 180

3-{3-[4-(6-(Methylamino)purin-9-yl)phenyl]ureido}-N-(2-morpholin-4-yl-ethyl)-5-(trifluoromethyl)benzamide (Table 2, Compound No. 58)

[Formula 255]

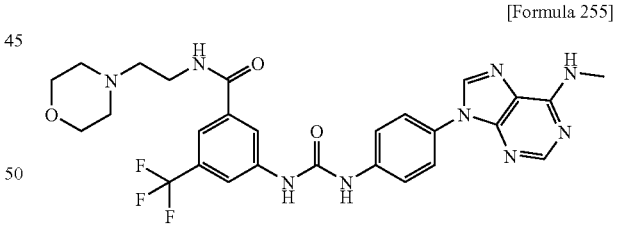

The title compound can be obtained by allowing 3-amino-5-trifluoromethylbenzoic acid benzyl ester and [9-(4-aminophenyl)-9H-purin-6-yl]-methylcarbamic acid tert-butyl ester to form a urea bonding, removing the benzyl group by catalytic reduction, performing amidation with 2-morpholin-4-yl-ethylamine and finally performing deprotection with trifluoroacetic acid by using the same techniques as in Example 176.

$^1$H-NMR (270 MHz, CD$_3$OD) δ (ppm): 2.48-2.61 (4H, m), 2.63 (2H, t, J=6.7 Hz), 3.14 (3H, br.s), 3.57 (2H, t, J=6.7 Hz), 3.72 (4H, t, J=4.7 Hz), 7.66 (2H, d, J=9.2 Hz), 7.71 (2H, d, J=9.2 Hz), 7.77 (1H, s), 8.09 (2H, s), 8.27 (1H, s), 8.31 (1H, s)

ESI (LC-MS positive mode) m/z 584 (M+H)

Example 181

1-(4-Dimethylaminomethyl-3-(trifluoromethyl)phenyl)-3-[4-(6-(methylamino)purin-9-yl)phenyl]urea (Table 2, Compound No. 59)

[Formula 256]

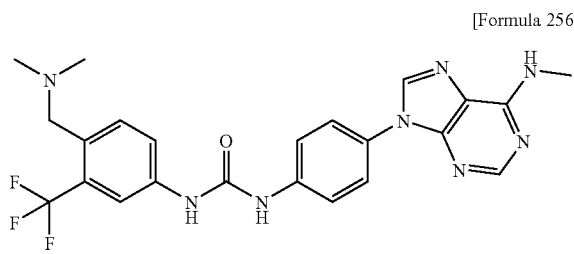 [SMILES: CNc1ncnc2c1ncn2-c1ccc(NC(=O)Nc2ccc(CN(C)C)c(C(F)(F)F)c2)cc1]

The title compound can be prepared from dimethylamine and (9-{4-[3-(4-formyl-3-(trifluoromethyl)phenyl)-ureido]phenyl}-9H-purin-6-yl)-methyl-carbamic acid tert-butyl ester by using the same techniques as in Example 168.

$^1$H-NMR (270 MHz, DMSO-d$_6$) δ (ppm): 2.23 (6H, s), 2.99 (3H, s), 3.48 (2H, s), 7.60-7.70 (4H, m), 7.76 (2H, d, J=8.9 Hz), 7.85 (1H, br.s), 7.95 (1H, s), 8.29 (1H, s), 8.50 (1H, s), 9.02 (1H, s), 9.09 (1H, s)

ESI (LC-MS positive mode) m/z 485 (M+H)

Example 182

1-(4-[(2-Dimethylamino-ethylamino)-methyl]-3-(trifluoromethyl)phenyl)-3-[4-(6-(methylamino)purin-9-yl)phenyl]urea (Table 2, Compound No. 60)

[Formula 257]

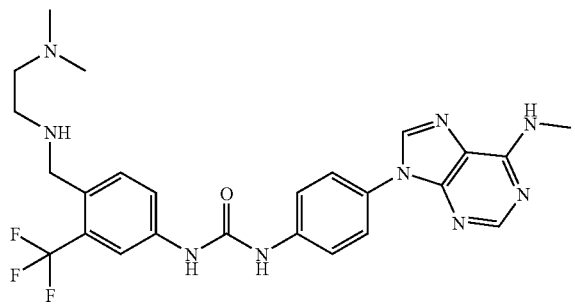

The title compound can be prepared from N,N-dimethylethylenediamine and (9-{4-[3-(4-formyl-3-(trifluoromethyl)phenyl)ureido]phenyl}-9H-purin-6-yl)methyl-carbamic acid tert-butyl ester by using the same techniques as in Example 168.

$^1$H-NMR (270 MHz, DMSO-d$_6$) δ (ppm): 2.14 (6H, s), 2.31 (2H, t, J=6.4 Hz), 2.55 (2H, t, J=6.4 Hz), 2.99 (3H, s), 3.80 (2H, s), 7.55-7.70 (4H, m), 7.79 (2H, d, J=8.9 Hz), 7.81 (1H, br.s), 7.95 (1H, d, J=1.8 Hz), 8.30 (1H, s), 8.50 (1H, s), 9.10 (1H, s), 9.15 (1H, s)

ESI (LC-MS positive mode) m/z 528 (M+H)

Example 183

1-[4-(6-Aminopurin-9-yl)-phenyl]-3-[4-(1-methylpiperidin-4-yloxy)-3-(trifluoromethyl)phenyl]urea (Table 2, Compound No. 61)

[Formula 258]

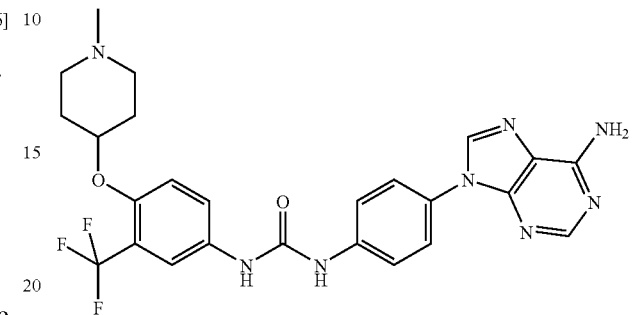

The title compound can be obtained by allowing 4-(1-methylpiperidin-4-yloxy)-3-(trifluoromethyl)aniline prepared from 2-fluoro-5-nitrobenzotrifluoride and 4-hydroxy-1-methylpiperidine to form a urea bonding with 6-di-tert-butoxycarbonylamino-9-(4-aminophenyl)-9H-purin and then performing deprotection with trifluoroacetic acid by using the same techniques as in Example 171.

$^1$H-NMR (270 MHz, DMSO-d$_6$) δ (ppm): 1.68 (2H, br), 1.88 (2H, br), 2.20 (3H, br), 4.52 (1H, br), 7.26 (1H, d, J=9.0 Hz), 7.37 (2H, s), 7.56 (1H, dd, J=2.5, 9.0 Hz), 7.65 (2H, d, J=9.0 Hz), 7.77 (2H, d, J=9.0 Hz), 7.85 (1H, d, J=2.5 Hz), 8.20 (1H, s), 8.51 (1H, s), 8.84 (1H, s), 8.96 (1H, s)

ESI (LC-MS positive mode) m/z 527 (M+H)

Example 184

1-[4-(6-(Methylamino)purin-9-yl)-phenyl]-3-[4-(1-methylpiperidin-4-yloxy)-3-(trifluoromethyl)phenyl]-urea (Table 2, Compound No. 62)

[Formula 259]

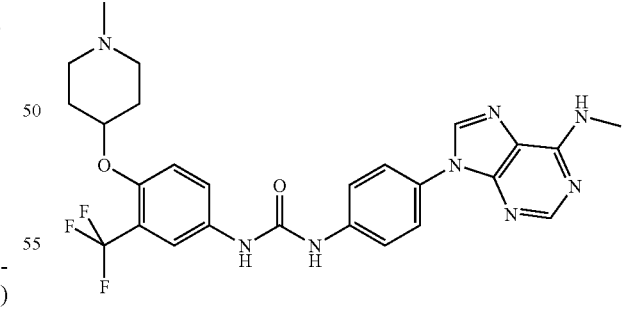

The title compound can be obtained by allowing 4-(1-methylpiperidin-4-yloxy)-3-(trifluoromethyl)aniline prepared from 2-fluoro-5-nitrobenzotrifluoride and 4-hydroxy-1-methylpiperidine to form a urea bonding with [9-(4-aminophenyl)-9H-purin-6-yl]methylcarbamic acid tert-butyl ester and then performing deprotection with trifluoroacetic acid by using the same techniques as in Example 171.

$^1$H-NMR (270 MHz, DMSO-d$_6$) δ (ppm): 1.70 (2H, br), 1.89 (2H, br), 2.25 (3H, br), 2.63 (4H, br), 2.99 (3H, br), 4.53

(1H, br), 7.25 (1H, d, J=8.8 Hz), 7.56 (2H, dd, J=2.5, 8.8 Hz), 7.65 (2H, d, J=9.0 Hz), 7.77 (2H, d, J=9.0 Hz), 7.84 (1H, d, J=2.5 Hz), 8.26 (1H, s), 8.50 (1H, s), 8.85 (1H, s), 8.96 (1H, s)

ESI (LC-MS positive mode) m/z 541 (M+H)

Example 185

1-[4-(2-Dimethylamino-ethyl)-3-(trifluoromethyl) phenyl]-3-[4-(6-(methylamino)purin-9-yl)phenyl] urea (Table 2, Compound No. 68)

Step A

Preparation of 3-trifluoromethyl-4-vinylaniline

[Formula 260]

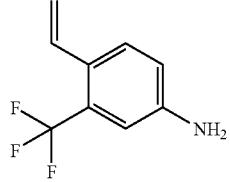

In 20 mL of isopropanol, 10 mL of water and 5 mL of t-butylamine, 4.0 g (16.7 mmol) of 4-bromo-3-(trifluoromethyl)aniline was dissolved, and 4.0 g (29.9 mmol) of potassium (trifluoro)vinylborate and 300 mg (0.37 mmol) of PdCl$_2$(dppf)$_2$•2(dichloromethane) complex were added thereto, and the mixture solution was stirred in an argon atmosphere at 80° C. for 20 hours. The reaction solution was concentrated and the residue was partitioned between water and ethyl acetate, and the organic layer was washed with a saturated sodium chloride solution and concentrated under reduced pressure. The product was purified by a silica gel column (n-hexane:ethyl acetate=6:1) to obtain 2.475 g (79%) of a target product as a pale yellow oil.

$^1$H-NMR (270 MHz, CDCl$_3$) δ (ppm): 3.84 (2H, s), 5.20 (1H, dd, J=1.8, 10.9 Hz), 5.56 (1H, d, J=17.1 Hz), 6.78 (1H, dd, J=10.9, 17.1 Hz), 6.88-7.04 (2H, m), 7.48 (1H, d, J=8.4 Hz)

ESI (LC-MS positive mode) m/z 188 (M+H)

Step B

Preparation of 4-(2-hydroxyethyl)-3-(trifluoromethyl)aniline

[Formula 261]

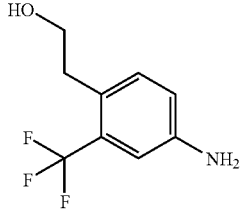

In 10 mL of anhydrous tetrahydrofuran, 2.47 g (13.2 mmol) of 3-trifluoromethyl-4-vinylaniline was dissolved, and 2.75 mL (30.0 mmol) of borane-dimethyl sulfide complex was added dropwise thereto in an argon atmosphere, and the mixture solution was stirred at room temperature four hours. To the reaction solution, 5 mL of a 1N sodium hydroxyl aqueous solution and 3 mL of a 30% hydrogen peroxide aqueous solution were added and the mixture solution was stirred at 0° C. for one hour. The reaction solution was concentrated and the residue was partitioned between water and ethyl acetate, and the organic layer was washed with a saturated sodium chloride solution and concentrated under reduced pressure. The product was purified by a silica gel column (n-hexane:ethyl acetate=2:1) to obtain 1.3 g (48%) of a target product as a pale yellow oil.

$^1$H-NMR (270 MHz, CDCl$_3$) δ (ppm): 2.90 (2H, t, J=5.7 Hz), 3.70-3.80 (4H, m), 6.86 (1H, dd, J=2.6, 8.2 Hz), 6.91 (1H, m), 7.15 (1H, d, J=8.2 Hz)

ESI (LC-MS positive mode) m/z 206 (M+H)

Step C

Preparation of [9-(4-{3-[4-(2-hydroxyethyl)-3-(trifluoromethyl)phenyl]ureido}phenyl)-9H-purin-6-yl]-methyl-carbamic acid tert-butyl ester

[Formula 262]

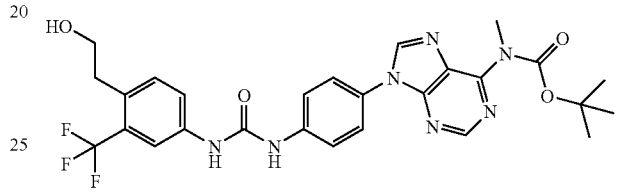

The title compound can be synthesized from 4-(2-hydroxyethyl)-3-(trifluoromethyl)aniline and [9-(4-aminophenyl)-9H-purin-6-yl]-methylcarbamic acid tert-butyl ester by using the same techniques as in Step A of Example 176.

ESI (LC-MS positive mode) m/z 572 (M+H)

Step D

Preparation of methyl-[9-(4-{3-[4-(2-oxoethyl)-3-(trifluoromethyl)phenyl]ureido}phenyl)-9H-purin-6-yl]-carbamic acid tert-butyl ester

[Formula 263]

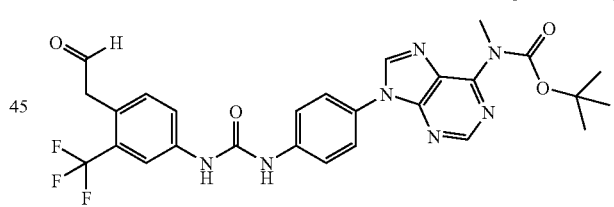

In 50 ml of dichloromethane, 300 mg (0.52 mmol) of [9-(4-{3-[4-(2-hydroxyethyl)-3-(trifluoromethyl)phenyl]-ureido}phenyl)-9H-purin-6-yl]-methyl-carbamic acid tert-butyl ester was dissolved, and 270 mg (0.64 mmol) of Dess-Martin periodinane was added thereto under cooling with ice and the solution was stirred at 0° C. for 20 hours. The reaction solution was partitioned between water and ethyl acetate and the organic layer was washed with a saturated sodium chloride solution and concentrated under reduced pressure. The product was purified by a silica gel column (ethyl acetate) to obtain 140 mg (47%) of a target product as a colorless amorphous substance.

$^1$H-NMR (270 MHz, CDCl$_3$) δ (ppm): 1.57 (9H, s), 3.60 (3H, s), 3.82 (2H, s), 7.18 (1H, d, J=8.4 Hz), 7.34-7.52 (4H, m), 7.62 (1H, d, J=8.4 Hz), 7.71 (1H, s), 8.06 (1H, s), 8.10 (1H, s), 8.15 (1H, s), 8.77 (1H, s), 9.69 (1H, s)

ESI (LC-MS positive mode) m/z 570 (M+H)

Step E

Preparation of 1-[4-(2-dimethylamino-ethyl)-3-(trifluoromethyl)phenyl]-3-[4-(6-(methylamino)purin-9-yl)phenyl]urea (Table 2, Compound No. 68)

[Formula 264]

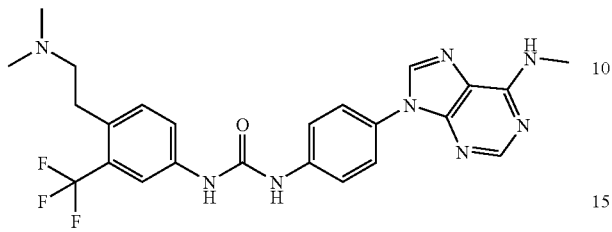

In 1 mL of ethanol, 25 mg (0.04 mmol) of methyl-[9-(4-{3-[4-(2-oxoethyl)-3-(trifluoromethyl)phenyl]ureido}-phenyl)-9H-purin-6-yl]-carbamic acid tert-butyl ester was dissolved, and 10 μL of acetic acid and 0.1 mL (0.20 mmol) of 2N dimethylamine were added thereto and the mixture solution was stirred at room temperature for 30 minutes. Furthermore, 7 mg (0.11 mmol) of sodium cyanoborohydride was added to the obtained solution and the mixture solution was stirred at room temperature for one hour. The reaction solution was concentrated and to the residue, 0.5 mL of trifluoroacetic acid was added and the mixture was stirred at room temperature for one hour. The reaction solution was concentrated, and a target product was obtained by a reversed phase HPLC (a product of Wako Pure Chemical, Combi ODS, 28 mm×50 mm, 0.05% acetonitrile-water, 30 mL/min). The fraction containing the target product was concentrated, and then dissolved in methanol and neutralized by addition of amino silica gel R 66030 B (a product of Silicycle), and then a solid was removed by filtration and the filtrate was concentrated to obtain 15 mg (52%) of a title compound.

$^1$H-NMR (270 MHz, CD$_3$OD) δ (ppm): 2.36 (6H, m), 2.54-2.66 (2H, m), 2.88-3.00 (2H, m), 3.14 (3H, br.s), 7.38 (1H, d, J=8.4 Hz), 7.56-7.73 (5H, m), 7.87 (1H, d, J=2.1 Hz), 8.27 (1H, s), 8.29 (1H, s)

ESI (LC-MS positive mode) m/z 499 (M+H)

The compounds of Examples 186, 187 and 230 to 237 can be prepared by using the same techniques as in Example 185.

Example 186

1-[4-(6-(Methylamino)purin-9-yl)phenyl]-3-{4-[2-(4-methylpiperazin-1-yl)-ethyl]-3-(trifluoromethyl)phenyl}urea (Table 2, Compound No. 69)

[Formula 265]

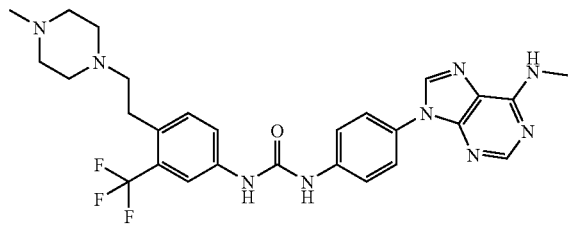

$^1$H-NMR (270 MHz, CD$_3$OD) δ (ppm): 2.55 (3H, s), 2.60-3.00 (12H, m), 3.15 (3H, br.s), 7.39 (1H, d, J=8.6 Hz), 7.58-7.72 (5H, m), 7.86 (1H, d, J=2.2 Hz), 8.27 (1H, s), 8.30 (1H, s)

ESI (LC-MS positive mode) m/z 554 (M+H)

Example 187

1-[4-(6-(Methylamino)purin-9-yl)phenyl]-3-[4-(2-morpholin-4-yl-ethyl)-3-(trifluoromethyl)phenyl]urea (Table 2, Compound No. 70)

[Formula 266]

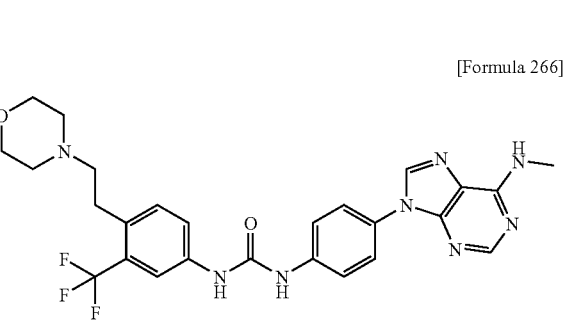

$^1$H-NMR (270 MHz, DMSO-d$_6$) δ (ppm): 2.33-2.59 (6H, m), 2.76-2.89 (2H, m), 3.16 (3H, br.s), 3.49 (4H, t, J=4.6 Hz), 7.42 (1H, d, J=8.2 Hz), 7.59 (1H, d, J=8.2 Hz), 7.67 (2H, d, J=9.1 Hz), 7.77 (2H, d, J=9.1 Hz), 7.83 (1H, br.s), 7.96 (1H, d, J=2.1 Hz), 8.28 (1H, s), 8.50 (1H, s), 9.30 (1H, s), 9.32 (1H, s)

ESI (LC-MS positive mode) m/z 541 (M+H)

The compounds of Examples 188 to 190, 227 and 228 can be prepared from 5-bromo-3-(trifluoromethyl)aniline by using the same techniques as in Example 185.

Example 188

1-[3-(2-Dimethylamino-ethyl)-5-(trifluoromethyl)phenyl]-3-[4-(6-(methylamino)purin-9-yl)phenyl]urea (Table 2, Compound No. 71)

[Formula 267]

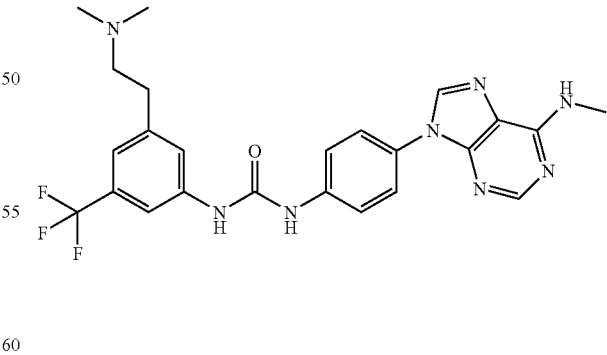

$^1$H-NMR (270 MHz, DMSO-d$_6$) δ (ppm): 2.19 (6H, s), 2.50 (2H, m), 2.78 (2H, t, J=4.9 Hz), 2.99 (3H, s), 7.20 (1H, s), 7.46 (1H, s), 7.65-7.83 (6H, m), 8.29 (1H, s), 8.50 (1H, s), 9.03 (1H, s), 9.06 (1H, s)

ESI (LC-MS positive mode) m/z 499 (M+H)

Example 189

1-[4-(6-(Methylamino)purin-9-yl)phenyl]-3-{3-(2-(4-methyl-piperazin-1-yl)-ethyl)-5-(trifluoromethyl)phenyl}urea (Table 2, Compound No. 72)

[Formula 268]

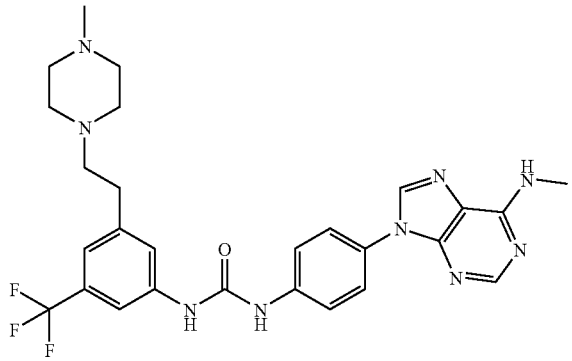

$^1$H-NMR (270 MHz, DMSO-d$_6$) δ (ppm): 2.23 (3H, s), 2.30-2.50 (8H, m), 2.55 (2H, m), 2.80 (2H, t, J=4.9 Hz), 2.99 (3H, s), 7.20 (1H, s), 7.46 (1H, s), 7.65-7.83 (6H, m), 8.29 (1H, s), 8.50 (1H, s), 9.03 (1H, s), 9.06 (1H, s)

ESI (LC-MS positive mode) m/z 554 (M+H)

Example 190

1-[4-(6-(Methylamino)purin-9-yl)phenyl]-3-[3-(2-morpholin-4-yl-ethyl)-5-(trifluoromethyl)phenyl]urea (Table 2, Compound No. 73)

[Formula 269]

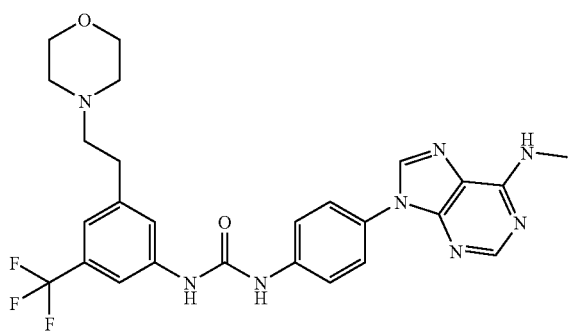

$^1$H-NMR (270 MHz, DMSO-d$_6$) δ (ppm): 2.32 (4H, s), 2.54 (2H, t, J=4.9 Hz), 2.81 (2H, t, J=4.9 Hz), 2.99 (3H, s), 3.57-3.59 (4H, m), 7.22 (1H, s), 7.49 (1H, s), 7.65-7.83 (6H, m), 8.29 (1H, s), 8.50 (1H, s), 9.07 (1H, s), 9.08 (1H, s)

ESI (LC-MS positive mode) m/z 541 (M+H)

Example 191

1-[4-(3-Dimethylamino-propyl)-3-(trifluoromethyl)phenyl]-3-[4-(6-methylamino)purin-9-yl]phenyl]urea (Table 2, Compound No. 74)

Step A

Preparation of 3-(4-nitro-2-(trifluoromethyl)phenyl)propionaldehyde

[Formula 270]

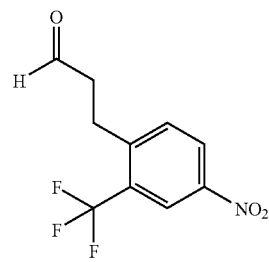

In 3 mL of dimethylformamide, 50 mg (0.19 mmol) of 4-bromo-3-(trifluoromethyl)nitrobenzene was dissolved, and 33 mg (0.56 mmol) of allyl alcohol, 43 mg (0.19 mmol) of tetrabutylammonium bromide, 2.1 mg (5 mol %) of palladium acetate and 52 μL (0.37 mmol) of triethylamine were added thereto and the mixture solution was stirred in an argon atmosphere at 90° C. for two hours. The reaction solution was partitioned between water and ethyl acetate, and the organic layer was washed with a saturated sodium chloride solution and concentrated under reduced pressure. The product was purified by a silica gel column (n-hexane:ethyl acetate=5:1) to obtain 78 mg (79%) of a target product as a pale yellow oil.

Step B

Preparation of 4-(3-dimethylamino-propyl)-3-(trifluoromethyl)aniline

[Formula 271]

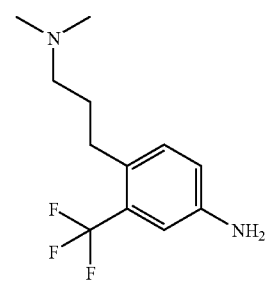

In 6 mL of tetrahydrofuran, 100 mg (0.41 mmol) of 3-(4-nitro-2-(trifluoromethyl)phenyl)propionaldehyde was dissolved, and 405 μL (0.81 mmol) of a 2N dimethylamine methanol solution, 171 mg (0.81 mmol) of sodium triacetoxy borohydride and 100 μL of acetic acid were added thereto and the mixture solution was stirred at room temperature overnight. The reaction solution was partitioned between water and ethyl acetate and the organic layer was washed with a saturated sodium chloride solution and concentrated to form an intermediate. This intermediate was dissolved in 10 mL of methanol and stirred on 10 mg of Pd/C (10%) in a hydrogen atmosphere for 20 hours. The catalyst was removed by filtration and the filtrated was concentrated and the obtained residue was purified by a silica gel column (n-hexane:ethyl acetate=5:1) to obtain 109 mg (quantitative) of a target object as a pale yellow oil.

ESI (LC-MS positive mode) m/z 247 (M+H)

Step C

Preparation of 1-[4-(3-dimethylamino-propyl)-3-(trifluoromethyl)phenyl]-3-[4-(6-(methylamino)purin-9-yl)-phenyl]urea (Table 2, Compound No. 74)

[Formula 272]

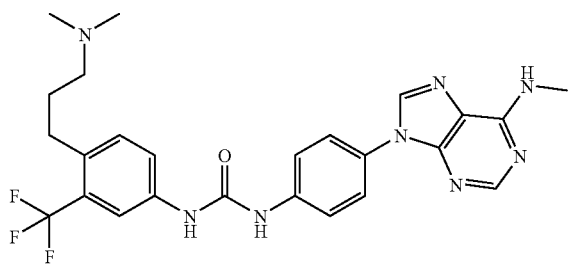

The title compound can be obtained by forming a urea bonding by using the same techniques as in Example 176 and successively performing deprotection with trifluoroacetic acid.

$^1$H-NMR (270 MHz, DMSO-d$_6$) δ (ppm): 1.72 (2H, m), 2.27 (6H, s), 2.41 (2H, m), 2.67 (2H, m), 2.99 (3H, s), 7.41 (1H, d, J=8.7 Hz), 7.56 (1H, dd, J=2.0, 8.4 Hz), 7.66-7.84 (5H, m), 8.29 (1H, s), 8.50 (1H, s), 9.07 (1H, s), 9.08 (1H, s)

ESI (LC-MS positive mode) m/z 513 (M+H)

The compounds of Examples 192 to 195 can be prepared by using the same techniques as in Example 191.

Example 192

1-[4-(6-(Methylamino)purin-9-yl)phenyl]-3-(4-[3-(4-methyl-piperazin-1-yl)-propyl]-3-(trifluoromethyl)phenyl)urea (Table 2, Compound No. 75)

[Formula 273]

$^1$H-NMR (270 MHz, DMSO-d$_6$) δ (ppm): 1.72 (2H, m), 2.23 (3H, s), 2.30-2.50 (8H, m), 2.41 (2H, m), 2.67 (2H, m), 2.99 (3H, s), 7.41 (1H, d, J=8.7 Hz), 7.56 (1H, dd, J=2.0, 8.4 Hz), 7.66-7.84 (5H, m), 7.95 (1H, m), 8.29 (1H, s), 8.50 (1H, s), 9.07 (1H, s), 9.08 (1H, s)

ESI (LC-MS positive mode) m/z 568 (M+H)

Example 193

1-[4-(6-(Methylamino)purin-9-yl)phenyl]-3-[4-[3-morpholin-4-yl-propyl]-3-(trifluoromethyl)phenyl]-urea (Table 2, Compound No. 76)

[Formula 274]

$^1$H-NMR (270 MHz, DMSO-d$_6$) δ (ppm): 1.90 (2H, m), 2.32 (4H, s), 2.41 (2H, m), 2.67 (2H, m), 2.99 (3H, s), 3.57-3.59 (4H, m), 7.41 (1H, d, J=8.7 Hz), 7.56 (1H, dd, J=2.0, 8.4 Hz), 7.66-7.84 (5H, m), 7.95 (1H, m), 8.29 (1H, s), 8.50 (1H, s), 9.11 (1H, s), 9.12 (1H, s)

ESI (LC-MS positive mode) m/z 555 (M+H)

Example 194

1-[4-(6-(Methylamino)purin-9-yl)phenyl]-3-[4-[3-pyrrolidin-1-yl-propyl]-3-(trifluoromethyl)phenyl]-urea (Table 2, Compound No. 77)

[Formula 275]

$^1$H-NMR (270 MHz, DMSO-d$_6$) δ (ppm): 1.76 (6H, m), 2.40-2.60 (8H, m), 2.99 (3H, s), 7.41 (1H, d, J=8.7 Hz), 7.56 (1H, dd, J=2.0, 8.4 Hz), 7.66-7.84 (5H, m), 7.95 (1H, m), 8.29 (1H, s), 8.50 (1H, s), 9.08 (1H, s), 9.09 (1H, s)

ESI (LC-MS positive mode) m/z 539 (M+H)

Example 195

1-[4-(6-(Methylamino)purin-9-yl)phenyl]-3-[4-[3-piperidin-1-yl-propyl]-3-(trifluoromethyl)phenyl]-urea (Table 2, Compound No. 78)

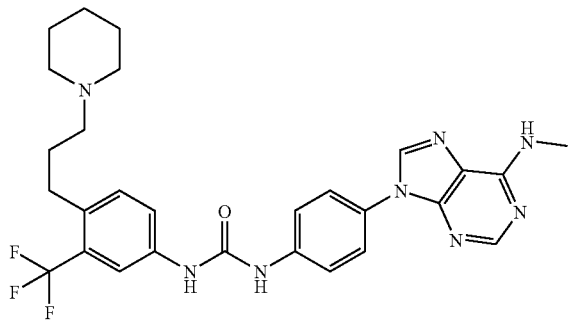

[Formula 276]

$^1$H-NMR (270 MHz, DMSO-d$_6$) δ (ppm): 1.40-1.80 (8H, m), 2.40-2.60 (8H, m), 2.99 (3H, s), 7.41 (1H, d, J=8.7 Hz), 7.56 (1H, dd, J=2.0, 8.4 Hz), 7.66-7.84 (5H, m), 7.95 (1H, m), 8.29 (1H, s), 8.50 (1H, s), 9.08 (1H, s), 9.09 (1H, s)
ESI (LC-MS positive mode) m/z 553 (M+H)

Example 196

1-[3-(2-Dimethylamino-ethoxy)-5-(trifluoromethyl)phenyl]-3-[4-(6-methylamino)purin-9-yl]phenyl]urea (Table 2, Compound No. 86)

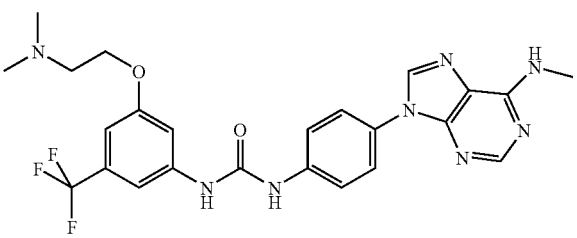

[Formula 277]

The title compound can be prepared from 3-fluoro-5-nitrobenzotrifluoride by using the same techniques as in Example 171.
$^1$H-NMR (270 MHz, DMSO-d$_6$) δ (ppm): 2.24 (6H, s), 2.66 (2H, m), 2.99 (3H, s), 4.13 (2H, m), 6.88 (1H, s), 7.30 (1H, s), 7.49 (1H, s), 7.65 (2H, d, J=9.1 Hz), 7.79 (2H, d, J=9.1 Hz), 7.85 (1H, m), 8.30 (1H, s), 8.53 (1H, s), 9.08 (1H, s), 9.11 (1H, s)
ESI (LC-MS positive mode) m/z 515 (M+H)

Example 197

1-[4-(6-(Methylamino)purin-9-yl)phenyl]-3-[3-(1-methyl-piperidin-4-yloxy)-5-(trifluoromethyl)phenyl]-urea (Table 2, Compound No. 91)

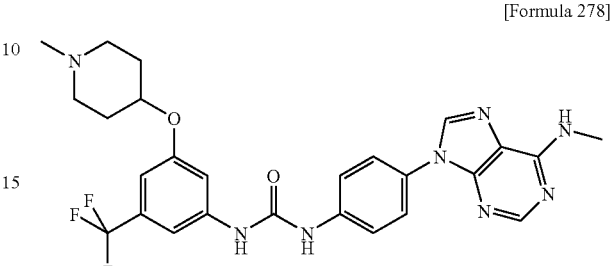

[Formula 278]

The title compound can be prepared from 3-fluoro-5-nitrobenzotrifluoride by using the same techniques as in Example 171.
$^1$H-NMR (270 MHz, DMSO-d$_6$) δ (ppm): 1.70 (2H, m), 2.00-2.10 (5H, m), 2.36 (4H, m), 2.99 (3H, s), 4.53 (1H, m), 6.86 (1H, s), 7.30 (1H, s), 7.49 (1H, s), 7.68-7.85 (5H, m), 8.29 (1H, s), 8.51 (1H, s), 9.08 (1H, s), 9.10 (1H, s)
ESI (LC-MS positive mode) m/z 541 (M+H)

Example 198

1-[4-(6-(Aminopurin-7-yl)phenyl)-3-(4-chloro-3-(trifluoromethyl)phenyl)urea hydrochloride (Table 3, Compound No. 1)

Step A

Preparation of 7-(4-aminophenyl)-6-di-tert-butoxycarbonylamino-7H-purine

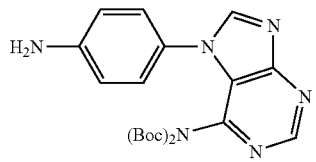

[Formula 279]

The title compound can be prepared by reducing 6-di-tert-butoxycarbonylamino-7-(4-nitrophenyl)-7H-purine obtained as a by-product in preparing 6-di-tert-butoxycarbonylamino-9-(4-nitrophenyl)-9H-purine in Step A of Example 29 in the same procedure as in Step B of Example 29.
$^1$H-NMR (270 MHz, DMSO-d$_6$) δ (ppm): 1.29 (18H, s), 5.59 (2H, s), 6.66 (2H, d, J=8.6 Hz), 7.12 (2H, d, J=8.6 Hz), 8.84 (1H, s), 8.98 (1H, s)
ESI (LC-MS positive mode) m/z 427 (M+H)

Step B

Preparation of 1-[4-(6-(aminopurin-7-yl)phenyl]-3-(4-chloro-3-(trifluoromethyl)phenyl)urea hydrochloride (Table 3, Compound No. 1)

The title compound can be prepared by performing deprotection of the intermediate prepared in the same procedure as in Step C of Example 29 with a 4N hydrogen chloride ethyl acetate solution.

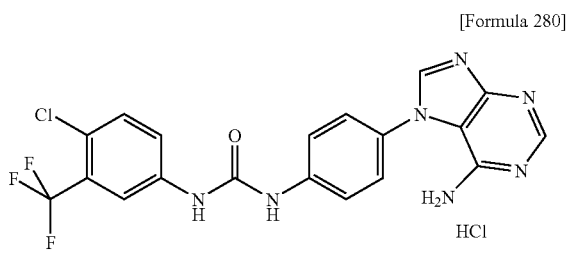 [SMILES: Nc1ncnc2ncn(-c3ccc(NC(=O)Nc4ccc(Cl)c(C(F)(F)F)c4)cc3)c12 ; Cl]

$^1$H-NMR (270 MHz, DMSO-$d_6$) δ (ppm): 7.54 (2H, d, J=8.9 Hz), 7.63 (2H, m), 7.72 (2H, d, J=8.9 Hz), 8.73 (1H, s), 8.80 (1H, s), 9.68 (1H, s), 9.80 (1H, s)

ESI (LC-MS positive mode) m/z 448 (M+H)

Example 199

1-(4-Chloro-3-(trifluoromethyl)phenyl)-3-[4-(6-(methylamino)purin-7-yl)phenyl]urea hydrochloride (Table 3, Compound No. 2)

Step A

Preparation of [7-(4-aminophenyl)-7H-purin-6-yl]-methylcarbamic acid tert-butyl ester

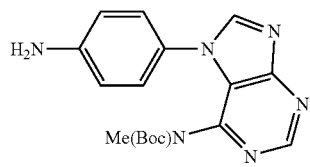

The title compound can be prepared by reducing [7-(4-nitrophenyl)-7H-purin-6-yl]-methylcarbamic acid tert-butyl ester obtained as a by-product in preparing [9-(4-aminophenyl)-9H-purin-6-yl]-methylcarbamic acid tert-butyl ester in Example 36 in the same procedure as in Step B of Example 29.

$^1$H-NMR (270 MHz, DMSO-$d_6$) δ (ppm): 1.10 (18H, s), 3.26 (3H, s), 5.40 (2H, s), 6.62 (1H, d, J=8.6 Hz), 7.16 (1H, d, J=8.6 Hz), 8.14 (1H, s), 8.78 (1H, s), 8.88 (1H, s)

ESI (LC-MS positive mode) m/z 341 (M+H)

Step B

Preparation of 1-(4-chloro-3-(trifluoromethyl)phenyl)-3-[4-(6-(methylamino)purin-7-yl)phenyl]urea hydrochloride (Table 3, Compound No. 2)

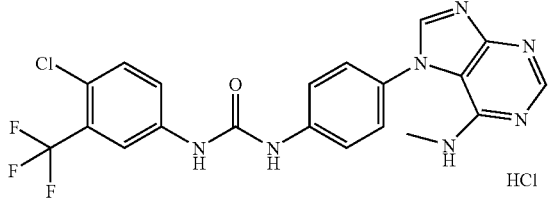

The title compound can be prepared by performing deprotection of the intermediate prepared in the same procedure as in Step C of Example 29 with a 4N hydrogen chloride ethyl acetate solution.

$^1$H-NMR (270 MHz, DMSO-$d_6$) δ (ppm): 3.01 (3H, d, J=4.6 Hz), 7.20 (1H, m), 7.55 (2H, d, J=8.9 Hz), 7.68 (2H, m), 7.78 (2H, d, J=8.9 Hz), 8.15 (1H, s), 8.74 (1H, s), 8.82 (1H, s), 9.98 (1H, s), 10.08 (1H, s)

ESI (LC-MS positive mode) m/z 462 (M+H)

Example 200

1-(7-{4-[3-(4-Chloro-3-(trifluoromethyl)phenyl) ureido]phenyl}-7H-purin-6-yl)-3-propylurea (Table 3, Compound No. 3)

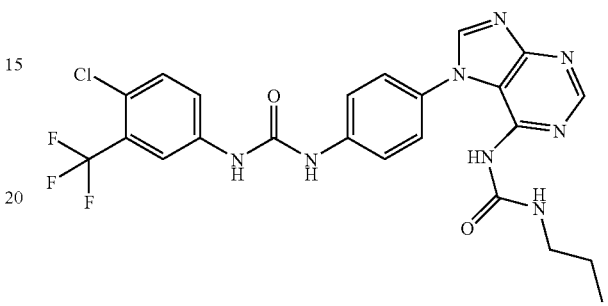

The title compound can be prepared from 1-[4-(6-aminopurin-7-yl)phenyl]-3-(4-chloro-3-(trifluoromethyl)phenyl)urea hydrochloride in the same procedure as in Example 119.

$^1$H-NMR (270 MHz, DMSO-$d_6$) δ (ppm): 0.83 (3H, t, J=4.9 Hz), 1.40 (2H, m), 2.02 (2H, m), 7.55-7.78 (6H, m), 8.20 (1H, s), 8.67 (1H, s), 8.72 (1H, s), 9.30 (1H, s), 9.40 (1H, s)

ESI (LC-MS positive mode) m/z 533 (M+H)

Example 201

1-[4-(6-(Aminopurin-7-yl)phenyl)-3-[3-(4-methylpiperazin-1-ylmethyl)-5-(trifluoromethyl)phenyl] urea (Table 3, Compound No. 4)

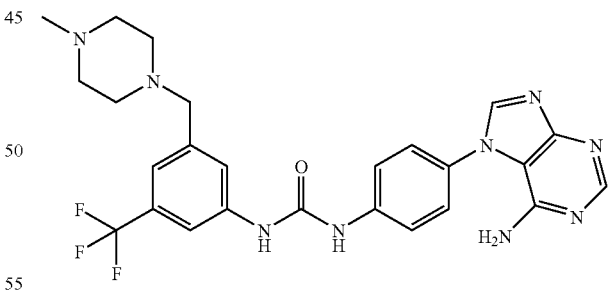

The title compound can be prepared by allowing 3-(methylpiperazin-1-ylmethyl)-5-(trifluoromethyl)aniline and 7-(4-aminophenyl)-6-di-tert-butoxycarbonylamino-7H-purine to form a urea bonding by using the techniques as in Step G of Example 147, then performing deprotection with an acid and subsequently effecting neutralization.

$^1$H-NMR (270 MHz, DMSO-$d_6$) δ (ppm): 2.16 (3H, s), 2.38 (8H, m), 3.52 (2H, s), 6.12 (2H, s), 7.21 (1H, s), 7.48 (1H, s), 7.55 (2H, d, J=8.7 Hz), 7.70 (2H, d, J=8.7 Hz), 7.83 (1H, s), 8.30 (1H, s), 8.46 (1H, s), 9.09 (1H, s), 9.19 (1H, s)

ESI (LC-MS positive mode) m/z 526 (M+H)

Example 202

9-{4-[3-(4-Chloro-3-(trifluoromethyl)phenyl)ureido]phenyl}-9H-purine-6-carboxylic acid methyl ester (Table 3, Compound No. 5)

[Formula 285]

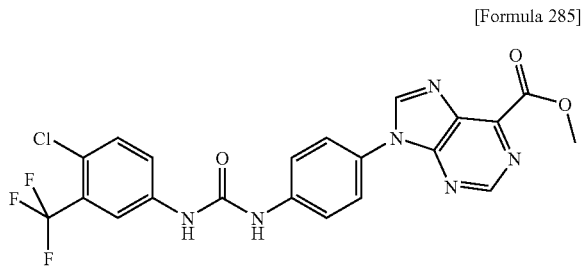 [SMILES: COC(=O)c1ncnc2c1ncn2-c1ccc(NC(=O)Nc2ccc(Cl)c(C(F)(F)F)c2)cc1]

The title compound can be prepared from 6-cyanopurine by using similar techniques as in Example 92

ESI (LC-MS positive mode) m/z 492 (M+H)

Example 203

9-{4-[3-(4-Chloro-3-(trifluoromethyl)phenyl)ureido]-phenyl}-9H-purine-6-carboxylic acid (Table 3, Compound No. 6)

[Formula 286]

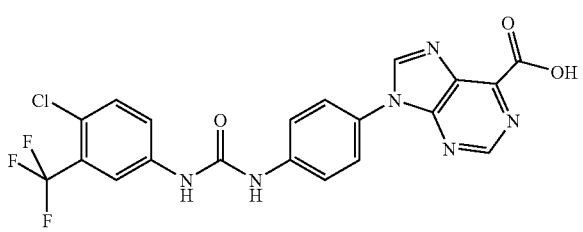

In 3 mL of methanol, 45 mg (0.092 mmol) of 9-{4-[3-(4-chloro-3-(trifluoromethyl)phenyl)ureido]phenyl}-9H-purine-6-carboxylic acid methyl ester, and 2 mL of a 0.1 N sodium hydroxide aqueous solution was added thereto and the mixture solution was stirred at room temperature overnight. The reaction solution was neutralized with 0.1 N hydro-chloric acid, and then the deposited product was washed with water to obtain 30 mg (69%) of a target product as a pale yellow solid.

ESI (LC-MS positive mode) m/z 477 (M+H)

Example 204

9-{4-[3-(4-Chloro-3-(trifluoromethyl)phenyl)ureido]phenyl}-9H-purine-6-carboxylic acid methylamide (Table 3, Compound No. 7)

[Formula 287]

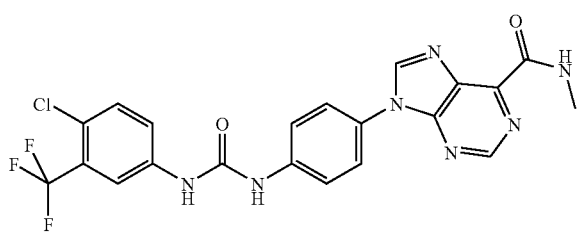

In 3 mL of dimethylformamide, 30 mg (0.063 mmol) of 9-{4-[3-(4-chloro-3-(trifluoromethyl)phenyl)ureido]phenyl}-9H-purine-6-carboxylic acid was dissolved, and 10 µL of 40% methylamine, 17 mg (0.13 mmol) of HATU and HOAt (0.13 mmol) were added thereto and the mixture solution was stirred at room temperature overnight. The reaction solution was partitioned between ethyl acetate and water and the organic layer was washed with water and a saturated sodium chloride solution in the order named, and then concentrated under reduced pressure. The coarse product was recrystallized from ethyl acetate to obtain 16 mg (52%) of a target product as a white solid.

ESI (LC-MS positive mode) m/z 490 (M+H)

Example 205

1-[4-(6-(Aminopurin-7-yl)phenyl)-3-(3-dimethylaminomethyl-5-trifluoromethyl-phenyl)urea (Table 3, Compound No. 8)

[Formula 288]

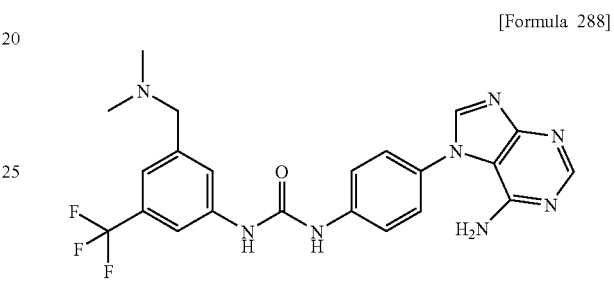

The title compound can be prepared from 3-(dimethylamino)methyl-5-(trifluoromethyl)aniline prepared in Example 151 in the same manner as in Example 201.

$^1$H-NMR (270 MHz, DMSO-$d_6$) δ (ppm): 2.18 (6H, s), 3.47 (2H, s), 6.12 (2H, s), 7.22 (1H, s), 7.48 (1H, s), 7.58 (2H, d, J=8.7 Hz), 7.70 (2H, d, J=8.7 Hz), 7.86 (1H, s), 8.29 (1H, s), 8.47 (1H, s), 9.09 (1H, s), 9.18 (1H, s)

ESI (LC-MS positive mode) m/z 471 (M+H)

Example 206

3-{3-[4-(6-Aminopurin-7-yl)phenyl]ureido}-N-(2-(dimethylamino)ethyl)-5-(trifluoromethyl)benzamide (Table 3, Compound No. 9)

[Formula 289]

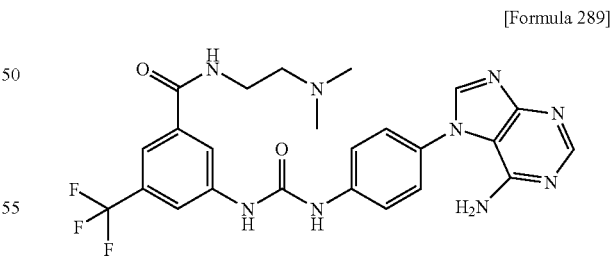

The title compound can be prepared from 3-amino-N-(2-(dimethylamino)ethyl)-5-(trifluoromethyl)benzamide prepared in Example 162 in the same manner as in Example 201.

$^1$H-NMR (270 MHz, DMSO-$d_6$) δ (ppm): 2.22 (6H, s), 2.39-2.57 (2H, m), 3.15-3.47 (2H, m), 6.12 (2H, bs), 7.52 (2H, d, J=8.7 Hz), 7.73 (2H, d, J=8.7 Hz), 7.80 (1H, s), 8.08 (1H, s), 8.17 (1H, s), 8.38 (1H, s), 8.46 (1H, s), 8.68 (1H, s), 9.35 (1H, s), 9.50 (1H, s)

ESI (LC-MS positive mode) m/z 528 (M+H)

Example 207

1-[4-(6-(Aminopurin-7-yl)phenyl)-3-[3-(4-methylpiperazine-1-carbonyl)-5-(trifluoromethyl)phenyl]urea (Table 3, Compound No. 10)

[Formula 290]

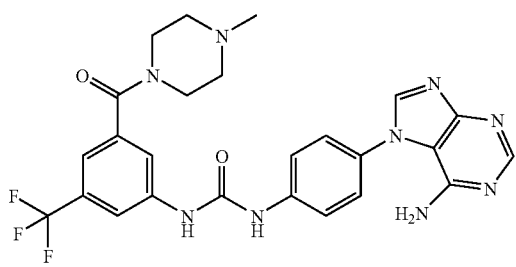

The title compound can be prepared from (3-amino-5-(trifluoromethyl)phenyl)-(4-methylpiperazin-1-yl)methanone prepared in Example 161 in the same manner as in Example 201.

$^1$H-NMR (270 MHz, CD$_3$OD) δ (ppm): 2.34 (3H, s), 2.47 (2H, bs), 2.54 (2H, bs), 3.49 (2H, bs), 3.80 (2H, bs), 7.37 (1H, s), 7.55 (2H, d, J=8.9 Hz), 7.76 (2H, d, J=8.9 Hz), 7.81 (1H, s), 7.95 (1H, s), 8.33 (1H, s), 8.38 (1H, s), 8.39 (1H, s)

ESI (LC-MS positive mode) m/z 540 (M+H)

Example 208

3-{3-[4-(6-Aminopurin-9-yl)phenyl]ureido}-N-(2-morpholin-4-yl-ethyl)-5-(trifluoromethyl)benzamide (Table 3, Compound No. 11)

[Formula 291]

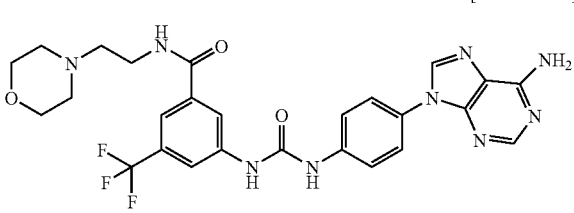

$^1$H-NMR (270 MHz, DMSO-d$_6$) δ (ppm): 2.39-2.50 (6H, m), 3.35 (2H, m), 3.58 (4H, m), 7.38 (2H, s), 7.68 (2H, d, J=9.1 Hz), 7.78 (1H, s), 7.80 (2H, d, J=9.2 Hz), 8.07 (1H, s), 8.16 (1H, s), 8.20 (1H, s), 8.53 (1H, s), 8.68 (1H, m), 9.19 (1H, s), 9.39 (1H, s)

ESI (LC-MS positive mode) m/z 570 (M+H)

The compounds shown in Examples 209 to 214, 216 to 226, 243, 246, 247 and 248 can be synthesized from the corresponding amines or their t-butoxycarbonyl-protected forms in the same manner as in Example 168.

Example 209

1-[4-(6-(Methylamino)purin-9-yl)phenyl]-3-(4-piperazin-1-ylmethyl-3-(trifluoromethyl)phenyl)urea (Table 3, Compound No. 12)

[Formula 292]

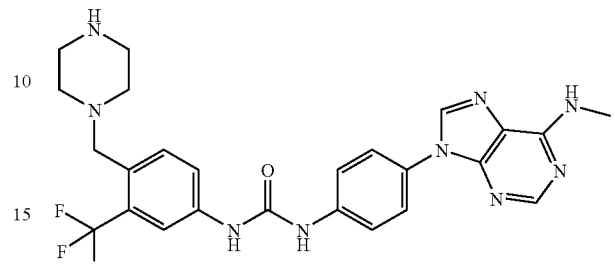

$^1$H-NMR (270 MHz, CD$_3$OD) δ (ppm): 2.42-2.56 (4H, m), 2.85-2.95 (4H, m), 3.15 (3H, br.s), 3.62 (2H, s), 7.60-7.74 (6H, m), 7.89 (1H, s), 8.28 (1H, s), 8.30 (1H, s)

ESI (LC-MS positive mode) m/z 526 (M+H)

Example 210

1-[4-(6-(Methylamino)purin-9-yl)phenyl]-3-(4-pyrrolidin-1-ylmethyl-3-(trifluoromethyl)phenyl)urea (Table 3, Compound No. 13)

[Formula 293]

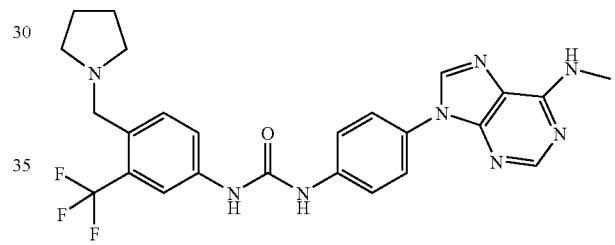

$^1$H-NMR (270 MHz, CD$_3$OD) δ (ppm): 2.64 (4H, s), 3.41 (4H, s), 3.94 (3H, br.s), 4.60 (2H, s), 8.36-8.57 (6H, m), 8.69 (1H, s), 9.07 (2H, s)

ESI (LC-MS positive mode) m/z 511 (M+H)

Example 211

1-[4-(4-Ethyl-piperazin-1-ylmethyl)-3-(trifluoromethyl)phenyl]-3-[4-(6-(methylamino)purin-9-yl)phenyl]urea (Table 3, Compound No. 14)

[Formula 294]

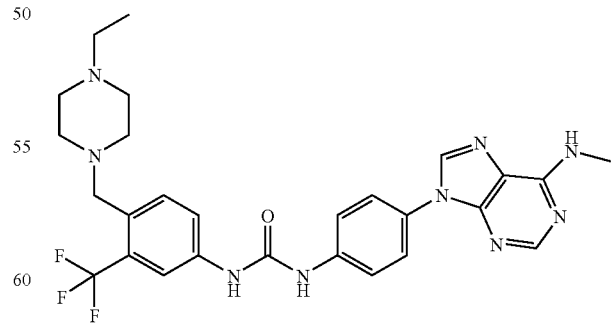

$^1$H-NMR (400 MHz, DMSO-d$_6$) δ (ppm): 1.16 (3H, t, J=7.2 Hz), 2.25-2.36 (10H, br.s), 2.29 (3H, br.s), 3.62 (2H, s), 7.60-7.71 (4H, m), 7.71-7.90 (3H, m), 7.99 (1H, s), 8.28 (1H, s), 8.50 (1H, s), 9.16 (1H, s), 9.24 (1H, s)

ESI (LC-MS positive mode) m/z 554 (M+H)

Example 212

1-[4-(6-(Methylamino)purin-9-yl)phenyl]-3-{4-[2-pyrrolidin-1-yl-ethylamino]methyl}-3-(trifluoromethyl)phenyl)urea (Table 3, Compound No. 15)

[Formula 295]

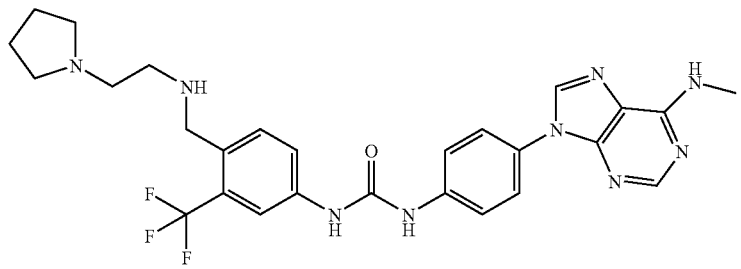

$^1$H-NMR (270 MHz, CD$_3$OD) δ (ppm): 1.81 (4H, br.s), 2.59 (4H, br.s), 2.61-2.81 (4H, m), 3.14 (3H, br.s), 3.90 (2H, s), 7.50-7.75 (6H, m), 7.91 (1H, s), 8.20-8.32 (2H, m)

ESI (LC-MS positive mode) m/z 554 (M+H)

Example 213

1-[4-(6-(Methylamino)purin-9-yl)phenyl]-3-(4-piperidin-1-ylmethyl-3-(trifluoromethyl)phenyl)urea (Table 3, Compound No. 16)

[Formula 296]

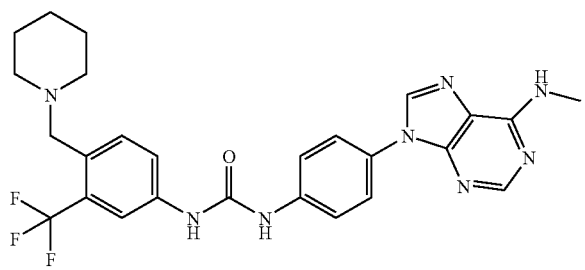

$^1$H-NMR (270 MHz, CD$_3$OD) δ (ppm): 1.43-1.58 (2H, s), 1.58-1.70 (4H, m), 2.50 (4H, br.s), 3.14 (3H, br.s), 3.64 (2H, s), 7.56-7.63 (6H, m), 7.89 (1H, d, J=2.1 Hz), 8.26 (1H, s), 8.28 (1H, s)

ESI (LC-MS positive mode) m/z 525 (M+H)

Example 214

1-(4-(Cyclohexylamino)methyl-3-(trifluoromethyl)phenyl)-3-[4-(6-(methylamino)purin-9-yl)phenyl]urea (Table 3, Compound No. 17)

[Formula 297]

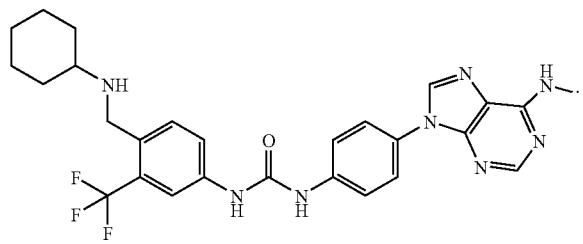

$^1$H-NMR (400 MHz, DMSO-d$_6$) δ (ppm): 1.10-1.33 (6H, m), 1.54-1.65 (1H, m), 1.75 (2H, br.s), 2.02 (2H, br.s), 3.00 (3H, br.s), 4.11 (2H, br.s), 7.60-7.89 (8H, m), 8.06 (1H, s), 8.29 (1H, s), 8.51 (1H, s), 9.31 (1H, s), 9.43 (1H, s)

ESI (LC-MS positive mode) m/z 539 (M+H)

Example 215

1-(4-Imidazo[4,5-c]pyridin-1-yl-phenyl)-3-[4-(4-methyl-piperazin-1-ylmethyl)-3-(trifluoromethyl)phenyl]urea (Table 3, Compound No. 18)

[Formula 298]

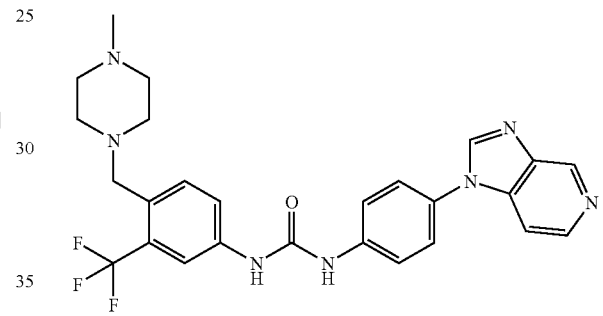

The title compound can be synthesized from 4-(imidazo[4,5-c]pyridin-1-yl)aniline prepared in Example 1 by using the same techniques as in Step G of Example 147.

$^1$H-NMR (270 MHz, DMSO-d$_6$) δ (ppm): 2.17 (3H, s), 2.25-2.45 (8H, m), 2.95-3.05 (3H, br.s), 3.53 (2H, s), 7.60-7.75 (7H, m), 7.99 (1H, s), 8.42 (1H, s), 8.69 (1H, s), 9.06 (1H, s), 9.13 (1H, s), 9.15 (1H, s)

ESI (LC-MS positive mode) m/z 510 (M+H)

Example 216

1-[4-(6-(Methylamino)purin-9-yl)phenyl]-3-{4-[(tetrahydro-pyran-4-ylamino)-methyl]-3-(trifluoromethyl)phenyl}urea (Table 3, Compound No. 19)

[Formula 299]

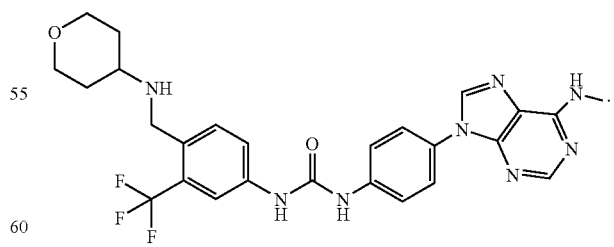

$^1$H-NMR (400 MHz, DMSO-d$_6$) δ (ppm): 1.27-1.49 (2H, m), 1.76-1.94 (2H, m), 3.00 (3H, br.s), 3.05 (1H, br.s), 3.21-3.31 (2H, m), 3.81-3.92 (2H, m), 3.96 (2H, br.s), 7.60-7.90 (8H, m), 8.01 (1H, s), 8.29 (1H, s), 8.51 (1H, s), 9.19 (1H, s), 9.27 (1H, s)

ESI (LC-MS positive mode) m/z 541 (M+H)

Example 217

1-{4-[(3-(Dimethylamino)propylamino)methyl]-3-(trifluoromethyl)phenyl}-3-[4-(6-(methylamino)purin-9-yl)phenyl]urea (Table 3, Compound No. 20)

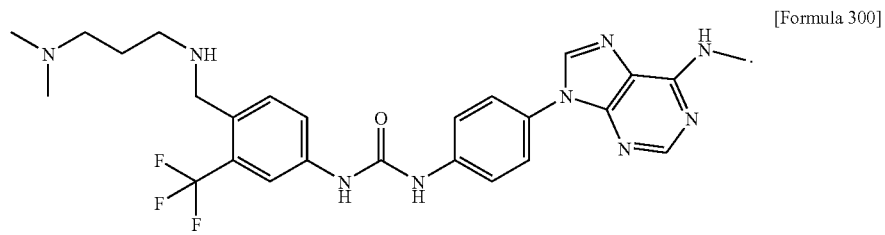
[Formula 300]

¹H-NMR (270 MHz, CD₃OD) δ (ppm): 1.80-1.93 (2H, m), 2.61 (6H, s), 2.83-2.96 (4H, m), 3.15 (3H, br.s), 3.99 (2H, s), 7.53-7.78 (6H, m), 7.94 (1H, s), 8.28 (1H, s), 8.30 (1H, m)
ESI (LC-MS positive mode) m/z 542 (M+H)

Example 218

1-[4-(6-(Methylamino)purin-9-yl)phenyl]-3-{4-[(3-morpholin-4-yl-propylamino)methyl]-3-(trifluoromethyl)phenyl}urea (Table 3, Compound No. 21)

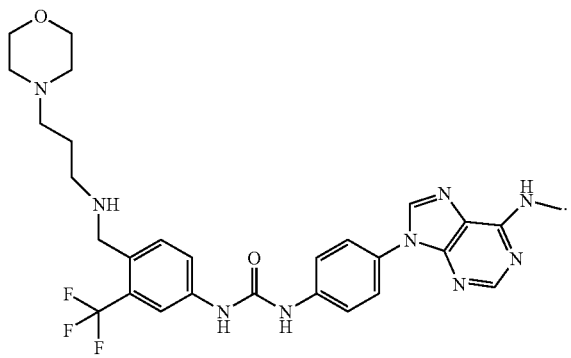
[Formula 301]

¹H-NMR (270 MHz, CD₃OD) δ (ppm): 1.84-1.98 (2H, m), 2.52 (4H, t, J=4.5 Hz), 2.59 (2H, t, H=6.4 Hz), 3.15 (3H, br.s), 3.17-3.26 (2H, m), 3.63 (4H, t, J=4.7 Hz), 4.30 (2H, s), 7.60-7.75 (5H, m), 7.86 (1H, d, J=8.6 Hz), 8.06 (1H, s), 8.28 (1H, s), 8.30 (1H, m)
ESI (LC-MS positive mode) m/z 584 (M+H)

Example 219

1-[4-(6-(Methylamino)purin-9-yl)phenyl]-3-[4-(piperidin-4-ylaminomethyl)-3-(trifluoromethyl)phenyl]urea (Table 3, Compound No. 22)

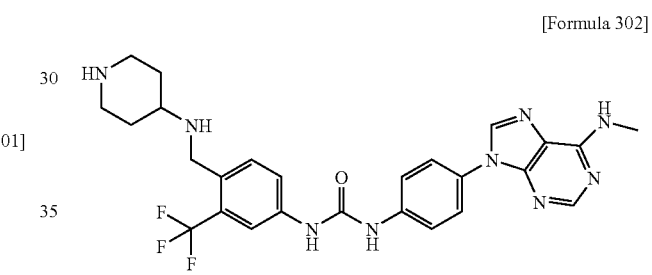
[Formula 302]

¹H-NMR (500 MHz, CD₃OD) δ (ppm): 1.57-1.70 (2H, m), 2.07-2.10 (2H, m), 2.85-3.07 (1H, m), 3.15 (3H, br.s), 3.36-3.47 (2H, m), 3.94 (2H, s), 7.60-7.75 (6H, m), 7.90 (1H, s), 8.27 (1H, s), 8.29 (1H, m)
ESI (LC-MS positive mode) m/z 540 (M+H)

Example 220

1-[4-(6-(Methylamino)purin-9-yl)phenyl]-3-(4-{[piperidin-4-ylmethyl]amino}methyl)-3-(trifluoromethyl)phenyl)urea (Table 3, Compound No. 23)

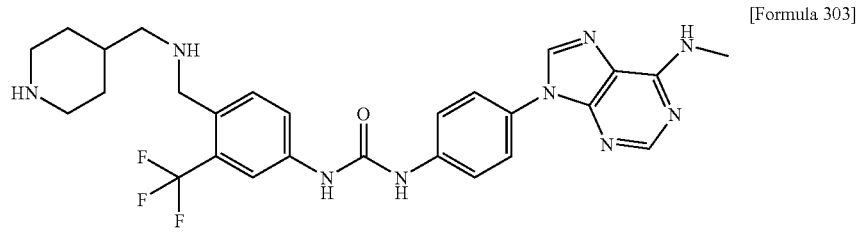 [SMILES: CNc1ncnc2c1ncn2-c1ccc(NC(=O)Nc2ccc(CNCC3CCNCC3)c(C(F)(F)F)c2)cc1]
[Formula 303]

¹H-NMR (500 MHz, CD₃OD) δ (ppm): 1.22-1.41 (2H, m), 1.75-1.85 (1H, m), 2.00 (2H, d, J=12.8 Hz), 2.54 (2H, d, J=6.9 Hz), 2.94 (2H, dt, J=3.2, 12.8 Hz), 3.10-3.19 (3H, m), 3.31-3.34 (2H, m), 7.57-7.73 (6H, m), 7.88 (1H, s), 8.27 (1H, s), 8.29 (1H, m)
ESI (LC-MS positive mode) m/z 554 (M+H)

Example 221

1-{4-[(Cyclohexyl-methylamino)methyl]-3-(trifluoromethyl)phenyl}-3-[4-(6-(methylamino)purin-9-yl)phenyl]urea (Table 3, Compound No. 24)

[Formula 304]

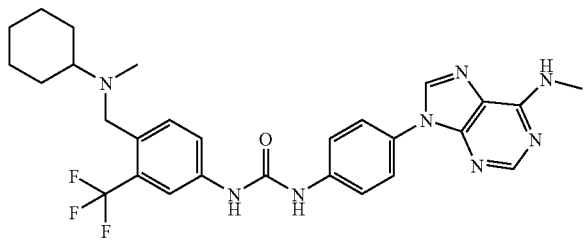

¹H-NMR (270 MHz, CD₃OD) δ (ppm): 1.11-2.06 (11H, m), 2.42 (3H, br.s), 3.14 (3H, br.s), 4.00 (2H, s), 7.61-7.77 (6H, m), 7.96 (1H, s), 8.28 (1H, s), 8.30 (1H, m)
ESI (LC-MS positive mode) m/z 553 (M+H)

Example 222

1-[4-(4-(Amino-piperidin-1-ylmethyl)-3-(trifluoromethyl)phenyl]-3-[4-(6-(methylamino)purin-9-yl)phenyl]urea (Table 3, Compound No. 25)

[Formula 305]

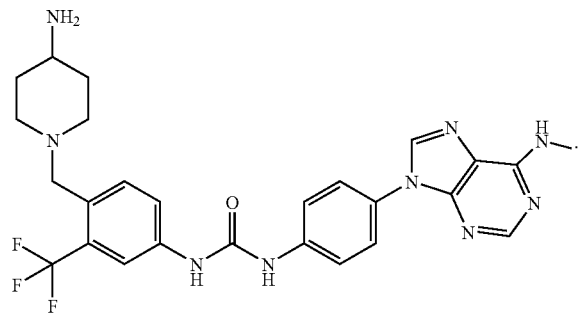

ESI (LC-MS positive mode) m/z 540 (M+H)

Example 223

1-[4-(4-(Hydroxy-piperidin-1-ylmethyl)-3-(trifluoromethyl)phenyl)-3-[4-(6-(methylamino)purin-9-yl)phenyl]urea (Table 3, Compound No. 26)

[Formula 306]

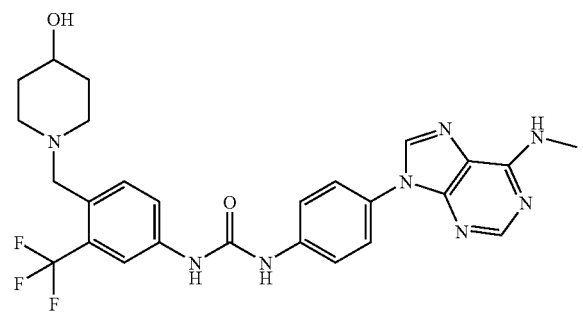

¹H-NMR (270 MHz, DMSO-d₆) δ (ppm): 1.31-1.50 (2H, m), 1.63-1.69 (2H, m), 2.00 (2H, d, J=10.0 Hz), 2.60-2.72 (2H, m), 2.99 (3H, br.s), 3.41-3.56 (1H, br.s), 3.51 (2H, s), 4.56 (1H, d, J=3.8 Hz), 7.55-7.91 (7H, m), 7.98 (1H, d, J=1.6 Hz), 8.28 (1H, s), 8.51 (1H, s), 9.12 (1H, s), 9.17 (1H, s)
ESI (LC-MS positive mode) m/z 541 (M+H)

Example 224

1-(4-{[(2-(Dimethylamino)ethyl)methylamino]methyl}-3-(trifluoromethyl)phenyl)-3-[4-(6-(methylamino)-purin-9-yl)phenyl]urea (Table 3, Compound No. 27)

[Formula 307]

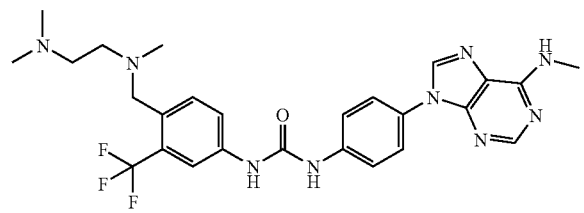

¹H-NMR (270 MHz, CD₃OD) δ (ppm): 2.26 (3H, s), 2.47 (6H, s), 2.63 (2H, t, J=6.8 Hz), 2.82 (2H, t, J=6.8 Hz), 3.15 (3H, br.s), 3.67 (2H, s), 7.61-7.78 (6H, m), 7.87 (1H, d, J=1.6 Hz), 8.27 (1H, s), 8.30 (1H, m)
ESI (LC-MS positive mode) m/z 542 (M+H)

Example 225

1-[4-(4-Isopropyl-piperazin-1-ylmethyl)-3-(trifluoromethyl)phenyl]-3-[4-(6-(methylamino)purin-9-yl)phenyl]urea (Table 3, Compound No. 28)

[Formula 308]

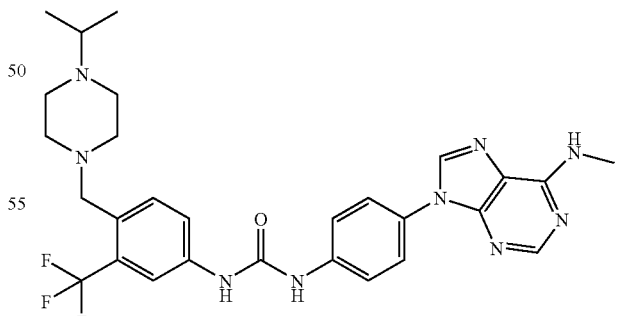

¹H-NMR (270 MHz, CD₃OD) δ (ppm): 1.21 (3H, s), 1.24 (3H, s), 1.23-1.37 (1H, m), 2.65 (4H, br.s), 2.94 (4H, br.s), 3.15 (3H, br.s), 3.67 (2H, s), 7.60-7.75 (6H, m), 7.88 (1H, d, J=1.6 Hz), 8.27 (1H, s), 8.30 (1H, m)
ESI (LC-MS positive mode) m/z 568 (M+H)

Example 226

1-(4-{[(3-(Dimethylamino)propyl)-methylamino]-methyl}-3-(trifluoromethyl)phenyl)-3-[4-(6-(methylamino)-purin-9-yl)phenyl]urea (Table 3, Compound No. 29)

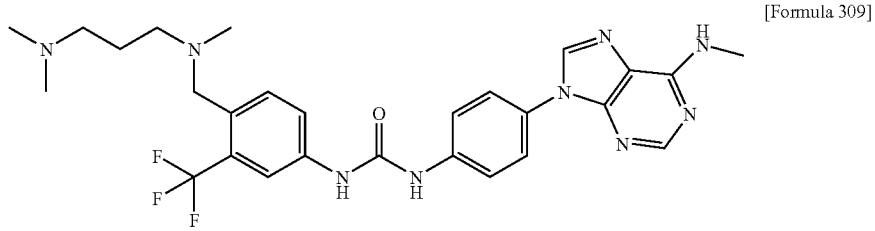
[Formula 309]

$^1$H-NMR (270 MHz, CD$_3$OD) δ (ppm): 1.80-1.95 (2H, m), 2.33 (3H, s), 2.54 (2H, t, J=6.6 Hz), 2.77 (6H, s), 2.99-3.08 (2H, m), 3.15 (3H, br.s), 3.65 (2H, s), 7.61-7.76 (6H, m), 7.87 (1H, d, J=2.2 Hz), 8.27 (1H, s), 8.30 (1H, m)
ESI (LC-MS positive mode) m/z 556 (M+H)

Example 227

1-[4-(6-(Methylamino)purin-9-yl)phenyl]-3-[3-(2-piperidin-1-yl-ethyl)-5-(trifluoromethyl)phenyl]urea (Table 3, Compound No. 30)

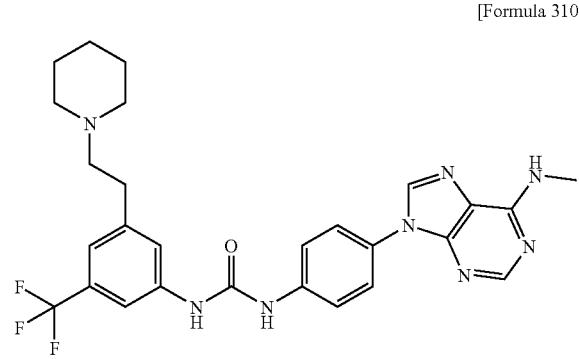 [SMILES: CNc1ncnc2c1ncn2-c1ccc(NC(=O)Nc2cc(CCN3CCCCC3)cc(C(F)(F)F)c2)cc1]
[Formula 310]

$^1$H-NMR (270 MHz, DMSO-d$_6$) δ (ppm): 1.39 (2H, m), 1.50 (4H, m), 2.40 (4H, m), 2.50 (2H, m), 2.80 (2H, t, J=4.9 Hz), 2.99 (3H, s), 7.20 (1H, s), 7.46 (1H, s), 7.65-7.83 (6H, m), 8.29 (1H, s), 8.50 (1H, s), 9.08 (1H, s), 9.09 (1H, s)
ESI (LC-MS positive mode) m/z 539 (M+H)

Example 228

1-[4-(6-(Methylamino)purin-9-yl)phenyl]-3-[3-(2-pyrrolidin-1-yl-ethyl)-5-(trifluoromethyl)phenyl]urea (Table 3, Compound No. 31)

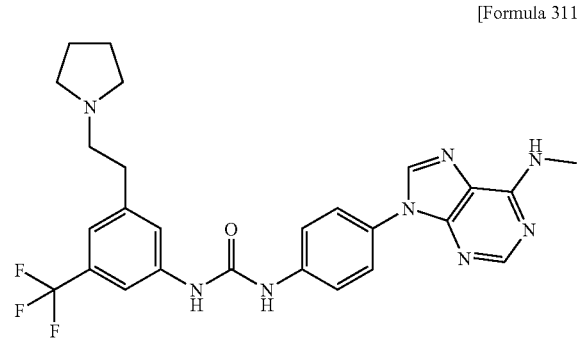
[Formula 311]

$^1$H-NMR (270 MHz, DMSO-d$_6$) δ (ppm): 1.70 (4H, s), 2.50 (4H, m), 2.68 (2H, m), 2.82 (2H, t, J=4.9 Hz), 2.99 (3H, s), 7.21 (1H, s), 7.48 (1H, s), 7.65-7.83 (6H, m), 8.29 (1H, s), 8.50 (1H, s), 9.06 (1H, s), 9.08 (1H, s)
ESI (LC-MS positive mode) m/z 525 (M+H)

Example 229

1-[4-(3-(Dimethylamino)propoxy)-3-(trifluoromethyl)phenyl]-3-[4-(6-(methylamino)purin-9-yl)phenyl]urea (Table 3, Compound No. 32)

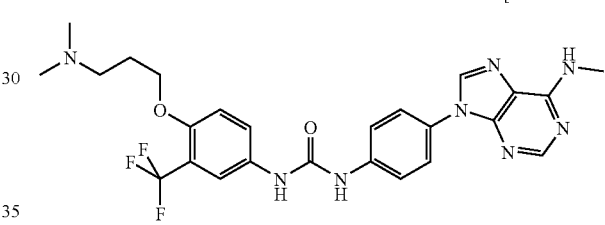
[Formula 312]

The title compound can be prepared from 2-fluoro-5-nitrobenzotrifluoride by using the same techniques as in Example 171.

$^1$H-NMR (270 MHz, DMSO-d$_6$) δ (ppm): 1.85 (2H, m), 2.18 (6H, s), 2.40 (2H, m), 2.99 (3H, s), 4.08 (2H, m), 7.20 (1H, d, J=9.6 Hz), 7.59 (1H, dd, J=9.6, 2.7 Hz), 7.62 (2H, d, J=9.1 Hz), 7.77 (2H, d, J=9.1 Hz), 7.87 (1H, d, J=2.7 Hz), 8.28 (1H, br.s), 8.50 (1H, s), 8.84 (1H, s), 8.96 (1H, s)
ESI (LC-MS positive mode) m/z 529 (M+H)

Example 230

1-[4-(6-(Methylamino)purin-9-yl)phenyl]-3-[4-(2-piperidin-1-yl-ethyl)-3-(trifluoromethyl)phenyl]urea (Table 3, Compound No. 33)

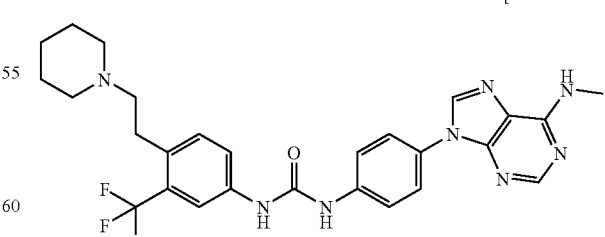
[Formula 313]

$^1$H-NMR (270 MHz, CD$_3$OD) δ (ppm): 1.50-1.62 (2H, m), 1.65-1.79 (4H, m), 2.69-2.89 (6H, m), 2.95-3.09 (2H, m), 3.14 (3H, br.s), 7.39 (1H, d, J=8.4 Hz), 7.57-7.73 (5H, m), 7.88 (1H, d, J=2.1 Hz), 8.27 (1H, s), 8.29 (1H, s)
ESI (LC-MS positive mode) m/z 539 (M+H)

Example 231

1-[4-(6-(Methylamino)purin-9-yl)phenyl]-3-[4-(2-pyrrolidin-1-yl-ethyl)-3-(trifluoromethyl)phenyl]urea (Table 3, Compound No. 34)

[Formula 314]

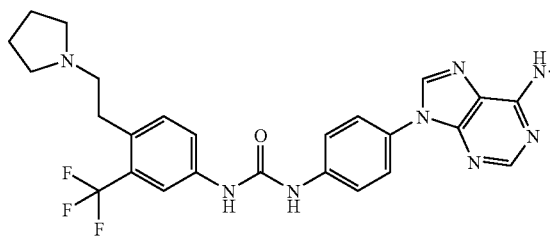

$^1$H-NMR (270 MHz, CD$_3$OD) δ (ppm): 1.83-1.97 (4H, m), 2.77-2.93 (6H, m), 2.99-3.07 (2H, m), 3.15 (3H, br.s), 7.40 (1H, d, J=8.6 Hz), 7.59-7.72 (5H, m), 7.88 (1H, d, J=2.1 Hz), 8.27 (1H, s), 8.30 (1H, s)
ESI (LC-MS positive mode) m/z 525 (M+H)

Example 232

1-{4-[2-(Cyclohexyl-methylamino)ethyl]-3-(trifluoromethyl)phenyl}-3-[4-(6-(methylamino)purin-9-yl)phenyl]urea (Table 3, Compound No. 35)

[Formula 315]

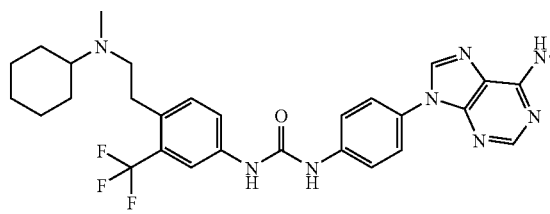

$^1$H-NMR (270 MHz, CD$_3$OD) δ (ppm): 1.23-1.47 (4H, m), 1.51-1.76 (2H, m), 1.85-2.00 (4H, m), 2.54 (3H, s), 2.76-2.85 (1H, m), 2.85-3.05 (4H, m), 3.15 (3H, br.s), 7.40 (1H, d, J=8.4 Hz), 7.60-7.77 (5H, m), 7.89 (1H, d, J=2.1 Hz), 8.27 (1H, s), 8.30 (1H, s)
ESI (LC-MS positive mode) m/z 567 (M+H)

Example 233

1-(4-{2-[(2-(Dimethylamino)ethyl)-methylamino]-ethyl}-3-(trifluoromethyl)phenyl)-3-[4-(6-(methylamino)-purin-9-yl)phenyl]urea (Table 3, Compound No. 36)

[Formula 316]

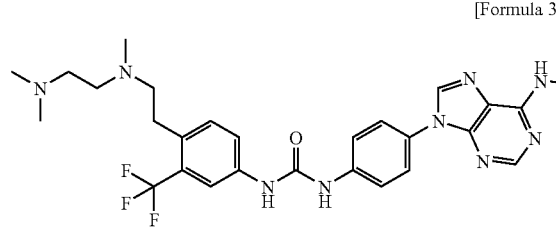

$^1$H-NMR (270 MHz, CD$_3$OD) δ (ppm): 2.41 (3H, s), 2.51 (6H, s), 2.64-2.85 (6H, m), 2.88-3.00 (2H, m), 3.14 (3H, br.s), 7.39 (1H, d, J=8.6 Hz), 7.60-7.72 (5H, m), 7.86 (1H, d, J=2.1 Hz), 8.27 (1H, s), 8.30 (1H, s)
ESI (LC-MS positive mode) m/z 556 (M+H)

Example 234

1-{4-[2-(4-Isopropyl-piperazin-1-yl)ethyl]-3-(trifluoromethyl)phenyl}-3-[4-(6-(methylamino)purin-9-yl)phenyl]urea (Table 3, Compound No. 37)

[Formula 317]

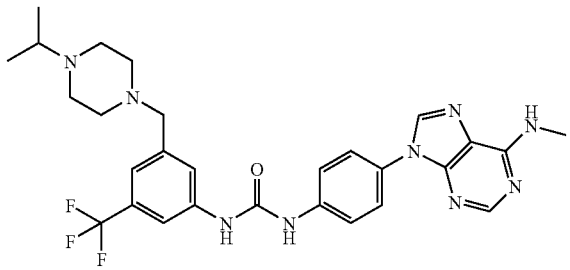

$^1$H-NMR (270 MHz, CD$_3$OD) δ (ppm): 1.26 (3H, s), 1.29 (3H, s), 2.61-3.24 (13H, m), 3.15 (3H, br.s), 7.39 (1H, d, J=8.4 Hz), 7.60-7.73 (5H, m), 7.86 (1H, d, J=2.1 Hz), 8.27 (1H, s), 8.29 (1H, s)
ESI (LC-MS positive mode) m/z 582 (M+H)

Example 235

1-(4-{2-[(3-(Dimethylamino)propyl)methylamino]ethyl}-3-(trifluoromethyl)phenyl)-3-[4-(6-(methylamino)purin-9-yl)phenyl]urea (Table 3, Compound No. 38)

[Formula 318]

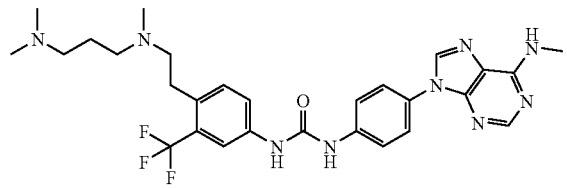

$^1$H-NMR (270 MHz, CD$_3$OD) δ (ppm): 1.72-1.89 (2H, m), 2.41 (3H, s), 2.48-2.77 (6H, m), 2.52 (6H, s), 2.88-3.00 (2H, m), 3.15 (3H, br.s), 7.39 (1H, d, J=8.9 Hz), 7.56-7.73 (5H, m), 7.86 (1H, d, J=2.1 Hz), 8.27 (1H, s), 8.29 (1H, s)
ESI (LC-MS positive mode) m/z 570 (M+H)

Example 236

1-{4-[2-(4-Ethyl-piperazin-1-yl)ethyl]-3-(trifluoromethyl)phenyl}-3-[4-(6-(methylamino)purin-9-yl)phenyl]urea (Table 3, Compound No. 39)

[Formula 319]

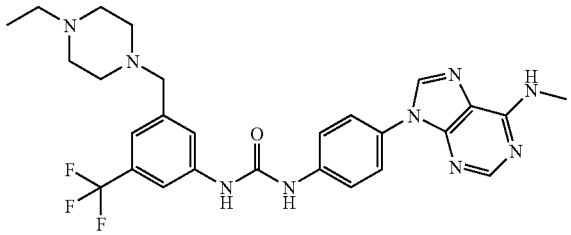

$^1$H-NMR (270 MHz, CD$_3$OD) δ (ppm): 1.12 (3H, t, J=7.3 Hz), 2.46 (2H, q, J=7.3 Hz), 2.50-2.72 (10H, m), 2.90-3.00 (2H, m), 3.15 (3H, br.s), 7.38 (1H, d, J=8.8 Hz), 7.55-7.72 (5H, m), 7.86 (1H, d, J=2.3 Hz), 8.27 (1H, s), 8.30 (1H, s)
ESI (LC-MS positive mode) m/z 568 (M+H)

Example 237

1-[4-(6-(Methylamino)purin-9-yl)phenyl]-3-[4-(2-piperazin-1-yl-ethyl)-3-(trifluoromethyl)phenyl]urea (Table 3, Compound No. 40)

[Formula 320]

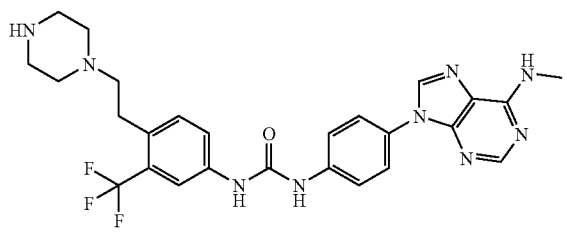

$^1$H-NMR (270 MHz, CD$_3$OD) δ (ppm): 2.55-2.68 (6H, m), 2.88-3.05 (6H, m), 3.15 (3H, br.s), 7.38 (1H, d, J=8.4 Hz), 7.56-7.72 (5H, m), 7.86 (1H, d, J=2.3 Hz), 8.27 (1H, s), 8.29 (1H, s)
ESI (LC-MS positive mode) m/z 540 (M+H)

Example 238

1-[4-(2-Methoxy-ethoxy)-3-(trifluoromethyl)phenyl]-3-[4-(6-(methylamino)purin-9-yl)phenyl]urea (Table 3, Compound No. 41)

[Formula 321]

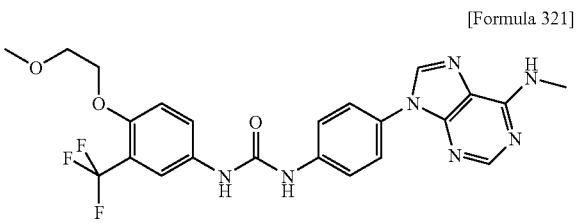

The title compound can be prepared from 2-fluoro-5-nitrobenzotrifluoride by using the same techniques as in Example 171.
$^1$H-NMR (270 MHz, DMSO-d$_6$) δ (ppm): 2.99 (3H, s), 3.68 (2H, m), 4.20 (2H, m), 7.24 (1H, d, J=9.6 Hz), 7.59 (1H, dd, J=9.6, 2.7 Hz), 7.62 (2H, d, J=9.1 Hz), 7.77 (2H, d, J=9.1 Hz), 7.87 (1H, d, J=2.7 Hz), 8.28 (1H, br.s), 8.50 (1H, s), 8.84 (1H, s), 8.96 (1H, s)
ESI (LC-MS positive mode) m/z 502 (M+H)

Example 239

1-{4-[2-(2-Methoxy-ethoxy)ethoxy]-3-(trifluoromethyl)phenyl}-3-[4-(6-(methylamino)purin-9-yl)phenyl]urea (Table 3, Compound No. 42)

[Formula 322]

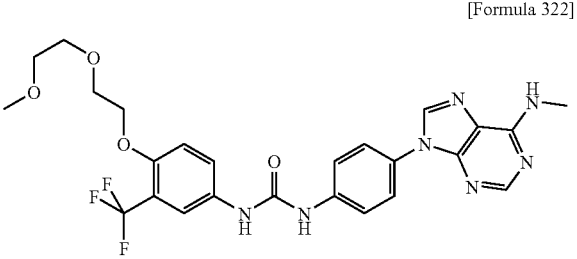

The title compound can be prepared from 2-fluoro-5-nitrobenzotrifluoride by using the same techniques as in Example 171.
ESI (LC-MS positive mode) m/z 546 (M+H)

Example 240

1-[4-(6-(Methylamino)purin-9-yl)phenyl]-3-[4-(2-piperidin-4-yl-ethoxy)-3-(trifluoromethyl)phenyl]urea (Table 3, Compound No. 43)

[Formula 323]

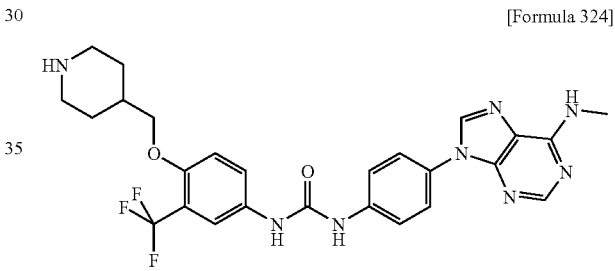

The title compound can be prepared from 2-fluoro-5-nitrobenzotrifluoride by using the same techniques as in Example 171.
ESI (LC-MS positive mode) m/z 555 (M+H)

Example 241

1-[4-(6-(Methylamino)purin-9-yl)phenyl]-3-[4-(piperidin-4-ylmethoxy)-3-(trifluoromethyl)phenyl]-urea (Table 3, Compound No. 44)

[Formula 324]

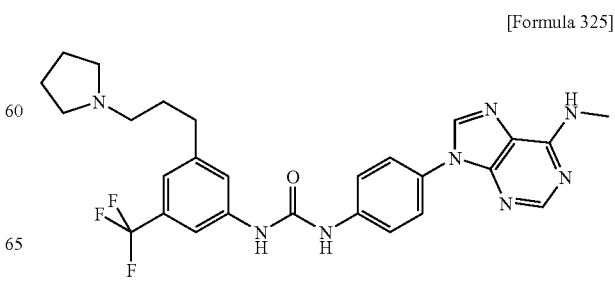

The title compound can be prepared from 2-fluoro-5-nitrobenzotrifluoride by using the same techniques as in Example 171.
$^1$H-NMR (270 MHz, DMSO-d$_6$) δ (ppm): 1.20 (1H, m), 1.70-1.90 (4H, m), 2.99 (3H, s), 3.01 (4H, m), 3.68 (2H, m), 3.90 (2H, m), 7.24 (1H, d, J=9.6 Hz), 7.59 (1H, dd, J=9.6, 2.7 Hz), 7.62 (2H, d, J=9.1 Hz), 7.77 (2H, d, J=9.1 Hz), 7.87 (1H, d, J=2.7 Hz), 8.28 (1H, br.s), 8.50 (1H, s), 8.94 (1H, s), 9.10 (1H, s)
ESI (LC-MS positive mode) m/z 541 (M+H)

Example 242

1-[4-(6-(Methylamino)purin-9-yl)phenyl]-3-[3-(3-pyrrolidin-1-yl-propyl)-5-(trifluoromethyl)phenyl]-urea (Table 3, Compound No. 45)

[Formula 325]

The title compound can be prepared from 5-bromo-3-(trifluoromethyl)nitrobenzene by using the same techniques as in Example 191.

$^1$H-NMR (270 MHz, DMSO-$d_6$) δ (ppm): 1.70-1.90 (6H, s), 2.60-2.70 (8H, m), 2.99 (3H, s), 7.21 (1H, s), 7.48 (1H, s), 7.65-7.83 (6H, m), 8.29 (1H, s), 8.50 (1H, s), 9.06 (1H, s), 9.08 (1H, s)

ESI (LC-MS positive mode) m/z 539 (M+H)

Example 243

1-[4-(3,5-Dimethyl-piperazin-1-ylmethyl)-3-(trifluoromethyl)phenyl]-3-[4-(6-(methylamino)purin-9-yl)phenyl]urea (Table 3, Compound No. 46)

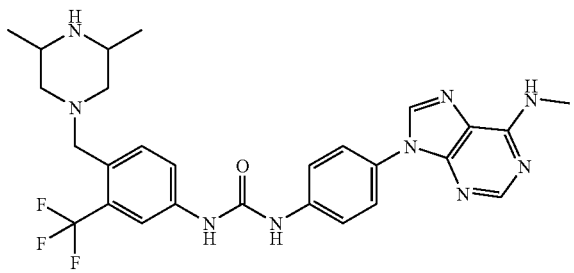

[Formula 326]

$^1$H-NMR (500 MHz, CD$_3$OD) δ (ppm): 1.11 (3H, s), 1.12 (3H, s), 1.82 (1H, t, J=11.5 Hz), 2.84 (1H, d, J=11.5 Hz), 3.03-3.08 (1H, m), 3.11 (3H, s), 3.63 (2H, s), 7.60-7.72 (6H, m), 7.88 (1H, d, J=2.0 Hz), 8.28 (1H, s), 8.30 (1H, s)

ESI (LC-MS positive mode) m/z 554 (M+H)

Example 244

1-[4-(6-(Methylamino)purin-9-yl)phenyl]-3-[4-(2-pyridin-4-yl-ethyl)-3-(trifluoromethyl)phenyl]-urea (Table 3, Compound No. 47)

Step A

Preparation of 4-(4-nitro-2-(trifluoromethyl)phenylethynyl)pyridine

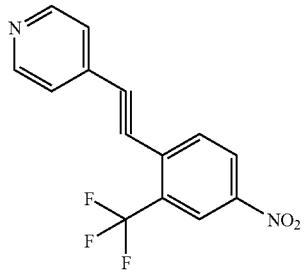

[Formula 327]

In 20 mL of dimethylformamide, 1.0 g (3.7 mmol) of 4-bromo-3-(trifluoromethyl)nitrobenzene was dissolved, and 0.502 g (3.7 mmol) of 4-ethynylpyridine, 43 mg (3 mol %) of copper iodide, 78 mg (3 mol %) of dichlorobis(triphenylphosphine)palladium and 2.06 mL (0.56 mmol) of triethylamine were added thereto and the mixture solution was stirred overnight at 50° C. in an argon atmosphere. The reaction solution was partitioned between water and ethyl acetate and the organic layer was washed with a saturated sodium chloride solution and concentrated under reduced pressure. The residue was purified by a silica gel column (n-hexane:ethyl acetate=3:1) to obtain 1.3 g (quantitative) of a target product as an pale yellow oil.

ESI (LC-MS positive mode) m/z 293 (M+H)

Step B

Preparation of 4-(2-pyridin-4-yl-ethyl)-3-(trifluoromethyl)aniline

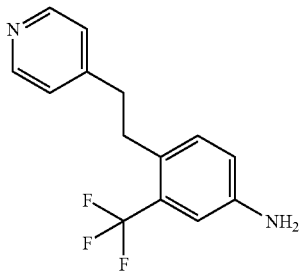

[Formula 328]

In 20 mL of ethanol, 1.3 g (4.45 mmol) of 4-(4-nitro-2-(trifluoromethyl)phenylethynyl)pyridine was dissolved and stirred on 100 mg of 10% palladium carbon overnight at room temperature in a hydrogen atmosphere. The catalyst was removed by filtration and the filtrate was concentrated and the residue was purified by a silica gel column (n-hexane:ethyl acetate=1:2) to obtain 1.0 g (85%) of a target product as a pale yellow oil.

ESI (LC-MS positive mode) m/z 266 (M+H)

Step C

Preparation of 1-[4-(6-(methylamino)purin-9-yl)phenyl]-3-[4-(2-pyridin-4-yl-ethyl)-3-(trifluoromethyl)phenyl]urea (Table 3, Compound No. 47)

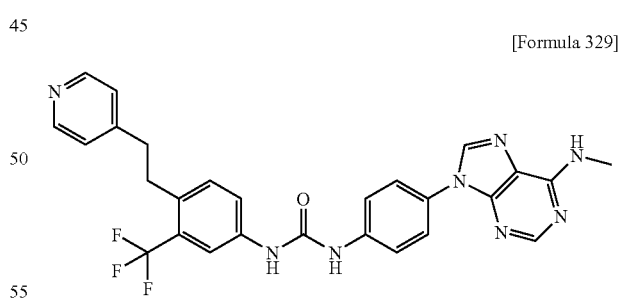

[Formula 329]

The title compound can be synthesized by allowing 4-(2-pyridin-4-yl-ethyl)-3-(trifluoromethyl)aniline and [9-(4-aminophenyl)-9H-purin-6-yl]-methylcarbamic acid tert-butyl ester to form a urea bonding by using the same techniques as in Step A of Example 176 and subsequently performing deprotection with trifluoroacetic acid.

$^1$H-NMR (270 MHz, DMSO-$d_6$) δ (ppm): 2.90-3.10 (5H, m), 3.40 (2H, m), 7.36-7.77 (8H, m), 7.86 (1H, br.s), 7.96 (1H, d, J=2.1 Hz), 8.28 (1H, s), 8.50-8.60 (3H, m), 9.08 (1H, s), 9.10 (1H, s)

ESI (LC-MS positive mode) m/z 533 (M+H)

Example 245

1-[4-(6-(Methylamino)purin-9-yl)phenyl]-3-[3-(3-morpholin-4-yl-propyl)-5-(trifluoromethyl)phenyl]-urea (Table 3, Compound No. 48)

[Formula 330]

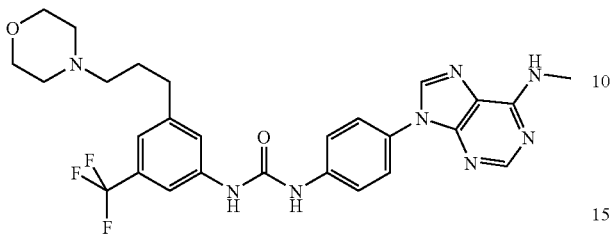

The title compound can be prepared from 5-bromo-3-(trifluoromethyl)nitrobenzene by using the same techniques as in Example 191.

ESI (LC-MS positive mode) m/z 555 (M+H)

Example 246

1-[4-(6-(Methylamino)purin-9-yl)phenyl]-3-[4-(4-pentanoyl-piperazin-1-ylmethyl)-3-(trifluoromethylphenyl)urea (Table 3, Compound No. 49)

[Formula 331]

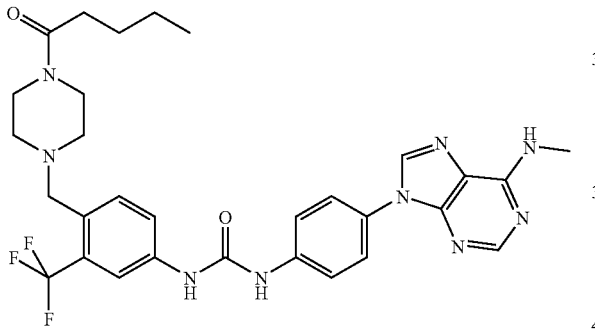

$^1$H-NMR (270 MHz, DMSO-d$_6$) δ (ppm): 0.88 (3H, t, J=5.6 Hz), 1.28 (2H, m), 1.46 (2H, m), 2.30 (4H, m), 2.99 (3H, s), 3.46 (4H, m), 3.56 (2H, s), 7.60-7.71 (4H, m), 7.71-7.90 (3H, m), 7.99 (1H, s), 8.29 (1H, s), 8.50 (1H, s), 9.04 (1H, s), 9.14 (1H, s)

ESI (LC-MS positive mode) m/z 610 (M+H)

Example 247

1-[4-(4-Acetyl-piperazin-1-ylmethyl)-3-(trifluoromethyl)phenyl]-3-[4-(6-(methylamino)purin-9-yl)phenyl]urea (Table 3, Compound No. 50)

[Formula 332]

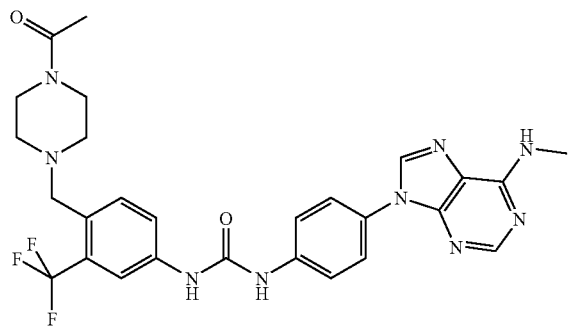

$^1$H-NMR (270 MHz, DMSO-d$_6$) δ (ppm): 1.99 (3H, s), 2.30 (4H, m), 2.99 (3H, s), 3.46 (4H, m), 3.56 (2H, s), 7.60-7.71 (4H, m), 7.71-7.90 (3H, m), 7.99 (1H, s), 8.29 (1H, s), 8.50 (1H, s), 9.04 (1H, s), 9.14 (1H, s)

ESI (LC-MS positive mode) m/z 568 (M+H)

Example 248

1-{4-[4-(2,2-Dimethyl-propionyl)-piperazin-1-ylmethyl]-3-(trifluoromethyl)phenyl}-3-[4-(6-methylamino-purin-9-yl)phenyl]urea (Table 3, Compound No. 51)

[Formula 333]

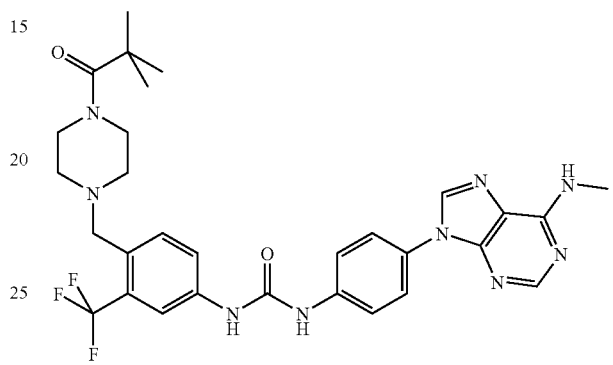

$^1$H-NMR (270 MHz, DMSO-d$_6$) δ (ppm): 1.02 (9H, s), 2.30 (4H, m), 2.99 (3H, s), 3.46 (4H, m), 3.56 (2H, s), 7.60-7.71 (4H, m), 7.71-7.90 (3H, m), 7.99 (1H, s), 8.29 (1H, s), 8.50 (1H, s), 9.04 (1H, s), 9.14 (1H, s)

ESI (LC-MS positive mode) m/z 610 (M+H)

Example 249

1-[4-(6-(Methylamino)purin-9-yl)phenyl]-3-(4-pyridin-4-ylmethyl-3-(trifluoromethyl)phenyl)urea (Table 3, Compound No. 52)

Step A

Preparation of 1-(4-bromo-3-trifluoromethyl-phenyl)-2,5-dimethyl-1H-pyrrole

[Formula 334]

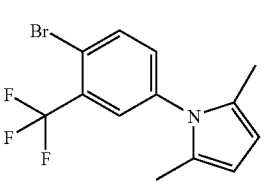

In 50 mL of toluene, 3.6 g (15 mmol) of 4-bromo-3-(trifluoromethyl)aniline was dissolved, and 2.06 g (18 mmol) of 2,5-hexanedione and 54 mg (0.28 mmol) of p-toluenesulfonic acid-hydrate were added thereto and the mixture solution was refluxed with stirring for two hours. The reaction solution was partitioned between a saturated sodium bicarbonate solution and ethyl acetate and the organic layer was washed with a saturated sodium chloride solution and concentrated under reduced pressure. The obtained residue was purified by a silica gel column (n-hexane:ethyl acetate=9:1) to obtain 4.66 g (97%) of a target product as a pale yellow oil.

ESI (LC-MS positive mode) m/z 319 (M+H)

Step B

Preparation of [4-(2,5-dimethylpyrrol-1-yl)-2-(trifluoromethyl)phenyl]-pyridin-4-yl-methanol

[Formula 335]

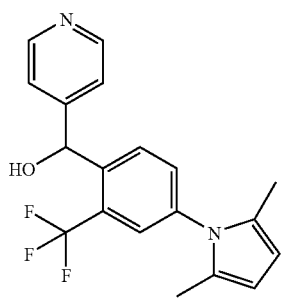

To 12 mL of an anhydrous ether solution of 1.08 g (3.4 mmol) of 1-(4-bromo-3-trifluoromethyl-phenyl)-2,5-dimethyl-1H-pyrrole, 1.4 mL of n-butyllithium (a tetrahydrofuran solution, 2.44 M) was added at one time at −60° C. and the mixture solution was stirred for one hour. Then, 5 mL of a tetrahydrofuran solution of 350 mg (3.27 mmol) of 4-formylpyridine was added thereto at −60° C. and the mixture solution was stirred while raising the temperature to room temperature over one hour. The reaction solution was partitioned between a saturated ammonium chloride aqueous solution and ethyl acetate and the organic layer was washed with a saturated sodium chloride solution and concentrated under reduced pressure. The obtained residue was purified by a silica gel column (n-hexane:ethyl acetate=1:1) to obtain 754 mg (66%) of a target product as a pale yellow oil.

ESI (LC-MS positive mode) m/z 347 (M+H)

Step C

Preparation of 4-[4-(2,5-dimethylpyrrol-1-yl)-2-trifluoromethyl-benzyl]-pyridine

[Formula 336]

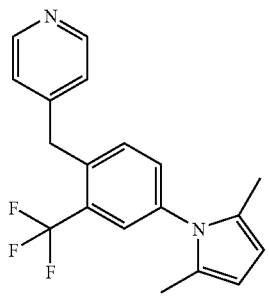

To 20 mL of an anhydrous tetrahydrofuran solution of 287 mg (0.83 mmol) of [4-(2,5-dimethylpyrrol-1-yl)-2-(trifluoromethyl)phenyl]pyridin-4-yl-methanol, 450 mg (2.52 mmol) of thiocarbonyldiimidazole was added and the mixture solution was refluxed with stirring for three hours. The reaction was concentrated under reduced pressure and the residue was purified by a silica gel column (ethyl acetate) to obtain 371 mg (98%) of a thiocarbonyl intermediate. To 6 mL of a toluene solution of 254 mg (0.56 mmol) of this intermediate, 454 mg (1.56 mmol) of tri-n-butyltin hydride was added and the mixture solution was refluxed with stirring for two hours. The reaction solution was concentrated under reduced pressure and the residue was purified by a silica gel column (n-hexane:ethyl acetate=1:1) to obtain 234 mg (87%) of a target product.

ESI (LC-MS positive mode) m/z 331 (M+H)

Step D

Preparation of 4-(pyridin-4-yl)methyl-3-(trifluoromethyl)aniline

[Formula 337]

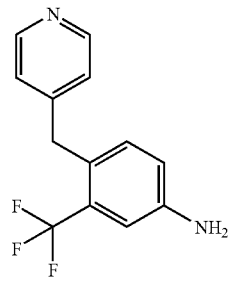

To 10 mL of an ethanol solution of 227 mg (0.69 mmol) of 4-[4-(2,5-dimethyl-pyrrol-1-yl)-2-trifluoromethyl-benzyl]-pyridine, 191 mg (2.75 mmol) of hydroxylamine hydrochloride and 200 μL of triethylamine were added and the mixture solution was refluxed with stirring for 18 hours. The reaction solution was partitioned between a saturated sodium bicarbonate solution and ethyl acetate and the organic layer was washed with a saturated sodium chloride solution and concentrated under reduced pressure. The obtained residue was purified by a silica gel column (n-hexane:ethyl acetate=1:1) to obtain 144 mg (83%) of a target product as a pale yellow oil.

ESI (LC-MS positive mode) m/z 253 (M+H)

Step E

[Formula 338]

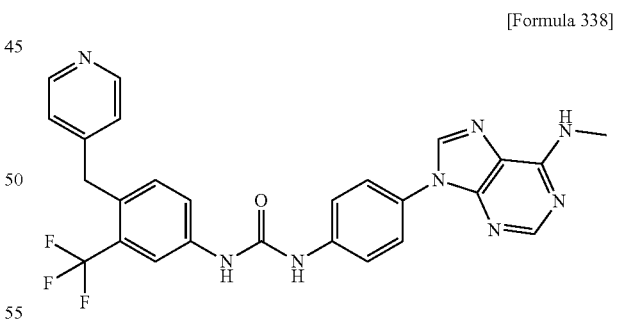

The title compound can be prepared by allowing 4-(pyridin-4-yl)methyl-3-(trifluoromethyl)aniline and [9-(4-aminophenyl)-9H-purin-6-yl]-methylcarbamic acid tert-butyl ester to form a urea bonding by using the techniques as in Step A of Example 176, and then performing deprotection with trifluoroacetic acid.

$^1$H-NMR (270 MHz, DMSO-$d_6$) δ (ppm): 3.00 (3H, s), 4.14 (2H, m), 7.13 (2H, m), 7.34 (1H, d, J=8.4 Hz), 7.56-7.87 (6H, m), 8.04 (1H, d, J=2.2 Hz), 8.28 (1H, s), 8.50-8.60 (3H, m), 9.08 (1H, s), 9.10 (1H, s)

ESI (LC-MS positive mode) m/z 519 (M+H)

Example 250

N-Methyl-3-(4-{3-[4-(6-(methylamino)purin-9-yl)phenyl]ureido}-2-(trifluoromethyl)phenyl)propionamide (Table 3, Compound No. 53)

Step A

Synthesis of (E)-3-(4-nitro-2-trifluoro-phenyl)acrylic acid ethyl ester

[Formula 339]

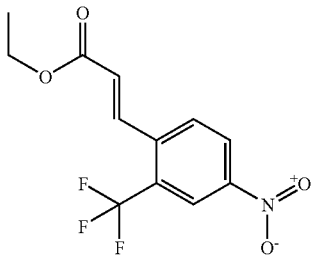

In 10 mL of dimethylformamide, 1.0 mg (3.7 mmol) of 4-bromo-3-(trifluoromethyl)nitrobenzene was dissolved, and 450 mg (4.5 mmol) of ethyl acrylate, 82 mg (0.37 mmol) of palladium acetate, 100 mg (0.37 mmol) of triphenyl-phosphine and 1.1 mL (7.9 mmol) of triethylamine were added thereto and the mixture solution was stirred in an argon atmosphere at 100° C. for two hours. The reaction solution was partitioned between water and ethyl acetate and the organic layer was washed with a saturated sodium chloride solution and concentrated under reduced pressure. The obtained residue was purified by a silica gel column (n-hexane:ethyl acetate=4:1) to obtain 500 mg (49%) of a target product as a pale yellow oil.

Step B

Preparation of 3-(4-amino-2-(trifluoromethyl)phenyl)propionic acid ethyl ester

[Formula 340]

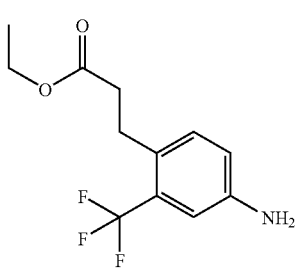

In 5 ml of ethanol, 100 mg (3.7 mmol) of (E)-3-(4-nitro-2-trifluoro-phenyl)acrylic acid ethyl ester was dissolved, and 10 mg of 10% palladium carbon was added thereto and the mixture solution was stirred in a hydrogen atmosphere at room temperature for two hours. The catalyst was removed by filtration and the reaction solution was concentrated under reduced pressure to obtain 90 mg (95%) of a target product as a pale yellow oil.

Step C

Preparation of N-methyl-3-(4-{3-[4-(6-(methylamino)purin-9-yl)-phenyl]ureido}-2-(trifluoromethyl)phenyl)propionamide (Table 3, Compound No. 53)

[Formula 341]

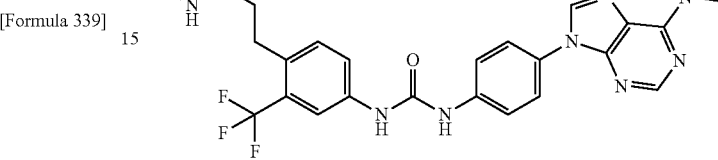

The title compound can be obtained by allowing 3-(4-amino-2-(trifluoromethyl)phenyl)propionic acid ethyl ester and [9-(4-aminophenyl)-9H-purin-6-yl]-methylcarbamic acid tert-butyl ester to form a urea bonding by using the same techniques as in Step A of Example 176, then subjecting the ester intermediate to alkali hydrolysis with lithium hydroxide by using the same techniques as in Example 203, amidating the obtained acid by using the same techniques as in Step C of Example 176, and subsequently performing deprotection with trifluoroacetic acid.

$^1$H-NMR (500 MHz, DMSO-$d_6$) δ (ppm): 2.35 (2H, t, J=7.8 Hz), 2.57 (3H, s), 2.91 (2H, t, J=7.8 Hz), 2.99 (3H, s), 7.36 (1H, d, J=8.5 Hz), 7.67 (2H, d, J=9.1 Hz), 7.76 (2H, d, J=9.1 Hz), 7.70-7.89 (1H, br.s), 7.96 (1H, d, J=2.1 Hz), 8.28 (1H, s), 8.50 (1H, s)

ESI (LC-MS positive mode) m/z 513 (M+H)

Example B-1

RAF-1 Enzyme Inhibition Test

With respect to the compounds relating to the present invention and the known compound (BAY 43-9006):

[Formula 342]

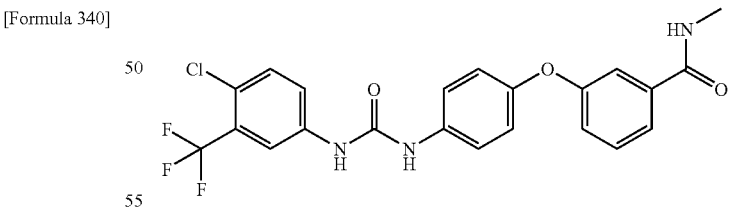

the Raf-1 protein inhibition activity was measured. The enzymatic reaction was measured by incorporation of $^{33}$P-phosphoric acid into MEK 1 protein by a recombinant Raf-1 protein. The activity was measured by preparing 50 μL of a reaction solution containing a dimethyl sulfoxide solution of the compound relating to the present invention or the compound BAY 43-9006 at a varied concentration [as the final concentration, the reaction solution containing 50 mL of TRIS hydrochloric buffer (pH 7.5), 1 mM of dithiothreitol, 100 mM of sodium chloride, 10 mM of potassium fluoride, 1 mM of sodium vanadate, 10 mM of magnesium chloride, 10

μM of adenosine triphosphate (ATP, containing $^{33}$P-ATP of 12580Bq), 2 μg of GST-MEK1 and 25 ng of an activated type GST-Raf-1]; keeping the reaction solution at 30° C. for 45 minutes; adding 100% trichloroacetic acid to the reaction solution in an amount twice the volume of the reaction solution to precipitate a proteinous component; recovering the precipitate on a glass filter; and measuring the radioactivity of the recovered product. The 50% inhibition concentration ($IC_{50}$) was obtained from the inhibition ratio to a sample-free reference.

The compound BAYT 43-9006 was prepared on the basis of the description (Example 41) of WO 00/42012. The results of measurement of Raf-1 inhibition activity are shown in Tables 4-1 to 4-3.

TABLE 4-1

50% Enzyme Inhibition Concentration ($IC_{50}$ value)/μM

| Compound | Raf-1 Enzyme Inhibition |
|---|---|
| BAY43-9006 | 0.027 |
| Table 1, Compound 18 | 0.047 |
| Table 1, Compound 30 | 0.033 |
| Table 1, Compound 36 | 0.110 |
| Table 1, Compound 46 | 0.067 |
| Table 1, Compound 93 | 0.053 |
| Table 1, Compound 95 | 0.042 |
| Table 1, Compound 96 | 0.044 |
| Table 1, Compound 104 | 0.074 |
| Table 1, Compound 119 | 0.013 |

TABLE 4-2

50% Enzyme Inhibition Concentration ($IC_{50}$ value)/μM

| Compound | Raf-1 Enzyme Inhibition |
|---|---|
| BAY43-9006 | 0.027 |
| Table 2, Compound 8 | 0.029 |
| Table 2, Compound 13 | 0.015 |
| Table 2, Compound 25 | 0.110 |
| Table 2, Compound 26 | 0.083 |
| Table 2, Compound 27 | 0.067 |
| Table 2, Compound 28 | 0.069 |
| Table 2, Compound 30 | 0.190 |
| Table 2, Compound 40 | 0.075 |
| Table 2, Compound 57 | 0.130 |

TABLE 4-3

50% Enzyme Inhibition Concentration ($IC_{50}$ value)/μM

| Compound | Raf-1 Enzyme Inhibition |
|---|---|
| BAY43-9006 | 0.027 |
| Table 2, Compound 71 | 0.190 |
| Table 2, Compound 73 | 0.084 |
| Table 2, Compound 78 | 0.140 |
| Table 2, Compound 91 | 0.270 |
| Table 3, Compound 1 | 0.051 |
| Table 3, Compound 4 | 0.053 |
| Table 3, Compound 9 | 0.085 |
| Table 3, Compound 30 | 0.170 |
| Table 3, Compound 31 | 0.130 |
| Table 3, Compound 45 | 0.073 |
| Table 3, Compound 46 | 0.041 |

As described in Table 4-1 to 4-3, the group of the compounds relating to the present invention has Raf-1 enzyme inhibition activity.

Example B-2

Cell Growth Inhibition Test

With respect to the compounds relating to the present invention and the known compound (BAY 43-9006), cell growth inhibition activity was measured.

A sample compound was in-series diluted with dimethyl sulfoxide, and then was 1/50 diluted with a $Ca^{2+}$- and $Mg^{2+}$-free phosphate-bufferized physiological saline and its 20 μL was poured to a 96-well plate. Cell suspensions having 3,000 cells/180 μL were prepared with a culture medium obtained by adding 10% bovine fetal serum to McCoy's 5a medium in measuring the grow inhibition of human colorectal cancer cell strain HCT 116; a culture medium obtained by adding 10% bovine fetal serum, 30 μg/mL of vein endothelial cell growth auxiliary and 50 μg/mL of heparin to PRMI 1640 medium in measuring the grow inhibition of VEGF nondependent human umbilical vein endothelial cells (HUVEC, purchased from Clonetics); and a culture medium obtained by adding 20 mg/mL of 10% bovine fetal serum and 20 ng/mL of VEGF to PRMI 1640 medium in measuring the grow inhibition of VEGF dependent HUVEC. Each of these cell suspensions was dividedly poured to the sample added plate in 180 μL/well and cultured in a 5% carbon dioxide incubator at 37° C. After 72 hours, 20 μL of WST-(HCT 116, a product of Dojin) or WST-1 (HUVEC, a product of Roche diagnostics) was added thereto to each well and the absorbance at 450 nm (reference wavelength: 650 nm) was measured. From the growth inhibition ratio of addition of the sample compound to no-addition of the sample compound as a reference, the 50% growth inhibition $IC_{50}$) of the sample compound was calculated.

With respect to the group of representative compounds of the present invention, the $IC_{50}$ values of HCT 116 and HUVEC (VEGF nondependent growth and VEGF dependent growth) are shown in Tables 5-1 to 5-3.

TABLE 5-1

50% Growth Inhibition Concentration ($IC_{50}$ value)/μM

| Compound | HUVEC (VEGF Nondependence) | HUVEC (VEGF Dependence) | HCT116 |
|---|---|---|---|
| Bay43-9006 | 4.6 | 0.021 | 3.0 |
| Table 1, Compound 1 | 2.1 | 0.092 | 1.2 |
| Table 1, Compound 35 | 2.4 | 0.46 | 2.8 |
| Table 1, Compound 36 | 0.25 | 0.079 | 0.7 |
| Table 1, Compound 49 | 4.1 | 0.19 | 7.3 |
| Table 1, Compound 53 | 2.8 | 0.44 | 3.4 |
| Table 1, Compound 95 | 2.6 | 0.47 | 3.1 |
| Table 1, Compound 96 | 3.2 | 0.091 | 2.2 |
| Table 1, Compound 104 | 7.4 | 0.93 | 3.9 |
| Table 1, Compound 119 | 0.97 | 0.064 | 3.7 |

TABLE 5-2

50% Growth Inhibition Concentration ($IC_{50}$ value)/μM

| Compound | HUVEC (VEGF Nondependence) | HUVEC (VEGF Dependence) | HCT116 |
|---|---|---|---|
| Bay43-9006 | 4.6 | 0.021 | 3.0 |
| Table 2, Compound 19 | 1.9 | 0.057 | 1.1 |
| Table 2, Compound 25 | 1.7 | 0.28 | 1.7 |
| Table 2, Compound 42 | 4.0 | 0.056 | 1.8 |
| Table 2, Compound 43 | 3.8 | 0.15 | 1.8 |
| Table 2, Compound 46 | 0.13 | 0.0025 | 0.24 |

TABLE 5-2-continued

50% Growth Inhibition Concentration ($IC_{50}$ value)/μM

| Compound | HUVEC (VEGF Nondependence) | HUVEC (VEGF Dependence) | HCT116 |
|---|---|---|---|
| Table 2, Compound 47 | 0.70 | 0.029 | 0.90 |
| Table 2, Compound 48 | 3.7 | 0.28 | 2.4 |
| Table 2, Compound 52 | 3.8 | 0.27 | 3.8 |
| Table 2, Compound 53 | 1.7 | 0.65 | 1.9 |

TABLE 5-3

50% Growth Inhibition Concentration ($IC_{50}$ value)/μM

| Compound | HUVEC (VEGF Nondependence) | HUVEC (VEGF Dependence) | HCT116 |
|---|---|---|---|
| Bay43-9006 | 4.6 | 0.021 | 3.0 |
| Table 2, Compound 62 | 0.9 | 0.011 | 0.7 |
| Table 2, Compound 74 | 0.9 | 0.083 | 1.2 |
| Table 2, Compound 76 | 1.0 | 0.057 | 0.9 |
| Table 3, Compound 14 | 0.2 | 0.004 | 0.3 |
| Table 3, Compound 18 | 3.1 | 0.026 | 2.7 |
| Table 3, Compound 28 | 0.3 | 0.008 | 0.2 |
| Table 3, Compound 41 | 0.9 | 0.076 | 0.8 |
| Table 3, Compound 46 | 4.2 | 0.290 | 2.8 |
| Table 3, Compound 48 | 3.2 | 0.039 | 2.5 |

As described in Tables 5-1 to 5-3, the group of the compounds relating to the present invention has growth inhibition action on human colorectal cancer strain HCT 116. Further, it has growth inhibition action on human umbilical vein endothelial cell (HUVEC).

Example B-3

Antitumor Test

With respect to the compounds relating to the present invention and the known compound (BAY 43-9006), cell growth inhibition activity was measured.

A cell suspension of a human colorectal cancer cell strain HCT 116 was prepared with a Hunks' balanced salt solution. Its $5.0 \times 10^6$ were inoculated subcutaneously to the flank of each male Balb/c nude mouse. When the mean volume of a tumor reached 200 to 250 mm$^3$, a sample compound was orally administered one time a day for 5 days. The tumor volume was calculated from the calculation formula: 0.5×(minor diameter)$^2$×(major diameter), and the tumor growth inhibition ratio was calculated from the ratio of the tumor growth of the sample administered group to that of a reference group. The dosage in the antitumor test, the tumor growth inhibition ratio on the final administration day and the reduction in body weight on day 7 after starting administration are shown in Tables 6-1 and 6-2

TABLE 6-1

Antitumor Test

| Compound | Dosage (mg/kg) | Tumor Inhibition Ratio (%) | Body Weight Reduction ratio (%) |
|---|---|---|---|
| Bay43-9006 | 100 | 83 | 17.0 |
| Table 1, Compound 36 | 200 | 81 | 5.9 |
| Table 1, Compound 93 | 200 | 79 | 6.0 |
| Table 1, Compound 119 | 200 | 89 | 8.5 |

TABLE 6-2

Antitumor Test

| Compound | Dosage (mg/kg) | Tumor Inhibition Ratio (%) | Body Weight Reduction ratio (%) |
|---|---|---|---|
| Bay43-9006 | 100 | 83 | 17.0 |
| Table 2, Compound 25 | 200 | 80 | 2.7 |
| Table 2, Compound 26 | 200 | 72 | 5.0 |
| Table 2, Compound 30 | 200 | 131 | 5.7 |

As described in Tables 6-1 and 6-2, the group of the compounds relating to the present invention has antitumor activity and is safe with a small reduction in body weight.

Example B-4

Method of Measuring Solubility to Fasted State Simulated Intestinal Fluid

To a 96-well plate, 2 μL of a dimethyl sulfoxide solution of the compound relating to the present invention or that of the compound BAY 43-9006 was poured at one time, respectively, and fasted state simulated intestinal fluid (pH 6.5) was added 200 μL by 200 μL, and the plate was shaken at 37° C. for 20 hours. The solution was filtered with a membrane filter and 101 μL of the filtrate was transferred to an UV plate, and 100 μL of a mixed solution of ethanol:water=2:1 was added thereto. On the other hand, as a standard solution, 2 μL of a dimethyl sulfoxide solution was added to a solution containing 4 μL of dimethyl sulfoxide, 400 μL of ethanol and 200 μL of water and the obtained solution was transferred 101 μL by 101 μL to the UV plate and to this UV plate, the simulated fasting bile-containing intestinal juice (pH 6.5) was added 100 μL by 100 μL. The solubility was calculated by the following equation.

Solubility=(absorbance of sample solution-blank)/(absorbance of standard solution-blank)×165 μL wherein
165 μL is a concentration of the standard solution.
Composition of Fasted State Simulated Intestinal Fluid Fasted state simulated intestinal fluid was prepared in accordance with E. Galia et al., Pharm. Res., 698, 1998.

To about 90 mL of water, 161 mg of taurocholic acid, 59 mg of L-α-phosphatidylcholine, 0.39 g of potassium dihydrogenphosphate and 0.77 g of potassium chloride were added and the pH of the mixture solution was adjusted to 100 mL and the mixture solution was filtered with a membrane filter.

The values relating to a representative group of the compounds of the present invention are shown in Tables 7-1 to 7-3.

TABLE 7-1

Solubility Test

| Compound | Solubility (μg/mL) |
|---|---|
| BAY43-9006 | 10 |
| Table 1, Compound 21 | 24 |
| Table 1, Compound 34 | 34 |
| Table 1, Compound 35 | 24 |
| Table 1, Compound 36 | 22 |
| Table 1, Compound 92 | 76 |
| Table 1, Compound 96 | 102 |
| Table 1, Compound 109 | 39 |
| Table 1, Compound 115 | 19 |
| Table 1, Compound 119 | 39 |

TABLE 7-2

Solubility Test

| Compound | Solubility (μg/mL) |
| --- | --- |
| BAY43-9006 | 10 |
| Table 2, Compound 11 | 38 |
| Table 2, Compound 12 | 265 |
| Table 2, Compound 21 | 120 |
| Table 2, Compound 25 | 158 |
| Table 2, Compound 26 | 61 |
| Table 2, Compound 28 | 238 |
| Table 2, Compound 30 | 105 |
| Table 2, Compound 32 | 175 |
| Table 2, Compound 33 | 193 |
| Table 2, Compound 35 | 149 |
| Table 2, Compound 39 | 48 |
| Table 2, Compound 52 | 126 |

TABLE 7-3

Solubility Test

| Compound | Solubility (μg/mL) |
| --- | --- |
| BAY43-9006 | 10 |
| Table 2, Compound 62 | 35 |
| Table 2, Compound 77 | 34 |
| Table 3, Compound 4 | 219 |
| Table 3, Compound 15 | 104 |
| Table 3, Compound 36 | 107 |
| Table 3, Compound 37 | 193 |
| Table 3, Compound 38 | 147 |
| Table 3, Compound 45 | 79 |
| Table 3, Compound 46 | 23 |

As described in Table 7-1 to Table 7-3, the group of the compounds relating to the present invention excels in the solubility in fasted state simulated intestinal fluid.

The invention claimed is:

1. A compound represented by formula (1):

Formula 1

(1)

wherein
  $R^1$, and $R^5$ are each independently selected from a hydrogen atom, a halogen atom, a $C_1$-$C_6$ alkyl group which may be substituted with one or more halogen atoms and a $C_1$-$C_6$ alkoxy group which may be substituted with one or more halogen atoms;
  $R^2$ is selected from the group consisting of halogen atom, a $C_1$-$C_6$ alkyl group which is substituent with one or more halogen atoms and a $C_1$-$C_6$ alkoxy group which is substituted with one or more halogen atoms;
  $R^3$ and $R^4$ are each independently selected from a hydrogen atom, a halogen atom, —NRfRg, —CONRfRg, a $C_1$-$C_6$ alkoxy group, a $C_1$-$C_6$ alkyl group and -T-$(OH_2)_k$—V, wherein the alkyl group and the alkoxy group may be substituted with one or more substituents selected from a hydroxyl group, a $C_1$-$C_5$ alkoxy group, a halogen atom and —NRfRg;
  wherein
    Rf and Rg are each independently selected from a hydrogen atom, $C_1$-$C_6$ alkyl group and $C_1$-$C_6$ alkylcarbonyl group, wherein the alkyl group and the alkylcarbonyl group may be substituted with one to three substituents selected from a hydroxyl group, a $C_1$-$C_6$ alkoxy group, a halogen atom and —NRhRi,
    Rh and Ri are each independently selected from a hydrogen atom and $C_1$-$C_6$ alkyl group, wherein the alkyl group may be substituted with one to three substituents selected from a hydroxyl group, a halogen atom and a $C_1$-$C_6$ alkoxy group, or
    Rf and Rg, and Rh and Ri together with a nitrogen atom to which they are attached may form a 4- to 7-heterocycle, wherein the heterocycle may be substituted with a $C_1$-$C_6$ alkyl group,
  T is an oxygen atom or a single bond; k is an integer selected from 0 to 4;
  V is a 5- to 6-membered heterocyclyl group which may be substituted with one or more substituents selected from the group consisting of
    —NRxRy,
    —C(=O)Rz, —ORz and a $C_1$-$C_6$ alkyl group, or V is
    —NRaRb, —CONRaRb,
    —C(=O)NRaRb, —SO$_2$NRaRb, —N(—Ra)C(=O)NRa'Rb', —N(—Ra)C(=O)ORd,
    —C(=O)ORd, —S(=O)$_m$-Rd, —O-Rd, —OC(=O)Rc, —N(—Ra) C(=O)Rc,
    —N(Ra)SO$_2$Rc, —C(=NRa)NRa'Rb',
    —C(=NORa)Rc or —C(=O)Rc;
  $R^6$ and $R^7$ are each independently selected from a hydrogen atom and a halogen atom;
  $Z^1$ and $Z^2$ are each independently selected from a hydrogen atom, a hydroxyl group and —O(CHR$^{11}$)OC(=O)R$^{12}$;
  wherein
    $R^{11}$ is a hydrogen atom or a $C_1$-$C_6$ alkyl group;
    $R^{12}$ is a pyrrolidinyl group, a piperidinyl group, a morpholinyl group, a piperazinyl group, an amino $C_1$-$C_6$ alkyl group, a mono- or di($C_1$-$C_6$ alkyl)amino $C_1$-$C_6$ alkyl group, an amino $C_1$-$C_6$ alkylamino group or a mono- or di($C_1$-$C_6$ alkyl)-amino $C_1$-$C_6$ alkylamino group;
  Q is a group of Formula 2 wherein
  $Y^1$ is selected from the group consisting of a hydrogen atom, a halogen atom, and a $C_2$-$C_6$ alkenyl group;
  W is —NRaRb, —N=C(-Rc)NRaRb, —N(—Ra)C(=O)NRa'Rb' or —N(—Ra)C(=O)Rc;
  Ra, Ra', Rb, Rb', Rc, and Rd are each independently selected from the group consisting of a hydrogen atom, a $C_1$-$C_{10}$ alkyl group, a $C_3$-$C_8$ cycloalkyl group, a $C_2$-$C_8$ alkenyl group, a $C_2$-$C_8$ alkynyl group, —[($C_1$-$C_6$ alkylene)-O]$_n$—($C_1$-$C_3$ alkyl), a tetrahydropyranyl group, a tetrahydrofuranyl group, an aryl group, a heteroaryl group, and a nitrogen-containing heterocyclyl group (wherein the nitrogen atom on the heterocyclyl group may be substituted with a $C_1$-$C_3$ alkyl group);

Ra and Rb, Ra' and Rb', Ra and Rd, Ra and Ra', Ra and Rc, and Rd and Ra' may form a saturated or unsaturated 5- to 6-membered heterocycle by ring-closing at the bonding position of each of these two groups and the heterocycle may be substituted with a $C_1$-$C_6$ alkyl group;

Ra, Ra', Rb, Rb', Rc, and Rd each may be substituted with one to three same or different substituents selected from $Y^3$;

m is an integer selected from 0 to 2;

n is an integer selected from 1 to 4;

$Y^3$ is a halogen atom, —NRxRy, —C(=O)ORz, —C(=O)Rz, —ORz, —C(=O)NRxRy, —OC(=O)NRxRY, —SO$_2$NRxRy, —N(-Rx)C(=O)NRx'Ry', —N(-Rx)C(=O)ORz, —S-Rz, —SO-Rz, —SO$_2$-Rz, —OC(=O)Rz, —N(Rx)C(=O)Rz, —C(=NORz)NRx'Ry', —C(=NRx)NRx'Ry', —C(=NORx)Rz, —[O—($C_1$-$C_6$ alkylene)]$_n$—O($C_1$-$C_3$ alkyl), —N(-Rx)-($C_1$-$C_6$ alkylene)-O($C_1$-$C_3$ alkyl), —C(=O)Rz, a $C_1$-$C_6$ alkyl group, a $C_2$-$C_8$ alkenyl group, a $C_2$-$C_8$ alkynyl group, an aryl group or a heteroaryl group;

Rx, Rx', Ry, Ry' and Rz are each independently selected from a hydrogen atom and a $C_1$-$C_4$ alkyl group;

Rx and Ry, Rx and Rx', Rx and Rz, and Rz and Rx' may form a saturated or unsaturated 5- to 6-membered heterocycle by ring-closing at the bonding position of each of these two groups; or a pharmaceutically acceptable salt thereof.

2. The compound of claim 1 or a pharmaceutically acceptable salt thereof wherein $R^2$ is selected from a halogen atom, a trifluoromethyl group and a trifluoromethoxy group.

3. The compound of claim 1 or a pharmaceutically acceptable salt thereof, wherein $R^1$, $R^2$, $R^3$, $R^4$ and $R^5$ are each independently selected from a hydrogen atom, a chlorine atom, a fluorine atom, a bromine atom and a trifluoromethyl group;

$R^6$ and $R^7$ are hydrogen atoms; and $Z^1$ and $Z^2$ are each independently selected from a hydrogen atom, and a hydroxyl group.

4. The compound of claim 1 or a pharmaceutically acceptable salt thereof, wherein $R^3$ and $R^4$ are each independently selected from a hydrogen atom, a halogen atom, a $C_1$-$C_6$ alkyl group which may be substituted with one or more hydroxyl groups or halogen atoms, a $C_1$-$C_6$ alkoxy group which may be substituted with one or more halogen atoms, and -T-(CH$_2$)$_k$—V;

T is an oxygen atom or a single bond; k is an integer selected from 0 to 4;

V is a 5- to 6-membered heterocyclyl group which may be substituted with one or more substituents selected from a hydroxy group, an amino group, $C_1$-$C_6$ alkyl group, $C_1$-$C_6$ alkoxy group and $C_1$-$C_6$ alkylcarbonyl group.

5. A pharmaceutical composition comprising a compound of claim 1 or a pharmaceutically acceptable salt thereof as an active ingredient.

6. The compound of claim 1, or a pharmaceutically acceptable salt thereof, wherein $R^1$ and $R^5$ are each independently selected from a hydrogen atom, and a halogen atom;

$R^2$ is a $C_1$-$C_6$ alkyl group which is substituted with one or more halogen atoms Rf and Rg are each independently selected from a hydrogen atom, and $C_1$-$C_6$ alkyl group, wherein the alkyl group may be substituted with one to three substituents selected from a hydroxyl group, and —NRhRi, Rh and Ri are each independently selected from $C_1$-$C_6$ alkyl group, or V is a 5- to 6-membered heterocyclyl group which may be substituted with one or more substituents selected from the group consisting of —C(=O)Rz, and a $C_1$-$C_6$ alkyl group, or V is —NRaRb, —CONRaRb, or —O-Rd;

$R^{11}$ is hydrogen atoms;

$R^{12}$ is a morpholinyl group;

Ra, Ra', Rb, Rb', Rc, and Rd are each independently selected from the group consisting of a hydrogen atom, a $C_1$-$C_{10}$ alkyl group, a $C_3$-$C_8$ cycloalkyl group, a $C_2$-$C_8$ alkenyl group, —[($C_1$-$C_6$ alkylene)-O]$_n$—($C_1$-$C_3$ alkyl), a tetrahydropyranyl group, and a nitrogen containing heterocyclyl group, wherein the nitrogen atom on the heterocyclyl group may be substituted with a $C_1$-$C_3$ alkyl group, and Ra, Ra', Rb, Rb', Rc and Rd each may be substituted with one to three same or different substituents selected from $Y^3$;

$Y^3$ is —NRxRy, —C(=O)ORz, —ORz, —SO$_2$-Rz, —[O—($C_1$-$C_6$ alkylene)]$_n$—O($C_1$-$C_3$ alkyl), or an aryl group.

* * * * *